(12) United States Patent
Garcia-Sastre et al.

(10) Patent No.: US 8,709,730 B2
(45) Date of Patent: Apr. 29, 2014

(54) METHODS OF PREVENTING AND TREATING VIRAL INFECTIONS BY INHIBITING THE DEISGYLATION ACTIVITY OF OTU DOMAIN-CONTAINING VIRAL PROTEINS

(75) Inventors: Adolfo Garcia-Sastre, New York, NY (US); Natalia Frias-Staheli, New York, NY (US); Herbert W. Virgin, Clayton, MO (US); Nadia Vicki Giannakopoulos, Seattle, WA (US)

(73) Assignees: Icahn School of Medicine at Mount Sinai, New York, NY (US); Washington University School of Medicine, St. Louis, MO (US)

( * ) Notice: Subject to any disclaimer, the term of this patent is extended or adjusted under 35 U.S.C. 154(b) by 658 days.

(21) Appl. No.: 12/594,774

(22) PCT Filed: Apr. 7, 2008

(86) PCT No.: PCT/US2008/004481
§ 371 (c)(1),
(2), (4) Date: Mar. 29, 2010

(87) PCT Pub. No.: WO2009/008924
PCT Pub. Date: Jan. 15, 2009

(65) Prior Publication Data
US 2011/0033498 A1    Feb. 10, 2011

Related U.S. Application Data

(60) Provisional application No. 60/922,273, filed on Apr. 5, 2007, provisional application No. 61/004,842, filed on Nov. 30, 2007.

(51) Int. Cl.
*G01N 33/53*    (2006.01)
*A61K 39/12*    (2006.01)

(52) U.S. Cl.
USPC ................ 435/7.1; 424/229.1; 424/204.1

(58) Field of Classification Search
None
See application file for complete search history.

(56) References Cited

U.S. PATENT DOCUMENTS

| 5,840,520 | A | 11/1998 | Clarke et al. |
| 2004/0209315 | A1 | 10/2004 | Zhang et al. |
| 2005/0287546 | A1 | 12/2005 | Plowman et al. |

FOREIGN PATENT DOCUMENTS

| WO | WO 92/21375 | 12/1992 |
| WO | WO 95/19438 | 7/1995 |
| WO | WO 02/072802 | 9/2002 |
| WO | WO 2009/008924 | 1/2009 |

OTHER PUBLICATIONS

Balakirev et al., Journal of Virology, 2002, 76(12):6323-6331.*
Deyde et al., Journal of Virology, 2006, 80(17):8834-8842.*
Balakirev et al., EMBO Reports, 2003, 4(5):517-522.*
Wilkinson et al., Methods in Enzymology, 2005, 399:37-51.*
BostonBiochem's ISG-AMC conjugate data sheet, Material Data Sheet from BostonBiochem's website: www.bostonbiochem.com/sites/bostonbiochem.com/files/datasheets/ul-553-isg15-amc_0.pdf, see Document Properties on that page, the date created/modified is Jan. 23, 2007.*
Allende et al., 1999, "North American and European porcine reproductive and respiratory syndrome viruses differ in non-structural protein coding regions", J Gen Virol., 80:307-315.
Amerik et al., 2004, "Mechanism and function of deubiquitinating enzymes". Biochem et Biophysica Acta, 1695:189-207.
Balakirev et al., 2002, "Deubiquitinating function of adenovirus proteinase," J Virol., 76:6323-6331.
Balakirev et al., 2003 "Otubains: a new family of cysteine proteases in the ubiquitin pathway", EMBO Rep. 4:517-522.
Barretto et al., 2005, "The papain-like protease of severe acute respiratory syndrome coronavirus has deubiquitinating activity", J Virol. 79:15189-15198.
Blomstrom et al., 1986, "Molecular characterization of the interferon-induced 15-kDa protein. Molecular cloning and nucleotide and amino acid sequence", J Biol Chem, 261:8811-8816.
Chen, 2005, "Ubiquitin signaling in the NF-κB pathway", Nat Cell Biol., 7:758-765.
Chen et al., 2006, "Viral hijacking of cellular ubiquitination pathways as an anti-innate immunity strategy", Viral Immunol., 19(3):349-362.
Dao et al., 2005, "ISG15: A ubiquitin-like enigma", Frontiers in Bioscience, 10:2701-2722.
Dastur et al., 2006, "Herc5, an interferon-induced HECT E3 enzyme, is required for conjugation of ISG15 in human cells", J Biol Chem., 281:4334-4338.
Deyde et al., 2006, "Crimean-Congo hemorrhagic fever virus genomics and global diversity", J Virol., 80:8834-8842.
Evans et al., 2003, "A novel type of deubiquitinating enzyme", J Biol Chem, 278:23180-23186.

(Continued)

*Primary Examiner* — Stacy B. Chen
(74) *Attorney, Agent, or Firm* — Jones Day

(57) ABSTRACT

Viruses having an impaired ability to deISGylate ISG15 conjugates, in particular, viral mutants comprising a mutation in the viral genome that reduces or eliminates the ability of the viral OTU domain-containing protein encoded by the viral genome to deISGylate ISG15 conjugates and/or deubiquitinate ubiquitinated proteins and/or deNeddylate Neddylated proteins are disclosed. Such viral mutants may be used in the formulation of immunogenic compositions for inducing an immune response and preventing, managing and/or treating a viral infection. Also disclosed are methods for identifying anti-viral compounds, in particular, methods of identifying compounds that reduce or inhibit the deISGylation activity and/or deubiquitination and/or deNeddylation activity of a viral OTU domain-containing protein. The compounds identified using such methods may be used as antiviral agents for the prevention, treatment and/or management of viral infections.

25 Claims, 28 Drawing Sheets

(56) References Cited

OTHER PUBLICATIONS

Figure 1A:
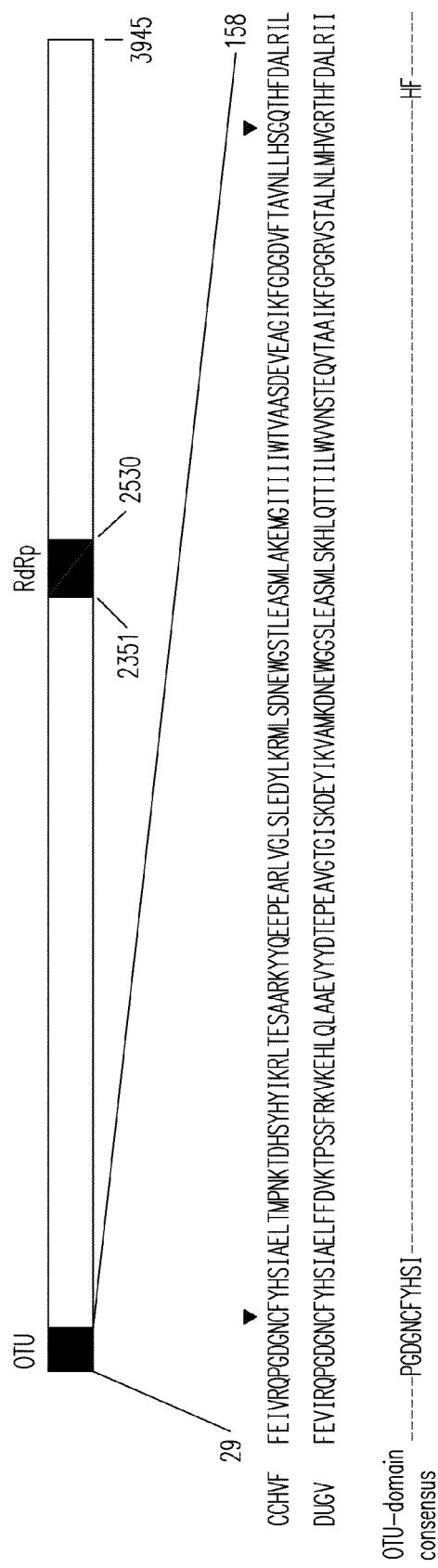

Evans et al., 2004, "Zinc-finger protein A20, a regulator of inflammation and cell survival, has de-ubiquitinating activity", Biochem J, 378:727-734.
Flick et al., 2005, "Crimean-Congo hemorrhagic fever virus", Curr Mol Med., 5:753-760.
Frias-Staheli et al., 2007, "Ovarian tumor (OUT)—domain containing viral proteases evade ubiquitin- and ISG15-dependent innate immune responses", Cell Host Microbe, 2(6):404-416.
GenBank Accession No. AY349168.
GenBank Accession. No. AY349167.
GenBank Accession. No. NC_002665.
Haas et al., 1987, "Interferon induces a 15-kilodalton protein exhibiting marked homology to ubiquitin," J Biol Chem., 262:11315-11323.
Haller et al., 1995, "Tick-borne thogoto virus infection in mice is inhibited by the orthomyxovirus resistance gene product Mx1", J Virol. 69:2596-2601.
Heise et al., 2000, "A single amino acid change in nsP1 attenuates neurovirulence of the Sindbis-group alphavirus S.A.AR86", J Virol., 74:4207-4213.
Honig et al., 2004, "Crimean-Congo hemorrhagic fever virus genome L RNA segment and encoded protein", Virology, 321:29-35.
International Search Report PCT/US2008/004481, dated Feb. 23, 2009.
James et al., 2011, "Structural basis for the removal of ubiquitin and interferon-stimulated gene 15 by a viral ovarian tumor domain-containing protease", PNAS, 108(6):2222-2227.
Kim et al., 2004, "Interferon-inducible ubiquitin E2, Ube8 is a conjugating enzyme for protein ISGylation", Mol Cell Biol., 24:9592-9600.
Kinsella et al., 2004, "Sequence determination of the Crimean-Congo hemorrhagic fever virus L segment", Virology, 321:23-28.
Korant et al., 1984, "Interferon-induced proteins. Purification and characterization of a 15,000-dalton protein from human and bovine cells induced by interferon", J Biol Chem., 259:14835-14839.
Lenschow et al., 2005, "Identification of interferon-stimulated gene 15 as an antiviral molecule during sindbis virus infection in vivo", J. Virol., 79:13974-13983.
Lenschow et al., 2007, "IFN-stimulated gene 15 functions as a critical antiviral molecule against influenza, herpes, and Sindbis viruses", Proc Natl Acad Sci USA., 104:1371-1376.
Levine et al., 1996, "Bcl-2 protects mice against fatal alphavirus encephalitis", Proc Natl Acad Sci USA, 93:4810-4815.
Lindner 2007, "Deubiquitination in virus infection", Virology, 362:245-256.
Lindner et al., 2005, "The papain-like protease from the severe acute respiratory syndrome coronavirus is a deubiquitinating enzyme", J Virol., 79:15199-15208.
Liu et al., 2005, "Immunity by ubiquitylation: a reversible process of modification", Nat Rev Immunol., 5:941-952.
Loeb et al., 1992, "The interferon-inducible 15-kDa ubiquitin homolog conjugates to intracellular proteins", J Biol Chem., 267:7806-7813.
Loureiro et al., 2006, "Antigen presentation and the ubiquitin-proteasome system in host-pathogen interactions", Adv Immunol., 92:225-305.
Makarova et al., 2000, "A novel superfamily of predicted cysteine proteases from eukaryotes, viruses and *Chlamydia pneumoniae*", Trends Biochem Sci., 25:50-52.
Malakhov et al., 2002, "UBP43 (USP18) specifically removes ISG15 from conjugated proteins", J Biol Chem., 277:9976-9981.
Malakhov et al., 2003, "High-throughput immunoblotting. Ubiquitin-like protein ISG15 modifies key regulators of signal transduction", J Biol Chem., 278:16608-16613.
Malakhov et al., 2006, "UBP43 is a novel regulator of interferon signaling independent of its ISG15 isopeptidase activity", EMBO J., 25:2358-2367.

Meurs et al., 1992, "Constitutive expression of human double-stranded RNA-activated p68 kinase in murine cells mediates phosphorylation of eukaryotic initiation factor 2 and partial resistance to encephalomyocarditis virus growth", J Virol., 66:5805-5814.
Nanao et al., 2004, "Crystal structure of human otubain 2", EMBO Rep., 5:783-788.
Narasimhan et al., 1996, "Conjugation of the 15-kDa interferon-induced ubiquitin homolog is distinct from that of ubiquitin", J Biol Chem., 271:324-330.
Narasimhan et al., 2005, "Crystal structure of the interferon-induced ubiquitin-like protein ISG15", J Biol Chem., 280:27356-27365.
Nijman et al., 2005, "A genomic and functional inventory of deubiquitinating enzymes", Cell, 123:773-786.
Nyman et al., 2000, "Proteome analysis reveals ubiquitin-conjugating enzymes to be a new family of interferon-alpha-regulated genes", Eur J Biochem., 267:4011-4019.
Okumura et al., 2006, "Innate antiviral response targets HIV-1 release by the induction of ubiquitin-like protein ISG15.", Proc Natl Acad Sci USA., 103:1440-1445.
Osiak et al., 2005, "ISG15, an interferon-stimulated ubiquitin-like protein, is not essential for STAT1 signaling and responses against vesicular stomatitis and lymphocytic choriomeningitis virus", Mol Cell Biol., 25:6338-6345.
Snijder et al., 1994, "Proteolytic processing of the replicase ORF1a protein of equine arteritis virus", J Virol., 68:5755:5764.
Snijder et al., 1995, "The arterivirus Nsp2 protease. An unusual cysteine protease with primary structure similarities to both papain-like and chymotrypsin-like proteases", J Biol Chem., 270:16671-16676.
Snijder et al., 1996, "The arterivirus nsp4 protease is the prototype of a novel group of chymotrypsin-like enzymes, the 3C-like serine proteases", J Biol Chem., 271:4864-4871.
Snijder et al., 2001, "Non-structural proteins 2 and 3 interact to modify host cell membranes during the formation of the arterivirus replication complex", J Gen Virol., 82:985-994.
Sulea et al., 2006, "Structural aspects of recently discovered viral deubiquitinating activities", Biol Chem., 387:853-862.
Van Kasteren et al., 2012, "Arterivirus and nairovirus ovarian tumor domain-containing Deubiquitinases target activated RIG-I to control innate immune signaling", J Virol., 86(2):773-85.
Wang et al., 2000, "Influenza A virus NS1 protein prevents activation of NF-kappaB and induction of alpha/beta interferon", J Virol., 74:11566-11573.
Wang et al., 2004, "VCIP135 acts as a deubiquitinating enzyme during p97-p47-mediated reassembly of mitotic Golgi fragments", J Cell Biol., 164:973-978.
Whitehouse 2004, "Crimean-Congo hemorrhagic fever", Antiviral Res., 64:145-160.
Written Opinion PCT/US2008/00448 I, dated Jan. 21, 2009.
Yuan et al., 2001, "Influenza B virus NS1 protein inhibits conjugation of the interferon (IFN)-induced ubiquitin-like ISG15 protein", EMBO J, 20:362-371.
Zhang et al., 2009, "Molecular responses of macrophages to porcine reproductive and respiratory syndrome virus infection", Virol. 262:152-162.
Zhao et al., 2004, "The UbcH8 ubiquitin E2 enzyme is also the E2 enzyme for ISG15, an IFN-alpha/beta-induced ubiquitin-like protein", Proc Natl Acad Sci USA, 101:7578-7582.
Zhao et al., 2005, "Human ISG15 conjugation targets both IFN-induced and constitutively expressed proteins functioning in diverse cellular pathways", Proc Natl Acad Sci USA, 102:10200-10205.
Ziebuhr et al., 2000, "Virus-encoded proteinases and proteolytic processing in the Nidovirales", J Gen Virol. 81:853-879.
Zou et al., 2006, "The interferon-inducible ubiquitin-protein isopeptide ligase (E3) EFP also functions as an ISG15 E3 ligase", J Biol Chem., 281:3989-3994.

* cited by examiner

OTU
CCHFV-L
L(1-1325)
L(1325-2590)
L(2582-3945)

L(1-354)
L(1-169)

L(1-169)SM
L(1-169)DM

FIG.2A

| | | | | | Host |
|---|---|---|---|---|---|
| −RNA viruses | AAQ98866 | Bunyavirus CCHFV(RdRp) | 30 EIVRQPGDGNCFYHSIAELT 49 | ---- | 148 GQTHFDALRI 157 | Humans |
| | Q66431 | DUGV(RdRp) | 30 EVIRQPGDGNCFYHSIAELF 49 | ---- | 148 GRTHFDALRI 157 | Cattle, humans |
| | BAA06677 | Tenuivirus RiceStV(RdRp) | 35 EETDVRGDGFCLYHSILYSM 54 | ---- | 145 GNYHFKSLET 154 | Plants |
| | P19811 | Arteriviruses EAV(Nsp2) | 260 GGYNPPGDGACGYRCLAFMN 279 | ---- | 329 DKQHWRVKRA 338 | Horses |
| | AAA85663 | LDV(Nsp2) | 380 YGYSPPGDGACGLHCISAII 399 | ---- | 453 VNQHWTVTKR 462 | Mice |
| | Q04561 | LELV(Nsp2) | 419 TTYSPPTDGSCGWHVLAAIM 438 | ---- | 495 NGVHWEVEVR 504 | Swine |
| | AAA68984 | Carlaviruses BBSV(RdRp) | 885 NVQCVPGDGNCFWHSLGSFT 904 | ---- | 981 KGSHFEPLEP 990 | Plants |
| | NP_955549 | PVM(RdRp) | 884 KRVSGPGDGCCCWHSFAYLV 903 | ---- | 981 ESEHYEPQVL 990 | Plants |
| | BAB13712 | HLV(RdRp) | 894 AALDVPGDGSCFWHSVGLLL 910 | ---- | 991 EGEHYMPMLI 1000 | Plants |
| | AAD10481 | SSMV(RdRp) | 848 TCINVPADGDCFWHSVSLYL 867 | ---- | 945 DHMHFCPAKF 954 | Plants |
| +RNA viruses | AAL68924 | Foveaviruses AOPRSV(RdRp) | 742 AIFPVPADGDCFWHAAGSVL 761 | ---- | 852 VTQHFDLALP 861 | Plants |
| | AAC35433 | CGRMV(RdRp) | 920 SVFPVKADGDCFWHAVSSIF 939 | ---- | 1029 RCHHFDLAVP 1038 | Plants |
| | AAC62910 | GRSPV(RdRp) | 1069 NTFSVPGDGNCFWHSVGFLL 1088 | ---- | 1171 KSNHFQPCAP 1180 | Plants |
| | Q00106 | Herpesvirus IcHV-1(ORF65) | 1285 KRVYIPGDGNCLYNTLRFIA 1304 | ---- | 1399 TNSHYEPLVT 1408 | Reptiles |
| ds DNA viruses | P22856 | Iridoviruses TIV(L96) | 684 SKPGTWGDFICLRVLSEILK 703 | ---- | 735 DDYHYTALTP 744 | Insects |
| | AAK82093 | CIV(232R) | 393 RMINVPLDGNCMFSVIGRAF 412 | ---- | 511 DNFHYIALEP 520 | Insects |
| | AAC70291 | Baculovirus LdMNPV(vp80) | 25 RVAHMKGDGACIFRAVAHVV 44 | ---- | 138 ESGHVDVYEL 147 | Insects |
| Bacteria | AAD18623 | C.pneum. | 256 YLVNVPGDGNCFYRAYAVGW 275 | ---- | 339 SQKHTATLIA 348 | |
| Humans | NP_006281 | A20 | 93 VALKTNGDGNCLMHATSQYM 112 | ---- | 252 DSHHFVPLVT 262 | |
| | NP_064590 | CEZANNE | 199 LPLATTGDGNCLLHAASLGM 218 | ---- | 369 DQAHFSALVS 379 | |
| | Q96FW1 | OTU1 | 81 YIRKTRPDGNCFYRAFGFSH 100 | ---- | 261 RPGHYDILYK 271 | |
| | Q96DC9 | OTU2 | 41 AIRKTKGDGNCFYRALGYSY 60 | ---- | 220 KTSHYNILYA 230 | |

FIG.5

FIG.7A

OTU proteins all including viral full length.apr
─────────────────────────────────────────────────────────────────────── Section 1

```
                                              1        10        20        30        40        50      63
Human Otubain 2                         (1)  ------------MSETSFNLISEKCDILSILRDHPENR-IYRRKIEELSKRFTAIRKTKGDGN
Ictalurid ORF 65 1240 to end            (1)  ------------RVLANVPVSSAVIINESLEEDQFTRLENTLYSMGLKRVYIPGDGN
CCHFV 1-200 L#2                         (1)  ------------MDFLRSLDWTQVIAGQYVSNPRFNISDYFEIVRQPGDGN
Dugbe L protein 1-200#2                 (1)  ------------MDFLDSLIWERVVDEQYITNPTFCVSDYFEVIRQPGDGN
Mse Otud1                               (1)  GFRHPRGAAASRPRTARRSCRTSRADPRDEKLALYLAEVERQDKYFTLRQRNKYRFHIIPDGN
VCIP135 210-390                         (1)  ------------LHDTLEDIKRANKSQECLFTIPVHVDGDGH
A20 61-270                              (1)  ------------QFREIIHKALIDRNIQATLESQK-----KLNWCREVRKLVALKTNGDGN
Tipular iridescent 610-790              (1)  ------------GNADRDLEILARRGYKVIPVKGDGN
Emilian protease 100 to end             (1)  ------------NALASHGLEKKSSPGDGN
Cezanne 2 160 to 390                    (1)  SVYSEDFFTRSFIERDLIEQATMVALEQAGRLNWWSTVCTSCKRLLPLATTGDGN
Unknown from herpesvirus lymphotropic 140 to end (1)  ------------EQWLFCYPTDPLPWLWLLFYGPKSFCTDGN
gHV68 gene 34 141 to end                (1)  ------------MKCPENWSGLHPVDPLACVWLLYFGPKSRCSEIA
EBV BGLF3 141 to end                    (1)  ------------LCDPGTWKGLLPDDPLPLLWLLFNGPASFCRADC
hum Otubain 1 40 to end                 (1)  ------------IAVQNPLVSERLELSVLYKEYAEDDNIYQQKIDLHKKYSYIRKTRPDGN
BHV4 140 to end                         (1)  ------------NPCHWEGYIPDDPLPLIWLLFYGKNSFCESPD
Saimiri 34 140 to end                   (1)  ------------IYPIDPLPYIWLLFYGKKSFCASPD
Consensus                               (1)             LI   LD   ILI    W GLIPIDPLPFLWLLFYGPKSTCGDGN
```

FIG.9A

OTU proteins all including viral full length.apr ——————————————Section 2

```
                                                 64         70          80          90         100         110         126
Human Otubain 2                             (51) CFYRALGY------SYLESLLG-KSREIFKFKERVLQTPNDLLAAGFEEHKFRNFFNAFYSVV
Ictalurid ORF 65 1240 to end                (46) CLYNTLRF------IAGADGESAIDFKKELLDDIRKYVRNQDPAERDLILTEIDNLAGPNVYG
CCHFV 1-200 L#2                             (40) CFYHSIAE------LTMPNKTD-HSYHYIKRLTESAARKYYQEEPEARLVGLSLEDYLKRMLS
Dugbe L protein 1-200#2                     (40) CFYHSIAE------LFFDVKTP-SSFRKVKEHLQLAAEVYYDTEPEAVGTGISKDEYIKVAMK
Mse Otud1                                   (64) CLYRAVSKTVYGDQSLHRELREQTVHYIADHLDHFSPLIEGDVFTGEFIIAAAQDGAWAGYPE
VCIP135 210-390                             (31) CLVHAVSR------ALVGRELFWHALRENLKQHFQQHLARYQALFHDFIDAAEWEFTDIINEC
A20 61-270                                  (45) CLFTMHATSQYMMGVQDTDLVLRKALFSTLKETDTRN-FKFRWQLESLKSQEFVETGLCYDTR
Tipular iridescent 610-790                  (27) CKFRAVGK---SLR---LNQNIKYSFTHEDLRAQVVTYLTSHKEFLEPYLEYVTESGDTT
Emilian protease 100 to end                 (19) CLYHSLTD------QINATGLYSECNHISMRRAIVAHIYRNYDFYGNFLEEKLVTKLRLGKWG
Cezanne 2 160 to 390                        (56) CLLHAASLGMMGFFTHDRDLVLRKALYTMMRTGAEREALKRRWRWQQTQQNKEEEWEREWTEL
Unknown from herpesvirus lymphotropic 140 to end (31) CLYAKFFH--------NSGLILFPPIIYQPSTDISSFMNMVCKYVCVLYKNQDLSKLIGDQVIPF
gHV68 gene 34 141 to end                    (35) CVSELFIG------KKGPILLPPHMYRGDTSVNSFAHHLCQYVKHLYADYEPEILS---CPL
EBV BGLF3 141 to end                        (35) CLYKQHCG------YPGPVLLPGHMYAPKRDLLSFVNHALKYTKFLYGDFSGTWAA-ACRPPF
hum Otubain 1 40 to end                     (51) CFYRAFGF------SHLEALLD-DSKELQRFKAVSAKSKEDLVSQGFTEFTIEDFHNTFMDLI
BHV4 140 to end                             (33) CLYMQRFK------HPGPILPPPHIYNPDGDISSFVNHVCHYVNFLYKERTESLTH-TTFLPF
Saimiri 34 140 to end                       (26) CIYLKKYN------VPGPMLLPPHMYRPDKNISSFISHVCQYVKILYEEVSEPIS--LEIVPF
Consensus                                   (64) CLYHALAK       SLGPILLPPHSYRPSKRISSFANHVCYYVSFLYFEVAISIE ALIVPF
```

FIG.9B

OTU proteins all including viral full length.apr
Section 3

| | | |
|---|---|---|
| | (127) | 127 140 150 160 170 189 |
| Human Otubain 2 | (107) | ELVEKDGSVSSLLKVFN---------DQSASDHIVQFLRLLTSAFIR--NRADFFRHFIDEEM |
| Ictalurid ORF 65 1240 to end | (103) | SGDLISFFQLLRGVGVT---------VVSWDKIGGRLVKLVATNQEG--IPPEYIILFTNSHY |
| CCHFV 1-200 L#2 | (96) | DNEWGSTLEASMLAKEM---------GITIIIWTVAASDEVEAGIKF--GDGDVFTAVNLLHS |
| Dugbe L protein 1-200#2 | (96) | DNEWGGSLEASMLSKHL---------QTTIILWVVNSTEQVTAAIKF--GPGRVSTALNLMHV |
| Mse Otud1 | (127) | LLAMGQMLNVNIHLTTG---------GRLESPTVSTMIHYLGPEDSLRPSETIWLSWLSNGHY |
| VCIP135 210-390 | (88) | DPLFVPPEGVPLGLRNI---------HIFGLANVLHRPIILLDSLSGMRSSGDYSATFLPGLF |
| A20 61-270 | (107) | NFTWNDEWDNLIKMASTDTP----MARSGLQYNSLEEIHIFVLCNILRRPIIVISDKMLRSLE |
| Tipular iridescent 610-790 | (81) | PQEYAKNVERYIKNISK---------PGTWGDFICFTLRVLSEILKVKFNLLILNTRNFQVIS |
| Emilian protease 100 to end | (76) | SHVDVSAASDLFNIKIT---------VIKYNGDDVILPRHNNPDSVVGSIFLCFQSELHYDST |
| Cezanne 2 160 to 390 | (119) | LKLASSEPRTHFTFSKNGGTGGGVDNSEDPVYESLEEFHVFVLAHILRRPIVVVADTMLRDSG |
| Unknown from herpesvirus lymphotropic 140 to end | (88) | DRSRLENVQSLISDMNY---------NDIHVTKLCLLCALYKQNQTTYHNVEHNQGCIILEC- |
| gHV68 gene 34 141 to end | (88) | DITRVKGCLSDLRQVAE---------SCVFLSQRCLLCHLYKQNAAVSKNILTASDCIILGGS |
| EBV BGLF3 141 to end | (91) | ATSRIQRVVSQMKIIDA---------SDTYISHTCLLCHIYQQNSIIAGQGTHVGGILLLSGK |
| hum Otubain 1 40 to end | (107) | EQVEKQTSVADLLASFN---------DQSTSDYLVVYLRLLTSGYLQ--RESKFFEHFIEGGR |
| BHV4 140 to end | (89) | EEQRLKRALELLEEVEN---------TATYISKTCLLCHLYKQNEILAAEGQSTHGCIILGGV |
| Saimiri 34 140 to end | (81) | DNCRIKEAVEELKQIDL---------PVAYLSNLCLLCTLHRQNMSASRGSGDMCGYIVLGGE |
| Consensus | (127) | DNVRIS LVSLLKIIEN SITYISWLCLLCHLLTQNIILARNIGDVSG IILGGS |

FIG.9C

OTU proteins all including viral full length.apr
　　　　　　　　　　　　　　　　　　　　　　　　　　　　　　　　　　　　　　　Section 4
                          190        200        210        220        230        240        252
Human Otubain 2                    (190) 190
Ictalurid ORF 65 1240 to end       (159) -DIKDFCTHEVE-----PMATECDHIQITALSQALSIALQVEYVDEMDT-ALNNHVFPEAATP
CCHFV 1-200 L#2                    (155) -EPLVTEDTMIP-----DSYLKDFIEWKRSLFLSAII-----
Dugbe L protein 1-200#2            (148) -GQTHFDALRIL-----PQFETDT--REALSLMDRVIAVDQLTSSSSDELQDYEDLALALTS
Mse Otud1                          (148) -GRTHFDALRII-----EQLENNQPQDRNRLDIADRIAAAEVYVRQSIEDNLQEDEFFD---
VCIP135 210-390                    (181) -DAVFDHSYPNPEYDNWCKQTQIQKKRDEELAKSMAISLSKMYIEQNACFTS-------
A20 61-270                         (142) -TIPAEKCTGKDGHLNKPICIAWSSSGRNHYIPLVGIKGA-------
Tipular iridescent 610-790         (166) SGSFTNFAPLKVGGIYLPLHMPAQECYRYPIVLGYDSHHFVPLVT-------
Emilian protease 100 to end        (135) -NNDTFKPLIPLGFIDDYHYTALTPLYAEPIAVLFTENETPTPSIAP-------
Cezanne 2 160 to 390               (130) -ARVEY-------
Unknown from herpesvirus lymphotropic 140 to end (182) -GEAFAPIPFFTGGIYLPLEVPPNRCGCSPLVLAYDQAHFSALVSMEQRD-------
gHV68 gene 34 141 to end           (141) -AEKYINNSVGR-----TKCLHTG---DIVLWPSYNIAAIVQHFKSHGKGTLE-------
EBV BGLF3 141 to end               (142) -GKSLLGTYMKS-----YKDPATH---DSILLPTYNLEAIVNYILEHYGHETAGQEINWE---
hum Otubain 1 40 to end            (145) -GTQYITGNVQT-----QRCPTTG---DYLIIPSYDIPAIITMIKENGLNQL-------
BHV4 140 to end                    (159) -TVKEFCQQEVE-----PMCKESDHIHIIALAQALSVSIQVEYMDRGEGGTTNPHIFPEGSEP
Saimiri 34 140 to end              (143) -GKQYITPQLHT-----TRSTHSG---DTILLPAYNLVGLMECVALDGVSKQEDS-------
Consensus                          (135) -GEKYITTNIIS-----KRCTVSG---DCLIVPSYNISLLMQNMEINYEQQ-------
                                   (190)   GKKYF ANIITG I   PKCT SG    HDSLLVPAYNIAAIVQYVE   G    L

FIG. 9D

OTU proteins all including viral full length.apr ———— Section 5

| | | 253 | 260 | 272 |
|---|---|---|---|---|
| Human Otubain 2 | (253) | S V Y L L Y K T S H Y N I L Y A A D K H |
| Ictalurid ORF 65 1240 to end | (215) | — — — — — — — — — — — — — — — — — — — — |
| CCHFV 1-200 L#2 | (186) | — — — — — — — — — — — — — — — — — — — — |
| Dugbe L protein 1-200#2 | (202) | — — — — — — — — — — — — — — — — — — — — |
| Mse Otud1 | (201) | — — — — — — — — — — — — — — — — — — — — |
| VCIP135 210-390 | (232) | — — — — — — — — — — — — — — — — — — — — |
| A20 61-270 | (181) | — — — — — — — — — — — — — — — — — — — — |
| Tipular iridescent 610-790 | (211) | — — — — — — — — — — — — — — — — — — — — |
| Emilian protease 100 to end | (181) | — — — — — — — — — — — — — — — — — — — — |
| Cezanne 2 160 to 390 | (135) | — — — — — — — — — — — — — — — — — — — — |
| Unknown from herpesvirus lymphotropic 140 to end | (231) | — — — — — — — — — — — — — — — — — — — — |
| gHV68 gene 34 141 to end | (185) | — — — — — — — — — — — — — — — — — — — — |
| EBV BGLF3 141 to end | (193) | — — — — — — — — — — — — — — — — — — — — |
| hum Otubain 1 40 to end | (188) | — — — — — — — — — — — — — — — — — — — — |
| BHV4 140 to end | (216) | K V Y L L Y R P G H Y D I L Y K — — — — |
| Saimiri 34 140 to end | (189) | — — — — — — — — — — — — — — — — — — — — |
| Consensus | (177) | — — — — — — — — — — — — — — — — — — — — |
| | (253) | |

FIG.9E

```
OTU cons        h-hh----sDstChh-sht-----h+t-h------------t---t-t-as-----hhth-h-hh------hh-------t--Hatshh---
                                       ▽                                                              ▽
CCHFV-L     29  FEIVRQPGDGNCFYHSIA-13-YIKRLTESAARK-17-YLKRMLSDNEWG-9--KEMGITIIIW-20-TAVNLLH-2--QTHFDALRIL 158
DUGV-L      29  FEIVRQPGDGNCFYHSIA-13-KVKEHLQLAAEV-17-YIKVAMKDNEWG-9--KHLQTIIILW-20-TALNLMH-2--RTHFDALRII 158

EAV-nsp2   259  YGGYNPPGDGACGYRCLA-----FMNGATVVSAG----------CSSDLWC-9--QLSPTFTVTI-8--AKYAMIC-1--KQHWRVKRAK 339
PRRSV-nsp2 426  LKRYSPPAEGNCGWHCIS-1--IANRMWNSKFK--2--LPERVRPPDDWA-9--QILRLPAAL-8--AKYVLKL-1--GEHWTATVTP 513

A20         92  LVALKTNGDGNCLMHATS-14-KALFSTLKETDT-22-CYDTRNWNDEWD-31-NILRRPIIVI-35-YPIVLGY-1--SHHFVPLVTL 263
Cez        183  LLPLATTGDGNCLLHAAS-14-KALYALMEKGVE-21-VYTEDEWQKEWN-44-HVLRRPIVVV-34-SPLVLAY-1--QAHFSALVSM 365
VCIP       207  LIPVHVDGDGHCLVHAVS-14-ENLKQHFQQHLA-4--LFHDFIDAAEWE-29-NVLHRPIILL-38-IAWSSSG----RNHYIPLVGI 360
OTUB1       80  SYIRKTRPDGNCFYRAFG-79-LLTSGYLQRESK-13-EFCQQEVEPMCK-11-QALSVSIQVE-21-KVYLLYR----PGHYDILYK- 271
OTUB2       40  TSIRKTKGDGNCFYRALG-79-LLTSAFIRNRAD-13-DFCTHEVEPMAM-11-QALNIALQVE-6--TALNHHV-14-TSHYNILYAA 231
```

FIG. 10

Figure 11A:
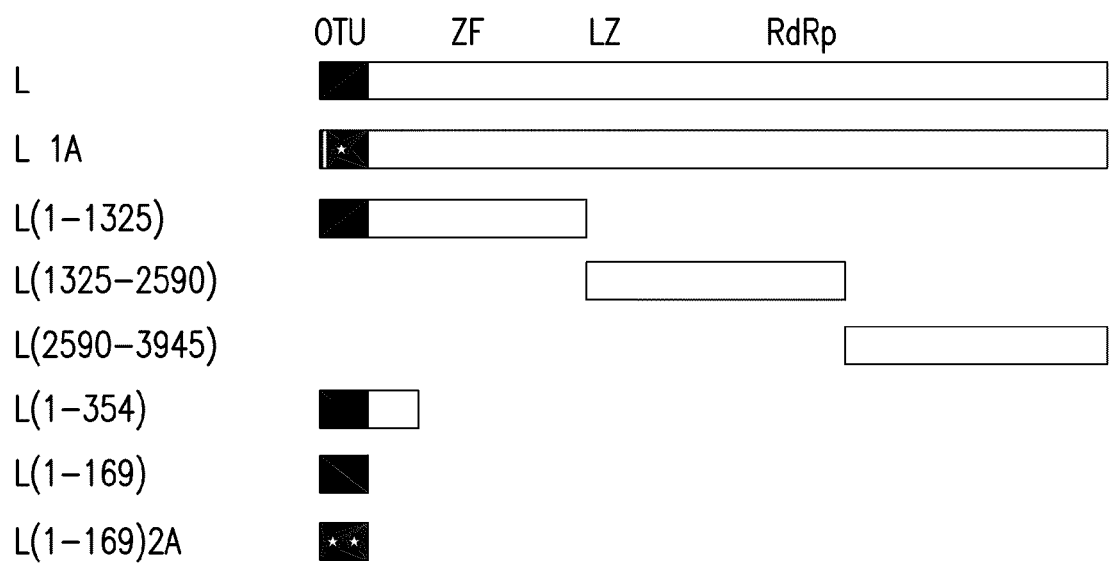

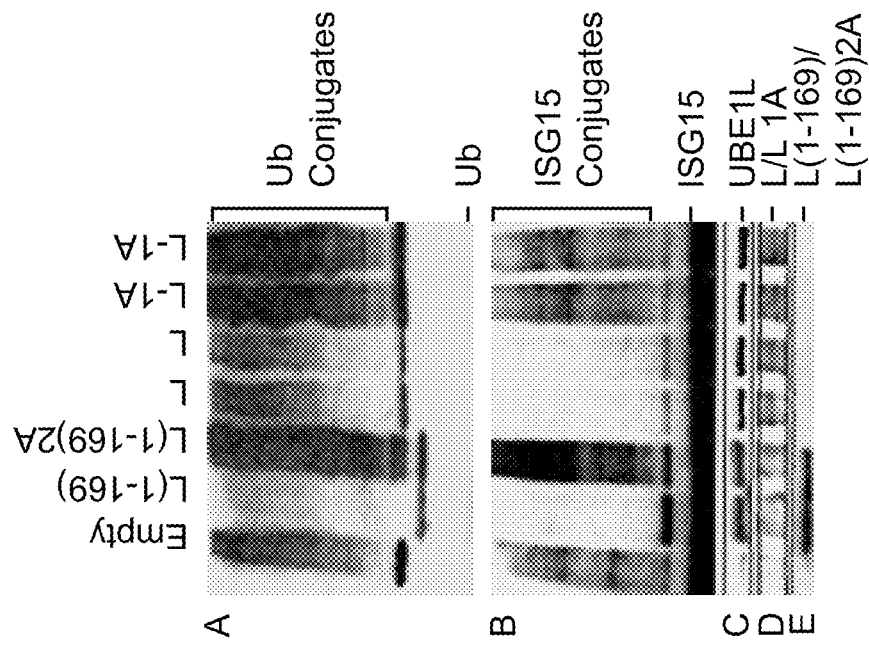
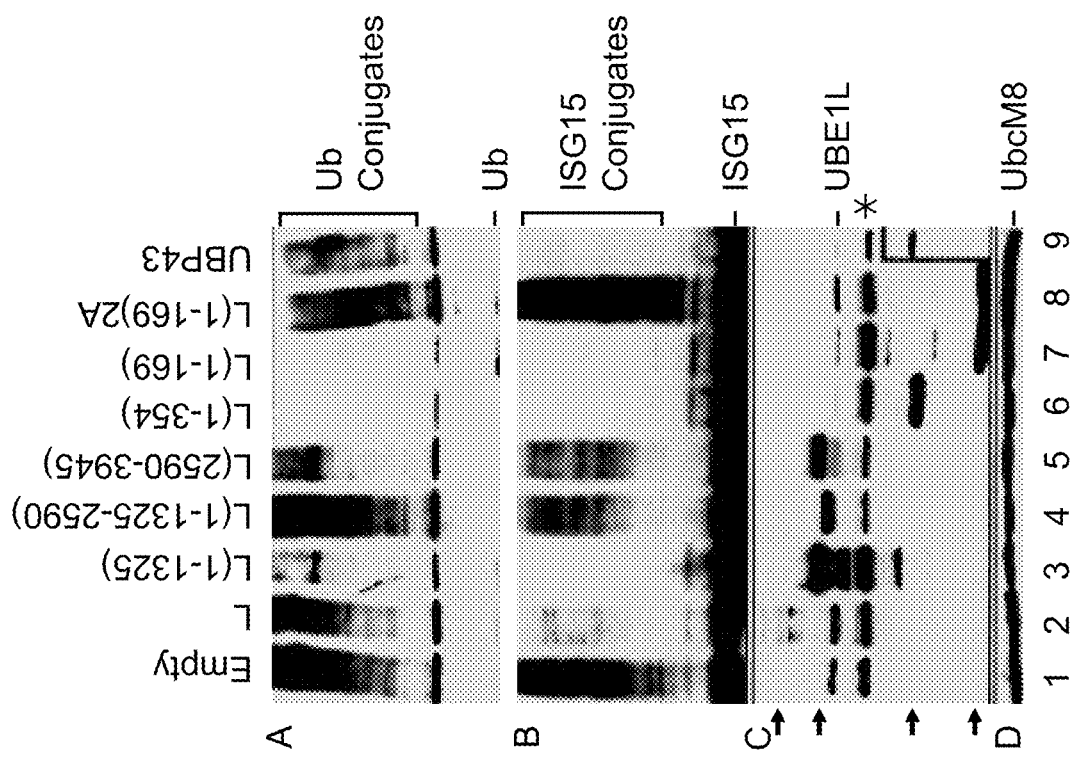
FIG. 11C
FIG. 11B

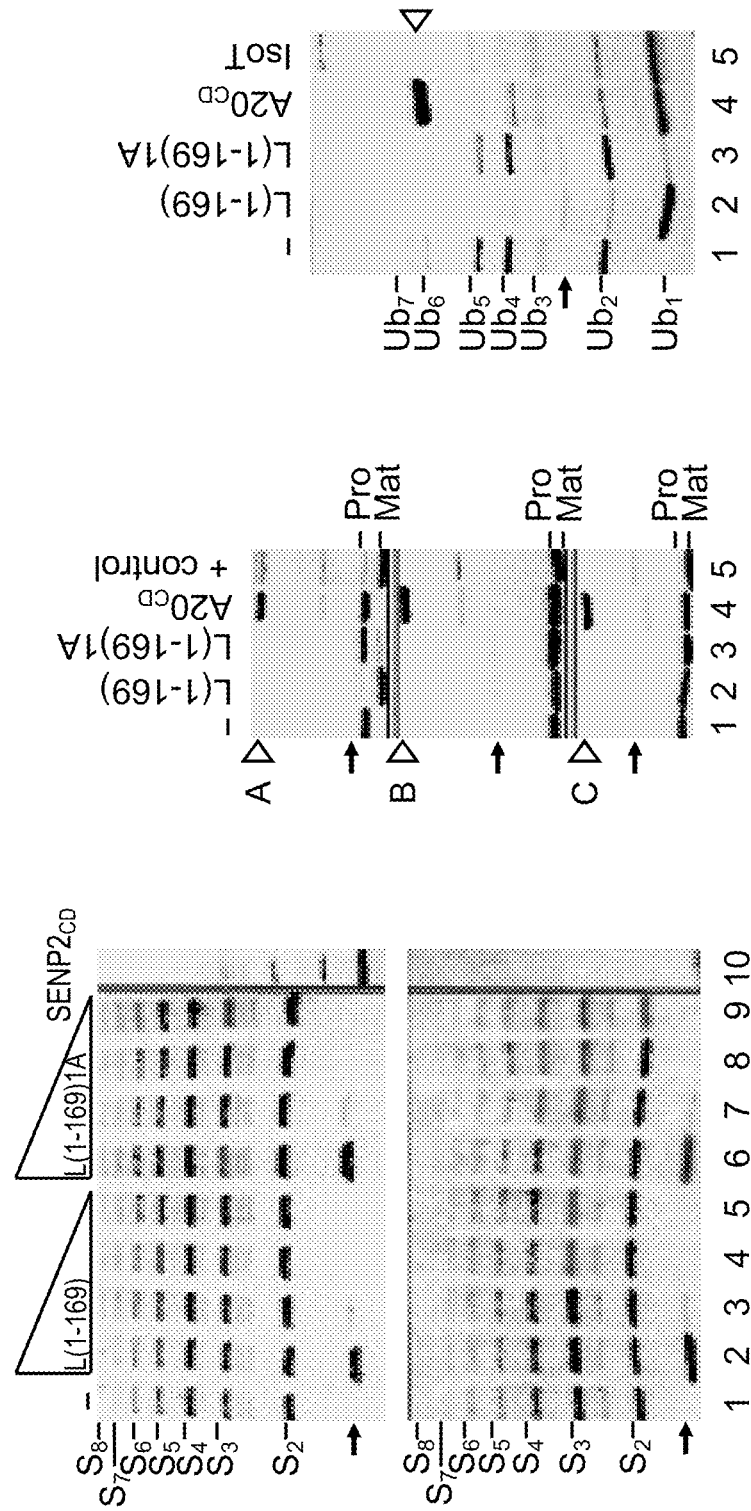

SEQUENCE LISTING

```
<160> NUMBER OF SEQ ID NOS: 82

<210> SEQ ID NO 1
<211> LENGTH: 6
<212> TYPE: PRT
<213> ORGANISM: Unknown
<220> FEATURE:
<223> OTHER INFORMATION: C-terminal residues found in Ubiquitin and
      ISG15

<400> SEQUENCE: 1

Leu Arg Leu Arg Gly Gly
1               5

<210> SEQ ID NO 2
<211> LENGTH: 254
<212> TYPE: PRT
<213> ORGANISM: Artificial Sequence
<220> FEATURE:
<223> OTHER INFORMATION: OTU domain amino acid motif defined by a
      bipartite pattern of conserved residues around
      the catalytic cysteine and histidine
<220> FEATURE:
<221> NAME/KEY: VARIANT
<222> LOCATION: 1, 3, 9
<223> OTHER INFORMATION: Xaa = small residue (s) (Ala,Cys,Ser,Thr,
      Asp,Val,Gly,Pro)
<220> FEATURE:
<221> NAME/KEY: VARIANT
<222> LOCATION: 4
<223> OTHER INFORMATION: Xaa = Any Amino Acid
<220> FEATURE:
<221> NAME/KEY: VARIANT
<222> LOCATION: 6, 10
<223> OTHER INFORMATION: Xaa = hydrophobic residue (h)
      (Ala,Cys,Phe,Leu,Ile,Met,Val,Trp,Tyr,Thr,Ser,Gly)
<220> FEATURE:
<221> NAME/KEY: VARIANT
<222> LOCATION: 7
<223> OTHER INFORMATION: Xaa =
      Ala/Cys/Phe/Leu/Ile/Met/Val/Trp/Tyr/Thr/Ser/Gly
<220> FEATURE:
<221> NAME/KEY: VARIANT
<222> LOCATION: 8, 11, 254
<223> OTHER INFORMATION: Xaa = residue with a high beta-turn-forming
      propensity (Ala,Cys,Ser,Thr,Asp,Glu,Asn,Val,Gly,Pro)
<220> FEATURE:
<221> NAME/KEY: VARIANT
<222> LOCATION: 253
<223> OTHER INFORMATION: Xaa = Phe/Tyr/Trp
<220> FEATURE:
<221> NAME/KEY: VARIANT
<222> LOCATION: (12)...(251)
<223> OTHER INFORMATION: Xaa = Any Amino Acid and deletions

<400> SEQUENCE: 2

Xaa Asp Xaa Xaa Cys Xaa Xaa Xaa Xaa Xaa Xaa Xaa Xaa Xaa Xaa
1               5                   10                  15
```

```
Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa
    210                 215                 220

Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa His Xaa Xaa
                245                 250

<210> SEQ ID NO 3
<211> LENGTH: 3945
<212> TYPE: PRT
<213> ORGANISM: Artificial Sequence
<220> FEATURE:
<223> OTHER INFORMATION: CCHFV-L USAMRIID sequence

<400> SEQUENCE: 3

Met Asp Phe Leu Arg Ser Leu Asp Trp Thr Gln Val Ile Ala Gly Gln
 1               5                  10                  15

Tyr Val Ser Asn Pro Arg Phe Asn Ile Ser Asp Tyr Phe Glu Ile Val
            20                  25                  30

Arg Gln Pro Gly Asp Gly Asn Cys Phe Tyr His Ser Ile Ala Glu Leu
        35                  40                  45

Thr Met Pro Asn Lys Thr Asp His Ser Tyr His Tyr Ile Lys Arg Leu
    50                  55                  60

Thr Glu Ser Ala Ala Arg Lys Tyr Tyr Gln Glu Pro Glu Ala Arg
65                  70                  75                  80

Leu Val Gly Leu Ser Leu Glu Asp Tyr Leu Lys Arg Met Leu Ser Asp
                85                  90                  95

Asn Glu Trp Gly Ser Thr Leu Glu Ala Ser Met Leu Ala Lys Glu Met
            100                 105                 110

Gly Ile Thr Ile Ile Ile Trp Thr Val Ala Ala Ser Asp Glu Val Glu
        115                 120                 125
```

```
Ala Gly Ile Lys Phe Gly Asp Gly Asp Val Phe Thr Ala Val Asn Leu
        130                 135                 140

Leu His Ser Gly Gln Thr His Phe Asp Ala Leu Arg Ile Leu Pro Gln
145                 150                 155                 160

Phe Glu Thr Asp Thr Arg Glu Ala Leu Ser Leu Met Asp Arg Val Ile
                165                 170                 175

Ala Val Asp Gln Leu Thr Ser Ser Ser Asp Glu Leu Gln Asp Tyr
                180                 185                 190

Glu Asp Leu Ala Leu Ala Leu Thr Ser Ala Glu Glu Ser Asn Arg Arg
            195                 200                 205

Ser Ser Leu Asp Glu Val Thr Leu Ser Lys Lys Gln Ala Glu Ile Leu
    210                 215                 220

Arg Gln Lys Ala Ser Gln Leu Ser Lys Leu Val Asn Lys Ser Gln Asn
225                 230                 235                 240

Ile Pro Thr Arg Val Gly Arg Val Leu Asp Cys Met Phe Asn Cys Lys
                245                 250                 255

Leu Cys Val Glu Ile Ser Ala Asp Thr Leu Ile Leu Arg Pro Glu Ser
                260                 265                 270

Lys Glu Lys Ile Gly Glu Ile Met Ser Leu Arg Gln Leu Gly His Lys
            275                 280                 285

Leu Leu Thr Arg Asp Lys Gln Ile Lys Gln Glu Phe Ser Arg Met Lys
    290                 295                 300

Leu Tyr Val Thr Lys Asp Leu Leu Asp His Leu Asp Val Gly Gly Leu
305                 310                 315                 320

Leu Arg Ala Ala Phe Pro Gly Thr Gly Ile Glu Arg His Met Gln Leu
                325                 330                 335

Leu His Ser Glu Met Ile Leu Asp Ile Cys Thr Val Ser Leu Gly Val
                340                 345                 350

Met Leu Ser Thr Phe Leu Tyr Gly Ser Asn Asn Lys Asn Lys Lys Lys
            355                 360                 365

Phe Ile Thr Asn Cys Leu Leu Ser Thr Ala Leu Ser Gly Lys Lys Val
    370                 375                 380

Tyr Lys Val Leu Gly Asn Leu Gly Asn Glu Leu Leu Tyr Lys Ala Pro
385                 390                 395                 400

Arg Lys Ala Leu Ala Thr Val Cys Ser Ala Leu Phe Gly Lys Gln Ile
                405                 410                 415

Asn Lys Leu Gln Asn Cys Phe Arg Thr Ile Ser Pro Val Ser Leu Leu
            420                 425                 430

Ala Leu Arg Asn Leu Asp Phe Asp Cys Leu Ser Val Gln Asp Tyr Asn
    435                 440                 445

Gly Met Ile Glu Asn Met Ser Lys Leu Asp Asn Thr Asp Val Glu Phe
450                 455                 460

Asn His Arg Glu Ile Ala Asp Leu Asn Gln Leu Thr Ser Arg Leu Ile
465                 470                 475                 480

Thr Leu Arg Lys Glu Lys Asp Thr Asp Leu Leu Lys Gln Trp Phe Pro
                485                 490                 495

Glu Ser Asp Leu Thr Arg Arg Ser Ile Arg Asn Ala Ala Asn Ala Glu
            500                 505                 510

Glu Phe Val Ile Ser Glu Phe Lys Lys Lys Asp Ile Met Lys Phe
    515                 520                 525

Ile Ser Thr Ser Gly Arg Ala Met Ser Ala Gly Lys Ile Gly Asn Val
    530                 535                 540

Leu Ser Tyr Ala His Asn Leu Tyr Leu Ser Lys Ser Ser Leu Asn Met
545                 550                 555                 560
```

```
Thr Ser Glu Asp Ile Ser Gln Leu Leu Ile Glu Ile Lys Arg Leu Tyr
            565                 570                 575

Ala Leu Gln Glu Asp Ser Glu Val Glu Pro Ile Ala Ile Cys Asp
        580                 585                 590

Gly Ile Glu Ser Asn Met Lys Gln Leu Phe Ala Ile Leu Pro Pro Asp
            595                 600                 605

Cys Ala Arg Glu Cys Glu Val Leu Phe Asp Asp Ile Arg Asn Ser Pro
            610                 615                 620

Thr His Ser Thr Ala Trp Lys His Ala Leu Arg Leu Lys Gly Thr Ala
625                 630                 635                 640

Tyr Glu Gly Leu Phe Ala Asn Cys Tyr Gly Trp Gln Tyr Ile Pro Glu
                645                 650                 655

Asp Ile Lys Pro Ser Leu Thr Met Leu Ile Gln Thr Leu Phe Pro Asp
            660                 665                 670

Lys Phe Glu Asp Phe Leu Asp Arg Thr Gln Leu His Pro Glu Phe Arg
        675                 680                 685

Asp Leu Thr Pro Asp Phe Ser Leu Thr Gln Lys Val His Phe Lys Arg
    690                 695                 700

Asn Gln Ile Pro Ser Val Glu Asn Val Gln Ile Ser Ile Asp Ala Thr
705                 710                 715                 720

Leu Pro Glu Ser Val Glu Ala Val Pro Val Thr Glu Arg Lys Met Phe
                725                 730                 735

Pro Leu Pro Glu Thr Pro Leu Ser Glu Val His Ser Ile Glu Arg Ile
            740                 745                 750

Met Glu Asn Phe Thr Arg Leu Met His Gly Gly Arg Leu Ser Thr Lys
            755                 760                 765

Lys Arg Asp Gly Asp Pro Ala Glu Gln Gly Asn Gln Gln Ser Ile Thr
        770                 775                 780

Glu His Glu Ser Ser Ser Ile Ser Ala Phe Lys Asp Tyr Gly Glu Arg
785                 790                 795                 800

Gly Ile Val Glu Glu Asn His Met Lys Phe Ser Gly Glu Asp Gln Leu
                805                 810                 815

Glu Thr Arg Gln Leu Leu Val Glu Val Gly Phe Gln Thr Asp Ile
            820                 825                 830

Asp Gly Lys Ile Arg Thr Asp His Lys Lys Trp Lys Asp Ile Leu Lys
        835                 840                 845

Leu Leu Glu Leu Leu Gly Ile Lys Cys Ser Phe Ile Ala Cys Ala Asp
    850                 855                 860

Cys Ser Thr Pro Pro Asp Arg Trp Trp Ile Thr Glu Asp Arg Val
865                 870                 875                 880

Arg Val Leu Lys Asn Ser Val Ser Phe Leu Phe Asn Lys Leu Ser Arg
                885                 890                 895

Asn Ser Pro Thr Glu Val Thr Asp Ile Val Val Gly Ala Ile Ser Thr
            900                 905                 910

Gln Lys Val Arg Ser Tyr Leu Lys Ala Gly Thr Ala Thr Lys Thr Pro
        915                 920                 925

Val Ser Thr Lys Asp Val Leu Glu Thr Trp Glu Lys Met Lys Glu His
    930                 935                 940

Ile Leu Asn Arg Pro Thr Gly Leu Thr Leu Pro Thr Ser Leu Glu Gln
945                 950                 955                 960

Ala Met Arg Lys Gly Leu Val Glu Gly Val Val Ile Ser Lys Glu Gly
                965                 970                 975

Ser Glu Ser Cys Ile Asn Met Leu Lys Glu Asn Leu Asp Arg Ile Thr
```

```
                980            985             990
Asp Glu Phe Glu Arg Thr Lys Phe Lys His Glu Leu Thr Gln Asn Ile
            995                 1000                1005
Thr Thr Ser Glu Lys Met Leu Leu Ser Trp Leu Ser Glu Asp Ile Lys
            1010                1015                1020
Ser Ser Arg Cys Gly Glu Cys Leu Ser Asn Ile Lys Lys Ala Val Asp
1025            1030                1035                1040
Glu Thr Ala Asn Leu Ser Glu Lys Ile Glu Leu Ala Tyr Asn Leu
            1045                1050                1055
Gln Leu Thr Asn His Cys Ser Asn Cys His Pro Asn Gly Val Asn Ile
            1060                1065                1070
Ser Asn Thr Ser Asn Val Cys Lys Arg Cys Pro Lys Ile Glu Val Val
            1075                1080                1085
Ser His Cys Glu Asn Lys Gly Phe Glu Asp Ser Asn Glu Cys Leu Thr
            1090                1095                1100
Asp Leu Asp Arg Leu Val Arg Leu Thr Leu Pro Gly Lys Thr Glu Lys
1105            1110                1115                1120
Glu Arg Arg Val Lys Arg Asn Val Glu Tyr Leu Ile Lys Leu Met Met
                1125                1130                1135
Ser Met Ser Gly Ile Asp Cys Ile Lys Tyr Pro Thr Gly Gln Leu Ile
            1140                1145                1150
Thr His Gly Arg Val Ser Ala Lys His Asn Asp Gly Asn Leu Lys Asp
            1155                1160                1165
Arg Ser Asp Asp Asp Gln Arg Leu Ala Glu Lys Ile Asp Thr Val Arg
            1170                1175                1180
Lys Glu Leu Ser Glu Ser Lys Leu Lys Asp Tyr Ser Thr Tyr Ala Arg
1185            1190                1195                1200
Gly Val Ile Ser Asn Ser Leu Lys Asn Leu Ser Arg Gln Gly Lys Ser
                1205                1210                1215
Lys Cys Ser Val Pro Arg Ser Trp Leu Glu Lys Val Leu Phe Asp Leu
            1220                1225                1230
Lys Val Pro Thr Lys Asp Glu Glu Val Leu Ile Asn Ile Arg Asn Ser
            1235                1240                1245
Leu Lys Ala Arg Ser Glu Phe Val Arg Asn Asn Asp Lys Leu Leu Ile
            1250                1255                1260
Arg Ser Lys Glu Glu Leu Lys Lys Cys Phe Asp Val Gln Ser Phe Lys
1265            1270                1275                1280
Leu Lys Lys Asn Lys Gln Pro Val Pro Phe Gln Val Asp Cys Ile Leu
                1285                1290                1295
Phe Lys Glu Val Ala Ala Glu Cys Met Lys Arg Tyr Ile Gly Thr Pro
            1300                1305                1310
Tyr Glu Gly Ile Val Asp Thr Leu Val Ser Leu Ile Asn Val Leu Thr
            1315                1320                1325
Arg Phe Thr Trp Phe Gln Glu Val Val Leu Tyr Gly Lys Ile Cys Glu
            1330                1335                1340
Thr Phe Leu Arg Cys Cys Thr Glu Phe Asn Arg Ser Gly Val Lys Leu
1345            1350                1355                1360
Val Lys Ile Arg His Cys Asn Ile Asn Leu Ser Val Lys Leu Pro Ser
                1365                1370                1375
Asn Lys Lys Glu Asn Met Leu Cys Cys Leu Tyr Ser Gly Asn Met Glu
            1380                1385                1390
Leu Leu Gln Gly Pro Phe Tyr Leu Asn Arg Arg Gln Ala Val Leu Gly
            1395                1400                1405
```

-continued

Ser Ser Tyr Leu Tyr Ile Val Ile Thr Leu Tyr Ile Gln Val Leu Gln
    1410            1415            1420

Gln Tyr Arg Cys Leu Glu Val Ile Asn Ser Val Ser Glu Lys Thr Leu
1425            1430            1435            1440

Gln Asp Ile Glu Asn His Ser Met Thr Leu Leu Glu Asp Ser Phe Arg
        1445            1450            1455

Glu Ile Thr Phe Ala Leu Glu Gly Arg Phe Ser Glu Ser Tyr Lys Ile
    1460            1465            1470

Arg Thr Ser Arg Cys Arg Ala Ser Gly Asn Phe Leu Asn Arg Ser Ser
        1475            1480            1485

Arg Asp His Phe Ile Ser Val Val Ser Gly Leu Asn Leu Val Tyr Gly
    1490            1495            1500

Phe Leu Ile Lys Asp Asn Leu Leu Ala Asn Ser Gln Gln Gln Asn Lys
1505            1510            1515            1520

Gln Leu Gln Met Leu Arg Phe Gly Met Leu Ala Gly Leu Ser Arg Leu
        1525            1530            1535

Val Cys Pro Asn Glu Leu Gly Lys Lys Phe Ser Thr Ser Cys Arg Arg
    1540            1545            1550

Ile Glu Asp Asn Ile Ala Arg Leu Tyr Leu Gln Thr Ser Ile Tyr Cys
        1555            1560            1565

Ser Val Arg Asp Val Glu Asp Asn Val Lys His Trp Lys Gln Arg Asp
    1570            1575            1580

Leu Cys Pro Glu Val Thr Ile Pro Cys Phe Thr Val Tyr Gly Thr Phe
1585            1590            1595            1600

Val Asn Ser Asp Arg Gln Leu Ile Phe Asp Ile Tyr Asn Val His Ile
        1605            1610            1615

Tyr Asn Lys Glu Met Asp Asn Phe Asp Glu Gly Cys Ile Ser Val Leu
    1620            1625            1630

Glu Glu Thr Ala Glu Arg His Met Leu Trp Glu Leu Asp Leu Met Asn
        1635            1640            1645

Ser Leu Cys Ser Asp Glu Lys Lys Asp Thr Arg Thr Ala Arg Leu Leu
    1650            1655            1660

Leu Gly Cys Pro Asn Val Arg Lys Ala Ala Asn Arg Glu Gly Lys Lys
1665            1670            1675            1680

Leu Leu Lys Leu Asn Ser Asp Thr Ser Thr Asp Thr Gln Ser Ile Ala
        1685            1690            1695

Ser Glu Val Ser Asp Arg Arg Ser Tyr Ser Ser Ser Lys Ser Arg Ile
    1700            1705            1710

Arg Ser Ile Phe Gly Arg Tyr Asn Ser Gln Lys Lys Pro Phe Glu Leu
        1715            1720            1725

Arg Ser Gly Leu Glu Val Phe Asn Asp Pro Phe Asn Asp Tyr Gln Gln
    1730            1735            1740

Ala Ile Thr Asp Ile Cys Gln Phe Ser Glu Tyr Thr Pro Asn Lys Glu
1745            1750            1755            1760

Ser Ile Leu Lys Asp Cys Leu Gln Ile Ile Arg Lys Asn Pro Ser His
        1765            1770            1775

Thr Met Gly Ser Phe Glu Leu Ile Gln Ala Ile Ser Glu Phe Gly Met
    1780            1785            1790

Ser Lys Phe Pro Pro Glu Asn Ile Asp Lys Ala Arg Arg Asp Pro Lys
        1795            1800            1805

Asn Trp Val Ser Ile Ser Glu Val Thr Glu Thr Thr Ser Ile Val Ala
    1810            1815            1820

Ser Pro Arg Thr His Met Met Leu Lys Asp Cys Phe Lys Ile Ile Leu
1825            1830            1835            1840

```
Gly Thr Glu Asn Lys Lys Ile Val Lys Met Leu Arg Gly Lys Leu Lys
                1845                1850                1855
Lys Leu Gly Ala Ile Ser Thr Asn Ile Glu Ile Gly Lys Arg Asp Cys
            1860                1865                1870
Leu Asp Leu Leu Ser Thr Val Asp Gly Leu Thr Asp Gln Gln Lys Glu
            1875                1880                1885
Asn Ile Val Asn Gly Ile Phe Glu Pro Ser Lys Leu Ser Phe Tyr His
            1890                1895                1900
Trp Lys Glu Leu Val Lys Lys Asn Ile Asp Glu Val Leu Leu Thr Glu
1905                1910                1915                1920
Asp Gly Asn Leu Ile Phe Cys Trp Leu Lys Thr Ile Ser Ser Ser Val
            1925                1930                1935
Lys Gly Ser Leu Lys Lys Arg Leu Lys Phe Met Asn Ile His Ser Pro
            1940                1945                1950
Glu Leu Met Pro Glu Asn Cys Leu Phe Ser Ser Glu Glu Phe Asn Glu
            1955                1960                1965
Leu Ile Lys Leu Lys Lys Leu Leu Leu Asn Glu Gln Gln Asp Glu Gln
            1970                1975                1980
Glu Leu Lys Gln Asp Leu Leu Ile Ser Ser Trp Ile Lys Cys Ile Thr
1985                1990                1995                2000
Ala Cys Lys Asp Phe Ala Ser Ile Asn Asp Lys Ile Gln Lys Phe Ile
            2005                2010                2015
Tyr His Leu Ser Glu Glu Leu Tyr Asp Ile Arg Leu Gln His Leu Glu
            2020                2025                2030
Leu Ser Lys Leu Lys Gln Glu His Pro Ser Val Ser Phe Thr Lys Glu
            2035                2040                2045
Glu Val Leu Ile Lys Arg Leu Glu Lys Asn Phe Leu Lys Gln His Asn
            2050                2055                2060
Leu Glu Ile Met Glu Thr Val Asn Leu Val Phe Phe Ala Ala Leu Ser
2065                2070                2075                2080
Ala Pro Trp Cys Leu His Tyr Lys Ala Leu Glu Ser Tyr Leu Val Arg
            2085                2090                2095
His Pro Glu Ile Leu Asp Cys Gly Ser Lys Glu Asp Cys Lys Leu Thr
            2100                2105                2110
Leu Leu Asp Leu Ser Val Ser Lys Leu Leu Val Cys Leu Tyr Gln Lys
            2115                2120                2125
Asp Asp Glu Glu Leu Ile Asn Ser Ser Ser Leu Lys Leu Gly Phe Leu
            2130                2135                2140
Val Lys Tyr Val Val Thr Leu Phe Thr Ser Asn Gly Glu Pro Phe Ser
2145                2150                2155                2160
Leu Ser Leu Asn Asp Gly Gly Leu Asp Leu Asp Leu His Lys Thr Thr
            2165                2170                2175
Asp Glu Lys Leu Leu His Gln Thr Lys Ile Val Phe Ala Lys Ile Gly
            2180                2185                2190
Leu Ser Gly Asn Ser Tyr Asp Phe Ile Trp Thr Thr Gln Met Ile Ala
            2195                2200                2205
Asn Ser Asn Phe Asn Val Cys Lys Arg Leu Thr Gly Arg Ser Thr Gly
            2210                2215                2220
Glu Arg Leu Pro Arg Ser Val Arg Ser Lys Val Ile Tyr Glu Met Val
2225                2230                2235                2240
Lys Leu Val Gly Glu Thr Gly Met Ala Ile Leu Gln Gln Leu Ala Phe
            2245                2250                2255
Ala Gln Ala Leu Asn Tyr Glu His Arg Phe Tyr Ala Val Leu Ala Pro
```

-continued

```
                2260                2265                2270
Lys Ala Gln Leu Gly Gly Ala Arg Asp Leu Leu Val Gln Glu Thr Gly
        2275                2280                2285

Thr Lys Val Met His Ala Thr Thr Glu Met Phe Ser Arg Asn Leu Leu
    2290                2295                2300

Lys Thr Thr Ser Asp Asp Gly Leu Thr Asn Pro His Leu Lys Glu Thr
2305                2310                2315                2320

Ile Leu Asn Val Gly Leu Asp Cys Leu Ala Asn Met Arg Asn Leu Asp
            2325                2330                2335

Gly Lys Pro Ile Ser Glu Gly Ser Asn Leu Val Asn Phe Tyr Lys Val
        2340                2345                2350

Ile Cys Ile Ser Gly Asp Asn Thr Lys Trp Gly Pro Ile His Cys Cys
    2355                2360                2365

Ser Phe Phe Ser Gly Met Met Gln Gln Val Leu Lys Asn Val Pro Asp
    2370                2375                2380

Trp Cys Ser Phe Tyr Lys Leu Thr Phe Ile Lys Asn Leu Cys Arg Gln
2385                2390                2395                2400

Val Glu Ile Pro Ala Gly Ser Ile Lys Lys Ile Leu Asn Val Leu Arg
            2405                2410                2415

Tyr Arg Leu Cys Ser Lys Gly Gly Val Glu Gln His Ser Glu Glu Asp
        2420                2425                2430

Leu Arg Arg Leu Leu Thr Asp Asn Leu Asp Ser Trp Asp Gly Asn Asp
        2435                2440                2445

Thr Val Lys Phe Leu Val Thr Thr Tyr Ile Ser Lys Gly Leu Met Ala
    2450                2455                2460

Leu Asn Ser Tyr Asn His Met Gly Gln Gly Ile His His Ala Thr Ser
2465                2470                2475                2480

Ser Val Leu Thr Ser Leu Ala Ala Val Leu Phe Glu Glu Leu Ala Ile
            2485                2490                2495

Phe Tyr Leu Lys Arg Ser Leu Pro Gln Thr Thr Val His Val Glu His
        2500                2505                2510

Ala Gly Ser Ser Asp Asp Tyr Ala Lys Cys Ile Val Val Thr Gly Ile
        2515                2520                2525

Leu Ser Lys Glu Leu Tyr Ser Gln Tyr Asp Glu Thr Phe Trp Lys His
    2530                2535                2540

Ala Cys Arg Leu Lys Asn Phe Thr Ala Ala Val Gln Arg Cys Cys Gln
2545                2550                2555                2560

Met Lys Asp Ser Ala Lys Thr Leu Val Ser Asp Cys Phe Leu Glu Phe
            2565                2570                2575

Tyr Ser Glu Phe Met Met Gly Tyr Arg Val Thr Pro Ala Val Ile Lys
        2580                2585                2590

Phe Met Phe Thr Gly Leu Ile Asn Ser Ser Val Thr Ser Pro Gln Ser
    2595                2600                2605

Leu Met Gln Ala Cys Gln Val Ser Ser Gln Ala Met Tyr Asn Ser
        2610                2615                2620

Val Pro Leu Val Thr Asn Thr Ala Phe Thr Leu Leu Arg Gln Gln Ile
2625                2630                2635                2640

Phe Phe Asn His Val Glu Asp Phe Ile Arg Arg Tyr Gly Ile Leu Thr
            2645                2650                2655

Leu Gly Thr Leu Ser Pro Phe Gly Arg Leu Phe Val Pro Thr Tyr Ser
        2660                2665                2670

Gly Leu Val Ser Ser Ala Val Ala Leu Glu Asp Ala Glu Val Ile Ala
        2675                2680                2685
```

-continued

```
Arg Ala Ala Gln Thr Leu Gln Met Asn Ser Val Ser Ile Gln Ser Ser
            2690                2695                2700

Ser Leu Thr Thr Leu Asp Ser Leu Gly Arg Ser Arg Thr Ser Ser Thr
2705                2710                2715                2720

Ala Glu Asp Ser Ser Ser Val Ser Asp Thr Thr Ala Ala Ser His Asp
            2725                2730                2735

Ser Gly Ser Ser Ser Ser Ser Phe Ser Phe Glu Leu Asn Arg Pro Leu
            2740                2745                2750

Ser Glu Thr Glu Leu Gln Phe Ile Lys Ala Leu Ser Ser Leu Lys Ser
            2755                2760                2765

Thr Gln Ala Cys Glu Val Ile Gln Asn Arg Ile Thr Gly Leu Tyr Cys
            2770                2775                2780

Asn Ser Asn Glu Gly Pro Leu Asp Arg His Asn Val Ile Tyr Ser Ser
2785                2790                2795                2800

Arg Met Ala Asp Ser Cys Asp Trp Leu Lys Asp Gly Lys Arg Arg Gly
                2805                2810                2815

Asn Leu Glu Leu Ala Asn Arg Ile Gln Ser Val Leu Cys Ile Leu Ile
                2820                2825                2830

Ala Gly Tyr Tyr Arg Ser Phe Gly Gly Glu Gly Thr Glu Lys Gln Val
            2835                2840                2845

Lys Ala Ser Leu Asn Arg Asp Asp Asn Lys Ile Ile Glu Asp Pro Met
2850                2855                2860

Ile Gln Leu Ile Pro Glu Lys Leu Arg Arg Glu Leu Glu Arg Leu Gly
2865                2870                2875                2880

Val Ser Arg Met Glu Val Asp Glu Leu Met Pro Ser Ile Ser Pro Asp
                2885                2890                2895

Asp Thr Leu Ala Gln Leu Val Ala Lys Lys Leu Ile Ser Leu Asn Val
            2900                2905                2910

Ser Thr Glu Glu Tyr Ser Ala Glu Val Ser Arg Leu Lys Gln Thr Leu
            2915                2920                2925

Thr Ala Arg Asn Val Leu His Gly Leu Ala Gly Gly Ile Lys Glu Leu
            2930                2935                2940

Ser Leu Pro Ile Tyr Thr Ile Phe Met Lys Ser Tyr Phe Phe Lys Asp
2945                2950                2955                2960

Asn Val Phe Leu Ser Leu Thr Asp Arg Trp Ser Thr Lys His Ser Thr
                2965                2970                2975

Asn Tyr Arg Asp Ser Cys Gly Lys Gln Leu Lys Gly Arg Ile Ile Thr
            2980                2985                2990

Lys Tyr Thr His Trp Leu Asp Thr Phe Leu Gly Cys Ser Val Ser Ile
            2995                3000                3005

Asn Arg His Thr Thr Val Lys Glu Pro Ser Leu Phe Asn Pro Asn Ile
            3010                3015                3020

Arg Cys Val Asn Leu Ile Thr Phe Glu Asp Gly Leu Arg Glu Leu Ser
3025                3030                3035                3040

Val Ile Gln Ser His Leu Lys Val Phe Glu Asn Glu Phe Thr Asn Leu
            3045                3050                3055

Asn Leu Gln Phe Ser Asp Pro Asn Arg Gln Lys Leu Arg Ile Val Glu
            3060                3065                3070

Ser Arg Pro Ala Glu Ser Glu Leu Glu Ala Asn Arg Ala Val Ile Val
            3075                3080                3085

Lys Thr Lys Leu Phe Ser Ala Thr Glu Gln Val Arg Leu Ser Asn Asn
            3090                3095                3100

Pro Ala Val Val Met Gly Tyr Leu Leu Asp Glu Ser Ala Ile Ser Glu
3105                3110                3115                3120
```

-continued

```
Val Lys Pro Thr Lys Val Asp Phe Ser Asn Leu Leu Lys Asp Arg Phe
            3125                3130                3135

Lys Ile Met Gln Phe Phe Pro Ser Val Phe Thr Leu Ile Lys Met Leu
            3140                3145                3150

Thr Asp Glu Ser Ser Asp Ser Glu Lys Ser Gly Leu Ser Pro Asp Leu
            3155                3160            3165

Gln Gln Val Ala Arg Tyr Ser Asn His Leu Thr Leu Leu Ser Arg Met
            3170                3175                3180

Ile Gln Gln Ala Lys Pro Thr Val Thr Val Phe Tyr Met Leu Lys Gly
3185                3190                3195                3200

Asn Leu Met Asn Thr Glu Pro Thr Val Ala Glu Leu Val Ser Tyr Gly
            3205                3210                3215

Ile Lys Glu Gly Arg Phe Phe Arg Leu Ser Asp Thr Gly Ile Asp Ala
            3220                3225                3230

Ser Thr Tyr Ser Val Lys Tyr Trp Lys Ile Leu His Cys Ile Ser Ala
            3235                3240                3245

Ile Gly Cys Leu Pro Leu Ser Gln Ala Asp Lys Ser Ser Leu Leu Met
            3250                3255                3260

Ser Phe Leu Asn Trp Arg Val Asn Met Asp Ile Arg Thr Ser Asp Cys
3265                3270                3275                3280

Pro Leu Ser Ser His Glu Ala Ser Ile Leu Ser Glu Phe Asp Gly Gln
            3285                3290                3295

Val Ile Ala Asn Ile Leu Ala Ser Glu Leu Ser Ser Val Lys Arg Asp
            3300                3305                3310

Ser Glu Arg Glu Gly Leu Thr Asp Leu Leu Asp Tyr Leu Asn Ser Pro
            3315                3320                3325

Thr Glu Leu Leu Lys Lys Lys Pro Tyr Leu Gly Thr Thr Cys Lys Phe
            3330                3335                3340

Asn Thr Trp Gly Asp Ser Asn Arg Ser Gly Lys Phe Thr Tyr Ser Ser
3345                3350                3355                3360

Arg Ser Gly Glu Ser Ile Gly Ile Phe Ile Ala Gly Lys Leu His Ile
            3365                3370                3375

His Leu Ser Ser Glu Ser Val Ala Leu Leu Cys Glu Thr Glu Arg Gln
            3380                3385                3390

Val Leu Ser Trp Met Ser Lys Arg Arg Thr Glu Val Ile Thr Lys Glu
            3395                3400                3405

Gln His Gln Leu Phe Leu Ser Leu Leu Pro Gln Ser His Glu Cys Leu
            3410                3415                3420

Gln Lys His Lys Asp Gly Ser Ala Leu Ser Val Ile Pro Asp Ser Ser
3425                3430                3435                3440

Asn Pro Arg Leu Leu Lys Phe Val Pro Leu Lys Lys Gly Leu Ala Val
            3445                3450                3455

Val Lys Ile Lys Lys Gln Ile Leu Thr Val Lys Lys Gln Val Val Phe
            3460                3465                3470

Asp Ala Glu Ser Glu Pro Arg Leu Gln Trp Gly His Gly Cys Leu Ser
            3475                3480                3485

Ile Val Tyr Asp Glu Thr Asp Thr Gln Thr Thr Tyr His Glu Asn Leu
            3490                3495                3500

Leu Lys Val Lys His Leu Val Asp Cys Ser Thr Asp Arg Lys Lys Leu
3505                3510                3515                3520

Leu Pro Gln Ser Val Phe Ser Asp Ser Lys Val Val Leu Ser Arg Ile
            3525                3530                3535

Lys Phe Lys Thr Glu Leu Leu Leu Asn Ser Leu Thr Leu Leu His Cys
```

```
                     3540            3545             3550
Phe Leu Lys His Ala Pro Ser Asp Ala Ile Met Glu Val Glu Ser Lys
            3555             3560             3565

Ser Ser Leu Leu His Lys Tyr Leu Lys Ser Gly Gly Val Arg Gln Arg
        3570            3575             3580

Asn Thr Glu Val Leu Phe Arg Glu Lys Leu Asn Lys Val Val Ile Lys
3585            3590            3595             3600

Asp Asn Leu Glu Gln Gly Val Glu Glu Ile Glu Phe Cys Asn Asn
            3605             3610             3615

Leu Thr Lys Thr Val Ser Glu Asn Pro Leu Pro Leu Ser Cys Trp Ser
            3620             3625             3630

Glu Val Gln Asn Tyr Ile Glu Asp Ile Gly Phe Asn Asn Val Leu Val
            3635             3640             3645

Asn Ile Asp Arg Asn Thr Val Lys Ser Glu Leu Leu Trp Lys Phe Thr
        3650            3655             3660

Leu Asp Thr Asn Val Ser Thr Thr Ser Thr Ile Lys Asp Val Arg Thr
3665            3670            3675             3680

Leu Val Ser Tyr Val Ser Thr Glu Thr Ile Pro Lys Phe Leu Leu Ala
            3685             3690             3695

Phe Leu Leu Tyr Glu Glu Val Leu Met Asn Leu Ile Asn Gln Cys Lys
            3700             3705             3710

Ala Val Lys Glu Leu Ile Asn Ser Thr Gly Leu Ser Asp Leu Glu Leu
            3715             3720             3725

Glu Ser Leu Leu Thr Leu Cys Ala Phe Tyr Phe Gln Ser Glu Cys Ser
            3730             3735             3740

Lys Arg Asp Gly Pro Arg Cys Ser Phe Ala Ala Leu Leu Ser Leu Ile
3745            3750            3755             3760

His Glu Asp Trp Gln Arg Ile Gly Lys Asn Ile Leu Val Arg Ala Asn
            3765             3770             3775

Asn Glu Leu Gly Asp Val Ser Leu Lys Val Asn Ile Val Leu Val Pro
            3780             3785             3790

Leu Lys Asp Met Ser Lys Pro Lys Ser Glu Arg Val Val Met Ala Arg
            3795             3800             3805

Arg Ser Leu Asn His Ala Leu Ser Leu Met Phe Leu Asp Glu Met Ser
            3810             3815             3820

Leu Pro Glu Leu Lys Ser Leu Ser Val Asn Cys Lys Met Gly Asn Phe
3825            3830            3835             3840

Glu Gly Gln Glu Cys Phe Glu Phe Thr Ile Leu Lys Asp Asn Ser Ala
            3845             3850             3855

Arg Leu Asp Tyr Asn Lys Leu Ile Asp His Cys Val Asp Met Glu Lys
            3860             3865             3870

Lys Arg Glu Ala Val Arg Ala Val Glu Asp Leu Ile Leu Met Leu Thr
            3875             3880             3885

Gly Arg Ala Val Lys Pro Ser Ala Val Thr Gln Phe Val His Gly Asp
            3890             3895             3900

Glu Gln Cys Gln Glu Gln Ile Ser Leu Asp Asp Leu Met Ala Asn Asp
3905            3910            3915             3920

Thr Val Thr Asp Phe Pro Asp Arg Glu Ala Glu Ala Leu Lys Thr Gly
            3925             3930             3935

Asn Leu Gly Phe Asn Trp Asp Ser Asp
            3940             3945

<210> SEQ ID NO 4
<211> LENGTH: 3945
```

```
<212> TYPE: PRT
<213> ORGANISM: Artificial Sequence
<220> FEATURE:
<223> OTHER INFORMATION: consensus sequence of CCHFV-L proteins from
      available complete L sequences and CCHFV-L USAMRIID (SEQ ID NO:3)

<400> SEQUENCE: 4
```

Met Asp Phe Leu Arg Ser Leu Asp Trp Thr Gln Val Ile Ala Gly Gln
 1               5                  10                  15

Tyr Val Ser Asn Pro Arg Phe Asn Ile Ser Asp Tyr Phe Glu Ile Val
             20                  25                  30

Arg Gln Pro Gly Asp Gly Asn Cys Phe Tyr His Ser Ile Ala Glu Leu
         35                  40                  45

Thr Met Pro Asn Lys Thr Asp His Ser Tyr His Tyr Ile Lys Arg Leu
 50                  55                  60

Thr Glu Ser Ala Ala Arg Lys Tyr Tyr Gln Glu Pro Glu Ala Arg
 65                  70                  75                  80

Leu Val Gly Leu Ser Leu Glu Asp Tyr Leu Lys Arg Met Leu Ser Asp
                 85                  90                  95

Asn Glu Trp Gly Ser Thr Leu Glu Ala Ser Met Leu Ala Lys Glu Met
            100                 105                 110

Gly Ile Thr Ile Ile Ile Trp Thr Val Ala Ala Ser Asp Glu Val Glu
        115                 120                 125

Ala Gly Ile Lys Phe Gly Asp Gly Asp Val Phe Thr Ala Val Asn Leu
    130                 135                 140

Leu His Ser Gly Gln Thr His Phe Asp Ala Leu Arg Ile Leu Pro Gln
145                 150                 155                 160

Phe Glu Thr Asp Thr Arg Glu Ala Leu Ser Leu Met Asp Arg Val Ile
                165                 170                 175

Ala Val Asp Gln Leu Thr Ser Ser Ser Asp Glu Leu Gln Asp Tyr
            180                 185                 190

Glu Asp Leu Ala Leu Ala Leu Thr Ser Ala Glu Ser Asn Arg Arg
        195                 200                 205

Ser Ser Leu Asp Glu Val Thr Leu Ser Lys Lys Gln Ala Glu Ile Leu
    210                 215                 220

Arg Gln Lys Ala Ser Gln Leu Ser Lys Leu Val Asn Lys Ser Gln Asn
225                 230                 235                 240

Ile Pro Thr Arg Val Gly Arg Val Leu Asp Cys Met Phe Asn Cys Lys
                245                 250                 255

Leu Cys Val Glu Ile Ser Ala Asp Thr Leu Ile Leu Arg Pro Glu Ser
            260                 265                 270

Lys Glu Lys Ile Gly Glu Ile Met Ser Leu Arg Gln Leu Gly His Lys
        275                 280                 285

Leu Leu Thr Arg Asp Lys Gln Ile Lys Gln Glu Phe Ser Arg Met Lys
    290                 295                 300

Leu Tyr Val Thr Lys Asp Leu Leu Asp His Leu Asp Val Gly Gly Leu
305                 310                 315                 320

Leu Arg Ala Ala Phe Pro Gly Thr Gly Ile Glu Arg His Met Gln Leu
                325                 330                 335

Leu His Ser Glu Met Ile Leu Asp Ile Cys Thr Val Ser Leu Gly Val
            340                 345                 350

Met Leu Ser Thr Phe Leu Tyr Gly Ser Asn Asn Lys Asn Lys Lys
        355                 360                 365

Phe Ile Thr Asn Cys Leu Leu Ser Thr Ala Leu Ser Gly Lys Lys Val
    370                 375                 380

```
Tyr Lys Val Leu Gly Asn Leu Gly Asn Glu Leu Leu Tyr Lys Ala Pro
385                 390                 395                 400

Arg Lys Ala Leu Ala Thr Val Cys Ser Ala Leu Phe Gly Lys Gln Ile
            405                 410                 415

Asn Lys Leu Gln Asn Cys Phe Arg Thr Ile Ser Pro Val Ser Leu Leu
        420                 425                 430

Ala Leu Arg Asn Leu Asp Phe Asp Cys Leu Ser Val Gln Asp Tyr Asn
    435                 440                 445

Gly Met Ile Glu Asn Met Ser Lys Leu Asp Asn Thr Asp Val Glu Phe
    450                 455                 460

Asn His Arg Glu Ile Ala Asp Leu Asn Gln Leu Thr Ser Arg Leu Ile
465                 470                 475                 480

Thr Leu Arg Lys Glu Lys Asp Thr Asp Leu Leu Lys Gln Trp Phe Pro
            485                 490                 495

Glu Ser Asp Leu Thr Arg Arg Ser Ile Arg Asn Ala Ala Asn Ala Glu
        500                 505                 510

Glu Phe Val Ile Ser Glu Phe Phe Lys Lys Asp Ile Met Lys Phe
    515                 520                 525

Ile Ser Thr Ser Gly Arg Ala Met Ser Ala Gly Lys Ile Gly Asn Val
    530                 535                 540

Leu Ser Tyr Ala His Asn Leu Tyr Leu Ser Lys Ser Ser Leu Asn Met
545                 550                 555                 560

Thr Ser Glu Asp Ile Ser Gln Leu Leu Ile Glu Ile Lys Arg Leu Tyr
            565                 570                 575

Ala Leu Gln Glu Asp Ser Glu Val Glu Pro Ile Ala Ile Ile Cys Asp
        580                 585                 590

Gly Ile Glu Ser Asn Met Lys Gln Leu Phe Ala Ile Leu Pro Pro Asp
    595                 600                 605

Cys Ala Arg Glu Cys Glu Val Leu Phe Asp Asp Ile Arg Asn Ser Pro
    610                 615                 620

Thr His Ser Thr Ala Trp Lys His Ala Leu Arg Leu Lys Gly Thr Ala
625                 630                 635                 640

Tyr Glu Gly Leu Phe Ala Asn Cys Tyr Gly Trp Gln Tyr Ile Pro Glu
            645                 650                 655

Asp Ile Lys Pro Ser Leu Thr Met Leu Ile Gln Thr Leu Phe Pro Asp
        660                 665                 670

Lys Phe Glu Asp Phe Leu Asp Arg Thr Gln Leu His Pro Glu Phe Arg
    675                 680                 685

Asp Leu Thr Pro Asp Phe Ser Leu Thr Gln Lys Val His Phe Lys Arg
    690                 695                 700

Asn Gln Ile Pro Ser Val Glu Asn Val Gln Ile Ser Ile Asp Ala Thr
705                 710                 715                 720

Leu Pro Glu Ser Val Glu Ala Val Pro Val Thr Glu Arg Lys Met Phe
            725                 730                 735

Pro Leu Pro Glu Thr Pro Leu Ser Glu Val His Ser Ile Glu Arg Ile
        740                 745                 750

Met Glu Asn Phe Thr Arg Leu Met His Gly Gly Arg Leu Ser Thr Lys
    755                 760                 765

Lys Arg Asp Gly Asp Pro Ala Glu Gln Gly Asn Gln Gln Ser Ile Thr
    770                 775                 780

Glu His Glu Ser Ser Ser Ile Ser Ala Phe Lys Asp Tyr Gly Glu Arg
785                 790                 795                 800

Gly Ile Val Glu Glu Asn His Met Lys Phe Ser Gly Glu Asp Gln Leu
            805                 810                 815
```

```
Glu Thr Arg Gln Leu Leu Leu Val Glu Val Gly Phe Gln Thr Asp Ile
            820                 825                 830
Asp Gly Lys Ile Arg Thr Asp His Lys Lys Trp Lys Asp Ile Leu Lys
            835                 840                 845
Leu Leu Glu Leu Leu Gly Ile Lys Cys Ser Phe Ile Ala Cys Ala Asp
        850                 855                 860
Cys Ser Ser Thr Pro Pro Asp Arg Trp Trp Ile Thr Glu Asp Arg Val
865                 870                 875                 880
Arg Val Leu Lys Asn Ser Val Ser Phe Leu Phe Asn Lys Leu Ser Arg
                885                 890                 895
Asn Ser Pro Thr Glu Val Thr Asp Ile Val Val Gly Ala Ile Ser Thr
            900                 905                 910
Gln Lys Val Arg Ser Tyr Leu Lys Ala Gly Thr Ala Thr Lys Thr Pro
            915                 920                 925
Val Ser Thr Lys Asp Val Leu Glu Thr Trp Glu Lys Met Lys Glu His
        930                 935                 940
Ile Leu Asn Arg Pro Thr Gly Leu Thr Leu Pro Thr Ser Leu Glu Gln
945                 950                 955                 960
Ala Met Arg Lys Gly Leu Val Glu Gly Val Ile Ser Lys Glu Gly
                965                 970                 975
Ser Glu Ser Cys Ile Asn Met Leu Lys Glu Asn Leu Asp Arg Ile Thr
            980                 985                 990
Asp Glu Phe Glu Arg Thr Lys Phe Lys His Glu Leu Thr Gln Asn Ile
            995                 1000                1005
Thr Thr Ser Glu Lys Met Leu Leu Ser Trp Leu Ser Glu Asp Ile Lys
        1010                1015                1020
Ser Ser Arg Cys Gly Cys Leu Ser Asn Ile Lys Lys Ala Val Asp
1025                1030                1035                1040
Glu Thr Ala Asn Leu Ser Glu Lys Ile Glu Leu Leu Ala Tyr Asn Leu
                1045                1050                1055
Gln Leu Thr Asn His Cys Ser Asn Cys His Pro Asn Gly Val Asn Ile
            1060                1065                1070
Ser Asn Thr Ser Asn Val Cys Lys Arg Cys Pro Lys Ile Glu Val Val
        1075                1080                1085
Ser His Cys Glu Asn Lys Gly Phe Glu Asp Ser Asn Glu Cys Leu Thr
        1090                1095                1100
Asp Leu Asp Arg Leu Val Arg Leu Thr Leu Pro Gly Lys Thr Glu Lys
1105                1110                1115                1120
Glu Arg Arg Val Lys Arg Asn Val Glu Tyr Leu Ile Lys Leu Met Met
                1125                1130                1135
Ser Met Ser Gly Ile Asp Cys Ile Lys Tyr Pro Thr Gly Gln Leu Ile
            1140                1145                1150
Thr His Gly Arg Val Ser Ala Lys His Asn Asp Gly Asn Leu Lys Asp
            1155                1160                1165
Arg Ser Asp Asp Asp Gln Arg Leu Ala Glu Lys Ile Asp Thr Val Arg
1170                1175                1180
Lys Glu Leu Ser Glu Ser Lys Leu Lys Asp Tyr Ser Thr Tyr Ala Arg
1185                1190                1195                1200
Gly Val Ile Ser Asn Ser Leu Lys Asn Leu Ser Arg Gln Gly Lys Ser
                1205                1210                1215
Lys Cys Ser Val Pro Arg Ser Trp Leu Glu Lys Val Leu Phe Asp Leu
            1220                1225                1230
Lys Val Pro Thr Lys Asp Glu Glu Val Leu Ile Asn Ile Arg Asn Ser
```

-continued

```
                1235                1240                1245
Leu Lys Ala Arg Ser Glu Phe Val Arg Asn Asn Asp Lys Leu Leu Ile
        1250                1255                1260
Arg Ser Lys Glu Glu Leu Lys Lys Cys Phe Asp Val Gln Ser Phe Lys
1265                1270                1275                1280
Leu Lys Lys Asn Lys Gln Pro Val Pro Phe Gln Val Asp Cys Ile Leu
            1285                1290                1295
Phe Lys Glu Val Ala Ala Glu Cys Met Lys Arg Tyr Ile Gly Thr Pro
        1300                1305                1310
Tyr Glu Gly Ile Val Asp Thr Leu Val Ser Leu Ile Asn Val Leu Thr
        1315                1320                1325
Arg Phe Thr Trp Phe Gln Glu Val Val Leu Tyr Gly Lys Ile Cys Glu
        1330                1335                1340
Thr Phe Leu Arg Cys Cys Thr Glu Phe Asn Arg Ser Gly Val Lys Leu
1345                1350                1355                1360
Val Lys Ile Arg His Cys Asn Ile Asn Leu Ser Val Lys Leu Pro Ser
            1365                1370                1375
Asn Lys Lys Glu Asn Met Leu Cys Cys Leu Tyr Ser Gly Asn Met Glu
            1380                1385                1390
Leu Leu Gln Gly Pro Phe Tyr Leu Asn Arg Arg Gln Ala Val Leu Gly
            1395                1400                1405
Ser Ser Tyr Leu Tyr Ile Val Ile Thr Leu Tyr Ile Gln Val Leu Gln
        1410                1415                1420
Gln Tyr Arg Cys Leu Glu Val Ile Asn Ser Val Ser Glu Lys Thr Leu
1425                1430                1435                1440
Gln Asp Ile Glu Asn His Ser Met Thr Leu Leu Glu Asp Ser Phe Arg
            1445                1450                1455
Glu Ile Thr Phe Ala Leu Glu Gly Arg Phe Asn Glu Ser Tyr Lys Ile
            1460                1465                1470
Arg Thr Ser Arg Cys Arg Ala Ser Gly Asn Phe Leu Asn Arg Ser Ser
        1475                1480                1485
Arg Asp His Phe Ile Ser Val Val Ser Gly Leu Asn Leu Val Tyr Gly
        1490                1495                1500
Phe Leu Ile Lys Asp Asn Leu Leu Ala Asn Ser Gln Gln Gln Asn Lys
1505                1510                1515                1520
Gln Leu Gln Met Leu Arg Phe Gly Met Leu Ala Gly Leu Ser Arg Leu
            1525                1530                1535
Val Cys Pro Asn Glu Leu Gly Lys Lys Phe Ser Thr Ser Cys Arg Arg
        1540                1545                1550
Ile Glu Asp Asn Ile Ala Arg Leu Tyr Leu Gln Thr Ser Ile Tyr Cys
        1555                1560                1565
Ser Val Arg Asp Val Glu Asp Asn Val Lys His Trp Lys Gln Arg Asp
    1570                1575                1580
Leu Cys Pro Glu Val Thr Ile Pro Cys Phe Thr Val Tyr Gly Thr Phe
1585                1590                1595                1600
Val Asn Ser Asp Arg Gln Leu Ile Phe Asp Ile Tyr Asn Val His Ile
            1605                1610                1615
Tyr Asn Lys Glu Met Asp Asn Phe Asp Glu Gly Cys Ile Ser Val Leu
            1620                1625                1630
Glu Glu Thr Ala Glu Arg His Met Leu Trp Glu Leu Asp Leu Met Asn
        1635                1640                1645
Ser Leu Cys Ser Asp Glu Lys Lys Asp Thr Arg Thr Ala Arg Leu Leu
    1650                1655                1660
```

```
Leu Gly Cys Pro Asn Val Arg Lys Ala Ala Asn Arg Glu Gly Lys Lys
1665                1670                1675                1680

Leu Leu Lys Leu Asn Ser Asp Thr Ser Thr Asp Thr Gln Ser Ile Ala
            1685                1690                1695

Ser Glu Val Ser Asp Arg Arg Ser Tyr Ser Ser Lys Ser Arg Ile
    1700                1705                1710

Arg Ser Ile Phe Gly Arg Tyr Asn Ser Gln Lys Lys Pro Phe Glu Leu
        1715                1720                1725

Arg Ser Gly Leu Glu Val Phe Asn Asp Pro Phe Asn Asp Tyr Gln Gln
        1730                1735                1740

Ala Ile Thr Asp Ile Cys Gln Phe Ser Glu Tyr Thr Pro Asn Lys Glu
1745                1750                1755                1760

Ser Ile Leu Lys Asp Cys Leu Gln Ile Ile Arg Lys Asn Pro Ser His
            1765                1770                1775

Thr Met Gly Ser Phe Glu Leu Ile Gln Ala Ile Ser Glu Phe Gly Met
            1780                1785                1790

Ser Lys Phe Pro Pro Glu Asn Ile Asp Lys Ala Arg Arg Asp Pro Lys
        1795                1800                1805

Asn Trp Val Ser Ile Ser Glu Val Thr Glu Thr Thr Ser Ile Val Ala
    1810                1815                1820

Ser Pro Arg Thr His Met Met Leu Lys Asp Cys Phe Lys Ile Ile Leu
1825                1830                1835                1840

Gly Thr Glu Asn Lys Lys Ile Val Lys Met Leu Arg Gly Lys Leu Lys
            1845                1850                1855

Lys Leu Gly Ala Ile Ser Thr Asn Ile Glu Ile Gly Lys Arg Asp Cys
            1860                1865                1870

Leu Asp Leu Leu Ser Thr Val Asp Gly Leu Thr Asp Gln Gln Lys Glu
        1875                1880                1885

Asn Ile Val Asn Gly Ile Phe Glu Pro Ser Leu Ser Phe Tyr His
    1890                1895                1900

Trp Lys Glu Leu Val Lys Lys Asn Ile Asp Glu Val Leu Leu Thr Glu
1905                1910                1915                1920

Asp Gly Asn Leu Ile Phe Cys Trp Leu Lys Thr Ile Ser Ser Ser Val
            1925                1930                1935

Lys Gly Ser Leu Lys Lys Arg Leu Lys Phe Met Asn Ile His Ser Pro
        1940                1945                1950

Glu Leu Met Pro Glu Asn Cys Leu Phe Ser Glu Glu Phe Asn Glu
        1955                1960                1965

Leu Ile Lys Leu Lys Lys Leu Leu Asn Glu Gln Gln Asp Glu Gln
    1970                1975                1980

Glu Leu Lys Gln Asp Leu Leu Ile Ser Ser Trp Ile Lys Cys Ile Thr
1985                1990                1995                2000

Ala Cys Lys Asp Phe Ala Ser Ile Asn Asp Lys Ile Gln Lys Phe Ile
            2005                2010                2015

Tyr His Leu Ser Glu Glu Leu Tyr Asp Ile Arg Leu Gln His Leu Glu
        2020                2025                2030

Leu Ser Lys Leu Lys Gln Glu His Pro Ser Val Ser Phe Thr Lys Glu
        2035                2040                2045

Glu Val Leu Ile Lys Arg Leu Glu Lys Asn Phe Leu Lys Gln His Asn
    2050                2055                2060

Leu Glu Ile Met Glu Thr Val Asn Leu Val Phe Phe Ala Ala Leu Ser
2065                2070                2075                2080

Ala Pro Trp Cys Leu His Tyr Lys Ala Leu Glu Ser Tyr Leu Val Arg
            2085                2090                2095
```

-continued

His Pro Glu Ile Leu Asp Cys Gly Ser Lys Glu Asp Cys Lys Leu Thr
            2100                2105                2110

Leu Leu Asp Leu Ser Val Ser Lys Leu Leu Val Cys Leu Tyr Gln Lys
         2115                2120                2125

Asp Asp Glu Glu Leu Ile Asn Ser Ser Leu Lys Leu Gly Phe Leu
     2130                2135                2140

Val Lys Tyr Val Val Thr Leu Phe Thr Ser Asn Gly Glu Pro Phe Ser
2145                2150                2155                2160

Leu Ser Leu Asn Asp Gly Gly Leu Asp Leu Asp Leu His Lys Thr Thr
             2165                2170                2175

Asp Glu Lys Leu Leu His Gln Thr Lys Ile Val Phe Ala Lys Ile Gly
         2180                2185                2190

Leu Ser Gly Asn Ser Tyr Asp Phe Ile Trp Thr Thr Gln Met Ile Ala
         2195                2200                2205

Asn Ser Asn Phe Asn Val Cys Lys Arg Leu Thr Gly Arg Ser Thr Gly
         2210                2215                2220

Glu Arg Leu Pro Arg Ser Val Arg Ser Lys Val Ile Tyr Glu Met Val
2225                2230                2235                2240

Lys Leu Val Gly Glu Thr Gly Met Ala Ile Leu Gln Gln Leu Ala Phe
             2245                2250                2255

Ala Gln Ala Leu Asn Tyr Glu His Arg Phe Tyr Ala Val Leu Ala Pro
         2260                2265                2270

Lys Ala Gln Leu Gly Gly Ala Arg Asp Leu Leu Val Gln Glu Thr Gly
             2275                2280                2285

Thr Lys Val Met His Ala Thr Thr Glu Met Phe Ser Arg Asn Leu Leu
         2290                2295                2300

Lys Thr Thr Ser Asp Asp Gly Leu Thr Asn Pro His Leu Lys Glu Thr
2305                2310                2315                2320

Ile Leu Asn Val Gly Leu Asp Cys Leu Ala Asn Met Arg Asn Leu Asp
             2325                2330                2335

Gly Lys Pro Ile Ser Glu Gly Ser Asn Leu Val Asn Phe Tyr Lys Val
             2340                2345                2350

Ile Cys Ile Ser Gly Asp Asn Thr Lys Trp Gly Pro Ile His Cys Cys
         2355                2360                2365

Ser Phe Phe Ser Gly Met Met Gln Gln Val Leu Lys Asn Val Pro Asp
     2370                2375                2380

Trp Cys Ser Phe Tyr Lys Leu Thr Phe Ile Lys Asn Leu Cys Arg Gln
2385                2390                2395                2400

Val Glu Ile Pro Ala Gly Ser Ile Lys Lys Ile Leu Asn Val Leu Arg
         2405                2410                2415

Tyr Arg Leu Cys Ser Lys Gly Gly Val Glu Gln His Ser Glu Glu Asp
         2420                2425                2430

Leu Arg Arg Leu Leu Thr Asp Asn Leu Asp Ser Trp Asp Gly Asn Asp
         2435                2440                2445

Thr Val Lys Phe Leu Val Thr Thr Tyr Ile Ser Lys Gly Leu Met Ala
     2450                2455                2460

Leu Asn Ser Tyr Asn His Met Gly Gln Gly Ile His His Ala Thr Ser
2465                2470                2475                2480

Ser Val Leu Thr Ser Leu Ala Ala Val Leu Phe Glu Glu Leu Ala Ile
             2485                2490                2495

Phe Tyr Leu Lys Arg Ser Leu Pro Gln Thr Thr Val His Val Glu His
         2500                2505                2510

Ala Gly Ser Ser Asp Asp Tyr Ala Lys Cys Ile Val Val Thr Gly Ile

-continued

```
              2515                2520                2525
Leu Ser Lys Glu Leu Tyr Ser Gln Tyr Asp Thr Phe Trp Lys His
    2530                2535                2540
Ala Cys Arg Leu Lys Asn Phe Thr Ala Val Gln Arg Cys Cys Gln
2545                2550                2555                2560
Met Lys Asp Ser Ala Lys Thr Leu Val Ser Asp Cys Phe Leu Glu Phe
            2565                2570                2575
Tyr Ser Glu Phe Met Met Gly Tyr Arg Val Thr Pro Ala Val Ile Lys
        2580                2585                2590
Phe Met Phe Thr Gly Leu Ile Asn Ser Ser Val Thr Ser Pro Gln Ser
            2595                2600                2605
Leu Met Gln Ala Cys Gln Val Ser Ser Gln Gln Ala Met Tyr Asn Ser
        2610                2615                2620
Val Pro Leu Val Thr Asn Thr Ala Phe Thr Leu Leu Arg Gln Gln Ile
2625                2630                2635                2640
Phe Phe Asn His Val Glu Asp Phe Ile Arg Arg Tyr Gly Ile Leu Thr
            2645                2650                2655
Leu Gly Thr Leu Ser Pro Phe Gly Arg Leu Phe Val Pro Thr Tyr Ser
            2660                2665                2670
Gly Leu Val Ser Ser Ala Val Ala Leu Glu Asp Ala Glu Val Ile Ala
        2675                2680                2685
Arg Ala Ala Gln Thr Leu Gln Met Asn Ser Val Ser Ile Gln Ser Ser
            2690                2695                2700
Ser Leu Thr Thr Leu Asp Ser Leu Gly Arg Ser Arg Thr Ser Ser Thr
2705                2710                2715                2720
Ala Glu Asp Ser Ser Ser Val Ser Asp Thr Thr Ala Ala Ser His Asp
            2725                2730                2735
Ser Gly Ser Ser Ser Ser Ser Phe Ser Phe Glu Leu Asn Arg Pro Leu
            2740                2745                2750
Ser Glu Thr Glu Leu Gln Phe Ile Lys Ala Leu Ser Ser Leu Lys Ser
            2755                2760                2765
Thr Gln Ala Cys Glu Val Ile Gln Asn Arg Ile Thr Gly Leu Tyr Cys
    2770                2775                2780
Asn Ser Asn Glu Gly Pro Leu Asp Arg His Asn Val Ile Tyr Ser Ser
2785                2790                2795                2800
Arg Met Ala Asp Ser Cys Asp Trp Leu Lys Asp Gly Lys Arg Arg Gly
            2805                2810                2815
Asn Leu Glu Leu Ala Asn Arg Ile Gln Ser Val Leu Cys Ile Leu Ile
        2820                2825                2830
Ala Gly Tyr Tyr Arg Ser Phe Gly Gly Glu Gly Thr Glu Lys Gln Val
        2835                2840                2845
Lys Ala Ser Leu Asn Arg Asp Asp Asn Lys Ile Ile Glu Asp Pro Met
    2850                2855                2860
Ile Gln Leu Ile Pro Glu Lys Leu Arg Arg Glu Leu Glu Arg Leu Gly
2865                2870                2875                2880
Val Ser Arg Met Glu Val Asp Glu Leu Met Pro Ser Ile Ser Pro Asp
            2885                2890                2895
Asp Thr Leu Ala Gln Leu Val Ala Lys Lys Leu Ile Ser Leu Asn Val
        2900                2905                2910
Ser Thr Glu Glu Tyr Ser Ala Glu Val Ser Arg Leu Lys Gln Thr Leu
            2915                2920                2925
Thr Ala Arg Asn Val Leu His Gly Leu Ala Gly Gly Ile Lys Glu Leu
    2930                2935                2940
```

-continued

```
Ser Leu Pro Ile Tyr Thr Ile Phe Met Lys Ser Tyr Phe Phe Lys Asp
2945                2950                2955                2960

Asn Val Phe Leu Ser Leu Thr Asp Arg Trp Ser Thr Lys His Ser Thr
            2965                2970                2975

Asn Tyr Arg Asp Ser Cys Gly Lys Gln Leu Lys Gly Arg Ile Ile Thr
        2980                2985                2990

Lys Tyr Thr His Trp Leu Asp Thr Phe Leu Gly Cys Ser Val Ser Ile
    2995                3000                3005

Asn Arg His Thr Thr Val Lys Glu Pro Ser Leu Phe Asn Pro Asn Ile
3010                3015                3020

Arg Cys Val Asn Leu Ile Thr Phe Glu Asp Gly Leu Arg Glu Leu Ser
3025                3030                3035                3040

Val Ile Gln Ser His Leu Lys Val Phe Glu Asn Glu Phe Thr Asn Leu
            3045                3050                3055

Asn Leu Gln Phe Ser Asp Pro Asn Arg Gln Lys Leu Arg Ile Val Glu
        3060                3065                3070

Ser Arg Pro Ala Glu Ser Glu Leu Glu Ala Asn Arg Ala Val Ile Val
    3075                3080                3085

Lys Thr Lys Leu Phe Ser Ala Thr Glu Gln Val Arg Leu Ser Asn Asn
3090                3095                3100

Pro Ala Val Val Met Gly Tyr Leu Leu Asp Glu Ser Ala Ile Ser Glu
3105                3110                3115                3120

Val Lys Pro Thr Lys Val Asp Phe Ser Asn Leu Leu Lys Asp Arg Phe
            3125                3130                3135

Lys Ile Met Gln Phe Phe Pro Ser Val Phe Thr Leu Ile Lys Met Leu
        3140                3145                3150

Thr Asp Glu Ser Ser Asp Ser Glu Lys Ser Gly Leu Ser Pro Asp Leu
    3155                3160                3165

Gln Gln Val Ala Arg Tyr Ser Asn His Leu Thr Leu Leu Ser Arg Met
3170                3175                3180

Ile Gln Gln Ala Lys Pro Thr Val Thr Val Phe Tyr Met Leu Lys Gly
3185                3190                3195                3200

Asn Leu Met Asn Thr Glu Pro Thr Val Ala Glu Leu Val Ser Tyr Gly
            3205                3210                3215

Ile Lys Glu Gly Arg Phe Phe Arg Leu Ser Asp Thr Gly Val Asp Ala
        3220                3225                3230

Ser Thr Tyr Ser Val Lys Tyr Trp Lys Ile Leu His Cys Ile Ser Ala
    3235                3240                3245

Ile Gly Cys Leu Pro Leu Ser Gln Ala Asp Lys Ser Ser Leu Leu Met
3250                3255                3260

Ser Phe Leu Asn Trp Arg Val Asn Met Asp Ile Arg Thr Ser Asp Cys
3265                3270                3275                3280

Pro Leu Ser Ser His Glu Ala Ser Ile Leu Ser Glu Phe Asp Gly Gln
            3285                3290                3295

Val Ile Ala Asn Ile Leu Ala Ser Glu Leu Ser Ser Val Lys Arg Asp
        3300                3305                3310

Ser Glu Arg Glu Gly Leu Thr Asp Leu Leu Asp Tyr Leu Asn Ser Pro
    3315                3320                3325

Thr Glu Leu Leu Lys Lys Lys Pro Tyr Leu Gly Thr Thr Cys Lys Phe
3330                3335                3340

Asn Thr Trp Gly Asp Ser Asn Arg Ser Gly Lys Phe Thr Tyr Ser Ser
3345                3350                3355                3360

Arg Ser Gly Glu Ser Ile Gly Ile Phe Ile Ala Gly Lys Leu His Ile
            3365                3370                3375
```

His Leu Ser Ser Glu Ser Val Ala Leu Leu Cys Glu Thr Glu Arg Gln
            3380                3385                3390

Val Leu Ser Trp Met Ser Lys Arg Arg Thr Glu Val Ile Thr Lys Glu
            3395                3400                3405

Gln His Gln Leu Phe Leu Ser Leu Leu Pro Gln Ser His Glu Cys Leu
            3410                3415                3420

Gln Lys His Lys Asp Gly Ser Ala Leu Ser Val Ile Pro Asp Ser Ser
3425                3430                3435                3440

Asn Pro Arg Leu Leu Lys Phe Val Pro Leu Lys Lys Gly Leu Ala Val
            3445                3450                3455

Val Lys Ile Lys Lys Gln Ile Leu Thr Val Lys Lys Gln Val Val Phe
            3460                3465                3470

Asp Ala Glu Ser Glu Pro Arg Leu Gln Trp Gly His Gly Cys Leu Ser
            3475                3480                3485

Ile Val Tyr Asp Glu Thr Asp Thr Gln Thr Thr Tyr His Glu Asn Leu
            3490                3495                3500

Leu Lys Val Lys His Leu Val Asp Cys Ser Thr Asp Arg Lys Lys Leu
3505                3510                3515                3520

Leu Pro Gln Ser Val Phe Ser Asp Ser Lys Val Val Leu Ser Arg Ile
            3525                3530                3535

Lys Phe Lys Thr Glu Leu Leu Leu Asn Ser Leu Thr Leu Leu His Cys
            3540                3545                3550

Phe Leu Lys His Ala Pro Ser Asp Ala Ile Met Glu Val Glu Ser Lys
            3555                3560                3565

Ser Ser Leu Leu His Lys Tyr Leu Lys Ser Gly Gly Val Arg Gln Arg
            3570                3575                3580

Asn Thr Glu Val Leu Phe Arg Gly Lys Leu Asn Lys Val Ile Lys
3585                3590                3595                3600

Asp Asn Leu Glu Gln Gly Val Glu Glu Ile Glu Phe Cys Asn Asn
            3605                3610                3615

Leu Thr Lys Thr Val Ser Glu Asn Pro Leu Pro Leu Ser Cys Trp Ser
            3620                3625                3630

Glu Val Gln Asn Tyr Ile Glu Asp Ile Gly Phe Asn Asn Val Leu Val
            3635                3640                3645

Asn Ile Asp Arg Asn Thr Val Lys Ser Glu Leu Leu Trp Lys Phe Thr
            3650                3655                3660

Leu Asp Thr Asn Val Ser Thr Thr Ser Thr Ile Lys Asp Val Arg Thr
3665                3670                3675                3680

Leu Val Ser Tyr Val Ser Thr Glu Thr Ile Pro Lys Phe Leu Leu Ala
            3685                3690                3695

Phe Leu Leu Tyr Glu Glu Val Leu Met Asn Leu Ile Asn Gln Cys Lys
            3700                3705                3710

Ala Val Lys Glu Leu Ile Asn Ser Thr Gly Leu Ser Asp Leu Glu Leu
            3715                3720                3725

Glu Ser Leu Leu Thr Leu Cys Ala Phe Tyr Phe Gln Ser Glu Cys Ser
            3730                3735                3740

Lys Arg Asp Gly Pro Arg Cys Ser Phe Ala Ala Leu Leu Ser Leu Ile
3745                3750                3755                3760

His Glu Asp Trp Gln Arg Ile Gly Lys Asn Ile Leu Val Arg Ala Asn
            3765                3770                3775

Asn Glu Leu Gly Asp Val Ser Leu Lys Val Asn Ile Val Leu Val Pro
            3780                3785                3790

Leu Lys Asp Met Ser Lys Pro Lys Ser Glu Arg Val Val Met Ala Arg

```
                  3795                3800                3805
Arg Ser Leu Asn His Ala Leu Ser Leu Met Phe Leu Asp Glu Met Ser
        3810                3815                3820
Leu Pro Glu Leu Lys Ser Leu Ser Val Asn Cys Lys Met Gly Asn Phe
3825                3830                3835                3840
Glu Gly Gln Glu Cys Phe Glu Phe Thr Ile Leu Lys Asp Asn Ser Ala
                3845                3850                3855
Arg Leu Asp Tyr Asn Lys Leu Ile Asp His Cys Val Asp Met Glu Lys
        3860                3865                3870
Lys Arg Glu Ala Val Arg Ala Val Glu Asp Leu Ile Leu Met Leu Thr
            3875                3880                3885
Gly Arg Ala Val Lys Pro Ser Ala Val Thr Gln Phe Val His Gly Asp
        3890                3895                3900
Glu Gln Cys Gln Glu Gln Ile Ser Leu Asp Asp Leu Met Ala Asn Asp
3905                3910                3915                3920
Thr Val Thr Asp Phe Pro Asp Arg Glu Ala Glu Ala Leu Lys Thr Gly
                3925                3930                3935
Asn Leu Gly Phe Asn Trp Asp Ser Asp
            3940                3945

<210> SEQ ID NO 5
<211> LENGTH: 6
<212> TYPE: PRT
<213> ORGANISM: Artificial Sequence
<220> FEATURE:
<223> OTHER INFORMATION: motif in SUMO carboxy-terminal

<400> SEQUENCE: 5

Gln Gln Gln Thr Gly Gly
 1               5

<210> SEQ ID NO 6
<211> LENGTH: 6
<212> TYPE: PRT
<213> ORGANISM: Artificial Sequence
<220> FEATURE:
<223> OTHER INFORMATION: motif in Nedd8 carboxy-terminal

<400> SEQUENCE: 6

Leu Ala Leu Arg Gly Gly
 1               5

<210> SEQ ID NO 7
<211> LENGTH: 6
<212> TYPE: PRT
<213> ORGANISM: Artificial Sequence
<220> FEATURE:
<223> OTHER INFORMATION: cleavage site of nsp2/3 junction of EAV by
      viral OTU domain-containing proteases

<400> SEQUENCE: 7

Phe Arg Leu Ile Gly Gly
 1               5

<210> SEQ ID NO 8
<211> LENGTH: 6
<212> TYPE: PRT
<213> ORGANISM: Artificial Sequence
<220> FEATURE:
<223> OTHER INFORMATION: cleavage site of nsp2/3 junction of PRSSV by
      viral OTU domain-containing proteases

<400> SEQUENCE: 8
```

Gly Arg Leu Leu Gly Gly
1               5

<210> SEQ ID NO 9
<211> LENGTH: 130
<212> TYPE: PRT
<213> ORGANISM: Crimean Congo Hemorrhagic Fever Virus (CCHFV)
<220> FEATURE:
<223> OTHER INFORMATION: CCHFV L protein OTU domain

<400> SEQUENCE: 9

Phe Glu Ile Val Arg Gln Pro Gly Asp Gly Asn Cys Phe Tyr His Ser
1               5                   10                  15

Ile Ala Glu Leu Thr Met Pro Asn Lys Thr Asp His Ser Tyr His Tyr
            20                  25                  30

Ile Lys Arg Leu Thr Glu Ser Ala Ala Arg Lys Tyr Tyr Gln Glu Glu
        35                  40                  45

Pro Glu Ala Arg Leu Val Gly Leu Ser Leu Glu Asp Tyr Leu Lys Arg
50                  55                  60

Met Leu Ser Asp Asn Glu Trp Gly Ser Thr Leu Glu Ala Ser Met Leu
65                  70                  75                  80

Ala Lys Glu Met Gly Ile Thr Ile Ile Ile Trp Thr Val Ala Ala Ser
                85                  90                  95

Asp Glu Val Glu Ala Gly Ile Lys Phe Gly Asp Gly Asp Val Phe Thr
            100                 105                 110

Ala Val Asn Leu Leu His Ser Gly Gln Thr His Phe Asp Ala Leu Arg
        115                 120                 125

Ile Leu
    130

<210> SEQ ID NO 10
<211> LENGTH: 130
<212> TYPE: PRT
<213> ORGANISM: Dugbe virus (DUGV)
<220> FEATURE:
<223> OTHER INFORMATION: DUGV L protein OTU domain

<400> SEQUENCE: 10

Phe Glu Val Ile Arg Gln Pro Gly Asp Gly Asn Cys Phe Tyr His Ser
1               5                   10                  15

Ile Ala Glu Leu Phe Phe Asp Val Lys Thr Pro Ser Ser Phe Arg Lys
            20                  25                  30

Val Lys Glu His Leu Gln Leu Ala Ala Glu Val Tyr Tyr Asp Thr Glu
        35                  40                  45

Pro Glu Ala Val Gly Thr Gly Ile Ser Lys Asp Glu Tyr Ile Lys Val
50                  55                  60

Ala Met Lys Asp Asn Glu Trp Gly Gly Ser Leu Glu Ala Ser Met Leu
65                  70                  75                  80

Ser Lys His Leu Gln Thr Thr Ile Ile Leu Trp Val Val Asn Ser Thr
                85                  90                  95

Glu Gln Val Thr Ala Ala Ile Lys Phe Gly Pro Gly Arg Val Ser Thr
            100                 105                 110

Ala Leu Asn Leu Met His Val Gly Arg Thr His Phe Asp Ala Leu Arg
        115                 120                 125

Ile Ile
    130

<210> SEQ ID NO 11
<211> LENGTH: 130

```
<212> TYPE: PRT
<213> ORGANISM: Artificial Sequence
<220> FEATURE:
<223> OTHER INFORMATION: conserved amino acids of CCHFV and DUGV OTU
      domain
<220> FEATURE:
<221> NAME/KEY: VARIANT
<222> LOCATION: 1.....6
<223> OTHER INFORMATION: Xaa = Any Amino Acid
<220> FEATURE:
<221> NAME/KEY: VARIANT
<222> LOCATION: 18....122
<223> OTHER INFORMATION: Xaa = Any Amino Acid
<220> FEATURE:
<221> NAME/KEY: VARIANT
<222> LOCATION: 125...130
<223> OTHER INFORMATION: Xaa = Any Amino Acid

<400> SEQUENCE: 11

Xaa Xaa Xaa Xaa Xaa Xaa Pro Gly Asp Gly Asn Cys Phe Tyr His Ser
 1               5                  10                  15

Ile Xaa Xaa Xaa Xaa Xaa Xaa Xaa Xaa Xaa Xaa Xaa Xaa Xaa Xaa Xaa
             20                  25                  30

Xaa Xaa Xaa Xaa Xaa Xaa Xaa Xaa Xaa Xaa Xaa Xaa Xaa Xaa Xaa
         35                  40                  45

Xaa Xaa Xaa Xaa Xaa Xaa Xaa Xaa Xaa Xaa Xaa Xaa Xaa Xaa Xaa
     50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
             85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa His Phe Xaa Xaa Xaa Xaa
        115                 120                 125

Xaa Xaa
   130

<210> SEQ ID NO 12
<211> LENGTH: 20
<212> TYPE: PRT
<213> ORGANISM: Crimean Congo hemorrhagic fever virus
<220> FEATURE:
<223> OTHER INFORMATION: conserved region of OTU domain-containing
      cysteine protease of CCHFV (RdRp) (positions 30-49)

<400> SEQUENCE: 12

Glu Ile Val Arg Gln Pro Gly Asp Gly Asn Cys Phe Tyr His Ser Ile
 1               5                  10                  15

Ala Glu Leu Thr
         20

<210> SEQ ID NO 13
<211> LENGTH: 10
<212> TYPE: PRT
<213> ORGANISM: Crimean Congo hemorrhagic fever virus
<220> FEATURE:
<223> OTHER INFORMATION: conserved region of OTU domain-containing
      cysteine protease of CCHFV (RdRp) (positions 148-157)

<400> SEQUENCE: 13

Gly Gln Thr His Phe Asp Ala Leu Arg Ile
 1               5                  10

<210> SEQ ID NO 14
```

```
<211> LENGTH: 20
<212> TYPE: PRT
<213> ORGANISM: Dugbe virus
<220> FEATURE:
<223> OTHER INFORMATION: conserved region of OTU domain-containing
      cysteine protease of DUGV (RdRp) (positions 30-49)

<400> SEQUENCE: 14

Glu Val Ile Arg Gln Pro Gly Asp Gly Asn Cys Phe Tyr His Ser Ile
1               5                   10                  15

Ala Glu Leu Phe
            20

<210> SEQ ID NO 15
<211> LENGTH: 10
<212> TYPE: PRT
<213> ORGANISM: Dugbe virus
<220> FEATURE:
<223> OTHER INFORMATION: conserved region of OTU domain-containing
      cysteine protease of DUGV (RdRp) (positions 148-157)

<400> SEQUENCE: 15

Gly Arg Thr His Phe Asp Ala Leu Arg Ile
1               5                   10

<210> SEQ ID NO 16
<211> LENGTH: 20
<212> TYPE: PRT
<213> ORGANISM: rice stripe virus
<220> FEATURE:
<223> OTHER INFORMATION: conserved region of OTU domain-containing
      cysteine protease of RiceStv (RdRp) (positions 35-54)

<400> SEQUENCE: 16

Glu Glu Thr Asp Val Arg Gly Asp Gly Phe Cys Leu Tyr His Ser Ile
1               5                   10                  15

Leu Tyr Ser Met
            20

<210> SEQ ID NO 17
<211> LENGTH: 10
<212> TYPE: PRT
<213> ORGANISM: rice stripe virus
<220> FEATURE:
<223> OTHER INFORMATION: conserved region of OTU domain-containing
      cysteine protease of RiceStv (RdRp) (positions 145-154)

<400> SEQUENCE: 17

Gly Asn Tyr His Phe Lys Ser Leu Glu Thr
1               5                   10

<210> SEQ ID NO 18
<211> LENGTH: 20
<212> TYPE: PRT
<213> ORGANISM: equine arteritis virus
<220> FEATURE:
<223> OTHER INFORMATION: conserved region of OTU domain-containing
      cysteine protease of EAV (Nsp2) (positions 260-279)

<400> SEQUENCE: 18

Gly Gly Tyr Asn Pro Pro Gly Asp Gly Ala Cys Gly Tyr Arg Cys Leu
1               5                   10                  15

Ala Phe Met Asn
            20

<210> SEQ ID NO 19
<211> LENGTH: 10
```

```
<212> TYPE: PRT
<213> ORGANISM: equine arteritis virus
<220> FEATURE:
<223> OTHER INFORMATION: conserved region of OTU domain-containing
      cysteine protease of EAV (Nsp2) (positions 329-338)

<400> SEQUENCE: 19

Asp Lys Gln His Trp Arg Val Lys Arg Ala
 1               5                  10

<210> SEQ ID NO 20
<211> LENGTH: 20
<212> TYPE: PRT
<213> ORGANISM: lactate dehydrogenase elevating virus
<220> FEATURE:
<223> OTHER INFORMATION: conserved region of OTU domain-containing
      cysteine protease of LDV (Nsp2) (positions 380-399)

<400> SEQUENCE: 20

Tyr Gly Tyr Ser Pro Pro Gly Asp Gly Ala Cys Gly Leu His Cys Ile
 1               5                  10                  15

Ser Ala Ile Ile
            20

<210> SEQ ID NO 21
<211> LENGTH: 10
<212> TYPE: PRT
<213> ORGANISM: lactate dehydrogenase elevating virus
<220> FEATURE:
<223> OTHER INFORMATION: conserved region of OTU domain-containing
      cysteine protease of LDV (Nsp2) (positions 453-462)

<400> SEQUENCE: 21

Val Asn Gln His Trp Thr Val Thr Lys Arg
 1               5                  10

<210> SEQ ID NO 22
<211> LENGTH: 20
<212> TYPE: PRT
<213> ORGANISM: Lelystad virus
<220> FEATURE:
<223> OTHER INFORMATION: conserved region of OTU domain-containing
      cysteine protease of LELV (Nsp2) (positions 419-438)

<400> SEQUENCE: 22

Thr Thr Tyr Ser Pro Pro Thr Asp Gly Ser Cys Gly Trp His Val Leu
 1               5                  10                  15

Ala Ala Ile Met
            20

<210> SEQ ID NO 23
<211> LENGTH: 10
<212> TYPE: PRT
<213> ORGANISM: Lelystad virus
<220> FEATURE:
<223> OTHER INFORMATION: conserved region of OTU domain-containing
      cysteine protease of LELV (Nsp2) (positions 495-504)

<400> SEQUENCE: 23

Asn Gly Val His Trp Glu Val Glu Val Arg
 1               5                  10

<210> SEQ ID NO 24
<211> LENGTH: 20
<212> TYPE: PRT
<213> ORGANISM: blueberry scorch virus
<220> FEATURE:
<223> OTHER INFORMATION: conserved region of OTU domain-containing
```

-continued cysteine protease of BBSV (RdRp) (positions 885-904)

<400> SEQUENCE: 24

Asn Val Gln Cys Val Pro Gly Asp Gly Asn Cys Phe Trp His Ser Leu
1               5                   10                  15

Gly Ser Phe Thr
            20

<210> SEQ ID NO 25
<211> LENGTH: 10
<212> TYPE: PRT
<213> ORGANISM: blueberry scorch virus
<220> FEATURE:
<223> OTHER INFORMATION: conserved region of OTU domain-containing
      cysteine protease of BBSV (RdRp) (positions 981-990)

<400> SEQUENCE: 25

Lys Gly Ser His Phe Glu Pro Leu Glu Pro
1               5                   10

<210> SEQ ID NO 26
<211> LENGTH: 20
<212> TYPE: PRT
<213> ORGANISM: potato virus M
<220> FEATURE:
<223> OTHER INFORMATION: conserved region of OTU domain-containing
      cysteine protease of PVM (RdRp) (positions 884-903)

<400> SEQUENCE: 26

Lys Arg Val Ser Gly Pro Gly Asp Gly Cys Cys Cys Trp His Ser Phe
1               5                   10                  15

Ala Tyr Leu Val
            20

<210> SEQ ID NO 27
<211> LENGTH: 10
<212> TYPE: PRT
<213> ORGANISM: potato virus M
<220> FEATURE:
<223> OTHER INFORMATION: conserved region of OTU domain-containing
      cysteine protease of PVM (RdRp) (positions 981-990)

<400> SEQUENCE: 27

Glu Ser Glu His Tyr Glu Pro Gln Val Leu
1               5                   10

<210> SEQ ID NO 28
<211> LENGTH: 20
<212> TYPE: PRT
<213> ORGANISM: hop latent virus
<220> FEATURE:
<223> OTHER INFORMATION: conserved region of OTU domain-containing
      cysteine protease of HLV (RdRp) (positions 894-910)

<400> SEQUENCE: 28

Ala Ala Leu Asp Val Pro Gly Asp Gly Ser Cys Phe Trp His Ser Val
1               5                   10                  15

Gly Leu Leu Leu
            20

<210> SEQ ID NO 29
<211> LENGTH: 10
<212> TYPE: PRT
<213> ORGANISM: hop latent virus
<220> FEATURE:
<223> OTHER INFORMATION: conserved region of OTU domain-containing
      cysteine protease of HLV (RdRp) (positions 991-1000)

-continued

```
<400> SEQUENCE: 29

Glu Gly Glu His Tyr Met Pro Met Leu Ile
1               5                   10

<210> SEQ ID NO 30
<211> LENGTH: 20
<212> TYPE: PRT
<213> ORGANISM: sugarcane striate mosaic virus
<220> FEATURE:
<223> OTHER INFORMATION: conserved region of OTU domain-containing
      cysteine protease of SSMV (RdRp) (positions 848-867)

<400> SEQUENCE: 30

Thr Cys Ile Asn Val Pro Ala Asp Gly Asp Cys Phe Trp His Ser Val
1               5                   10                  15

Ser Leu Tyr Leu
            20

<210> SEQ ID NO 31
<211> LENGTH: 10
<212> TYPE: PRT
<213> ORGANISM: sugarcane striate mosaic virus
<220> FEATURE:
<223> OTHER INFORMATION: conserved region of OTU domain-containing
      cysteine protease of SSMV (RdRp) (positions 945-954)

<400> SEQUENCE: 31

Asp His Met His Phe Cys Pro Ala Lys Phe
1               5                   10

<210> SEQ ID NO 32
<211> LENGTH: 20
<212> TYPE: PRT
<213> ORGANISM: African oil palm ringspot virus
<220> FEATURE:
<223> OTHER INFORMATION: conserved region of OTU domain-containing
      cysteine protease of AOPRSV (RdRp) (positions 742-761)

<400> SEQUENCE: 32

Ala Ile Phe Pro Val Pro Ala Asp Gly Asp Cys Phe Trp His Ala Ala
1               5                   10                  15

Gly Ser Val Leu
            20

<210> SEQ ID NO 33
<211> LENGTH: 10
<212> TYPE: PRT
<213> ORGANISM: African oil palm ringspot virus
<220> FEATURE:
<223> OTHER INFORMATION: conserved region of OTU domain-containing
      cysteine protease of AOPRSV (RdRp) (positions 852-861)

<400> SEQUENCE: 33

Val Thr Gln His Phe Asp Leu Ala Leu Pro
1               5                   10

<210> SEQ ID NO 34
<211> LENGTH: 20
<212> TYPE: PRT
<213> ORGANISM: cherry green ring mottle virus
<220> FEATURE:
<223> OTHER INFORMATION: conserved region of OTU domain-containing
      cysteine protease of CGRMV (RdRp) (positions 920-939)

<400> SEQUENCE: 34

Ser Val Phe Pro Val Lys Ala Asp Gly Asp Cys Phe Trp His Ala Val
```

```
                1               5                  10                  15

Ser Ser Ile Phe
            20

<210> SEQ ID NO 35
<211> LENGTH: 10
<212> TYPE: PRT
<213> ORGANISM: cherry green ring mottle virus
<220> FEATURE:
<223> OTHER INFORMATION: conserved region of OTU domain-containing
      cysteine protease of CGRMV (RdRp) (positions 1029-1038)

<400> SEQUENCE: 35

Arg Cys His His Phe Asp Leu Ala Val Pro
1               5                   10

<210> SEQ ID NO 36
<211> LENGTH: 20
<212> TYPE: PRT
<213> ORGANISM: grapevine Rupestris stem pitting associated virus
<220> FEATURE:
<223> OTHER INFORMATION: conserved region of OTU domain-containing
      cysteine protease of GRSPV (RdRp) (positions 1069-1088)

<400> SEQUENCE: 36

Asn Thr Phe Ser Val Pro Gly Asp Gly Asn Cys Phe Trp His Ser Val
1               5                   10                  15

Gly Phe Leu Leu
            20

<210> SEQ ID NO 37
<211> LENGTH: 10
<212> TYPE: PRT
<213> ORGANISM: grapevine Rupestris stem pitting associated virus
<220> FEATURE:
<223> OTHER INFORMATION: conserved region of OTU domain-containing
      cysteine protease of GRSPV (RdRp) (positions 1171-1180)

<400> SEQUENCE: 37

Lys Ser Asn His Phe Gln Pro Cys Ala Pro
1               5                   10

<210> SEQ ID NO 38
<211> LENGTH: 20
<212> TYPE: PRT
<213> ORGANISM: Ictalurid herpesvirus 1
<220> FEATURE:
<223> OTHER INFORMATION: conserved region of OTU domain-containing
      cysteine protease of IcHV-1 (ORF65) (positions 1285-1304)

<400> SEQUENCE: 38

Lys Arg Val Tyr Ile Pro Gly Asp Gly Asn Cys Leu Tyr Asn Thr Leu
1               5                   10                  15

Arg Phe Ile Ala
            20

<210> SEQ ID NO 39
<211> LENGTH: 10
<212> TYPE: PRT
<213> ORGANISM: Ictalurid herpesvirus 1
<220> FEATURE:
<223> OTHER INFORMATION: conserved region of OTU domain-containing
      cysteine protease of IcHV-1 (ORF65) (positions 1399-1408)

<400> SEQUENCE: 39

Thr Asn Ser His Tyr Glu Pro Leu Val Thr
1               5                   10
```

```
<210> SEQ ID NO 40
<211> LENGTH: 20
<212> TYPE: PRT
<213> ORGANISM: Tipula iridescent virus
<220> FEATURE:
<223> OTHER INFORMATION: conserved region of OTU domain-containing
      cysteine protease of TIV (L96) (positions 684-703)

<400> SEQUENCE: 40

Ser Lys Pro Gly Thr Trp Gly Asp Phe Ile Cys Leu Arg Val Leu Ser
 1               5                  10                  15

Glu Ile Leu Lys
            20

<210> SEQ ID NO 41
<211> LENGTH: 10
<212> TYPE: PRT
<213> ORGANISM: Tipula iridescent virus
<220> FEATURE:
<223> OTHER INFORMATION: conserved region of OTU domain-containing
      cysteine protease of TIV (L96) (positions 735-744)

<400> SEQUENCE: 41

Asp Asp Tyr His Tyr Thr Ala Leu Thr Pro
 1               5                  10

<210> SEQ ID NO 42
<211> LENGTH: 20
<212> TYPE: PRT
<213> ORGANISM: Chilo iridescent virus
<220> FEATURE:
<223> OTHER INFORMATION: conserved region of OTU domain-containing
      cysteine protease of CIV (232R) (positions 393-412)

<400> SEQUENCE: 42

Arg Met Ile Asn Val Pro Leu Asp Gly Asn Cys Met Phe Ser Val Ile
 1               5                  10                  15

Gly Arg Ala Phe
            20

<210> SEQ ID NO 43
<211> LENGTH: 10
<212> TYPE: PRT
<213> ORGANISM: Chilo iridescent virus
<220> FEATURE:
<223> OTHER INFORMATION: conserved region of OTU domain-containing
      cysteine protease of CIV (232R) (positions 511-520)

<400> SEQUENCE: 43

Asp Asn Phe His Tyr Ile Ala Leu Glu Pro
 1               5                  10

<210> SEQ ID NO 44
<211> LENGTH: 20
<212> TYPE: PRT
<213> ORGANISM: Lymantria dispar multicapsid nucleopolyhedrovirus
<220> FEATURE:
<223> OTHER INFORMATION: conserved region of OTU domain-containing
      cysteine protease of LdMNPV (Vp80) (positions 25-44)

<400> SEQUENCE: 44

Arg Val Ala His Met Lys Gly Asp Gly Ala Cys Ile Phe Arg Ala Val
 1               5                  10                  15

Ala His Val Val
            20
```

```
<210> SEQ ID NO 45
<211> LENGTH: 10
<212> TYPE: PRT
<213> ORGANISM: Lymantria dispar multicapsid nucleopolyhedrovirus
<220> FEATURE:
<223> OTHER INFORMATION: conserved region of OTU domain-containing
      cysteine protease of LdMNPV (Vp80) (positions 138-147)

<400> SEQUENCE: 45

Glu Ser Gly His Val Asp Val Tyr Glu Leu
1               5                   10

<210> SEQ ID NO 46
<211> LENGTH: 20
<212> TYPE: PRT
<213> ORGANISM: Chlamydophila pneumoniae
<220> FEATURE:
<223> OTHER INFORMATION: conserved region of OTU domain-containing
      cysteine protease of C. pneum (positions 256-275)

<400> SEQUENCE: 46

Tyr Leu Val Asn Val Pro Gly Asp Gly Asn Cys Phe Tyr Arg Ala Tyr
1               5                   10                  15

Ala Val Gly Trp
            20

<210> SEQ ID NO 47
<211> LENGTH: 10
<212> TYPE: PRT
<213> ORGANISM: Chlamydophila pneumoniae
<220> FEATURE:
<223> OTHER INFORMATION: conserved region of OTU domain-containing
      cysteine protease of C. pneum (positions 339-348)

<400> SEQUENCE: 47

Ser Gln Lys His Thr Ala Thr Leu Ile Ala
1               5                   10

<210> SEQ ID NO 48
<211> LENGTH: 20
<212> TYPE: PRT
<213> ORGANISM: homo sapiens
<220> FEATURE:
<223> OTHER INFORMATION: conserved region of OTU domain-containing
      cysteine protease of A20 (positions 93-112)

<400> SEQUENCE: 48

Val Ala Leu Lys Thr Asn Gly Asp Gly Asn Cys Leu Met His Ala Thr
1               5                   10                  15

Ser Gln Tyr Met
            20

<210> SEQ ID NO 49
<211> LENGTH: 10
<212> TYPE: PRT
<213> ORGANISM: homo sapiens
<220> FEATURE:
<223> OTHER INFORMATION: conserved region of OTU domain-containing
      cysteine protease of A20 (positions 252-262)

<400> SEQUENCE: 49

Asp Ser His His Phe Val Pro Leu Val Thr
1               5                   10

<210> SEQ ID NO 50
<211> LENGTH: 20
<212> TYPE: PRT
```

```
<213> ORGANISM: homo sapiens
<220> FEATURE:
<223> OTHER INFORMATION: conserved region of OTU domain-containing
      cysteine protease of Cezanne (positions 199-218)

<400> SEQUENCE: 50

Leu Pro Leu Ala Thr Thr Gly Asp Gly Asn Cys Leu Leu His Ala Ala
 1               5                  10                  15

Ser Leu Gly Met
            20

<210> SEQ ID NO 51
<211> LENGTH: 10
<212> TYPE: PRT
<213> ORGANISM: homo sapiens
<220> FEATURE:
<223> OTHER INFORMATION: conserved region of OTU domain-containing
      cysteine protease of Cezanne (positions 369-379)

<400> SEQUENCE: 51

Asp Gln Ala His Phe Ser Ala Leu Val Ser
 1               5                  10

<210> SEQ ID NO 52
<211> LENGTH: 20
<212> TYPE: PRT
<213> ORGANISM: homo sapiens
<220> FEATURE:
<223> OTHER INFORMATION: conserved region of OTU domain-containing
      cysteine protease of Otubain 1 (OTU1) (positions 81-100)

<400> SEQUENCE: 52

Tyr Ile Arg Lys Thr Arg Pro Asp Gly Asn Cys Phe Tyr Arg Ala Phe
 1               5                  10                  15

Gly Phe Ser His
            20

<210> SEQ ID NO 53
<211> LENGTH: 10
<212> TYPE: PRT
<213> ORGANISM: homo sapiens
<220> FEATURE:
<223> OTHER INFORMATION: conserved region of OTU domain-containing
      cysteine protease of Otubain 1 (OTU1) (positions 261-271)

<400> SEQUENCE: 53

Arg Pro Gly His Tyr Asp Ile Leu Tyr Lys
 1               5                  10

<210> SEQ ID NO 54
<211> LENGTH: 20
<212> TYPE: PRT
<213> ORGANISM: homo sapiens
<220> FEATURE:
<223> OTHER INFORMATION: conserved region of OTU domain-containing
      cysteine protease of Otubain 2 (OTU2)(positions 41-60)

<400> SEQUENCE: 54

Ala Ile Arg Lys Thr Lys Gly Asp Gly Asn Cys Phe Tyr Arg Ala Leu
 1               5                  10                  15

Gly Tyr Ser Tyr
            20

<210> SEQ ID NO 55
<211> LENGTH: 10
<212> TYPE: PRT
<213> ORGANISM: homo sapiens
```

```
<220> FEATURE:
<223> OTHER INFORMATION: conserved region of OTU domain-containing
      cysteine protease of Otubain 2 (OTU2) (positions 220-230)

<400> SEQUENCE: 55

Lys Thr Ser His Tyr Asn Ile Leu Tyr Ala
 1               5                  10

<210> SEQ ID NO 56
<211> LENGTH: 234
<212> TYPE: PRT
<213> ORGANISM: homo sapiens
<220> FEATURE:
<223> OTHER INFORMATION: human otubain 2 OTU domain

<400> SEQUENCE: 56

Met Ser Glu Thr Ser Phe Asn Leu Ile Ser Lys Cys Asp Ile Leu
 1               5                  10                  15

Ser Ile Leu Arg Asp His Pro Glu Asn Arg Ile Tyr Arg Arg Lys Ile
                20                  25                  30

Glu Glu Leu Ser Lys Arg Phe Thr Ala Ile Arg Lys Thr Lys Gly Asp
            35                  40                  45

Gly Asn Cys Phe Tyr Arg Ala Leu Gly Tyr Ser Tyr Leu Glu Ser Leu
 50                  55                  60

Leu Gly Lys Ser Arg Glu Ile Phe Lys Phe Lys Glu Arg Val Leu Gln
 65                  70                  75                  80

Thr Pro Asn Asp Leu Leu Ala Ala Gly Phe Glu Glu His Lys Phe Arg
                85                  90                  95

Asn Phe Phe Asn Ala Phe Tyr Ser Val Val Glu Leu Val Glu Lys Asp
                100                 105                 110

Gly Ser Val Ser Ser Leu Leu Lys Val Phe Asn Asp Gln Ser Ala Ser
            115                 120                 125

Asp His Ile Val Gln Phe Leu Arg Leu Leu Thr Ser Ala Phe Ile Arg
130                 135                 140

Asn Arg Ala Asp Phe Phe Arg His Phe Ile Asp Glu Glu Met Asp Ile
145                 150                 155                 160

Lys Asp Phe Cys Thr His Glu Val Glu Pro Met Ala Thr Glu Cys Asp
                165                 170                 175

His Ile Gln Ile Thr Ala Leu Ser Gln Ala Leu Ser Ile Ala Leu Gln
                180                 185                 190

Val Glu Tyr Val Asp Glu Met Asp Thr Ala Leu Asn His His Val Phe
            195                 200                 205

Pro Glu Ala Ala Thr Pro Ser Val Tyr Leu Leu Tyr Lys Thr Ser His
210                 215                 220

Tyr Asn Ile Leu Tyr Ala Ala Asp Lys His
225                 230

<210> SEQ ID NO 57
<211> LENGTH: 185
<212> TYPE: PRT
<213> ORGANISM: Ictalurid herpesvirus 1
<220> FEATURE:
<223> OTHER INFORMATION: Ictalurid ORF 65 (position 1240 to end)

<400> SEQUENCE: 57

Arg Val Leu Ala Asn Val Pro Val Ser Ser Ala Val Ile Ile Asn Glu
 1               5                  10                  15

Ser Leu Glu Glu Asp Gln Phe Thr Arg Leu Glu Asn Thr Leu Tyr Ser
                20                  25                  30
```

```
Met Gly Leu Lys Arg Val Tyr Ile Pro Gly Asp Gly Asn Cys Leu Tyr
             35                  40                  45

Asn Thr Leu Arg Phe Ile Ala Gly Ala Asp Gly Glu Ser Ala Ile Asp
 50                  55                  60

Phe Lys Lys Glu Leu Leu Asp Asp Ile Arg Lys Tyr Val Arg Asn Gln
 65                  70                  75                  80

Asp Pro Ala Glu Arg Asp Leu Ile Leu Thr Glu Ile Asp Asn Leu Ala
                 85                  90                  95

Gly Pro Asn Val Tyr Gly Ser Gly Asp Leu Ile Ser Phe Phe Gln Leu
                100                 105                 110

Leu Arg Gly Val Gly Val Thr Val Ser Trp Asp Lys Ile Gly Gly
            115                 120                 125

Arg Leu Val Lys Leu Val Ala Thr Asn Gln Glu Gly Ile Pro Pro Glu
130                 135                 140

Tyr Ile Ile Leu Phe Thr Asn Ser His Tyr Glu Pro Leu Val Thr Glu
145                 150                 155                 160

Asp Thr Met Ile Pro Asp Ser Tyr Leu Lys Asp Phe Ile Glu Trp Lys
                165                 170                 175

Arg Ser Leu Phe Leu Ser Ala Ile Ile
            180                 185

<210> SEQ ID NO 58
<211> LENGTH: 201
<212> TYPE: PRT
<213> ORGANISM: Crimean Congo hemorrhagic fever virus
<220> FEATURE:
<223> OTHER INFORMATION: CCHFV 1-200 L#2

<400> SEQUENCE: 58

Met Asp Phe Leu Arg Ser Leu Asp Trp Thr Gln Val Ile Ala Gly Gln
  1               5                  10                  15

Tyr Val Ser Asn Pro Arg Phe Asn Ile Ser Asp Tyr Phe Glu Ile Val
                 20                  25                  30

Arg Gln Pro Gly Asp Gly Asn Cys Phe Tyr His Ser Ile Ala Glu Leu
             35                  40                  45

Thr Met Pro Asn Lys Thr Asp His Ser Tyr His Tyr Ile Lys Arg Leu
 50                  55                  60

Thr Glu Ser Ala Ala Arg Lys Tyr Tyr Gln Glu Glu Pro Glu Ala Arg
 65                  70                  75                  80

Leu Val Gly Leu Ser Leu Glu Asp Tyr Leu Lys Arg Met Leu Ser Asp
                 85                  90                  95

Asn Glu Trp Gly Ser Thr Leu Glu Ala Ser Met Leu Ala Lys Glu Met
                100                 105                 110

Gly Ile Thr Ile Ile Ile Trp Thr Val Ala Ala Ser Asp Glu Val Glu
            115                 120                 125

Ala Gly Ile Lys Phe Gly Asp Gly Asp Val Phe Thr Ala Val Asn Leu
130                 135                 140

Leu His Ser Gly Gln Thr His Phe Asp Ala Leu Arg Ile Leu Pro Gln
145                 150                 155                 160

Phe Glu Thr Asp Thr Arg Glu Ala Leu Ser Leu Met Asp Arg Val Ile
                165                 170                 175

Ala Val Asp Gln Leu Thr Ser Ser Ser Asp Glu Leu Gln Asp Tyr
            180                 185                 190

Glu Asp Leu Ala Leu Ala Leu Thr Ser
            195                 200
```

<210> SEQ ID NO 59
<211> LENGTH: 200
<212> TYPE: PRT
<213> ORGANISM: Dugbe virus
<220> FEATURE:
<223> OTHER INFORMATION: Dugbe L protein 1-200#2

<400> SEQUENCE: 59

```
Met Asp Phe Leu Asp Ser Leu Ile Trp Glu Arg Val Val Asp Glu Gln
 1               5                  10                  15

Tyr Ile Thr Asn Pro Thr Phe Cys Val Ser Asp Tyr Phe Glu Val Ile
            20                  25                  30

Arg Gln Pro Gly Asp Gly Asn Cys Phe Tyr His Ser Ile Ala Glu Leu
        35                  40                  45

Phe Phe Asp Val Lys Thr Pro Ser Ser Phe Arg Lys Val Lys Glu His
    50                  55                  60

Leu Gln Leu Ala Ala Glu Val Tyr Tyr Asp Thr Glu Pro Glu Ala Val
65                  70                  75                  80

Gly Thr Gly Ile Ser Lys Asp Glu Tyr Ile Lys Val Ala Met Lys Asp
                85                  90                  95

Asn Glu Trp Gly Gly Ser Leu Glu Ala Ser Met Leu Ser Lys His Leu
            100                 105                 110

Gln Thr Thr Ile Ile Leu Trp Val Val Asn Ser Thr Glu Gln Val Thr
        115                 120                 125

Ala Ala Ile Lys Phe Gly Pro Gly Arg Val Ser Thr Ala Leu Asn Leu
    130                 135                 140

Met His Val Gly Arg Thr His Phe Asp Ala Leu Arg Ile Ile Glu Gln
145                 150                 155                 160

Leu Glu Asn Asn Gln Pro Gln Asp Arg Asn Arg Leu Asp Ile Ala Asp
                165                 170                 175

Arg Ile Ala Ala Ala Glu Val Tyr Val Arg Gln Ser Ile Glu Asp Asn
            180                 185                 190

Leu Gln Glu Asp Glu Phe Phe Asp
        195                 200
```

<210> SEQ ID NO 60
<211> LENGTH: 231
<212> TYPE: PRT
<213> ORGANISM: Mouse
<220> FEATURE:
<223> OTHER INFORMATION: Mouse Otud1 OTU domain

<400> SEQUENCE: 60

```
Gly Phe Arg His Pro Arg Gly Ala Ala Ala Ser Arg Pro Arg Thr Ala
 1               5                  10                  15

Arg Arg Ser Cys Arg Thr Ser Arg Ala Asp Pro Arg Asp Glu Lys Leu
            20                  25                  30

Ala Leu Tyr Leu Ala Glu Val Glu Arg Gln Asp Lys Tyr Phe Thr Leu
        35                  40                  45

Arg Gln Arg Asn Lys Tyr Arg Phe His Ile Ile Pro Asp Gly Asn Cys
    50                  55                  60

Leu Tyr Arg Ala Val Ser Lys Thr Val Tyr Gly Asp Gln Ser Leu His
65                  70                  75                  80

Arg Glu Leu Arg Glu Gln Thr Val His Tyr Ile Ala Asp His Leu Asp
                85                  90                  95

His Phe Ser Pro Leu Ile Glu Gly Asp Val Phe Thr Gly Glu Phe Ile
            100                 105                 110

Ile Ala Ala Ala Gln Asp Gly Ala Trp Ala Gly Tyr Pro Glu Leu Leu
```

```
                115             120             125
Ala Met Gly Gln Met Leu Asn Val Asn Ile His Leu Thr Thr Gly Gly
            130             135             140

Arg Leu Glu Ser Pro Thr Val Ser Thr Met Ile His Tyr Leu Gly Pro
145             150             155             160

Glu Asp Ser Leu Arg Pro Ser Phe Thr Ile Trp Leu Ser Trp Leu Ser
                165             170             175

Asn Gly His Tyr Asp Ala Val Phe Asp His Ser Tyr Pro Asn Pro Glu
            180             185             190

Tyr Asp Asn Trp Cys Lys Gln Thr Gln Ile Gln Lys Lys Arg Asp Glu
                195             200             205

Glu Leu Ala Lys Ser Met Ala Ile Ser Leu Ser Lys Met Tyr Ile Glu
            210             215             220

Gln Asn Ala Cys Phe Thr Ser
225             230
```

<210> SEQ ID NO 61
<211> LENGTH: 180
<212> TYPE: PRT
<213> ORGANISM: homo sapiens
<220> FEATURE:
<223> OTHER INFORMATION: VCIP135 210-390

<400> SEQUENCE: 61

```
Leu His Asp Thr Leu Glu Asp Ile Lys Arg Ala Asn Lys Ser Gln Glu
1               5               10              15

Cys Leu Phe Thr Ile Pro Val His Val Asp Gly Asp Gly His Cys Leu
            20              25              30

Val His Ala Val Ser Arg Ala Leu Val Gly Arg Glu Leu Phe Trp His
        35              40              45

Ala Leu Arg Glu Asn Leu Lys Gln His Phe Gln Gln His Leu Ala Arg
    50              55              60

Tyr Gln Ala Leu Phe His Asp Phe Ile Asp Ala Ala Glu Trp Glu Phe
65              70              75              80

Thr Asp Ile Ile Asn Glu Cys Asp Pro Leu Phe Val Pro Pro Glu Gly
                85              90              95

Val Pro Leu Gly Leu Arg Asn Ile His Ile Phe Gly Leu Ala Asn Val
            100             105             110

Leu His Arg Pro Ile Ile Leu Leu Asp Ser Leu Ser Gly Met Arg Ser
        115             120             125

Ser Gly Asp Tyr Ser Ala Thr Phe Leu Pro Gly Leu Phe Thr Ile Pro
    130             135             140

Ala Glu Lys Cys Thr Gly Lys Asp Gly His Leu Asn Lys Pro Ile Cys
145             150             155             160

Ile Ala Trp Ser Ser Ser Gly Arg Asn His Tyr Ile Pro Leu Val Gly
                165             170             175

Ile Lys Gly Ala
            180
```

<210> SEQ ID NO 62
<211> LENGTH: 210
<212> TYPE: PRT
<213> ORGANISM: homo sapiens
<220> FEATURE:
<223> OTHER INFORMATION: A20 61-270

<400> SEQUENCE: 62

```
Gln Phe Arg Glu Ile Ile His Lys Ala Leu Ile Asp Arg Asn Ile Gln
```

```
1               5                   10                  15

Ala Thr Leu Glu Ser Gln Lys Lys Leu Asn Trp Cys Arg Glu Val Arg
            20                  25                  30

Lys Leu Val Ala Leu Lys Thr Asn Gly Asp Gly Asn Cys Leu Phe Thr
        35                  40                  45

Met His Ala Thr Ser Gln Tyr Met Trp Gly Val Gln Asp Thr Asp Leu
    50                  55                  60

Val Leu Arg Lys Ala Leu Phe Ser Thr Leu Lys Glu Thr Asp Thr Arg
65                  70                  75                  80

Asn Phe Lys Phe Arg Trp Gln Leu Glu Ser Leu Lys Ser Gln Glu Phe
                85                  90                  95

Val Glu Thr Gly Leu Cys Tyr Asp Thr Arg Asn Phe Thr Trp Asn Asp
            100                 105                 110

Glu Trp Asp Asn Leu Ile Lys Met Ala Ser Thr Asp Thr Pro Met Ala
        115                 120                 125

Arg Ser Gly Leu Gln Tyr Asn Ser Leu Glu Glu Ile His Ile Phe Val
    130                 135                 140

Leu Cys Asn Ile Leu Arg Arg Pro Ile Ile Val Ile Ser Asp Lys Met
145                 150                 155                 160

Leu Arg Ser Leu Glu Ser Gly Ser Phe Thr Asn Phe Ala Pro Leu Lys
                165                 170                 175

Val Gly Gly Ile Tyr Leu Pro Leu His Trp Pro Ala Gln Glu Cys Tyr
            180                 185                 190

Arg Tyr Pro Ile Val Leu Gly Tyr Asp Ser His His Phe Val Pro Leu
        195                 200                 205

Val Thr
    210

<210> SEQ ID NO 63
<211> LENGTH: 180
<212> TYPE: PRT
<213> ORGANISM: Tipular iridescent virus
<220> FEATURE:
<223> OTHER INFORMATION: Tipular iridescent 610-790

<400> SEQUENCE: 63

Gly Asn Ala Asp Arg Asp Leu Glu Ile Leu Ala Arg Arg Arg Gly Tyr
1               5                   10                  15

Lys Val Ile Pro Val Lys Gly Asp Gly Asn Cys Leu Phe Arg Ala Val
            20                  25                  30

Gly Lys Ser Leu Arg Leu Asn Gln Asn Ile Lys Tyr Ser Phe Thr His
        35                  40                  45

Glu Asp Leu Arg Ala Gln Val Val Thr Tyr Leu Thr Ser His Lys Glu
    50                  55                  60

Phe Leu Glu Pro Tyr Leu Glu Tyr Val Thr Glu Ser Gly Asp Thr Thr
65                  70                  75                  80

Pro Gln Glu Tyr Ala Lys Asn Val Glu Arg Tyr Ile Lys Asn Ile Ser
                85                  90                  95

Lys Pro Gly Thr Trp Gly Asp Phe Ile Cys Phe Thr Leu Arg Val Leu
            100                 105                 110

Ser Glu Ile Leu Lys Val Lys Phe Asn Leu Leu Ile Leu Asn Thr Arg
        115                 120                 125

Asn Phe Gln Val Ile Ser Asn Asn Asp Thr Phe Lys Pro Leu Ile Pro
    130                 135                 140

Leu Gly Phe Ile Asp Asp Tyr His Tyr Thr Ala Leu Thr Pro Leu Tyr
145                 150                 155                 160
```

```
Ala Glu Pro Ile Ala Val Leu Phe Thr Glu Asn Glu Thr Pro Thr Pro
                165                 170                 175

Ser Ile Ala Pro
            180

<210> SEQ ID NO 64
<211> LENGTH: 134
<212> TYPE: PRT
<213> ORGANISM: Emiliania huxleyi virus
<220> FEATURE:
<223> OTHER INFORMATION: Emilian protease 100 to end

<400> SEQUENCE: 64

Asn Ala Leu Ala Ser His Gly Leu Glu Lys Lys Ser Pro Gly Asp
  1               5                  10                  15

Gly Asn Cys Leu Tyr His Ser Leu Thr Asp Gln Ile Asn Ala Thr Gly
                 20                  25                  30

Leu Tyr Ser Glu Cys Asn His Ile Ser Met Arg Arg Ala Ile Val Ala
             35                  40                  45

His Ile Tyr Arg Asn Tyr Asp Phe Tyr Gly Asn Phe Leu Glu Glu Lys
         50                  55                  60

Leu Val Thr Lys Leu Arg Leu Gly Lys Trp Gly Ser His Val Asp Val
 65                  70                  75                  80

Ser Ala Ala Ser Asp Leu Phe Asn Ile Lys Ile Thr Val Ile Lys Tyr
                 85                  90                  95

Asn Gly Asp Asp Val Ile Leu Pro Arg His Asn Asn Pro Asp Ser Val
            100                 105                 110

Val Gly Ser Ile Phe Leu Cys Phe Gln Ser Glu Leu His Tyr Asp Ser
        115                 120                 125

Thr Ala Arg Val Glu Tyr
    130

<210> SEQ ID NO 65
<211> LENGTH: 230
<212> TYPE: PRT
<213> ORGANISM: Homo sapiens
<220> FEATURE:
<223> OTHER INFORMATION: Cezanne 2 160 to 390

<400> SEQUENCE: 65

Ser Val Tyr Ser Glu Asp Phe Phe Thr Arg Ser Phe Ile Glu Arg Asp
  1               5                  10                  15

Leu Ile Glu Gln Ala Thr Met Val Ala Leu Glu Gln Ala Gly Arg Leu
                 20                  25                  30

Asn Trp Trp Ser Thr Val Cys Thr Ser Cys Lys Arg Leu Leu Pro Leu
             35                  40                  45

Ala Thr Thr Gly Asp Gly Asn Cys Leu Leu His Ala Ala Ser Leu Gly
         50                  55                  60

Met Trp Gly Phe Phe Thr His Asp Arg Asp Leu Val Leu Arg Lys Ala
 65                  70                  75                  80

Leu Tyr Thr Met Met Arg Thr Gly Ala Glu Arg Glu Ala Leu Lys Arg
                 85                  90                  95

Arg Trp Arg Trp Gln Gln Thr Gln Gln Asn Lys Glu Glu Trp Glu
            100                 105                 110

Arg Glu Trp Thr Glu Leu Leu Lys Leu Ala Ser Ser Glu Pro Arg Thr
        115                 120                 125

His Phe Thr Phe Ser Lys Asn Gly Gly Thr Gly Gly Val Asp Asn
    130                 135                 140
```

```
Ser Glu Asp Pro Val Tyr Glu Ser Leu Glu Glu Phe His Val Phe Val
145                 150                 155                 160

Leu Ala His Ile Leu Arg Arg Pro Ile Val Val Ala Asp Thr Met
            165                 170                 175

Leu Arg Asp Ser Gly Gly Glu Ala Phe Ala Pro Ile Pro Phe Phe Thr
            180                 185                 190

Gly Gly Ile Tyr Leu Pro Leu Glu Val Pro Pro Asn Arg Cys His Cys
            195                 200                 205

Ser Pro Leu Val Leu Ala Tyr Asp Gln Ala His Phe Ser Ala Leu Val
        210                 215                 220

Ser Met Glu Gln Arg Asp
225                 230

<210> SEQ ID NO 66
<211> LENGTH: 184
<212> TYPE: PRT
<213> ORGANISM: herpesvirus
<220> FEATURE:
<223> OTHER INFORMATION: unknown from herpesvirus lymphotropic 140 to
      end

<400> SEQUENCE: 66

Glu Gln Trp Leu Phe Cys Tyr Pro Thr Asp Pro Leu Pro Trp Leu Trp
1               5                   10                  15

Leu Leu Phe Tyr Gly Pro Lys Ser Phe Cys Thr Asp Gly Asn Cys Leu
            20                  25                  30

Tyr Ala Lys Phe Phe His Asn Ser Gly Leu Ile Leu Phe Pro Pro Ile
        35                  40                  45

Ile Tyr Gln Pro Ser Thr Asp Ile Ser Ser Phe Met Asn Met Val Cys
    50                  55                  60

Lys Tyr Val Cys Val Leu Tyr Lys Asn Gln Asp Leu Ser Lys Leu Ile
65                  70                  75                  80

Gly Asp Gln Val Ile Pro Phe Asp Arg Ser Arg Leu Glu Asn Val Gln
                85                  90                  95

Ser Leu Ile Ser Asp Met Asn Tyr Asn Asp Ile His Val Thr Lys Leu
            100                 105                 110

Cys Leu Leu Cys Ala Leu Tyr Lys Gln Asn Gln Thr Thr Tyr His Asn
        115                 120                 125

Val Glu His Asn Gln Gly Cys Ile Ile Leu Glu Cys Ala Glu Lys Tyr
    130                 135                 140

Ile Asn Asn Ser Val Gly Arg Thr Lys Cys Leu His Thr Gly Asp Ile
145                 150                 155                 160

Val Leu Trp Pro Ser Tyr Asn Ile Ala Ala Ile Val Gln His Phe Lys
                165                 170                 175

Ser His Gly Lys Gly Thr Leu Glu
            180

<210> SEQ ID NO 67
<211> LENGTH: 192
<212> TYPE: PRT
<213> ORGANISM: murine gamma herpesvirus type 68
<220> FEATURE:
<223> OTHER INFORMATION: gHV68 gene 34 141 to end

<400> SEQUENCE: 67

Met Lys Cys Pro Glu Asn Trp Ser Gly Leu His Pro Val Asp Pro Leu
1               5                   10                  15

Ala Cys Val Trp Leu Leu Tyr Phe Gly Pro Lys Ser Arg Cys Ser Glu
```

```
                    20                  25                  30

Ile Ala Cys Val Ser Glu Leu Phe Ile Gly Lys Lys Gly Pro Ile Leu
            35                  40                  45

Leu Pro Pro His Met Tyr Arg Gly Asp Thr Ser Val Asn Ser Phe Ala
    50                  55                  60

His His Leu Cys Gln Tyr Val Lys His Leu Tyr Ala Asp Tyr Glu Pro
65                  70                  75                  80

Glu Ile Leu Ser Cys Pro Leu Asp Ile Thr Arg Val Lys Gly Cys Leu
                85                  90                  95

Ser Asp Leu Arg Gln Val Ala Glu Ser Cys Val Phe Leu Ser Gln Arg
            100                 105                 110

Cys Leu Leu Cys His Leu Tyr Lys Gln Asn Ala Ala Val Ser Lys Asn
            115                 120                 125

Ile Leu Thr Ala Ser Asp Cys Ile Ile Leu Gly Gly Ser Gly Lys Ser
        130                 135                 140

Leu Leu Gly Thr Tyr Met Lys Ser Tyr Lys Asp Pro Ala Thr His Asp
145                 150                 155                 160

Ser Ile Leu Leu Pro Thr Tyr Asn Leu Glu Ala Ile Val Asn Tyr Ile
                165                 170                 175

Leu Glu His Tyr Gly His Glu Thr Ala Gly Gln Glu Ile Asn Trp Glu
            180                 185                 190

<210> SEQ ID NO 68
<211> LENGTH: 187
<212> TYPE: PRT
<213> ORGANISM: Epstein-Barr Virus
<220> FEATURE:
<223> OTHER INFORMATION: EBV BGLF3 141 to end

<400> SEQUENCE: 68

Leu Cys Asp Pro Gly Thr Trp Lys Gly Leu Leu Pro Asp Asp Pro Leu
1               5                   10                  15

Pro Leu Leu Trp Leu Leu Phe Asn Gly Pro Ala Ser Phe Cys Arg Ala
            20                  25                  30

Asp Cys Cys Leu Tyr Lys Gln His Cys Gly Tyr Pro Gly Pro Val Leu
            35                  40                  45

Leu Pro Gly His Met Tyr Ala Pro Lys Arg Asp Leu Leu Ser Phe Val
    50                  55                  60

Asn His Ala Leu Lys Tyr Thr Lys Phe Leu Tyr Gly Asp Phe Ser Gly
65                  70                  75                  80

Thr Trp Ala Ala Ala Cys Arg Pro Pro Phe Ala Thr Ser Arg Ile Gln
                85                  90                  95

Arg Val Val Ser Gln Met Lys Ile Ile Asp Ala Ser Asp Thr Tyr Ile
            100                 105                 110

Ser His Thr Cys Leu Leu Cys His Ile Tyr Gln Gln Asn Ser Ile Ile
            115                 120                 125

Ala Gly Gln Gly Thr His Val Gly Gly Ile Leu Leu Leu Ser Gly Lys
        130                 135                 140

Gly Thr Gln Tyr Ile Thr Gly Asn Val Gln Thr Gln Arg Cys Pro Thr
145                 150                 155                 160

Thr Gly Asp Tyr Leu Ile Ile Pro Ser Tyr Asp Ile Pro Ala Ile Ile
                165                 170                 175

Thr Met Ile Lys Glu Asn Gly Leu Asn Gln Leu
            180                 185

<210> SEQ ID NO 69
```

```
<211> LENGTH: 231
<212> TYPE: PRT
<213> ORGANISM: homo sapiens
<220> FEATURE:
<223> OTHER INFORMATION: human otubain 1 40 to end

<400> SEQUENCE: 69

Ile Ala Val Gln Asn Pro Leu Val Ser Glu Arg Leu Glu Leu Ser Val
 1               5                  10                  15

Leu Tyr Lys Glu Tyr Ala Glu Asp Asp Asn Ile Tyr Gln Gln Lys Ile
             20                  25                  30

Lys Asp Leu His Lys Lys Tyr Ser Tyr Ile Arg Lys Thr Arg Pro Asp
         35                  40                  45

Gly Asn Cys Phe Tyr Arg Ala Phe Gly Phe Ser His Leu Glu Ala Leu
     50                  55                  60

Leu Asp Asp Ser Lys Glu Leu Gln Arg Phe Lys Ala Val Ser Ala Lys
 65                  70                  75                  80

Ser Lys Glu Asp Leu Val Ser Gln Gly Phe Thr Glu Phe Thr Ile Glu
                 85                  90                  95

Asp Phe His Asn Thr Phe Met Asp Leu Ile Glu Gln Val Glu Lys Gln
            100                 105                 110

Thr Ser Val Ala Asp Leu Leu Ala Ser Phe Asn Asp Gln Ser Thr Ser
        115                 120                 125

Asp Tyr Leu Val Val Tyr Leu Arg Leu Leu Thr Ser Gly Tyr Leu Gln
130                 135                 140

Arg Glu Ser Lys Phe Phe Glu His Phe Ile Glu Gly Gly Arg Thr Val
145                 150                 155                 160

Lys Glu Phe Cys Gln Gln Glu Val Glu Pro Met Cys Lys Glu Ser Asp
                165                 170                 175

His Ile His Ile Ile Ala Leu Ala Gln Ala Leu Ser Val Ser Ile Gln
            180                 185                 190

Val Glu Tyr Met Asp Arg Gly Gly Gly Thr Thr Asn Pro His Ile
        195                 200                 205

Phe Pro Glu Gly Ser Glu Pro Lys Val Tyr Leu Leu Tyr Arg Pro Gly
210                 215                 220

His Tyr Asp Ile Leu Tyr Lys
225                 230

<210> SEQ ID NO 70
<211> LENGTH: 188
<212> TYPE: PRT
<213> ORGANISM: Bovine Herpesvirus 4
<220> FEATURE:
<223> OTHER INFORMATION: BHV4 140 to end

<400> SEQUENCE: 70

Asn Pro Cys His Trp Glu Gly Tyr Ile Pro Asp Asp Pro Leu Pro Leu
 1               5                  10                  15

Ile Trp Leu Leu Phe Tyr Gly Lys Asn Ser Phe Cys Glu Ser Pro Asp
             20                  25                  30

Cys Leu Tyr Met Gln Arg Phe Lys His Pro Gly Pro Ile Leu Phe Pro
         35                  40                  45

Pro His Ile Tyr Asn Pro Asp Gly Asp Ile Ser Ser Phe Val Asn His
     50                  55                  60

Val Cys His Tyr Val Asn Phe Leu Tyr Lys Glu Arg Thr Phe Ser Leu
 65                  70                  75                  80

Thr His Thr Thr Phe Leu Pro Phe Glu Glu Gln Arg Leu Lys Arg Ala
                 85                  90                  95
```

```
Leu Glu Leu Leu Glu Glu Val Glu Asn Thr Ala Thr Tyr Ile Ser Lys
            100                 105                 110

Thr Cys Leu Leu Cys His Leu Tyr Lys Gln Asn Glu Ile Leu Ala Ala
            115                 120                 125

Glu Gly Gln Ser Thr His Gly Cys Ile Ile Leu Gly Gly Val Gly Lys
            130                 135                 140

Gln Tyr Ile Thr Pro Gln Leu His Thr Thr Arg Ser Thr His Ser Gly
145                 150                 155                 160

Asp Thr Leu Leu Leu Pro Ala Tyr Asn Leu Val Gly Leu Met Glu Cys
                165                 170                 175

Val Ala Leu Asp Gly Val Ser Lys Gln Glu Asp Ser
            180                 185
```

<210> SEQ ID NO 71
<211> LENGTH: 176
<212> TYPE: PRT
<213> ORGANISM: Squirrel monkey herpesvirus
<220> FEATURE:
<223> OTHER INFORMATION: Saimiri34 140 to end

<400> SEQUENCE: 71

```
Ile Tyr Pro Ile Asp Pro Leu Pro Tyr Ile Trp Leu Leu Phe Tyr Gly
1               5                   10                  15

Lys Lys Ser Phe Cys Ala Ser Pro Asp Cys Ile Tyr Leu Lys Lys Tyr
            20                  25                  30

Asn Val Pro Gly Pro Met Leu Leu Pro Pro His Met Tyr Arg Pro Asp
            35                  40                  45

Lys Asn Ile Ser Ser Phe Ile Ser His Val Cys Gln Tyr Val Lys Ile
        50                  55                  60

Leu Tyr Glu Glu Val Ser Glu Pro Ile Ser Leu Glu Ile Val Pro Phe
65                  70                  75                  80

Asp Asn Cys Arg Ile Lys Glu Ala Val Glu Glu Leu Lys Gln Ile Asp
                85                  90                  95

Leu Pro Val Ala Tyr Leu Ser Asn Leu Cys Leu Leu Cys Thr Leu His
            100                 105                 110

Arg Gln Asn Met Ser Ala Ser Arg Gly Ser Gly Asp Met Cys Gly Tyr
            115                 120                 125

Ile Val Leu Gly Gly Glu Gly Glu Lys Tyr Ile Thr Thr Asn Ile Ile
            130                 135                 140

Ser Lys Arg Cys Thr Val Ser Gly Asp Cys Leu Ile Val Pro Ser Tyr
145                 150                 155                 160

Asn Ile Ser Leu Leu Met Gln Asn Met Glu Ile Asn Tyr Glu Gln Gln
                165                 170                 175
```

<210> SEQ ID NO 72
<211> LENGTH: 241
<212> TYPE: PRT
<213> ORGANISM: Artificial Sequence
<220> FEATURE:
<223> OTHER INFORMATION: consensus sequence of representative proteins
      with an OTU domain of viral, human, murine and other origin
<220> FEATURE:
<221> NAME/KEY: VARIANT
<222> LOCATION: (1)..(19), (22)..(24), (27)..(29), 33, 35, 37,
      (72)..(77), 119, 122, 133, (144)..(152), 183, 190, 196, 203,
      (205)..(206), 211, (214)..(215), (235)..(236), (238)..(240)
<223> OTHER INFORMATION: Xaa = Any Amino Acid or deletions

<400> SEQUENCE: 72

```
Xaa Xaa Xaa Xaa Xaa Xaa Xaa Xaa Xaa Xaa Xaa Xaa Xaa Xaa Xaa Xaa
```

```
                1               5                   10                  15
Xaa Xaa Xaa Leu Ile Xaa Xaa Leu Asp Xaa Xaa Ile Leu Ile
                20                  25                  30

Xaa Leu Xaa Trp Xaa Gly Leu Ile Pro Ile Asp Pro Leu Pro Phe Leu
            35                  40                  45

Trp Leu Leu Phe Tyr Gly Pro Lys Ser Thr Cys Gly Asp Gly Asn Cys
 50                  55                  60

Leu Tyr His Ala Leu Ala Lys Xaa Xaa Xaa Xaa Xaa Ser Leu Gly
 65                  70                  75                  80

Pro Ile Leu Leu Pro Pro His Ser Tyr Arg Pro Ser Lys Arg Ile Ser
            85                  90                  95

Ser Phe Ala Asn His Val Cys Tyr Tyr Val Ser Phe Leu Tyr Phe Glu
            100                 105                 110

Val Ala Ile Ser Ile Glu Xaa Ala Leu Xaa Ile Val Pro Phe Asp Asn
            115                 120                 125

Val Arg Ile Ser Xaa Leu Val Ser Leu Leu Lys Ile Ile Glu Asn Xaa
            130                 135                 140

Xaa Xaa Xaa Xaa Xaa Xaa Xaa Xaa Ser Ile Thr Tyr Ile Ser Trp Leu
145                 150                 155                 160

Cys Leu Leu Cys His Leu Leu Thr Gln Asn Ile Ile Leu Ala Arg Asn
            165                 170                 175

Ile Gly Asp Val Ser Gly Xaa Ile Ile Leu Gly Gly Ser Xaa Gly Lys
            180                 185                 190

Lys Tyr Phe Xaa Ala Asn Ile Ile Thr Gly Xaa Ile Xaa Xaa Pro Lys
            195                 200                 205

Cys Thr Xaa Ser Gly Xaa Xaa His Asp Ser Leu Leu Val Pro Ala Tyr
            210                 215                 220

Asn Ile Ala Ala Ile Val Gln Tyr Val Glu Xaa Xaa Gly Xaa Xaa Xaa
225                 230                 235                 240

Leu
```

<210> SEQ ID NO 73
<211> LENGTH: 130
<212> TYPE: PRT
<213> ORGANISM: Crimean Congo hemorrhagic fever virus
<220> FEATURE:
<223> OTHER INFORMATION: OTU domain of CCHFV-L (29-158)
<220> FEATURE:
<221> NAME/KEY: VARIANT
<222> LOCATION: (19)..(31), (44)..(60), (73)..(81), (92)..(111),
      (119)..(120)
<223> OTHER INFORMATION: Xaa = Any Amino Acid

<400> SEQUENCE: 73

```
Phe Glu Ile Val Arg Gln Pro Gly Asp Gly Asn Cys Phe Tyr His Ser
 1               5                   10                  15

Ile Ala Xaa Xaa Xaa Xaa Xaa Xaa Xaa Xaa Xaa Xaa Xaa Xaa Tyr
            20                  25                  30

Ile Lys Arg Leu Thr Glu Ser Ala Ala Arg Lys Xaa Xaa Xaa Xaa
            35                  40                  45

Xaa Xaa Xaa Xaa Xaa Xaa Xaa Xaa Xaa Xaa Tyr Leu Lys Arg
 50                  55                  60

Met Leu Ser Asp Asn Glu Trp Gly Xaa Xaa Xaa Xaa Xaa Xaa
 65                  70                  75                  80

Xaa Lys Glu Met Gly Ile Thr Ile Ile Trp Xaa Xaa Xaa Xaa
            85                  90                  95

Xaa Xaa Xaa Xaa Xaa Xaa Xaa Xaa Xaa Xaa Xaa Xaa Xaa Xaa Thr
```

```
                    100                 105                 110

Ala Val Asn Leu Leu His Xaa Xaa Gln Thr His Phe Asp Ala Leu Arg
            115                 120                 125

Ile Leu
    130

<210> SEQ ID NO 74
<211> LENGTH: 130
<212> TYPE: PRT
<213> ORGANISM: Dugbe virus
<220> FEATURE:
<223> OTHER INFORMATION: OTU domain of DUGV-L (29-158)
<220> FEATURE:
<221> NAME/KEY: VARIANT
<222> LOCATION: (19)..(31), (44)..(60), (73)..(81), (92)..(111),
      (119)..(120)
<223> OTHER INFORMATION: Xaa = Any Amino Acid

<400> SEQUENCE: 74

Phe Glu Val Ile Arg Gln Pro Gly Asp Gly Asn Cys Phe Tyr His Ser
 1               5                  10                  15

Ile Ala Xaa Xaa Xaa Xaa Xaa Xaa Xaa Xaa Xaa Xaa Xaa Xaa Xaa Lys
            20                  25                  30

Val Lys Glu His Leu Gln Leu Ala Ala Glu Val Xaa Xaa Xaa Xaa Xaa
        35                  40                  45

Xaa Xaa Xaa Xaa Xaa Xaa Xaa Xaa Xaa Xaa Xaa Xaa Tyr Ile Lys Val
    50                  55                  60

Ala Met Lys Asp Asn Glu Trp Gly Xaa Xaa Xaa Xaa Xaa Xaa Xaa Xaa
65                  70                  75                  80

Xaa Lys His Leu Gln Thr Thr Ile Ile Leu Trp Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Thr
                    100                 105                 110

Ala Leu Asn Leu Met His Xaa Xaa Arg Thr His Phe Asp Ala Leu Arg
            115                 120                 125

Ile Ile
    130

<210> SEQ ID NO 75
<211> LENGTH: 81
<212> TYPE: PRT
<213> ORGANISM: equine arteritis virus
<220> FEATURE:
<223> OTHER INFORMATION: OTU domain of EAV-nsp2 (259-339)
<220> FEATURE:
<221> NAME/KEY: VARIANT
<222> LOCATION: (37)..(45), (56)..(63), 71
<223> OTHER INFORMATION: Xaa = Any Amino Acid

<400> SEQUENCE: 75

Tyr Gly Gly Tyr Asn Pro Pro Gly Asp Gly Ala Cys Gly Tyr Arg Cys
 1               5                  10                  15

Leu Ala Phe Met Asn Gly Ala Thr Val Val Ser Ala Gly Cys Ser Ser
            20                  25                  30

Asp Leu Trp Cys Xaa Xaa Xaa Xaa Xaa Xaa Xaa Xaa Xaa Gln Leu Ser
            35                  40                  45

Pro Thr Phe Thr Val Thr Ile Xaa Xaa Xaa Xaa Xaa Xaa Xaa Xaa Ala
        50                  55                  60

Lys Tyr Ala Met Ile Cys Xaa Lys Gln His Trp Arg Val Lys Arg Ala
65                  70                  75                  80

Lys
```

```
<210> SEQ ID NO 76
<211> LENGTH: 88
<212> TYPE: PRT
<213> ORGANISM: porcine respiratory and reproductive syndrome virus
<220> FEATURE:
<223> OTHER INFORMATION: OTU domain of PRRSV-nsp2 (426-513)
<220> FEATURE:
<221> NAME/KEY: VARIANT
<222> LOCATION: 19, (31)..(32), (45)..(53), (63)..(70), 78
<223> OTHER INFORMATION: Xaa = Any Amino Acid

<400> SEQUENCE: 76

Leu Lys Arg Tyr Ser Pro Pro Ala Glu Gly Asn Cys Gly Trp His Cys
 1               5                  10                  15

Ile Ser Xaa Ile Ala Asn Arg Met Val Asn Ser Lys Phe Lys Xaa Xaa
            20                  25                  30

Leu Pro Glu Arg Val Arg Pro Pro Asp Asp Trp Ala Xaa Xaa Xaa Xaa
        35                  40                  45

Xaa Xaa Xaa Xaa Xaa Gln Ile Leu Arg Leu Pro Ala Ala Leu Xaa Xaa
    50                  55                  60

Xaa Xaa Xaa Xaa Xaa Xaa Ala Lys Tyr Val Leu Lys Leu Xaa Gly Glu
65                  70                  75                  80

His Trp Thr Ala Thr Val Thr Pro
                85

<210> SEQ ID NO 77
<211> LENGTH: 172
<212> TYPE: PRT
<213> ORGANISM: Homo sapiens
<220> FEATURE:
<223> OTHER INFORMATION: OTU domain of A20 (92-263)
<220> FEATURE:
<221> NAME/KEY: VARIANT
<222> LOCATION: (19)..(32), (45)..(66), (79)..(109), (120)..(154), 162
<223> OTHER INFORMATION: Xaa = Any Amino Acid

<400> SEQUENCE: 77

Leu Val Ala Leu Lys Thr Asn Gly Asp Gly Asn Cys Leu Met His Ala
 1               5                  10                  15

Thr Ser Xaa Xaa Xaa Xaa Xaa Xaa Xaa Xaa Xaa Xaa Xaa Xaa Xaa Xaa
            20                  25                  30

Lys Ala Leu Phe Ser Thr Leu Lys Glu Thr Asp Thr Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Cys Tyr Asp Thr Arg Asn Trp Asn Asp Glu Trp Asp Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Asn Ile Leu
            100                 105                 110

Arg Arg Pro Ile Ile Val Ile Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Tyr Pro Ile Val Leu Gly
145                 150                 155                 160

Tyr Xaa Ser His His Phe Val Pro Leu Val Thr Leu
        165                 170
```

<210> SEQ ID NO 78
<211> LENGTH: 183
<212> TYPE: PRT
<213> ORGANISM: homo sapiens
<220> FEATURE:
<223> OTHER INFORMATION: OTU domain of Cezanne (183-365)
<220> FEATURE:
<221> NAME/KEY: VARIANT
<222> LOCATION: (19)..(32), (45)..(65), (78)..(121), (132)..(165), 173
<223> OTHER INFORMATION: Xaa = Any Amino Acid

<400> SEQUENCE: 78

Leu Leu Pro Leu Ala Thr Thr Gly Asp Gly Asn Cys Leu Leu His Ala
 1               5                  10                  15

Ala Ser Xaa Xaa Xaa Xaa Xaa Xaa Xaa Xaa Xaa Xaa Xaa Xaa Xaa Xaa
             20                  25                  30

Lys Ala Leu Tyr Ala Leu Met Glu Lys Gly Val Glu Xaa Xaa Xaa Xaa
         35                  40                  45

Xaa Xaa Xaa Xaa Xaa Xaa Xaa Xaa Xaa Xaa Xaa Xaa Xaa Xaa Xaa Xaa
     50                  55                  60

Xaa Val Tyr Thr Glu Asp Glu Trp Gln Lys Glu Trp Asn Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                 85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa His Val Leu Arg Arg Pro Ile
        115                 120                 125

Val Val Val Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Ser Pro Leu Val Leu Ala Tyr Xaa Gln Ala His
                165                 170                 175

Phe Ser Ala Leu Val Ser Met
            180

<210> SEQ ID NO 79
<211> LENGTH: 154
<212> TYPE: PRT
<213> ORGANISM: Homo sapiens
<220> FEATURE:
<223> OTHER INFORMATION: OTU domain of VCIP (207-360)
<220> FEATURE:
<221> NAME/KEY: VARIANT
<222> LOCATION: (19)..(32), (45)..(48), (61)..(89), (100)..(137)
<223> OTHER INFORMATION: Xaa = Any Amino Acid

<400> SEQUENCE: 79

Leu Ile Pro Val His Val Asp Gly Asp Gly His Cys Leu Val His Ala
 1               5                  10                  15

Val Ser Xaa Xaa Xaa Xaa Xaa Xaa Xaa Xaa Xaa Xaa Xaa Xaa Xaa Xaa
             20                  25                  30

Glu Asn Leu Lys Gln His Phe Gln Gln His Leu Ala Xaa Xaa Xaa Xaa
         35                  40                  45

Leu Phe His Asp Phe Ile Asp Ala Ala Glu Trp Glu Xaa Xaa Xaa Xaa
     50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Asn Val Leu His Arg Pro Ile

```
            85                  90                  95
Ile Leu Leu Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa
            115                 120                 125

Xaa Xaa Xaa Xaa Xaa Xaa Xaa Xaa Ile Ala Trp Ser Ser Gly
            130                 135             140

Arg Asn His Tyr Ile Pro Leu Val Gly Ile
145                 150

<210> SEQ ID NO 80
<211> LENGTH: 192
<212> TYPE: PRT
<213> ORGANISM: Homo sapiens
<220> FEATURE:
<223> OTHER INFORMATION: OTU domain of OTUB1 (80-271)
<220> FEATURE:
<221> NAME/KEY: VARIANT
<222> LOCATION: (19)..(97), (110)..(122), (135)..(145), (156)..(176)
<223> OTHER INFORMATION: Xaa = Any Amino Acid

<400> SEQUENCE: 80

Ser Tyr Ile Arg Lys Thr Arg Pro Asp Gly Asn Cys Phe Tyr Arg Ala
1               5                   10                  15

Phe Gly Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa
            50                  55                  60

Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa
            85                  90                  95

Xaa Leu Leu Thr Ser Gly Tyr Leu Gln Arg Glu Ser Lys Xaa Xaa Xaa
            100                 105                 110

Xaa Xaa Xaa Xaa Xaa Xaa Xaa Xaa Xaa Glu Phe Cys Gln Gln Glu
            115                 120                 125

Val Glu Pro Met Cys Lys Xaa Xaa Xaa Xaa Xaa Xaa Xaa Xaa
            130                 135                 140

Xaa Gln Ala Leu Ser Val Ser Ile Gln Val Glu Xaa Xaa Xaa Xaa
145                 150                 155             160

Xaa Xaa Xaa Xaa Xaa Xaa Xaa Xaa Xaa Xaa Xaa Xaa Xaa Xaa
            165                 170                 175

Lys Val Tyr Leu Leu Tyr Arg Pro Gly His Tyr Asp Ile Leu Tyr Lys
            180                 185                 190

<210> SEQ ID NO 81
<211> LENGTH: 192
<212> TYPE: PRT
<213> ORGANISM: Homo sapiens
<220> FEATURE:
<223> OTHER INFORMATION: OTU domain of OTUB2 (40-231)
<220> FEATURE:
<221> NAME/KEY: VARIANT
<222> LOCATION: (19)..(97), (110)..(122), (135)..(145), (156)..(161),
       (169)..(182)
<223> OTHER INFORMATION: Xaa = Any Amino Acid

<400> SEQUENCE: 81

Thr Ser Ile Arg Lys Thr Lys Gly Asp Gly Asn Cys Phe Tyr Arg Ala
```

```
                1               5                   10                  15
Leu Gly Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa
                35                  40                  45

Xaa Xaa Xaa Xaa Xaa Xaa Xaa Xaa Xaa Xaa Xaa Xaa Xaa Xaa
                50                  55                  60

Xaa Xaa Xaa Xaa Xaa Xaa Xaa Xaa Xaa Xaa Xaa Xaa Xaa Xaa
 65                 70                  75                  80

Xaa Xaa Xaa Xaa Xaa Xaa Xaa Xaa Xaa Xaa Xaa Xaa Xaa Xaa
                85                  90                  95

Xaa Leu Leu Thr Ser Ala Phe Ile Arg Asn Arg Ala Asp Xaa Xaa Xaa
                100                 105                 110

Xaa Xaa Xaa Xaa Xaa Xaa Xaa Xaa Xaa Xaa Asp Phe Cys Thr His Glu
                115                 120                 125

Val Glu Pro Met Ala Met Xaa Xaa Xaa Xaa Xaa Xaa Xaa Xaa
                130                 135                 140

Xaa Gln Ala Leu Asn Ile Ala Leu Gln Val Glu Xaa Xaa Xaa Xaa
145                 150                 155                 160

Xaa Thr Ala Leu Asn His His Val Xaa Xaa Xaa Xaa Xaa Xaa Xaa
                165                 170                 175

Xaa Xaa Xaa Xaa Xaa Xaa Thr Ser His Tyr Asn Ile Leu Tyr Ala Ala
                180                 185                 190

<210> SEQ ID NO 82
<211> LENGTH: 266
<212> TYPE: PRT
<213> ORGANISM: Artificial Sequence
<220> FEATURE:
<223> OTHER INFORMATION: consensus sequence of OTU across viral and
      mammalian proteins
<220> FEATURE:
<221> NAME/KEY: VARIANT
<222> LOCATION: 1, (3)..(4), (13)..(14), 17, 99, 103, (189)..(190), 192,
      194, (196)..(197), (237)..(238), (263)..(264)
<223> OTHER INFORMATION: Xaa = h which indicates hydrophobic residues
      (Ala,Cys,Phe,Leu,Ile,Met,Val,Trp,Tyr,Thr,Ser,Gly)
<220> FEATURE:
<221> NAME/KEY: VARIANT
<222> LOCATION: 8, 10, 16, 143, 262
<223> OTHER INFORMATION: Xaa = s which indicates small residues
      (Ala,Cys,Ser,Thr,Asp,Val,Gly,Pro)
<220> FEATURE:
<221> NAME/KEY: VARIANT
<222> LOCATION: 100
<223> OTHER INFORMATION: Xaa = + which indicates positively charged
      residues (Arg,Lys)
<220> FEATURE:
<221> NAME/KEY: VARIANT
<222> LOCATION: 11, 18, 101, 134, 138, 140, 191, 257, 261
<223> OTHER INFORMATION: Xaa = t which indicates residues with high
      beta-turn-forming propensity
      (Ala,Cys,Ser,Thr,Asp,Glu,Asn,Val,Gly,Pro)
<220> FEATURE:
<221> NAME/KEY: VARIANT
<222> LOCATION: 142,260
<223> OTHER INFORMATION: Xaa = a which indicates aromatic residues
      (Trp,Tyr,Phe,His)
<220> FEATURE:
<221> NAME/KEY: VARIANT
<222> LOCATION: (19)..(97), (110)..(131), (144)..(187), (198)..(235),
      (243)..(256)
<223> OTHER INFORMATION: Xaa = Any Amino Acid and deletions
<220> FEATURE:
<221> NAME/KEY: VARIANT
<222> LOCATION: 2,(5)..(8), 15, 98, 102, (104)..(109), (132)..(133),
      (135)..(137), 139, 141, 188, 193, 195, 236, (239)-(242), 258,
      (265)..(266)
```

<223> OTHER INFORMATION: Xaa = Any Amino Acid

<400> SEQUENCE: 82

```
Xaa Xaa Xaa Xaa Xaa Xaa Xaa Xaa Asp Xaa Xaa Cys Xaa Xaa Xaa Xaa
  1               5                  10                  15
Xaa Xaa Xaa Xaa Xaa Xaa Xaa Xaa Xaa Xaa Xaa Xaa Xaa Xaa Xaa Xaa
             20                  25                  30
Xaa Xaa Xaa Xaa Xaa Xaa Xaa Xaa Xaa Xaa Xaa Xaa Xaa Xaa Xaa Xaa
         35                  40                  45
Xaa Xaa Xaa Xaa Xaa Xaa Xaa Xaa Xaa Xaa Xaa Xaa Xaa Xaa Xaa Xaa
     50                  55                  60
Xaa Xaa Xaa Xaa Xaa Xaa Xaa Xaa Xaa Xaa Xaa Xaa Xaa Xaa Xaa Xaa
 65                  70                  75                  80
Xaa Xaa Xaa Xaa Xaa Xaa Xaa Xaa Xaa Xaa Xaa Xaa Xaa Xaa Xaa Xaa
                 85                  90                  95
Xaa Xaa Xaa Xaa Xaa Xaa Xaa Xaa Xaa Xaa Xaa Xaa Xaa Xaa Xaa Xaa
             100                 105                 110
Xaa Xaa Xaa Xaa Xaa Xaa Xaa Xaa Xaa Xaa Xaa Xaa Xaa Xaa Xaa Xaa
         115                 120                 125
Xaa Xaa Xaa Xaa Xaa Xaa Xaa Xaa Xaa Xaa Xaa Xaa Xaa Xaa Xaa Xaa
     130                 135                 140
Xaa Xaa Xaa Xaa Xaa Xaa Xaa Xaa Xaa Xaa Xaa Xaa Xaa Xaa Xaa Xaa
145                 150                 155                 160
Xaa Xaa Xaa Xaa Xaa Xaa Xaa Xaa Xaa Xaa Xaa Xaa Xaa Xaa Xaa Xaa
                165                 170                 175
Xaa Xaa Xaa Xaa Xaa Xaa Xaa Xaa Xaa Xaa Xaa Xaa Xaa Xaa Xaa Xaa
            180                 185                 190
Xaa Xaa Xaa Xaa Xaa Xaa Xaa Xaa Xaa Xaa Xaa Xaa Xaa Xaa Xaa Xaa
        195                 200                 205
Xaa Xaa Xaa Xaa Xaa Xaa Xaa Xaa Xaa Xaa Xaa Xaa Xaa Xaa Xaa Xaa
    210                 215                 220
Xaa Xaa Xaa Xaa Xaa Xaa Xaa Xaa Xaa Xaa Xaa Xaa Xaa Xaa Xaa Xaa
225                 230                 235                 240
Xaa Xaa Xaa Xaa Xaa Xaa Xaa Xaa Xaa Xaa Xaa Xaa Xaa Xaa Xaa Xaa
                245                 250                 255
Xaa Xaa His Xaa Xaa Xaa Xaa Xaa Xaa Xaa
            260                 265
```

METHODS OF PREVENTING AND TREATING VIRAL INFECTIONS BY INHIBITING THE DEISGYLATION ACTIVITY OF OTU DOMAIN-CONTAINING VIRAL PROTEINS

This application is a national stage application under 35 U.S.C. §371 of International Patent Application No. PCT/US2008/004481, filed Apr. 7, 2008, which claims the benefit of U.S. Provisional Application No. 60/922,273, filed Apr. 5, 2007, and U.S. Provisional Application No. 61/004,842, filed Nov. 30, 2007, each of which is incorporated by reference herein in its entirety.

This invention was made with government support under award numbers U54AI057158 and U54AI057160 awarded by the National Institutes of Health and award number W81XWH-04-1-0876 awarded by the ARMY/MRMC Medical Research and Material Command. The U.S. Government has certain rights in the invention.

1. INTRODUCTION

The present invention provides viruses having an impaired ability to deISGylate ISG15 conjugates. In particular, the present invention provides viral mutants comprising a mutation in the viral genome that reduces or eliminates the ability of the viral Ovarian Tumor-related protease (OTU) domain-containing protein encoded by the viral genome to deISGylate ISG15 conjugates, to deubiquitinate ubiquitinated proteins, and/or to deNeddylate Neddylated proteins. The invention provides for the use of such viral mutants in the formulation of immunogenic compositions for inducing an immune response and preventing, managing and/or treating a viral infection.

The present invention provides methods for identifying anti-viral compounds. In particular, the methods of the invention identify compounds that reduce or inhibit the deISGylation activity and/or deubiquitination activity of a viral OTU domain-containing protein. The compounds identified using such methods may be used as antiviral agents for the prevention, treatment and/or management of viral infections.

2. BACKGROUND

2.1 Interferon Stimulated Gene ISG15

The type I interferon (IFN) pathway plays an essential role in anti-viral immunity by inducing the expression of hundreds of genes. Some interferon stimulated genes (ISG) have well-characterized anti-viral functions, but for the majority of ISGs, their mechanism of action is unknown. ISG15 was first identified as a 15 kDa protein induced by IFN treatment that cross-reacted with anti-ubiquitin antibodies (Blomstrom et al., 1986; Haas et al., 1987; Korant et al., 1984). A member of the ubiquitin-like (Ubl) family, ISG15 possesses significant homology to a di-ubiquitin sequence. The crystal structure of ISG15 revealed two ubiquitin folds joined by a linker sequence (Narasimhan et al., 2005). Like ubiquitin, ISG15 is linked to target proteins via an isopeptide bond between the terminal carboxyl group of ISG15 and the ε-amino group of lysines of target proteins (Ritchie and Zhang, 2004; Welchman et al., 2005).

ISG15 utilizes a series of IFN-induced enzymes to conjugate to target proteins. The activating enzyme (E1) and the conjugating enzyme (E2) have been identified as UBE1L (Yuan and Krug, 2001) and UbcH8 (Zhao et al., 2004), respectively. More recently, Herc5 (Dastur et al., 2006) and EFP (Zou and Zhang, 2006) have been found to be ISG15 ligases (E3). DeISGylation is catalyzed by UBP43, an ISG15-specific deconjugating enzyme (Malakhov et al., 2002). To date, the only ISG15-specific isopeptidase that had been identified is UBP43. No viral protein has been demonstrated to have deISGylating activity, however it has been demonstrated that the de-ubiquitinating proteases Severe Acute Respiratory Syndrome-associated Coronavirus (SARS-CoV) PLpro and the adenovirus protease can process ISG15 fusion proteins (Balakirev et al., 2002; Barretto et al., 2005; Lindner et al., 2005). Proteomic approaches have identified target proteins for ISGylation (Giannakopoulos et al., 2005; Zhao et al., 2005). Some of these proteins, such as STAT-1, PKR, Mx and RIG-I, are also IFNα/β-inducible and have known anti-viral functions (Haller et al., 1995; Meurs et al., 1992; Yoneyama et al., 2004). The existence of an IFN-inducible pathway that mirrors ubiquitin conjugation suggests that protein ISGylation may be an important component of the IFN-induced innate immune response.

2.2 Anti-Viral Properties of ISG15

Numerous studies have suggested that ISG15 has anti-viral properties in vivo. When ISG15 was heterologously expressed from a recombinant Sindbis virus, the Sindbis virus was no longer lethal to IFNαβR1$^{-/-}$ mice (Lenschow et al., 2005). ISG15$^{-/-}$ mice display increased susceptibility to infection with Sindbis, herpes simplex, influenza A and influenza B viruses (Lenschow et al., 2007), although they have no defect in the antiviral response against vesicular stomatitis virus (VSV) or lymphocytic choriomeningitis virus (LCMV) (Osiak et al., 2005). ISGylation has been reported to inhibit HIV budding (Okumura et al., 2006). In addition, the NS1 of influenza B virus specifically binds ISG15 and blocks cellular protein ISGylation by inhibiting the ISG15-UBE1L interaction, most likely as an immune evasion mechanism (Yuan et al., 2002; Yuan and Krug, 2001).

2.3 Ovarian-Tumor (OTU) Domain-Containing Proteins of the Deubiquitinating (DUB) Superfamily Ubiquitin (Ub) conjugation and deconjugation have been shown to play an essential role in the regulation of numerous biological processes, including protein degradation, signal transduction and endocytosis. The deubiquitinating (DUB) superfamily of proteases includes more than 500 members, most of them specific for Ub, and only a few of them displaying activity towards Ubl molecules (Nyman et al., 2000). Some mammalian proteins (such as Otubains, Cezanne, and A20) belonging to the Ovarian Tumor (OTU) family of cysteine proteases have been described as a DUB (Balakirev et al., 2003; Evans et al., 2004; Evans et al., 2003).

2.4 Crimean Congo Hemorrhagic Fever Virus (CCHFV)

Crimean Congo Hemorrhagic Fever Virus (CCHFV) is a human pathogen distributed mainly in Africa, Asia and Eastern Europe. It is the causative agent for a tick-borne hemorrhagic fever with high mortality rates (Flick and Whitehouse, 2005). CCHFV is a segmented negative-stranded RNA virus belonging to the nairovirus genus in the bunyaviridae family. Nairoviruses differ from other bunyaviruses in the relative sizes of their tri-segmented genome and particularly in the large L segment that encodes a putative RNA dependent RNA polymerase (RdRp) of 450 kDa.

3. SUMMARY OF THE INVENTION

The present invention provides viruses having an impaired ability to deISGylate ISG15 conjugates. In particular, the present invention provides viral mutants comprising a mutation in the viral genome that reduces or eliminates the ability of the viral OTU domain-containing protein encoded by the viral genome to deISGylate ISG15 conjugates. In some embodiments, the mutation in the viral genome reduces or eliminates the ability of the viral OTU domain-containing protein encoded by the viral genome to deISGylate ISG15 conjugates and to deubiquitinate ubiquitinated proteins. In some embodiments, the mutation in the viral genome reduces or eliminates the ability of the viral OTU domain-containing protein encoded by the viral genome to deISGylate ISG15 conjugates and deNeddylate Neddylated proteins. In certain aspects, the reduced or impaired ability of the virus to deISGylate ISG15 conjugates reduces the virus' ability to antagonize the cellular interferon response. In some aspects, the reduced or impaired ability of the virus to deubiquitinate ubiquitinated proteins reduces the virus' ability to antagonize the cellular interferon (IFN) response. In some aspects, the reduced or impaired ability of the virus to deNeddylate Neddylated proteins reduces the virus' ability to replicate and/or to counteract one or more antiviral host responses. In one embodiment, the mutant viruses have a reduced IFN antagonist activity and have an IFN-inducing phenotype. In another embodiment, the mutant viruses have a reduced or impaired ability to downregulate the NF-κB pathway. In another embodiment, the mutant viruses have a reduced or impaired ability to evade the tumor necrosis factor (TNF)α pathway. In a specific embodiment, the mutant viruses have a reduced ability to evade a host immune response and the mutant viruses have an enhanced immunity-inducing phenotype. In some embodiments, the mutant viruses have a reduced ability to evade the innate and the adaptive cellular immune system. In some embodiments, the mutant viruses have a reduced ability to modulate MHC class I and/or II antigen presentation. In some embodiments, the mutant viruses have a reduced ability to modulate TLR/IL1 signaling. In some embodiments, the mutant viruses have a reduced ability to induce type I IFN by the cellular viral sensor RIGI. In some embodiments, the mutant viruses have a reduced ability to modulate the proteasome-mediated protein degradation system, signal transduction events, and/or or cell cycle progress. Accordingly, the virus is less virulent and useful in immunogenic compositions to induce an immune response to the virus and/or a heterologous antigen encoded by the viral genome.

The present invention provides mutants of viruses comprising an OTU domain-containing protein, wherein the mutants comprise a mutation in the viral gene encoding the OTU domain-containing protein that reduces or inhibits the deISGylation activity of the OTU domain-containing protein. The present invention also provides mutants of viruses comprising an OTU domain-containing protein, wherein the mutants comprise a mutation in the viral gene encoding the OTU domain-containing protein that reduces or inhibits the deubiquitination activity of the OTU domain-containing protein. The present invention also provides mutants of viruses comprising an OTU domain-containing protein, wherein the mutants comprise a mutation in the viral gene encoding the OTU domain-containing protein that reduces or inhibits the deISGylation activity and deubiquitination activity of the OTU domain-containing protein. The present invention also provides mutants of viruses comprising an OTU domain-containing protein, wherein the mutants comprise a mutation in the viral gene encoding the OTU domain-containing protein that reduces or inhibits the deNeddylation activity of the OTU domain-containing protein. The present invention also provides mutants of viruses comprising an OTU domain-containing protein, wherein the mutants comprise a mutation in the viral gene encoding the OTU domain-containing protein that reduces or inhibits the deISGylation and deNeddylation activity of the OTU domain-containing protein. In a preferred embodiment, the viral mutants are attenuated.

The present invention also provides mutants of viruses comprising an OTU domain-containing protein, wherein the mutants comprise a mutation in the viral gene encoding the OTU domain-containing protein that reduces or inhibits the deISGylation and deubiquitination and deNeddylation activity of the OTU domain-containing protein. In a preferred embodiment, the viral mutants are attenuated.

In a specific embodiment, the mutation in the gene encoding the OTU domain-containing protein reduces the deISGylation activity of the viral OTU domain-containing protein by about 5% to about 25%, about 10% to about 30%, about 10% to about 50%, about 25% to about 50%, about 25% to about 75%, or about 30% to about 90% as measured in an assay known to one of skill in the art or described herein. In another embodiment, the mutation in the gene encoding the OTU domain-containing protein reduces the deubiquitination activity of the viral OTU domain-containing protein by about 5% to about 25%, about 10% to about 30%, about 10% to about 50%, about 25% to about 50%, about 25% to about 75%, or about 30% to about 90% as measured in an assay known to one of skill or described herein. In another embodiment, the mutation in the gene encoding the OTU domain-containing protein reduces the deNeddylation activity of the viral OTU domain-containing protein by about 5% to about 25%, about 10% to about 30%, about 10% to about 50%, about 25% to about 50%, about 25% to about 75%, or about 30% to about 90% as measured in an assay known to one of skill or described herein.

Any mutation that results in the desired phenotype (i.e., an impaired deISGylation activity and, in some embodiments, an impaired deubiquitination activity and/or deNeddylation activity) can be introduced into the virus gene encoding the OTU domain-containing protein or into a gene that affects the function of the OTU domain-containing protein. Examples of the types of mutations that can be included in or introduced into the gene include, but are not limited to, deletions, substitutions, insertions and combinations thereof. One or more mutations can be located anywhere throughout the coding region, non-coding region, and/or the regulatory element. In one embodiment, the mutation in the viral gene encoding an OTU domain-containing protein is in the region of the gene encoding the catalytic region of the OTU domain. In a specific embodiment, the mutation in the viral gene encoding an OTU domain-containing protein results in the substitution or deletion of the catalytic cysteine, histidine and/or aspartic acid residues. In a more specific embodiment, the mutation in the viral gene encoding an OTU domain-containing protein results in the substitution of the catalytic cysteine, histidine and/or aspartic acid residues for alanine residues. In another embodiment, the mutation in the viral gene encoding the OTU domain-containing protein is a deletion of the catalytic region of the OTU domain or a fragment thereof.

In one embodiment, the virus is a mutant of an arterivirus, such as equine arteritis virus (EAV), porcine reproductive and respiratory syndrome virus (PRRSV), such as Lelystad virus (LELV), or lactate dehydrogenase elevating virus (LDV) and the viral OTU domain-containing protein is the nsp2 protein of such viruses. In another embodiment, the virus is a mutant of a nairovirus. In another embodiment, the virus is a mutant of CCHFV or Dugbe virus (DUGV) and the viral OTU domain-containing protein is the L protein (the RNA dependent RNA polymerase) of CCHFV or DUGV. In another embodiment, the viral OTU domain-containing protein is the L protein (the RNA dependent RNA polymerase) of CCHFV. In another embodiment, the viral OTU domain-containing protein is the L protein (the RNA dependent RNA polymerase) of DUGV. In accordance with these embodiments, a mutation to the nsp2 protein of an arterivirus or L protein of CCHFV or DUGV is, in some embodiments, in the catalytic cysteine, histidine and/or aspartic acid of the L protein. In a specific embodiment, the catalytic cysteine (Cys40) of CCHFV L is mutated. In another embodiment, the catalytic His151 is mutated. In another embodiment, the predicted catalytic Asp37 is mutated. In some embodiments, the CCHFV L domain has one or a combination of these mutations. In some embodiments, the CCHFV L domain has the mutations Cys40Ala and His151Ala. In a specific embodiment, one or more residues in the region spanning amino acids 1 to 169 of CCHFV L are mutated. In one embodiment, amino acids 1 to 169 of CCHFV L are deleted. In another specific embodiment, the catalytic cysteine (Cys40) of DUGV L is mutated. In another embodiment, the catalytic His151 is mutated. In another embodiment, the predicted catalytic Asp37 is mutated. In some embodiments, the DUGV L domain has one or a combination of these mutations. In some embodiments, replication of the mutant viruses is facilitated by complementation. In some embodiments, replication of the mutant viruses is complemented by expressing a wild-type OTU domain-containing protein in trans.

In a specific embodiment, a mutation in the viral gene encoding an OTU domain-containing protein does not reduce or does not significantly reduce one or more activities other than the deISGylation activity (and in some embodiments, the deubiquitination and/or deNeddylation activities) of the OTU domain-containing protein as assessed by an assay known to one of skill (see Table 2 infra). In another embodiment, a mutation in the viral gene encoding an OTU domain-containing protein reduces the one or more activities other than the deISGylation activity (and in some embodiments, the deubiquitination and/or deNeddylation activities) of the OTU domain-containing protein by no more than about 75%, preferably no more than about 50%, 45%, 40%, 35%, 30%, or 25% as assessed by an assay known to one of skill in the art.

In a particular embodiment, a mutation in the L protein of CCHFV or DUGV does not reduce or does not significantly reduce the activity of the RNA dependent RNA polymerase of the protein as assessed by an assay known to one of skill in the art. In one embodiment, the RNA dependent RNA polymerase is tested for its ability to support virus replication in cells. In a specific embodiment, the virus is tested for its ability to replicate in ISG15 deficient cells. In specific embodiments, the activity of the RNA dependent RNA polymerase is assessed by a plaque assay for propagation of the virus in tissue culture, e.g., in SW13 cells or Vero cells, or in ISG15 deficient cells. In another embodiment, RNA dependent RNA polymerase activity is tested by assessing virulence of the virus in vivo, e.g., by infecting an ISG15-deficient mouse or cells derived from such mouse and assessing survival of the mouse or mouse cells. In another embodiment, the activity of the RNA dependent RNA polymerase is tested using a mini-replicon or mini-genome assay, see, e.g., U.S. Pat. No. 5,840,520 which describes mini-replicon and mini-genome assays.

In a specific embodiment, a mutation in the L protein of CCHFV or DUGV does not reduce the RNA dependent RNA polymerase activity of the protein by more than about 75%, preferably no more than about 50%, 45%, 40%, 35%, 30%, or 25% as assessed by an assay known to one of skill in the art. In one embodiment, the RNA dependent RNA polymerase is tested for its ability to support virus replication in cells. In a specific embodiment, the virus is tested for its ability to replicate in ISG15 deficient cells. In specific embodiments, activity of the RNA dependent RNA polymerase is assessed by a plaque assay for propagation of the virus in tissue culture, e.g., in SW13 cells or Vero cells, or in ISG15 deficient cells. In another embodiment, RNA dependent RNA polymerase activity is tested by assessing virulence of the virus in vivo, e.g., by infecting an ISG15-deficient mouse or cells derived from such mouse and assessing survival of the mouse or mouse cells.

In another embodiment, a mutation in the nsp2 protein of EAV, PRRSV, LELV, or LDV does not reduce or does not significantly reduce activities of the nsp2 protein other than its deISGylation activity as assessed by an assay known to one of skill in the art. In another embodiment, a mutation in the nsp2 protein of EAV, PRRSV, LELV, or LDV does not reduce or does not significantly reduce the activity, other than deISGylation activity, of the polyprotein precursor that contains the nsp2 protein as assessed by an assay known to one of skill in the art. In one embodiment, the replicase function of nsp2 is tested. In one such embodiment, in vitro generated viral RNA transcripts are introduced into cells and RNA replication is assessed. In another embodiment, viral RNA replication is tested with the use of DNA launch plasmids. In another embodiment, a GFP tag is inserted between the nsp1 and nsp2 sequences of the polyprotein, and genome replication is assessed by monitoring the fluorescence of the cells. In some embodiments, replicase function is assessed in ISG15-deficient cells. In another embodiment, a mutation in the nsp2 protein of EAV, PRRSV, LELV, or LDV does not reduce replicase activity by more than about 75%, preferably no more than about 50%, 45%, 40%, 35%, 30%, or 25% as assessed by an assay known to one of skill in the art. In one embodiment, the sites in the polyprotein that depend on the function of nsp2 for cleavage are mutated so that they are recognizable by different viral proteases, so as to separate the deISGylation and/or deubiquitination activities from the function of nsp2 in polyprotein processing.

In some embodiments, a mutation that abrogates deISGylation function (and in some embodiments, the deubiquitination and/or deNeddylation function) of the OTU domain-containing viral protein also abrogates the other functions of the protein. In alternative embodiments, a mutation that abrogates deISGylation function (and in some embodiments, the deubiquitination and/or deNeddylation function) of the OTU domain-containing viral protein does not abrogate the other functions of the protein.

In a specific embodiment, the viral mutants described herein are attenuated. In a preferred embodiment, the viral mutants described herein replicate in vivo to provide subclinical levels of infection and are not pathogenic. Such viruses are ideal candidates for live viral vaccines.

An attenuated virus having the desired phenotype can itself be used as the active ingredient in an immunogenic composition (e.g., a vaccine) or a pharmaceutical composition. Alternatively, the virus can be used as the vector or "backbone" of recombinantly produced immunogenic compositions. To this end, the genetic engineering techniques can be used to engineer mutations or introduce heterologous sequences, such as foreign epitopes into the attenuated virus, which would serve as the "parental" strain. In this way, vaccines can be designed for immunization against strain variants, or in the alternative, against completely different infectious agents or disease antigens (e.g., tumor-associated antigens or bacteria). In some embodiments, the virus mutants of the present invention may be a chimeric virus that expresses a heterologous sequence, e.g., antigens of other pathogens. In some embodiments, the virus mutants of the invention are isolated. The present invention encompasses substrates (such as cells) infected with a mutant virus of the invention.

The mutant viruses of the invention can be used in active immunization in a subject. In one aspect, the mutant viruses of the invention can be used to prevent, manage and/or treat one or more diseases. The mutant viruses of the invention can also be used to produce antibodies which can be used in diagnostic immunoassays, passive immunotherapy, and generation of antiidiotypic antibodies.

The present invention provides immunogenic compositions comprising a mutant virus of the invention, and a physiological carrier or excipient. The invention provides methods for producing such immunogenic compositions, comprising propagating in a substrate a mutant virus of the invention and collecting the virus. The invention provides methods of inducing an immune response, comprising administering to a subject an effective amount of an immunogenic composition of the invention. The invention provides methods of preventing, managing and/or treating a viral infection, comprising administering an effective amount of an immunogenic composition of the invention. In some embodiments, the viral infection to be prevented, managed and/or treated is a nairovirus, e.g., CCHFV or DUGV. In other embodiments, the viral infection to be prevented, managed and/or treated is an arterivirus infection. In yet other embodiments, the viral infection to be prevented, managed and/or treated is a herpes virus infection.

The present invention provides methods of identifying novel anti-viral compounds. In particular, the methods of the invention identify compounds that reduce or inhibit the deISGylation activity of a viral OTU domain-containing protein. The invention also provides methods for identifying compounds that reduce or inhibit the deubiquitination activity of a viral OTU domain-containing protein. Further, the invention provides methods for identifying compounds that reduce or inhibit the deconjugation of ubiquitin-like molecules (e.g., Nedd8 and/or SUMO) from target proteins. In some embodiments, a compound is identified that reduces or inhibits the deubiquitination and/or deISGylation activity of a viral OTU domain-containing protein but not the deubiquitination activity of a cellular OTU domain-containing protein.

The present invention provides methods for identifying a compound that modulates the deISGylation activity of a viral OTU domain-containing protein, the methods comprising: (a) contacting a compound with a composition comprising ISG15 conjugated protein and a viral OTU domain-containing protein or an OTU domain-containing fragment thereof; and (b) measuring the amount of ISG15 conjugated protein, wherein an alteration in the amount of ISG15 conjugated protein relative to a negative control (e.g., a composition comprising ISG15 conjugated protein and a viral OTU domain-containing protein or an OTU domain-containing fragment thereof not contacted with the compound) or a predetermined reference range indicates that the compound modulates the deISGylation activity of the viral OTU domain-containing protein. In a specific embodiment, the invention provides methods for identifying a compound that reduces or inhibits the deISGylation activity of a viral OTU domain-containing protein, the methods comprising: (a) contacting a compound with a composition comprising ISG15 conjugated protein and a viral OTU domain-containing protein or an OTU domain-containing fragment thereof; and (b) measuring the amount of ISG15 conjugated protein, wherein an increase in the amount of ISG15 conjugated protein relative to a negative control (e.g., a composition comprising ISG15 conjugated protein and a viral OTU domain-containing protein or an OTU domain-containing fragment thereof not contacted with the compound) or a predetermined reference range indicates that the compound reduces or inhibits the deISGylation activity of the viral OTU domain-containing protein.

In one embodiment, the invention provides methods for identifying a compound that reduces or inhibits the deISGylation activity of a viral OTU domain-containing protein or an OTU domain-containing fragment thereof, the methods comprising: (a) contacting a compound with a composition comprising an artificial substrate that mimics the ISG15 cleavage and a viral OTU domain-containing protein or OTU domain-containing fragment thereof; and (b) measuring the amount of cleavage of the artificial substrate, wherein a decrease in the cleavage of the artificial substrate relative to a negative control (e.g., the composition comprising an artificial substrate that mimics the ISG15 cleavage and the viral OTU domain-containing protein or OTU domain-containing fragment thereof not contacted with the compound) or a predetermined reference range indicates that the compound reduces or inhibits the deISGylation activity of the viral OTU domain-containing protein or OTU domain-containing fragment thereof. In certain embodiments, the artificial substrate is a small synthetic fluorogenic substrate such as 7-amido-4-methylcoumarin (AMC) or 7-amino-4-trifluoromethylcoumarin (AFC) that incorporates the C-terminal four (or six) residues found in Ub and ISG15 (LRGG) or (LRLRGG) (SEQ ID NO:1). (Lindner, H et al. J Virol. December 2005 Vol 79 p 15199-15208), (Blakirev, M et al, J Virol, June 2002, Vol 76 p 6323-6331). In other embodiments, the artificial substrate has DABCYL and EDANS moieties on opposite ends of a 12-(or other) mer peptide that can be detected by FRET (as used in: Barretto et al, J Virol, December 2005, Vol 79 p 15189-15198), in which such peptide has the cleavage site of interest (e.g., LRLRGG (SEQ ID NO:1)).

In another embodiment, the invention provides methods for identifying a compound that reduces or inhibits the deISGylation activity of a viral OTU domain-containing protein or an OTU domain-containing fragment thereof, the methods comprising: (a) contacting a compound with an ISG15-fluorogenic substrate (such as, e.g., ISG15-AMC or ISGI5-AFC available from Boston Biochem, Inc., Cambridge, Mass.), and a viral OTU domain-containing protein or an OTU domain-containing fragment thereof; and (b) measuring the fluorescence of the mixture, wherein a decrease in the fluorescence relative to a negative control (e.g., the composition comprising an ISG15-fluorogenic substrate and the viral OTU domain-containing protein or OTU domain-containing fragment thereof not contacted with the compound) or a predetermined reference range indicates that the compound reduces or inhibits the deISGylation activity of the viral OTU domain-containing protein or OTU domain-containing fragment thereof.

The present invention provides methods for identifying a compound that modulates the deubiquitination activity of a viral OTU domain-containing protein, the methods comprising: (a) contacting a compound with a composition comprising ubiquitinated protein and a viral OTU domain-containing protein or an OTU domain-containing fragment thereof, and (b) measuring the amount of ubiquitinated protein, wherein an alteration in the amount of ubiquitinated protein relative to a negative control (e.g., a composition comprising ubiquitinated protein and a viral OTU domain-containing viral protein or an OTU domain-containing fragment thereof not contacted with the compound) or a predetermined reference range indicates that the compound modulates the deubiquitination activity of the viral OTU domain-containing protein.

In a specific embodiment, the invention provides methods for identifying a compound that reduces or inhibits the deubiquitination activity of a viral OTU domain-containing protein, the methods comprising: (a) contacting a compound with a composition comprising ubiquitinated protein and a viral OTU domain-containing protein or an OTU domain-containing fragment thereof; and (b) measuring the amount of ubiquitinated protein, wherein an increase in the amount of ubiquitinated protein relative to a negative control (e.g., a composition comprising ubiquitinated protein and an viral OTU domain-containing protein or an OTU domain-containing fragment thereof not contacted with the compound) or a predetermined reference range indicates that the compound reduces or inhibits the deubiquitination activity of the viral OTU domain-containing protein.

In one embodiment, the invention provides methods for identifying a compound that reduces or inhibits the deubiquitination activity of a viral OTU domain-containing protein or an OTU domain-containing fragment thereof, the methods comprising: (a) contacting a compound with a composition comprising an artificial substrate that mimics the ubiquitin cleavage and a viral OTU domain-containing protein or OTU domain-containing fragment thereof; and (b) measuring the amount of cleavage of the artificial substrate, wherein a decrease in the cleavage of the artificial substrate relative to a negative control (e.g., the composition comprising an artificial substrate that mimics the ubiquitin cleavage and the viral OTU domain-containing protein or OTU domain-containing fragment thereof not contacted with the compound) or a predetermined reference range indicates that the compound reduces or inhibits the deubiquitination activity of the viral OTU domain-containing protein or OTU domain-containing fragment thereof. In certain embodiments, the artificial substrate is a small synthetic fluorogenic substrate, such as AMC or AFC, that incorporates the C-terminal four (or six) residues found in Ub and ISG15 (LRGG) or (LRLRGG) (SEQ ID NO:1). (Lindner, H et al. J Virol. December 2005 Vol 79 p 15199-15208), (Blakirev, M et al, J Virol, June 2002, Vol 76 p 6323-6331). In other embodiments, the artificial substrate has DABCYL and EDANS moieties on opposite ends of a 12-(or other) mer peptide that can be detected by FRET (as used in: Barretto et al, J Virol, December 2005, Vol 79 p 15189-15198), in which such peptide has the cleavage site of interest (e.g., LRLRGG) (SEQ ID NO:1).

In another embodiment, the invention provides methods for identifying a compound that reduces or inhibits the deubiquitination activity of a viral OTU domain-containing protein or an OTU domain-containing fragment thereof, the methods comprising: (a) contacting a compound with an ubiquitin-fluorogenic substrate (such as, e.g., ubiquitin-AMC or ubiquitin-AFC available from Boston Biochem, Inc., Cambridge, Mass.), and a viral OTU domain-containing protein or an OTU domain-containing fragment thereof; and (b) measuring the fluorescence of the mixture, wherein a decrease in the fluorescence relative to a negative control (e.g., the composition comprising an ubiquitin-fluorogenic substrate and the viral OTU domain-containing protein or OTU domain-containing fragment thereof not contacted with the compound) or a predetermined reference range indicates that the compound reduces or inhibits the ubiquitination activity of the viral OTU domain-containing protein or OTU domain-containing fragment thereof.

In some embodiments, compounds identified as inhibitors of the deISGylation and/or deubiquitination activity of a viral OTU domain-containing protein are further screened in a series of secondary assays designed to select for the ability to specifically inhibit viral replication. The methods of the invention further provide for the synthesis of novel compounds based on the identified inhibitors. The novel compounds are designed using structure activity relationship analyses combined with molecular modeling approaches. The novel compounds represent compounds optimized for their ability to inhibit viral replication while maintaining low toxicity with respect to eukaryotic cells, preferably mammalian cells. In some embodiments, compounds are identified that selectively inhibit viral OTU domain-containing proteins but not cellular OTU domain-containing proteins based on the fact that the viral OTU domain-containing protein deconjugates ISG15 conjugates and ubiquitinated proteins but the cellular OTU domain-containing proteins have only Ub deconjugation activity. In some embodiments, a compound is identified that reduces or inhibits the deubiquitination and/or deISGylation activity of a viral OTU domain-containing protein but not the deubiquitination activity of a cellular OTU domain-containing protein.

The compounds screened and identified by the methods of the invention include, but are not limited to, peptides; peptoids; random biooligomers; diversomers such as hydantoins, benzodiazepines and dipeptides; vinylogous polypeptides; nonpeptidal peptidomimetics; oligocarbamates; peptidyl phosphonates; nucleic acids (e.g., RNAi and antisense); antibodies; carbohydrates; and small molecules. In certain embodiments, the compound is an attenuated virus mutant.

In specific embodiments, the compounds of the invention are useful as inhibitors of the deISGylation activity and/or deubiquitination activity of a viral OTU domain-containing protein. In preferred embodiments, the compounds of the invention exhibit specificity for viral OTU domain-containing proteins compared to cellular OTU domain-containing proteins. In a specific embodiment, a compound of the invention is an inhibitor of viral replication. In another embodiment, a compound of the invention exhibits low cytotoxicity in eukaryotic cells, preferably mammalian cells. In one embodiment, a compound of the invention reduces or inhibits a viral infection. In a specific embodiment, a compound eliminates or reduces the amount of virus by 75%, 80%, 85%, 90%, 95%, 98%, 99%, 75-99.5%, 85-99.5%, or 90-99.8% in a subject as determined by an assay described herein or known to one of skill in the art. Accordingly, the compounds of the invention are useful in methods of preventing, treating and/or managing viral infections. In a particular embodiment, a compound of the invention is useful in preventing, treating and/or managing a viral infection caused by a strain of virus that exhibits resistance to other antiviral agents.

The present invention provides compositions comprising a compound identified in accordance with the methods of the invention or a pharmaceutically acceptable salt thereof. In some embodiments, the invention provides compositions (including pharmaceutical compositions) comprising a compound and a pharmaceutically acceptable carrier, excipient, or diluent. In certain embodiments, the invention provides a pharmaceutical composition comprising an effective amount of a compound and a pharmaceutically acceptable carrier, excipient, or diluent. The pharmaceutical compositions are suitable for veterinary and/or human administration.

The present invention also provides kits comprising a compound of the invention.

3.1 Definitions

As used herein, the term "about" or "approximately" when used in conjunction with a number refers to any number within 1, 5 or 10% of the referenced number.

As used herein, the phrase "cysteine protease" refers to a protein or peptide with a protease, peptidase or isopeptidase activity, which is catalyzed in part by a conserved cysteine residue. A catalytic triad may be formed by the cysteine in cooperation with a histidine residue and an aspartic acid residue.

As used herein, the term "deISGylation" refers to the removal of ISG15 from conjugated peptides and proteins through a protease, peptidase, or isopeptidase activity of a deISGylating enzyme. In one embodiment, the protease activity is a peptidase activity. In another embodiment, the protease activity is an isopeptidase activity. In some embodiments, a protein with deISGylating activity can process a pro-ISG15 protein into its mature form.

As used herein, the term "deNeddylation" refers to the removal of Nedd8 molecules from conjugated peptides and proteins through a protease, peptidase or isopeptidase activity of a deNeddylating enzyme. In one embodiment, the protease activity is a peptidase activity. In another embodiment, the protease activity is an isopeptidase activity. In some embodiments, a protein with deNeddylation activity can process a pro-Nedd8 protein into its mature form.

As used herein, the term "deubiquitinating (DUB) enzyme(s)" refers to an enzyme of the DUB superfamily of proteases, and which are specific for ubiquitin. DUB enzymes are known to have one or both of the activities of cleaving the C-terminus of ubiquitin to generate their mature forms or removing ubiquitin from conjugated peptides or proteins through a protease, peptidase or isopeptidase activity. In one embodiment, the protease activity is a peptidase activity. In another embodiment, the protease activity is an isopeptidase activity.

As used herein, the term "deubiquitination" refers to the removal of ubiquitin molecules from conjugated peptides and proteins through a protease, peptidase or isopeptidase activity of a deubiquitinating enzyme. In one embodiment, the protease activity is a peptidase activity. In another embodiment, the protease activity is an isopeptidase activity. In some embodiments, a protein with deubiquitinating activity can process an immature ubiquitin protein into its mature form.

As used herein, the terms "disease" and "disorder" are used interchangeably to refer to a condition in a subject. In some embodiments, the condition is a viral infection. In certain embodiments, the condition is a disease in a subject which benefits from inducing an immune response in the subject by administering a mutated virus. Non-limiting examples of such conditions include cancer, bacterial infections, parasitic infections, fungal infections and viral infections.

As used herein, the term "effective amount" in the context of administering a therapy to a subject refers to the amount of a therapy which is sufficient to have a prophylactic and/or therapeutic effect alone or in combination with another therapy. In specific embodiments, the term "effective amount" in the context of administering a therapy to a subject refers to the amount of a therapy which is sufficient to achieve one, two, three, or more or all of the following effects: (i) to reduce and/or ameliorate the severity of a condition (e.g., a viral infection or a condition or symptom associated therewith, or a condition in which an attenuated virus can be used as a vector to induce an immune response to a particular antigen associated with the condition); (ii) to reduce the duration of a condition (e.g., a viral infection or a condition or symptom associated therewith, or a condition in which an attenuated virus can be used as a vector to induce an immune response to a particular antigen associated with the condition); (iii) prevent the advancement of a condition (e.g., a viral infection or a condition or symptom associated therewith, or a condition in which an attenuated virus can be used as a vector to induce an immune response to a particular antigen associated with the condition) (iv) cause regression of a condition (e.g., a viral infection or a condition or symptom associated therewith, or a condition in which an attenuated virus can be used as a vector to induce an immune response to a particular antigen associated with the condition); (v) prevent the recurrence, development, or onset of one or more symptoms associated with a condition (e.g., a viral infection or a condition or symptom associated therewith, or a condition in which attenuated viruses can be used as a vector to induce an immune response to a particular antigen associated with the condition); (vi) reduce the titer of a virus; and/or (vii) enhance or improve the prophylactic and/or therapeutic effect(s) of another therapy. In another specific embodiment, an effective amount of a therapy of the invention reduces cellular death, reduces organ failure, reduces hospitalization of subjects, reduces the length of hospitalization, reduces the duration of a viral infection or symptom associated therewith, reduces the spread of a virus or another pathogen from one cell, organ, tissue or subject to another cell, organ, tissue or subject, reduces the recurrence of viral infection and/or increases the survival of subjects.

As used herein, the term "effective amount" in the context of a disinfectant or household or industrial product refers to an amount of a compound which is sufficient to reduce the viral titer on a surface, or prevent or inhibit the replication of a virus on a surface.

As used herein, the term "epitopes" refers to sites or fragments of a polypeptide or protein having antigenic or immunogenic activity in an animal, preferably in a mammal, and most preferably in a human. An epitope having immunogenic activity is a site or fragment of a polypeptide or protein that elicits an antibody response in an animal. An epitope having antigenic activity is a site or fragment of a polypeptide or protein to which an antibody immunospecifically binds as determined by any method well-known to one of skill in the art, for example by immunoassays.

As used herein, the terms "ISG15 conjugate" or "ISGylated protein" are used interchangeably to refer to a peptide, protein, polypeptide, or other proteinaceous substance to which one or more ISG15 moieties are attached.

As used herein, the term "fragment" in the context of a proteinaceous agent refers to a peptide or polypeptide comprising an amino acid sequence of at least 2 contiguous amino acid residues, at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, at least 250 contiguous amino acid residues, at least 300 contiguous amino acid residues, at least 300 contiguous amino acid residues, at least 500 contiguous amino acid residues, at least 750 contiguous amino acid residues, at least 1000 contiguous amino acid residues, or between 8 to 75 contiguous amino acid residues, between 25 to 150 contiguous amino acid residues, or between 25 to 300 contiguous amino acid residues of the amino acid sequence of a peptide, polypeptide or protein. In one embodiment, a fragment of a full-length protein retains an activity of the full-length protein, e.g., deISGylation activity. In another embodiment, the fragment of the full-length protein does not retain an activity of the full-length protein, e.g., deISGylation. In a specific embodiment, a fragment of CCHFV L protein or DUGV L protein lacks deISGylation activity and/or deubiquitination activity but retains polymerase activity. In another embodiment, a fragment of CCHFV L protein or DUGV L protein lacks deISGylation activity and/or deubiquitination activity but retains limited polymerase activity. In another embodiment, a fragment of an arterivirus nsp2 protein lacks deISGylation activity and/or deubiquitination activity but the replicase polyprotein remains functional.

As used herein, the term "fragment" in the context of a nucleic acid refers to a nucleic acid comprising an nucleic acid sequence of at least 2 contiguous nucleotides, at least 5 contiguous nucleotides, at least 10 contiguous nucleotides, at least 15 contiguous nucleotides, at least 20 contiguous nucleotides, at least 25 contiguous nucleotides, at least 30 contiguous nucleotides, at least 35 contiguous nucleotides, at least 40 contiguous nucleotides, at least 50 contiguous nucleotides, at least 60 contiguous nucleotides, at least 70 contiguous nucleotides, at least contiguous 80 nucleotides, at least 90 contiguous nucleotides, at least 100 contiguous nucleotides, at least 125 contiguous nucleotides, at least 150 contiguous nucleotides, at least 175 contiguous nucleotides, at least 200 contiguous nucleotides, at least 250 contiguous nucleotides, at least 300 contiguous nucleotides, at least 350 contiguous nucleotides, at least 380 contiguous nucleotides, or between 8 to 75 contiguous nucleotides, between 25 to 150 contiguous nucleotides, or between 25 to 300 contiguous nucleotides of the nucleic acid sequence encoding a peptide, polypeptide or protein. In one embodiment, a fragment of a nucleic acid encodes a peptide or polypeptide that retains an activity of the full-length protein, e.g., deISGylation activity. In another embodiment, the fragment of the nucleic acid encodes a peptide or polypeptide that does not retain an activity of the full-length protein, e.g., deISGylation. In a specific embodiment, a nucleic acid fragment encodes a CCHFV L protein or DUGV L protein that lacks deISGylation activity and/or deubiquitination activity but retains polymerase activity. In another embodiment, a nucleic acid fragment encodes a CCHFV L protein or DUGV L protein that lacks deISGylation activity and/or deubiquitination activity but retains limited polymerase activity. In another embodiment, a nucleic acid fragment encodes an arterivirus nsp2 protein that lacks deISGylation activity and/or deubiquitination activity but the replicase polyprotein remains functional.

As used herein, the phrase "heterologous sequence" refers to any nucleic acid sequence or protein, polypeptide or peptide sequence that is not normally found in nature or not normally associated in nature with a nucleic acid, protein, polypeptide or peptide sequence of interest. For example, a "heterologous sequence" may refer to a sequence derived from a different species.

As used herein, the term "in combination," in the context of the administration of two or more therapies to a subject, refers to the use of more than one therapy (e.g., more than one prophylactic agent and/or therapeutic agent). The use of the term "in combination" does not restrict the order in which therapies are administered to a subject with a condition (e.g., a viral infection or a condition or symptom associated therewith). A first therapy (e.g., a first prophylactic or therapeutic agent) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject with a condition (e.g., a viral infection or a condition or symptom associated therewith).

As used herein, the term "infection" means the invasion by and presence of a virus in a cell or a subject. In one embodiment, an infection is an "active" infection, i.e., one in which the virus is replicating in a cell or a subject. Such an infection is characterized by the spread of the virus to other cells, tissues, and/or organs, from the cells, tissues, and/or organs initially infected by the virus. An infection may also be a latent infection, i.e., one in which the virus is not replicating. In one embodiment, an infection refers to the pathological state resulting from the presence of the virus in a cell or a subject, or by the invasion of a cell or subject by the virus.

As used herein, the phrase "interferon antagonist activity" refers to a protein or polypeptide, or fragment, derivative, or analog thereof that reduces or inhibits the cellular interferon immune response. In particular, a protein or polypeptide, or fragment, derivative, or analog thereof that has interferon antagonist activity reduces or inhibits interferon expression and/or activity. A viral protein or polypeptide with interferon antagonist activity may preferentially affect the expression and/or activity of one or two types of interferon (IFN). In one embodiment, the expression and/or activity of IFN-α is affected. In another embodiment, the expression and/or activity of IFN-β is affected. In certain embodiments, the expression and/or activity of IFN-α and/or IFN-β is reduced at least 25%, at least 50%, at least 75%, at lease 95%, or 5-10%, 10-20%, 20-30%, 30-40%, 40-50%, 50-60%, 60-70%, 70-80%, 80-90% or more by a protein, polypeptide, virus, etc. with an interferon antagonist activity when compared to a control (e.g., PBS or a protein without interferon antagonist activity) in IFN-competent systems, e.g., a wild-type cell or animal under the same conditions. In certain embodiments, the expression and/or activity of IFN-α and/or IFN-β is reduced approximately 1 to approximately 100 fold, approximately 5 to approximately 80 fold, approximately 20 to approximately 80 fold, approximately 1 to approximately 10 fold, or approximately 1 to approximately 5 fold, or approximately 40 to approximately 80 fold, or 1, 2, 3, 4, 5, 7, 10, 15, 20, 25, 30, 35, 40, 45, 50, 55, 60, 65, 70, 75, 80, 85, 90, 95 or 100 fold by a protein, polypeptide, virus, etc. with an interferon antagonist activity when compared to a control (e.g., PBS or a protein without interferon antagonist activity) in IFN-competent systems under the same conditions.

As used herein, the phrases "IFN deficient systems" or "IFN-deficient substrates" refer to systems, e.g., cells, cell lines and animals, such as pigs, mice, chickens, turkeys, rabbits, rats, etc., which do not produce IFN or produce low levels of IFN (i.e., a reduction in IFN expression of 5-10%, 10-20%, 20-30%, 30-40%, 40-50%, 50-60%, 60-70%, 70-80%, 80-90% or more when compared to IFN-competent systems under the same conditions), do not respond or respond less efficiently to IFN, and/or are deficient in the activity of one or more antiviral genes induced by IFN.

As used herein, the phrase "IFN inducing phenotype" refers to a phenotype whereby a virus demonstrates an increased cellular interferon response compared to a wild-type virus, which typically inhibits or reduces cellular interferon mediated responses.

As used herein, the term "ISG15" refers to a ubiquitin-like modifier encoded by an interferon stimulated gene. In some embodiments, ISG15 is induced by IFN-α. In some embodiments, it is induced by IFN-β. In other embodiments, ISG15 is induced by another stress-related signal. ISG15 has roles in, among other things, the innate immune response, regulation of interferon signaling, pregnancy, and cancer. ISG15 contains two ubiquitin-like domains connected to one another, and can become covalently conjugated to proteins in a manner similar to ubiquitin and other ubiquitin-like modifiers. In some embodiments, ISG15 refers to the immature precursor form, which is a ~17 kDa protein of 165 amino acids. In some embodiments, ISG15 refers to the mature form, formed by the removal of 8 amino acids from the carboxyl terminus of the precursor. In some embodiments, mature ISG15 lacks an amino-terminal methionine. In certain embodiments, ISG15 refers to the form of ISG15 that has at its carboxyl terminus the amino acids Leu Arg Leu Arg Gly Gly (LRLRGG) (SEQ ID NO:1). In some embodiments, the LRLRGG (SEQ ID NO:1) motif plays a role in substrate recognition and specific cleavage by viral OTU domain-containing proteins. In some embodiments, ISG15 does not exist in a precursor form. In some embodiments, ISG15 is conjugated to a protein. In some embodiments, ISG15 is found in its free form. In some embodiments, free ISG15 is extracellular. In some embodiments, ISG15 is found in serum. In certain embodiments, the ISG15 activating enzyme (E1) is UBE1L. In some embodiments, the conjugating enzyme (E2) is UBCH8 (human) or UBCM8 (mouse). In some embodiments, ISGylation is accomplished with elements of the ubiquitination machinery. In some embodiments, the ISG15 specific protease is UBP43/USP18. In some embodiments, deISGylation is accomplished by UBP43. In other embodiments, deISGylation is accomplished by an OTU domain or a viral OTU domain or OTU domain-containing protein. The nucleotide and/or amino acid sequences of ISG15 can be found in the literature or public databases, or the nucleotide and/or amino acid sequences can be determined using cloning and sequencing techniques known to one of skill in the art. Non-limiting examples of nucleotide and amino acid sequences of ISG15 are listed in Table 1, infra.

TABLE 1

ISG15 Sequences From Various Species

| Species | gene ID | exemplary cDNA sequence (GenBank Accession No.) | exemplary amino acid sequence (GenBank Accession No.) |
|---|---|---|---|
| human | 9636 | BC009507 | AAH09507 |
| mouse | 53606 | NM_015783 | NP_056598.1 |
| cow | 281871 | NM_174366 | NP_776791.1 |
| sheep | 443057 | NM_001009735 | NP_001009735 |
| dog | 479575 | XM_536714 | XP_536714 |

As used herein the term "ISGylation" refers to the covalent attachment of ISG15 to a protein or a peptide. ISG15 is a ubiquitin-like modifier (Ubl). Other Ubls include Nedd8, SUMO, Atg8, and others yet to be defined by either their sequence homology to ubiquitin or by homology with regard to their mode of conjugation to targets.

As used herein, the term "isolated," in the context of viruses, refers to a virus that is derived from a single parental virus. A virus can be isolated using routine methods known to one of skill in the art including, but not limited to, those based on plaque purification and limiting dilution.

As used herein, the term "isolated" in the context of a compound other than a proteinaceous agent or a nucleic acid refers to a compound that is substantially free of chemical precursors or other chemicals when chemically synthesized. The phrase "substantially free of chemical precursors or other chemicals" includes preparations of a compound that have less than about 30%, 25%, 20%, 10%, 5%, or 1% (by dry weight) of chemical precursors or other chemicals. In a specific embodiment, the compound is about 60%, preferably 65%, 70%, 75%, 80%, 85%, 90% or 99% free of other different compounds. In another specific embodiment, a compound disclosed herein is isolated.

As used herein, the term "isolated" in the context of a proteinaceous agent (e.g., a protein, polypeptide or peptide) refers to a proteinaceous agent which is substantially free of cellular material or contaminating proteins from the cell or tissue source from which it is derived, or substantially free of chemical precursors or other chemicals when chemically synthesized. The phrase "substantially free of cellular material" includes preparations of a proteinaceous agent in which the proteinaceous agent is separated from cellular components of the cells from which it is isolated or recombinantly produced. Thus, a proteinaceous agent that is substantially free of cellular material includes preparations of a proteinaceous agent having less than about 30%, 25%, 20%, 15%, 10%, or 5% (by dry weight) of a contaminating protein (e.g., a heterologous protein, polypeptide, or peptide). When the proteinaceous agent is recombinantly produced, it is also preferably substantially free of culture medium, i.e., culture medium represents less than about 20%, 15%, 10%, or 5% of the volume of the protein preparation. When the proteinaceous agent is produced by chemical synthesis, it is preferably substantially free of chemical precursors or other chemicals, i.e., it is separated from chemical precursors or other chemicals which are involved in the synthesis of the proteinaceous agent. Accordingly, such preparations of a proteinaceous agent have less than about 30%, 20%, 10%, 5% (by dry weight) of chemical precursors or compounds other than the proteinaceous agent of interest. In a specific embodiment, a proteinaceous agent disclosed herein is isolated.

As used herein, the term "isolated" in the context of a nucleic acid (e.g., DNA, RNA, cDNA, etc.) refers to a nucleic acid that is substantially free of cellular material or contaminating nucleic acids from the cell or tissue source from which it is derived, or substantially free of chemical precursors or other chemicals when chemically synthesized. The phrase "substantially free of cellular material" includes preparations of a nucleic acid in which the nucleic acid is separated from cellular components of the cells from which it is isolated or produced. Thus, a nucleic acid that is substantially free of cellular material includes preparations of a nucleic acid having less than about 30%, 25%, 20%, 15%, 10%, or 5% (by dry weight) of a contaminating nucleic acid (e.g., a heterologous nucleic acid). When the nucleic acid is produced by chemical synthesis, it is preferably substantially free of chemical precursors or other chemicals, i.e., it is separated from chemical precursors or other chemicals which are involved in the synthesis of the nucleic acid. Accordingly, such preparations of a nucleic acid have less than about 30%, 20%, 10%, 5% (by dry weight) of chemical precursors or compounds other than the nucleic acid of interest. In a specific embodiment, a nucleic acid agent disclosed herein is isolated.

As used herein, the term "library" refers to a plurality of compounds. A library can be a combinatorial library, e.g., a collection of compounds synthesized using combinatorial chemistry techniques, or a collection of unique chemicals of low molecular weight (less than 1000 daltons).

As used herein, the term "limited polymerase activity" refers to 25% or less, 15% or less, 10% or less, 5% or less, or 5 to 25% of the polymerase activity of the wild-type protein.

As used herein, the terms "manage," "managing," and "management," in the context of the administration of a therapy to a subject, refer to the beneficial effects that a subject derives from a therapy, which does not result in a cure of the disease. In certain embodiments, a subject is administered one or more therapies to "manage" a disease so as to prevent the progression or worsening of the disease.

As used herein, the phrase "multiplicity of infection" or "MOI" is the average number of virus per infected cell. The MOI is determined by dividing the number of virus added (ml added×PFU) by the number of cells added (ml added×cells/ml).

As used herein, the terms "Nedd8 conjugate" or "Neddylated protein" are used interchangeably to refer to a peptide, protein, polypeptide, or other proteinaceous substance to which one or more Nedd8 moieties are attached.

As used herein, the phrase "NF-κB antagonist activity" refers to a protein or polypeptide, or fragment, derivative, or analog thereof that reduces or inhibits the NF-κB pathway. In particular, a protein or polypeptide, or fragment, derivative, or analog thereof that has NF-κB antagonist activity reduces or inhibits expression of components of the NF-κB complex or NF-κB activity, including NF-κB signaling. In one embodiment, an NF-κB antagonist activity results in decreased activation of an NF-κB responsive promoter. In another embodiment, an NF-κB antagonist activity results in decreased NF-κB activation as measured by a decrease in p65 nuclear translocation. In certain embodiments, the activity of NF-κB is reduced at least 25%, at least 50%, at least 75% percent, or at least 95%, or 5-10%, 10-20%, 20-30%, 30-40%, 40-50%, 50-60%, 60-70%, 70-80%, 80-90% or more by a protein, polypeptide, virus, etc. with an NF-κB antagonist activity when compared to a control (e.g., PBS or a protein without NF-κB antagonist activity). In certain embodiments, the activity of NF-κB is reduced approximately 1 to approximately 100 fold, approximately 5 to approximately 80 fold, approximately 20 to approximately 80 fold, approximately 1 to approximately 10 fold, or approximately 1 to approximately 5 fold, or approximately 40 to approximately 80 fold, or 1, 2, 3, 4, 5, 7, 10, 15, 20, 25, 30, 35, 40, 45, 50, 55, 60, 65, 70, 75, 80, 85, 90, 95 or 100 fold by a protein, polypeptide, virus, etc. with an NF-κB antagonist activity when compared to a control (e.g., PBS or a protein without NF-κB antagonist activity) under the same conditions.

As used herein, the terms "non-responsive" and "refractory" describe subjects or patients treated with a currently available therapy for a viral infection or condition associated therewith, which is not clinically adequate to eradicate such infection or condition and/or relieve one or more symptoms thereof. Typically, such patients suffer from severe, persistently active viral infection and require additional therapy to ameliorate the symptoms associated with the infection.

As used herein, the phrase "Ovarian tumor-related protease (OTU) domain" and "OTU domain" refer to an amino acid motif defined by a bipartite pattern of conserved residues around the catalytic cysteine and histidine: sDsxCh[A/C/F/L/I/M/V/W/Y/T/S/G]tshtx$_n$H[F/Y/W]t (SEQ ID NO:2), where: s, small residue; h, hydrophobic residue; t, residue with a high β-turn-forming propensity.

As used herein, the term "pool" in the context of a "pool of compounds," i.e., for use in a high throughput assay, refers to a number of compounds in excess of one compound. In certain embodiments, a pool of compounds is a number of compounds in the range of 1-5, 5-10, 10-25, 25-50, 50-100, 100-150, 150-200, 250-300, 350-400, 200-2,000, 500-2,000, 1,000-5,000 compounds.

As used herein, the term "OTU domain-containing fragment" in the context of a viral OTU domain-containing protein refers to a fragment of a viral OTU domain-containing protein. In a specific embodiment, the fragment retains the OTU domain. In certain embodiments, a fragment of a viral OTU domain-containing protein is used in the assays described herein.

As used herein, the term "premature human infant" refers to a human infant born at less than 37 weeks of gestational age.

As used herein, the term "human infant" refers to a newborn to 1 year old year human.

As used herein, the term "human child" refers to a human that is 1 year to 18 years old.

As used herein, the term "human adult" refers to a human that is 18 years or older.

As used herein, the term "elderly human" refers to a human 65 years or older.

As used herein, the terms "prevent," "preventing" and "prevention" in the context of the administration of a therapy to a subject refer to the inhibition of the recurrence, development or onset of a condition (e.g., a viral infection or a condition or symptom associated therewith, or a condition in which an attenuated virus can be used as a vector to induce an immune response to a particular antigen associated with the condition), or the prevention of the recurrence, onset, or development of one or more symptoms of a condition (e.g., a viral infection or a condition or symptom associated therewith, or a condition in which an attenuated virus can be used as a vector to induce an immune response to a particular antigen associated with the condition) in a subject resulting from the administration of a therapy, or the administration of a combination of therapies.

As used herein, the term "previously determined reference range" refers to a reference range for the readout of a particular assay. In a specific embodiment, the term refers to a reference range for deISGylation activity in an assay described herein. In some embodiments, each laboratory establishes its own reference range for each particular assay. In a preferred embodiment, at least one positive control and at least one negative control are included in each batch of compounds analyzed.

As used herein, the terms "prophylactic agent" and "prophylactic agents" refer to any agent(s) which can be used in the prevention of a condition (e.g., a viral infection or a condition or symptom associated therewith). In a specific embodiment, a prophylactic agent is an agent which is known to be useful to or has been or is currently being used to prevent or impede the onset, development, progression and/or severity of a viral infection or a condition or symptom associated therewith.

As used herein, the term "prophylactically effective amount" refers to the amount of a therapy (e.g., prophylactic agent) which is sufficient to result in the prevention of the development, recurrence, or onset of a condition (e.g., a viral infection or a condition or symptom associated therewith) or to enhance or improve the prophylactic effect(s) of another therapy (e.g., a prophylactic agent).

As used herein, the phrase "purified" in the context of viruses refers to a virus which is substantially free of cellular material and culture media from the cell or tissue source from which the virus is derived. The language "substantially free of cellular material" includes preparations of virus in which the virus is separated from cellular components of the cells from which it is isolated or recombinantly produced. Thus, virus that is substantially free of cellular material includes preparations of protein having less than about 30%, 25%, 20%, 15%, 10%, or 5% (by dry weight) of cellular protein (also referred to herein as a "contaminating protein"). The virus is also substantially free of culture medium, i.e., culture medium represents less than about 20%, 15%, 10%, or 5% of the volume of the virus preparation. A virus can be purified using routine methods known to one of skill in the art including, but not limited to, chromatography and centrifugation.

As used herein, the term "does not significantly reduce" refers to a 25% or less, 15% or less, 10% or less, 5% or less or 5 to 25% reduction.

As used herein, the term "small molecules" and analogous terms include, but are not limited to, peptides, peptidomimetics, amino acids, amino acid analogs, polynucleotides, polynucleotide analogs, nucleotides, nucleotide analogs, other organic and inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, organic or inorganic compounds having a molecular weight less than about 100 grams per mole, and salts, esters, and other pharmaceutically acceptable forms of such compounds. Salts, esters, and other pharmaceutically acceptable forms of such compounds are also encompassed.

As used herein, the terms "subject" or "patient" are used interchangeably. As used herein, the terms "subject" and "subjects" refer to an animal (e.g., birds, reptiles, and mammals), preferably a mammal including a non-primate (e.g., a camel, donkey, zebra, cow, pig, horse, goat, sheep, cat, dog, rat, and mouse) and a primate (e.g., a monkey, chimpanzee, and a human), and most preferably a human. In certain embodiments, the subject or patient has a viral infection. In certain embodiments, the subject or patient has a nairovirus infection. In certain embodiments, the subject or patient has an arterivirus infection. In certain embodiments, the subject or patient has a herpes virus infection.

In certain embodiments, the subject is a mammal which is 0 to 6 months old, 6 to 12 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In certain embodiments, the patient is a human at risk for a virus infection. In certain embodiments, the patient is a human with a virus infection. In certain embodiments, the patient is a human 0 to 6 months old, 6 to 12 months old, 1 to 5 years old, 5 to 10 years old, 5 to 12 years old, 10 to 15 years old, 15 to 20 years old, 13 to 19 years old, 20 to 25 years old, 25 to 30 years old, 20 to 65 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In some embodiments, the subject is a human infant. In other embodiments, the subject is a human child. In other embodiments, the subject is a human adult. In yet other embodiments, the subject is an elderly human.

In certain embodiments, the subject is a pig at risk for a virus infection. In certain embodiments, the subject is a pig with a virus infection. In certain embodiments, the subject or patient is a pig 0 to 6 months old, 6 to 12 months old, 1 to 5 years old, 5 to 10 years old or 10 to 15 years old. The natural lifespan of a pig is 8-12 years.

In certain embodiments, the subject is a cow at risk for a virus infection. In certain embodiments, the subject is a cow with a virus infection. In certain embodiments, the subject or patient is a cow or bull 0 to 6 months old, 6 to 12 months old, 1 to 5 years old, 5 to 10 years old or 10 to 15 years old. The natural lifespan of a cow is 8-12 years.

In certain embodiments, the subject is a horse at risk for a virus infection. In certain embodiments, the subject is a horse with a virus infection. In certain embodiments, the subject or patient is a horse 0 to 6 months old, 6 to 12 months old, 1 to 5 years old, 5 to 10 years old, 10 to 15 years old or 15-25 years old. The natural lifespan of a horse is 15-25 years.

In certain embodiments, the subject is a sheep at risk for a virus infection. In certain embodiments, the subject or patient is a sheep 0 to 6 months old, 6 to 12 months old, 1 to 5 years old, 5-10 years old or 10 to 15 years old. The natural lifespan of a sheep is 10-15 years.

In certain embodiments, the subject is a goat at risk for a virus infection. In certain embodiments, the subject or patient is a goat 0 to 6 months old, 6 to 12 months old, 1 to 5 years old, 5-10 years old or 10 to 15 years old. The natural lifespan of a goat is 10-15 years.

In certain embodiments, the subject is a dog at risk for a virus infection. In certain embodiments, the subject is a dog with a virus infection. In certain embodiments, the subject or patient is a dog 0 to 6 months old, 6 to 12 months old, 1 to 5 years old, 5 to 10 years old or 10 to 15 years old. The natural lifespan of a dog is 10-15 years.

In certain embodiments, the subject is a cat at risk for a virus infection. In certain embodiments, the subject is a cat with a virus infection. In certain embodiments, the subject or patient is a cat 0 to 6 months old, 6 to 12 months old, 1 to 5 years old, 5 to 10 years old or 10 to 15 years old. The natural lifespan of a cat is 10-15 years.

In certain embodiments, the subject or patient is a primate, preferably a human, or another mammal, preferably a pig, cow, horse, sheep, goat, dog, or cat, but might be also a rodent, in an immunocompromised state or at risk for becoming immunocompromised. In certain embodiments, the subject or patient is recovering from immunosuppressive therapy. In certain embodiments, the subject or patient has or is at risk of getting cancer, AIDS, another virus, or a bacterial infection. In certain embodiments, the subject or patient is pregnant or likely to become pregnant.

As used herein, the terms "therapies" and "therapy" can refer to any protocol(s), method(s), compositions, formulations, and/or agent(s) that can be used in the prevention, treatment, management, and/or amelioration of a condition (e.g., a viral infection or a condition or symptom associated therewith, or a condition in which the attenuated viruses can be used as a vector to induce an immune response to a particular antigen associated with the condition). In certain embodiments, the terms "therapies" and "therapy" refer to biological therapy, supportive therapy, and/or other therapies useful in treatment, management, prevention, and/or amelioration of a condition (e.g., viral infection or a condition or symptom associated therewith, or a condition in which an attenuated virus can be used as a vector to induce an immune response to a particular antigen associated with the condition), known to one of skill in the art. In a specific embodiment, a therapy is a compound that reduces or inhibits the deISGylation activity and/or deubiquitination activity of an OTU domain-containing viral protein. In another embodiment, a therapy is an attenuated virus or an inactivated virus mutant.

As used herein, the term "synergistic," in the context of the effect of therapies, refers to a combination of therapies which is more effective than the additive effects of any two or more single therapies. In a specific embodiment, a synergistic effect of a combination of therapies permits the use of lower dosages of one or more of therapies and/or less frequent administration of said therapies to a subject with a condition (e.g., a viral infection). In certain embodiments, the ability to utilize lower dosages of therapies (e.g., prophylactic or therapeutic agents) and/or to administer said therapies less frequently reduces the toxicity associated with the administration of said therapies to a subject without reducing the efficacy of said therapies in the prevention or treatment of a condition (e.g., viral infection). In addition, a synergistic effect can result in improved efficacy of therapies (e.g., prophylactic or therapeutic agents) in the prevention or treatment of a condition (e.g., a viral infection). Finally, a synergistic effect of a combination of therapies (e.g., prophylactic or therapeutic agents) may avoid or reduce adverse or unwanted side effects associated with the use of any single therapy.

As used herein, the term "therapeutically effective amount" refers to the amount of a therapy, which is sufficient alone or in combination with another therapy to treat and or manage a condition (e.g., a viral infection, or a condition or symptom associated therewith, or a condition in which an attenuated virus can be used as a vector to induce an immune response to a particular antigen associated with the condition). In specific embodiments, the term "therapeutically effective amount" refers to the amount of a therapy which is sufficient to achieve one, two, three or more or all of the following effects: (i) reduce the severity of a condition (e.g., a viral infection, or a condition or symptom associated therewith, or a condition in which an attenuated virus can be used as a vector to induce an immune response to a particular antigen associated with the condition); (ii) reduce the duration of a condition (e.g., a viral infection or a condition or symptom associated therewith, or a condition in which an attenuated virus can be used as a vector to induce an immune response to a particular antigen associated with the condition); (iii) reduce the titer of virus or reduce the number of other pathogens; (iv) reduce or inhibit the spread of virus or another pathogen from one cell, tissue or organ to another cell, tissue or organ, or from one subject to another subject; (v) ameliorate one or more symptoms of a condition (e.g., a viral infection or a condition or symptom associated therewith, or a condition in which an attenuated virus can be used as a vector to induce an immune response to a particular antigen associated with the condition); (vi) prevent the advancement of a condition (e.g., a viral infection, or a condition or symptom associated therewith, or a condition in which an attenuated virus can be used as a vector to induce an immune response to a particular antigen associated with the condition); (vii) cause regression of a condition (e.g., a viral infection or a condition or symptom associated therewith, or a condition in which an attenuated virus can be used as a vector to induce an immune response to a particular antigen associated with the condition); or (viii) enhance or improve the therapeutic effect(s) of another therapy.

As used herein, the terms "therapeutic agent" and "therapeutic agents" refer to any agent(s) which can be used in the prevention, treatment, management and/or amelioration of a condition or a symptom thereof (e.g., a viral infection or a condition or symptom associated therewith, or a condition in which an attenuated virus can be used as a vector to induce an immune response to a particular antigen associated with the condition). In a specific embodiment, a therapeutic agent is an agent which is known to be useful for, or has been or is currently being used for the prevention, treatment, management, and/or amelioration of a viral infection or a condition or symptom associated therewith.

The term "tumor-associated antigen" as used herein refers to a molecule on a tumor cell that can be specifically recognized by immune T cells or antibodies. A tumor-associated antigen includes those present only on tumor cells (tumor specific antigens) as well as those present on normal cells but expressed preferentially or aberrantly on tumor cells (tumor associated antigens). Examples of tumor-associated antigens include, but are not limited to, antigens of sarcoids, prostate cancer, fibrosarcoma, self-differentiation antigens such as oncofetal, or differentiation, antigens which are expressed by malignant cells, including but not limited to oncofetal antigens such as carcinoembryonio antigens (CEA) of the colon, alpha-fetoprotein, the human antigenic counterpart or functional equivalent of the 175 kDa murine antigen of transitional cell bladder carcinomas, the melanoma associated antigen p97 or GD3, and differentiation antigens of human lung carcinomas such as L6 and L20.

As used herein, the terms "treat," "treatment," and "treating" refer in the context of administration of a therapy to a subject to the eradication or control of virus replication or the replication of another pathogen (e.g., a bacteria), the reduction in the titer of a virus, the reduction in the numbers of a pathogen, the reduction or amelioration of the progression, severity and/or duration of a condition (e.g., a virus infection or a condition or symptom associated therewith, or a condition in which an attenuated virus can be used as a vector to induce an immune response to a particular antigen associated with the condition), prevents the advancement of a condition (e.g., a virus infection or a condition or symptom associated therewith, or a condition in which an attenuated virus can be used as a vector to induce an immune response to a particular antigen associated with the condition), or the amelioration of one or more symptoms resulting from the administration of one or more therapies. In certain embodiments, treatment with a therapy reduces cellular death, reduces organ failure, reduces hospitalization, reduces the length of hospitalization, reduces the recurrence of viral infection, reduce the spread of a virus or another pathogen from one cell, organ, tissue or subject to another cell, organ, tissue or subject, and/or increases survival of subjects.

As used herein, the phrase "TNFα antagonist activity" refers to a protein or polypeptide, or fragment, derivative, or analog thereof that reduces or inhibits a cellular immune response that occurs as a result of the TNFα pathway. In particular, a protein or polypeptide, or fragment, derivative, or analog thereof that has TNFα antagonist activity reduces or inhibits TNFα expression and/or activity, including TNFα signaling. In one embodiment, a TNFα antagonist activity results in decreased activation of an NF-κB responsive promoter after TNFα treatment. In another embodiment, a TNFα antagonist activity results in decreased NF-κB activation as measured by a decrease in p65 nuclear translocation. In certain embodiments, the expression and/or activity of TNFα is reduced at least 25%, at least 50%, at least 75%, or at least 95% or 5-10%, 10-20%, 20-30%, 30-40%, 40-50%, 50-60%, 60-70%, 70-80%, 80-90% or more by a protein, polypeptide, virus, etc. with a TNFα antagonist activity when compared to a control (e.g., PBS or a protein without TNFα antagonist activity). In certain embodiments, the expression and/or activity of TNFα is reduced approximately 1 to approximately 100 fold, approximately 5 to approximately 80 fold, approximately 20 to approximately 80 fold, approximately 1 to approximately 10 fold, or approximately 1 to approximately 5 fold, or approximately 40 to approximately 80 fold, or 1, 2, 3, 4, 5, 7, 10, 15, 20, 25, 30, 35, 40, 45, 50, 55, 60, 65, 70, 75, 80, 85, 90, 95 or 100 fold by a protein, polypeptide, virus, etc. with a TNFα antagonist activity when compared to a control (e.g., PBS or a protein without TNFα antagonist activity) under the same conditions. In certain embodiments, NF-κB activity is reduced at least 25%, at least 50%, at least 75%, or at least 90% or 5-10%, 10-20%, 20-30%, 30-40%, 40-50%, 50-60%, 60-70%, 70-80%, 80-90% or more by a protein, polypeptide, virus, etc. with a TNFα antagonist activity when compared to a control (e.g., PBS or a protein without TNFα antagonist activity). In certain embodiments, the activity of NF-κB is reduced approximately 1 to approximately 100 fold, approximately 5 to approximately 80 fold, approximately 20 to approximately 80 fold, approximately 1 to approximately 10 fold, or approximately 1 to approximately 5 fold, or approximately 40 to approximately 80 fold, or 1, 2, 3, 4, 5, 7, 10, 15, 20, 25, 30, 35, 40, 45, 50, 55, 60, 65, 70, 75, 80, 85, 90, 95 or 100 fold by a protein, polypeptide, virus, etc. with a TNFα antagonist activity when compared to a control (e.g., PBS or a protein without TNFα antagonist activity) under the same conditions.

As used herein, "ubiquitination" refers to the covalent attachment of ubiquitin to a target protein or peptide. Ubiquitin can be covalently attached to a target protein or peptide by an enzymatic cascade involving the activity of proteins designated E1, E2, and E3. Attachment can also be catalyzed independent of one or all such activities. The attachment may be reversible. In some embodiments, ubiquitin is attached at several sites on a target. In some embodiments, a single ubiquitin is attached at a particular position (mono-ubiquitin). In other embodiments, ubiquitin forms a chain on the target residue (poly-ubiquitin). In some embodiments, ubiquitin is covalently conjugated to a lysine residue of the target. In other embodiments, ubiquitin is conjugated to the terminal amino group of a peptide or protein. The attachment/removal of ubiquitin is referred to herein as ubiquitination/deubiquitination. In some embodiments, ubiquitin requires carboxyl-terminal processing in order to become active. In other embodiments, ubiquitin is a recombinant and is already active.

As used herein, the terms "ubiquitin conjugate" or "ubiquitinated protein" are used interchangeably to refer to a peptide, protein, polypeptide, or other proteinaceous substance to which one or more ubiquitin moieties are attached.

As used herein, the phrase "ubiquitin-like modifier (Ubl)" refers to a protein or polypeptide that is similar to ubiquitin, either by virtue of its sequence or its function in becoming covalently attached to a protein or peptide target. Attachment can be through an enzymatic cascade involving the activity of proteins designated E1, E2, and E3. Attachment can also be catalyzed independent of one or all such activities. The attachment may be reversible. In some embodiments, the Ubl is covalently conjugated to a lysine residue of the target. In other embodiments, the Ubl is conjugated to the terminal amino group of a peptide or protein. Ubls include ISG15, Nedd8, SUMO, Atg8, and others yet to be defined by either their sequence homology to ubiquitin or by homology with regard to their mode of conjugation to targets. The attachment/removal of Ubls to/from a target is referred to herein as ISGylation/deISGylation (for ISG15); Neddylation/deNeddylation (for Nedd8); SUMOylation/deSUMOylation (for SUMO, which may refer to poly-SUMO chains), etc. In some embodiments, the Ubl requires carboxyl-terminal processing in order to become active. In other embodiments, the Ubl is already present in an active form.

As used herein, the phrase "wild-type virus" refers to the types of a virus that are prevalent, circulating naturally and producing typical outbreaks of disease.

4. DESCRIPTION OF THE FIGURES

FIG. 1. Cloning, sequencing and expression of the full length CCHFV-L protein. (A) The upper panel shows the approximate location of the OTU and RdRp motifs in the L protein. The middle panel shows the amino acid sequences of the CCHFV and DUGV OTU domain (SEQ ID NOS:9 and 10). At the bottom, the conserved amino acids that define the OTU domain are shown (SEQ ID NO:11). The closed triangles indicate the catalytic residues (Cys40 and His151). (B) 293T cells were transfected with full length CCHFV-L or empty (HA) plasmids. Lane 2 shows expression of the full CCHFV-L tagged with the HA epitope at the amino and carboxy terminus (HA-L-HA). Lane 3 shows expression of the full length CCHFV-L tagged with HA only at its carboxy terminus (L-HA). After 24 hours, the cells were harvested, immunoprecipitated using anti-HA antibody and separated in a 4-20% SDS-PAGE. Proteins were detected by Western blotting using anti-HA antibody. (C) Immunofluorescence in HeLa cells transfected with HA-tagged CCHFV-L plasmid (HA-L-HA). 24 hours post-transfection, the cells were fixed and stained using anti-HA antibody. The HA signal is shown as the bright stain (on two cells). Nuclear staining is shown as the lighter staining circular pattern in ten cells (DAPI staining).

FIG. 2. Total levels of ubiquitinated and ISGylated proteins in 293T cells transfected with full length or deletion mutant CCHFV-L plasmids. (A) CCHFV-L constructs utilized in studies. The dark grey box represents a single mutation in the OTU domain (Cys40A1a) and light grey represents a double mutation (Cys40Ala and His151Ala). (B) 293T cells were transfected with HA-Ub (top panel) or ISG15, UBE1L and UbcM8 (middle panel) together with empty plasmid (HA), full length CCHFV-L (HA-L-HA), different CCHFV-L truncation mutants or UBP43. Samples were Western blotted for HA (top panel) or ISG15 (middle panel). Samples transfected with components of the ISG15 conjugation system were also probed with anti-HA (or anti-FLAG for UBP43) (lower panel) or anti-FLAG (bottom panel) to show expression of UBE1L, HA-L-HA (line), HA-L(1-1325), L(1325-2590)-HA and L(2582-3945)-HA (arrow), HA-L(1-354) and UBP43 (closed triangle), HA-L(1-169) and HA-L(1-169) DM (open triangle) or UbcM8 (bottom). Asterisks indicate non-specific bands.

FIG. 3. Recombinant L(1-169) protein of CCHFV hydrolyzes ISG15 conjugates in vitro. (A) L(1-169) and L(1-169) SM expression from E. coli. Left panel: GST-L(1-169) protein (lane 1) was purified from bacteria by affinity chromatography using Glutathione Sepharose and then the GST was cleaved off using Prescission™ protease enzyme. The untagged L(1-169) protein (lane 2) was used for the in vitro experiments. Right panel: The GST(L-169)SM (lane 1) was purified using the same conditions as described above. Only the L(1-169)SM protein showed in lane 3 was used for the assays. Lane 2 shows GST protein alone used as purification control. (B) Upper panel: ISG15 conjugates obtained from IFN-treated UBP43$^{-/-}$ MEFs were either incubated with reaction buffer (−) or treated with decreasing amounts of either CCHFV-L(1-169) or CCHFV-L (1-169) SM recombinant proteins. Both E. coli-purified proteins were added in decreasing ten-fold dilutions, starting with 1 μg to 1 ng. The reaction products were separated on 4-15% SDS-PAGE and total levels of ISGylated proteins were detected by Western blot with anti-ISG15 antibodies. Coomassie staining at the bottom of the Western blot shows the expression of L(1-169) and L(1-169)SM recombinant proteins (black arrow). Lower panel: 293T cells were transfected with a mixture of His-tagged ISG15 and UBE1L and UbcH8 expression plasmids. 24 hours later, the cells were lysed and the His-ISG15 conjugates were purified using Ni-NTA chromatography. Decreasing ten-fold dilutions of the L(1-169) and L(1-169)SM recombinant proteins, starting with 1 μg of protein per reaction, were incubated with the ISG15 conjugates and the total level of ISGylated proteins was visualized by Western blot using anti-ISG15 antibody. As negative control, no protein was added to the reaction (−).

Figure 4A:
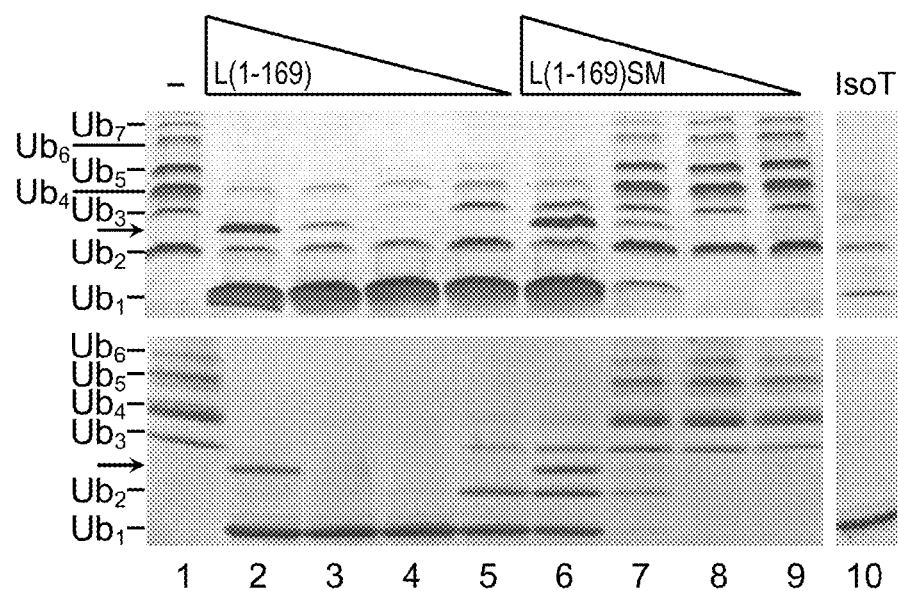

FIG. 4. CCHFV-L(1-169) deconjugates polyubiquitin chains and is unable to hydrolyze poly-SUMO chains in vitro (A) Upper panel: Ten-fold dilutions of the L(1-169) and L(1-169)SM recombinant proteins, starting with 1 μg of protein per reaction, were incubated with an excess of branched K48-linked polyubiquitin chains as described in Materials and Methods (Section 6.1.8. infra.) 100 mM of purified isopeptidase-T (IsoT) served as a positive control for the reaction whereas polyubiquitin chains incubated with reaction buffer was used as negative control (−). Following hydrolysis, ubiquitin was visualized by Coomassie staining The expression of the IsoT and the L(1-169) and L(1-169)SM proteins can be visualized (black arrows). Lower panel: Same experimental condition as in upper panel but using K63 Ub3-7 chains as substrate. Ub hydrolysis was visualized by Coomassie staining The arrow in upper and lower panels indicate the L(1-169) and L(1-169)SM recombinant proteins. (B) CCHFV-L(1-169) is not able to hydrolyze poly-SUMO chains in vitro. Upper panel: Experiments were performed as described in FIG. 4A using poly-SUMO-$2_{2-8}$ as substrate. SUMO hydrolysis was visualized by Coomassie staining Lower panel: Experiments were performed as described in FIG. 4A using poly-SUMO-$3_{2-8}$ as substrate. SUMO hydrolysis was visualized by Western blotting using anti-SUMO3 antibody. The arrow indicates the L(1-169) and L(1-169)SM recombinant proteins. As negative control no protein was added (−) and as positive control, 100 mM of deSUMOylating (SENP2$_{CD}$) enzyme was added to the reaction.

FIG. 5. Multiple alignment of conserved regions of OTU domain-containing cysteine proteases of viral, bacterial and human origin. Representative examples of OTU domain-containing proteins are shown. The GenBank accession numbers and amino acid positions are indicated. Highly conserved residues are shown in bold. CCHFV, Crimean Congo hemorrhagic fever virus; DUGV, Dugbe virus; RiceStrV, rice stripe virus; EAV, equine arteritis virus; LDV, lactate dehydrogenase elevating virus; LELV, Lelystad virus; BBSV, blueberry scorch virus; PVM, potato virus M; HLV, hop latent virus; SSMV, sugarcane striate mosaic virus; AOPRSV, African oil palm ringspot virus; CGRMV, cherry green ring mottle virus; GRSPV, grapevine Rupestris stem pitting associated virus; IcHV-1, Ictalurid herpesvirus 1; TIV, Tipula iridescent virus; CIV, Chilo iridescent virus; LdMNPV, Lymantria dispar multicapsid nucleopolyhedrovirus; C. pneum., Chlamydophila pneumoniae; OTU1 and OTU2, Otubains 1 and 2, respectively (SEQ ID NOS:12-55).

Figure 6:
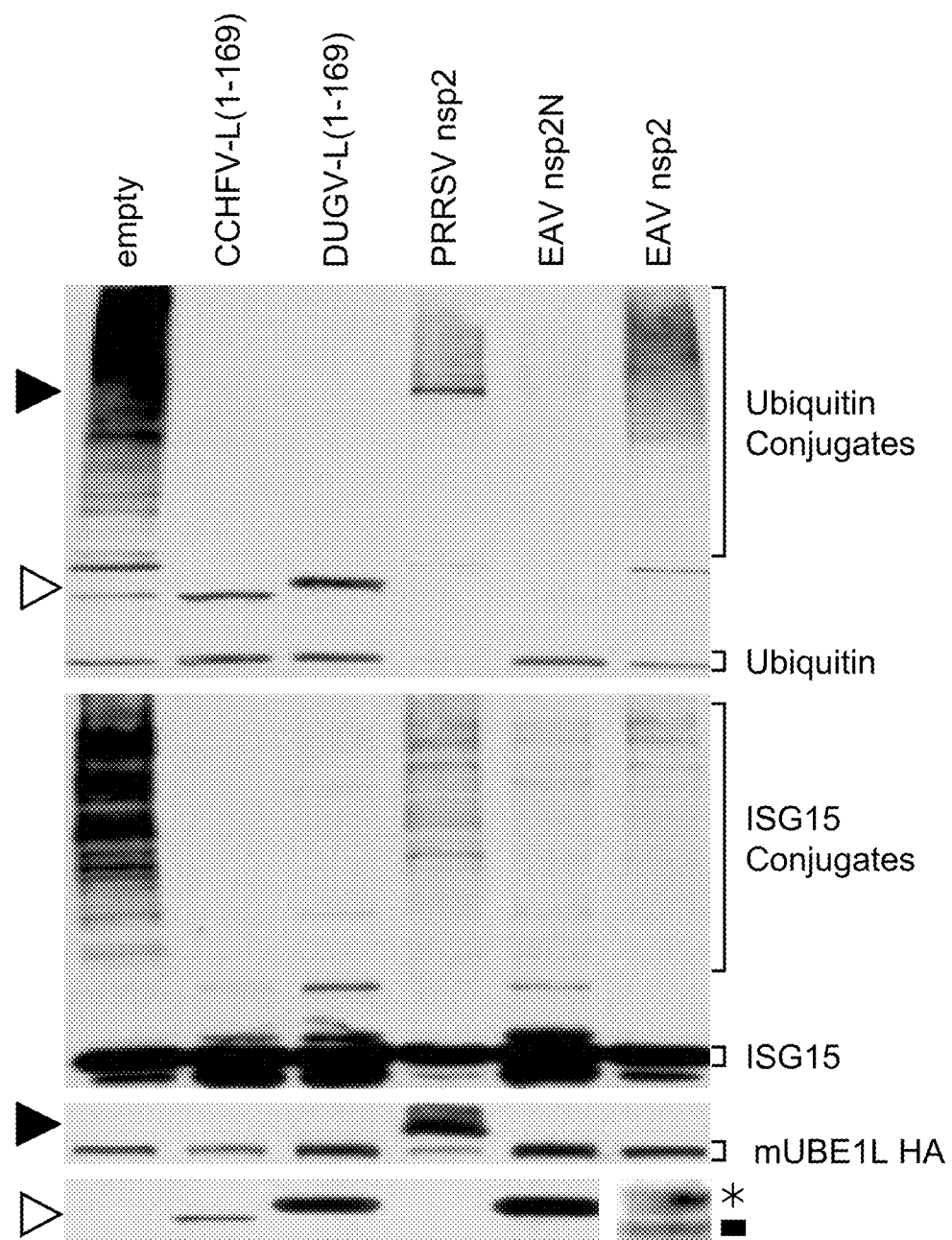

FIG. 6. OTU domain-containing proteins from other viruses can also deconjugate ubiquitin and ISG15 conjugates. CCHFV-L(1-169), DUGV-L(1-169), PRRSV nsp2, EAV nsp2N or EAV nsp2 were co-transfected into 293T cells with either HA-Ub (top panel) or ISG15, mUBE1L HA, untagged UbcM8 and Herc5 (lower three panels). Samples were Western blotted for HA (top panel) or ISG15 (second panel). ISG15-transfected samples were also probed with anti-HA (third panel) or anti-FLAG plus anti-HA (bottom panel) to show expression of mUBE1L, PRRSV nsp2 (closed triangle), CCHFV-L(1-169), DUGV-L(1-169), or EAV nsp2N (open triangle), or EAV nsp2 (square). Asterisk indicates non-specific band.

FIG. 7. Design and characterization of OTU domain-containing Sindbis viruses. (A) Structure of recombinant double subgenomic (SG) Sindbis viruses generated by cloning CCHFV-L(1-169) [169], L(1-169)2A [MT], ISG15-IRES-L(1-169) [169GG] or ISG15-IRES-L(1-169)2A [MTGG] into the BstEII site of dsTE12Q. (B) BHK-21 cells were infected with viruses as indicated and samples were Western blotted for OTU domain expression (top panel), ISG15 expression (middle panel) and expression of Sindbis viral proteins (bottom panel). (C) Single step growth curve of recombinant Sindbis viruses in BHK-21 cells. Data is represented as mean+/−SEM for three (dsTE12Q) or six replicates (recombinant viruses). There are no significant differences between the medians of different viruses (P=0.9407).

FIG. 8. OTU domain-containing Sindbis viruses can deconjugate ubiquitin and ISG15 conjugates and inhibit ISG15-mediated protection of Ifnar$^{-/-}$ mice. (A) BHK-21 cells were transfected with constructs as indicated and subsequently infected with recombinant Sindbis viruses. Samples were harvested and Western blotted for ISG15 (left and middle panels) or HA (right panel). (B) Ifnar$^{-/-}$ mice were infected with recombinant Sindbis viruses and monitored for survival. Data is pooled from four independent experiments and numbers of mice are indicated in parenthesis. P values represent comparisons between indicated viruses.

FIG. 9. Alignment of representative proteins with an OTU domain of viral, human, murine and other origin (SEQ ID NOS:56-72).

FIG. 10. The OTU-Domain Sequence is Conserved Across Viral and Mammalian Proteins. Multiple alignment of the OTU domains present in the proteins used in this study. In the consensus (SEQ ID NO:82) (Makarova et al., 2000), h indicates hydrophobic residues (A, C, F, L, I, M, V, W, Y, T, S, G); s indicates small residues (A, C, S, T, D, V, G, P); + indicates positively charged residues (R, K); a indicates aromatic residues (W, Y, F, H); t indicates residues with high β-turn-forming propensity (A, C, S, T, D, E, N, V, G, P). Highly conserved residues are shaded in black. Numbers at the beginning and end of each sequence indicate the positions of the first and last aligned residue in the respective protein sequences; the numbers between aligned blocks indicate the numbers of residues that are not shown. CCHFV, Crimean Congo hemorrhagic fever virus; DUGV, Dugbe virus; EAV, equine arteritis virus; PRRSV, porcine respiratory and reproductive syndrome virus; Cez, Cezanne, OTUB1 and OTUB2, Otubains 1 and 2, respectively (SEQ ID NOS:73-81).

FIG. 11. Levels of Ubiquitinated and ISGylated Proteins in Cells Expressing CCHFV-L and CCHFV-L Mutants. (A) Schematic representation of the CCHFV-L constructs utilized in these studies. Predicted protein domains within the protein: OTU domain; ZF, zinc finger; LZ, leucine zipper; RdRp, RNA dependent RNA polymerase conserved motifs. White stars represent mutations in the OTU domain: 1A (C40A) or 2A (C40A and H151A). All constructs were HA-tagged. (B) 293T cells were transfected with either HA-Ub (panel A) or His-ISG15, HA-mUBE1L and Flag-UbcM8 (panels B-D along with HA-tagged CCHFV-L constructs, Flag-UBP43 or empty plasmid. Total protein ubiquitination was visualized by immunoblotting with anti-HA (panel A) and protein ISGylation was visualized by anti-ISG15 immunoblot (panel B). ISG15-transfected samples were also probed with anti-HA or anti-Flag (panels C and D) for detection of the CCHFV-L constructs (left arrows), mUbE1L, UBP43 (inset) and UbcM8. Asterisk indicates a non-specific band. (C) L and 1A were analyzed for their effect on total ubiquitination (panel A) or ISGylation (panel B) as described in (B). Expression of HA-tagged UBE1L (panel C), L and L 1A (panel D) and L(1-169) and L(1-169)2A (panel E) is shown.

Figure 12C:
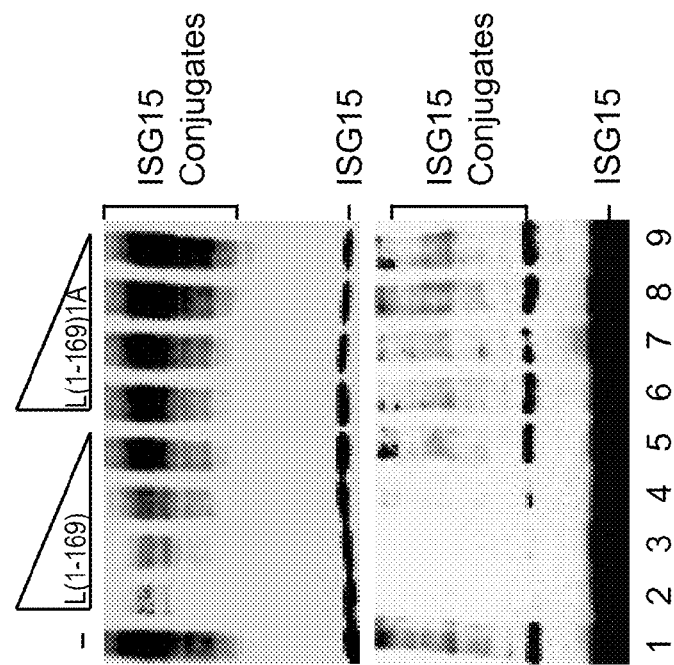
Figure 12B:
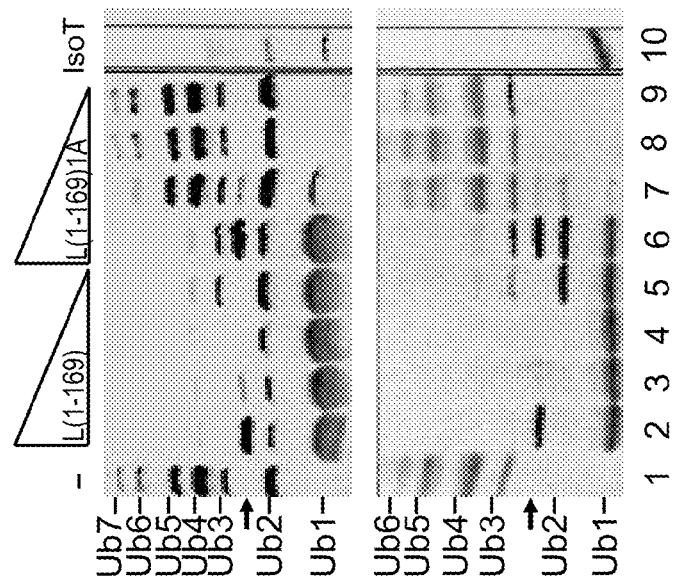
Figure 12A:
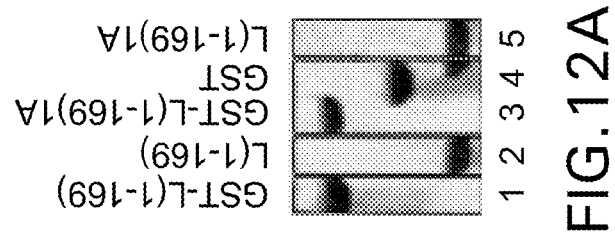

FIG. 12. In vitro Ub- and ISG15-deconjugation Activities of CCHFV-L OTU Domain. (A) Coomassie-stained gel of GST-L(1-169), L(1-169), GST-L(1-169)1A and L(1-169)1A recombinant proteins. L(1-169) and L(1-169)1A proteins were used for the in vitro experiments. (B) K48-(top panel) or K63-(bottom panel) linked poly-Ub chains were incubated with reaction buffer (lane 1) or 10-fold dilutions of L(1-169) or L(1-169)1A recombinant proteins, subjected to SDS-PAGE and visualized by Coomassie staining Isopeptidase T (IsoT) was used as a positive control. Black arrows indicate L(1-169) and L(1-169)1A proteins. (C) Lysates of UBP43−/− MEFs (top panel) or ISG15 conjugates purified from ISG15, HAmUBE1L and Flag-UbcM8 transfected 293T cells (bottom panel) were incubated with reaction buffer (lane 1) or 10-fold dilutions of L(1-169) or L(1-169)1A protein. ISG15 conjugates were visualized by anti-ISG15 immunoblot. (D) SUMO-2 (top panel) or SUMO-3 (bottom panel) chains were incubated with reaction buffer (lane 1) or 10-fold dilutions of L(1-169) or L(1-169)1A and visualized by Coomassie staining His6-SENP2CD was used as a positive control. Black arrows indicate L(1-169) and L(1-169)1A proteins. S2-8 indicates number of SUMO 2 or SUMO 3 molecules. (E) ProISG15 (panel A), proNedd8 (panel B), proSUMO-1 (panel C) or (F) K48-linked Ub chains were incubated with reaction buffer, L(1-169), L(1-169)1A or A20 catalytic domain (A20CD) and visualized by Coomassie staining Positive controls indicate incubation with UBP43 (panel A), NEDP1 (panel B), SENP2CD (panel C) or (F) IsoT. Black arrows indicate L(1-169) and L(1-169)1A proteins and white arrowhead indicates A20CD. Pro indicated the pro-Ubl molecule form and Mat indicates the mature protein.

Figure 13A:
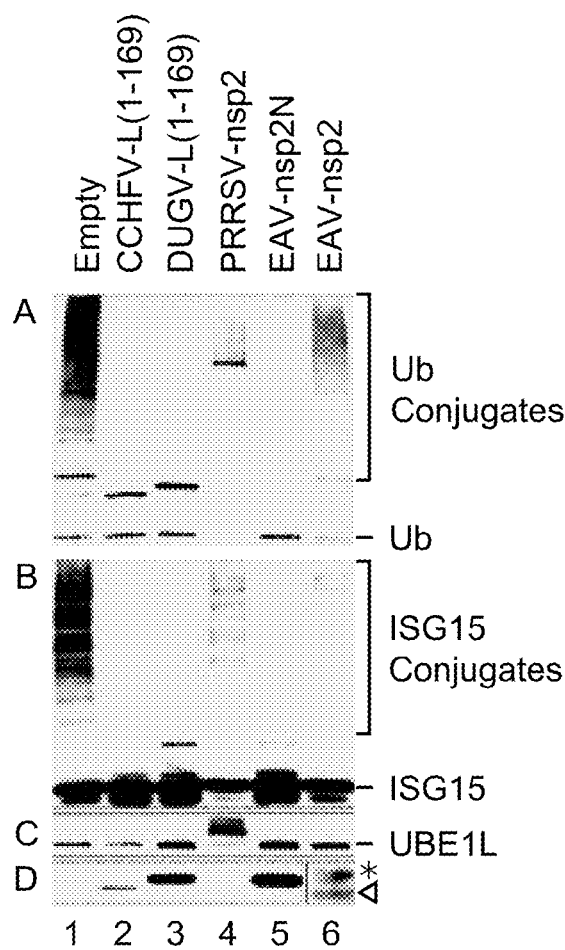

FIG. 13. Ub- and ISG15-deconjugation activity of OTU Domain-containing Polypeptides of Viral and Mammalian Origin. (A) CCHFV-L(1-169), DUGV-L(1-169), PPRSV-nsp2, EAV-nsp2N or EAV-nsp2 were cotransfected into 293T cells with either HA-Ub (panel A) or ISG15, HA-mUBE1L-HA, Flag-UbcM8 and Herc5 plasmids (panels B-D). Samples were immunoblotted for HA (panel A) or ISG15 (panel B). ISG15-transfected samples were also probed with anti-HA (panel C) or anti-Flag plus anti-HA (panel D) to show expression of HA-mUBE1L, PPRSV-nsp2, CCHFV-L(1-169), DUGV-L(1-169), or EAV-nsp2N, or EAV-nsp2 (inset, open triangle). Asterisk indicates a non-specific band. (B) Otubain1, Otubain2, Cezanne, VCIP135, A20 or UBP43 were analyzed for their effect on total ubiquitination (panel A) or ISGylation (panels B-D) as described in (A). Expression of HA tagged Cezanne and VCIP135 (panel C) and Flag-tagged Otubain1 and 2 and UBP43 (panel D) is shown.

FIG. 14. Expression of L(1-1325) Transgene Correlates with Increased Susceptibility to Sindbis Virus Infection. (A, B) Expression of L(1-1325) transgene and actin in (A) MEFs and (B) brain lysates. + indicates a transgene positive mouse and − indicates a C57/BL6 mouse. The arrows indicate L(1-1325) protein and open triangles denote actin. (C) Survival of L(1-1325) transgenic mice following infection with Sindbis virus AR86. Transgene negative littermates from 1836, 1854 and 2929 served as C57/BL6 controls. Numbers of mice in each group are indicated in parenthesis. Comparison by statistical analysis were made between 1836+ and C57/BL6 (P=0.0011).

FIG. 15. Sindbis Viruses Expressing CCHFV-L OTU Domain Deconjugate Ub and ISG15 and Inhibit ISG15-mediated Antiviral Effects in Mice. (A) Schematic diagram representing the CCHFV OTU-domain expressing Sindbis viruses utilized in these studies. G: genomic promoter; SG: subgenomic promoter. (B) BHK-21 cells were transfected with UBE1L, UbcM8 and Herc5 (left panel); UBE1L, UbcM8, Herc5 and ISG15 (middle panel) or HA-Ub (right panel) and subsequently infected with recombinant Sindbis viruses as indicated. Cells lysates were immunoblotted with anti-ISG15 (left and middle panels) or anti-HA (right panel) antibodies. − indicates untransfected cells. (C) IFNαβR−/− mice were infected with recombinant Sindbis viruses as indicated and monitored for survival. Data are pooled from four independent experiments and numbers of mice in each group are indicated in parenthesis. Differences in survival were analyzed by the log rank test: 169GG and 169 (P<0.0001), 169GG and MT (P=0.0032), 169GG and MTGG (P=0.0015), MTGG and 169 (P<0.0001) and MTGG and MT (P<0.0001).

Figures 16A, 16B:
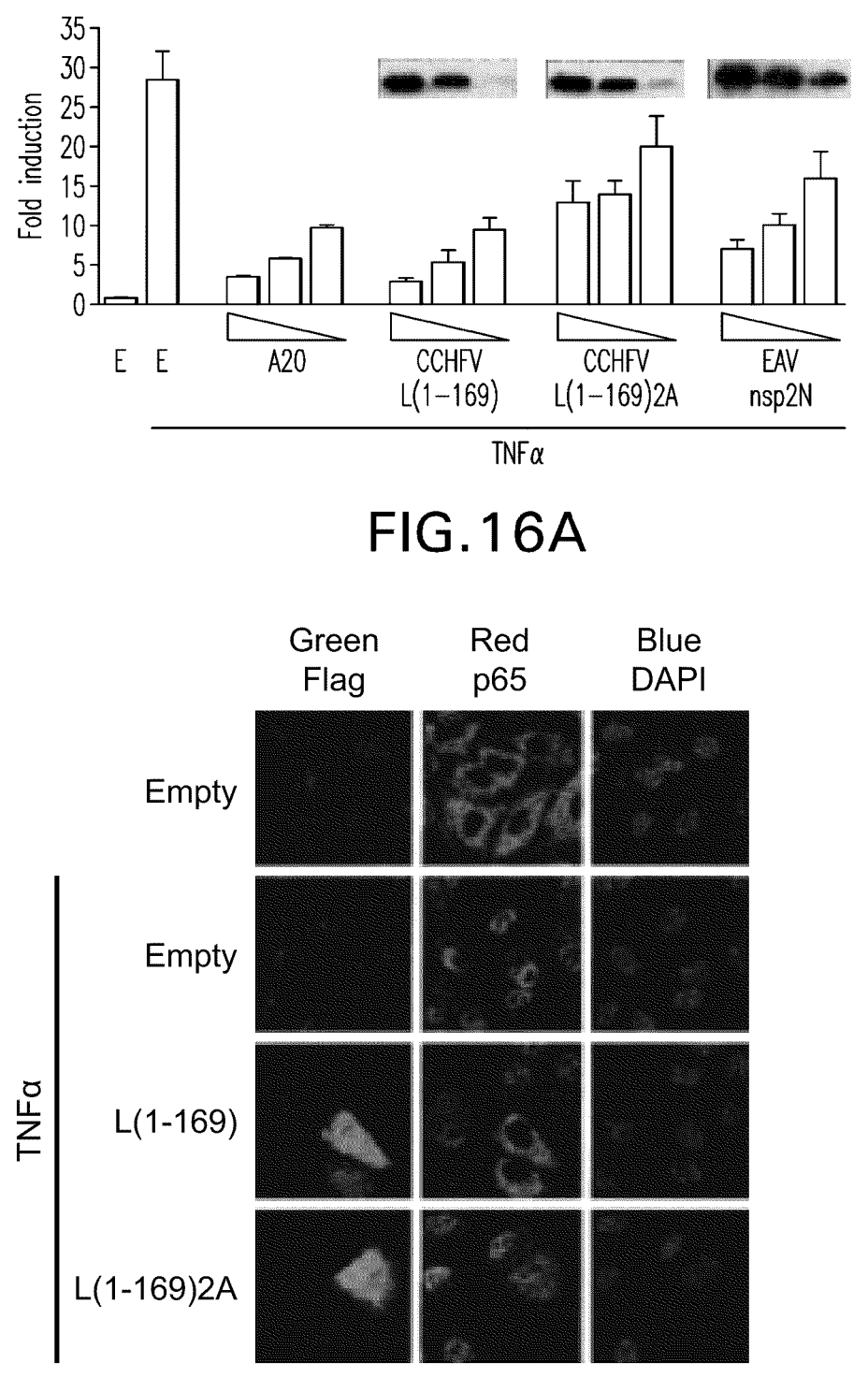

FIG. 16. CCHFV-L and EAV-nsp2 OTU Domains Inhibit TNFα-mediated NF-κB Activation. (A) NF-κB reporter assay in 293T cells transfected with OTU domains and treated with TNFα. Results shown are an average of three independent experiments. The western blot indicates expression of viral OTU proteins as detected with anti-HA (CCHFV-L(1-169) and CCHFV-L(1-169)2A) or anti-Flag antibodies (EAV-nsp2N). E indicates empty plasmid. (B) A549 cells were transfected with indicated plasmids, stimulated with TNFα and stained for p65 (red) and L(1-169) or L(1-169)2A (green). Nuclei were stained with DAPI (blue). (C) L(1-169) or L(1-169)2A transfected cells in (B) were scored according to subcellular distribution of p65. Differences in p65 nuclear accumulation in TNFα-treated cells were analyzed by the T student test: E and L(1-169) (P<0.0001); E and L(1-169)2A (P=0.0007) and L(1-169) and L(1-169)2A (P=0.0045). E indicates empty plasmid.

Figures 16C, 17:
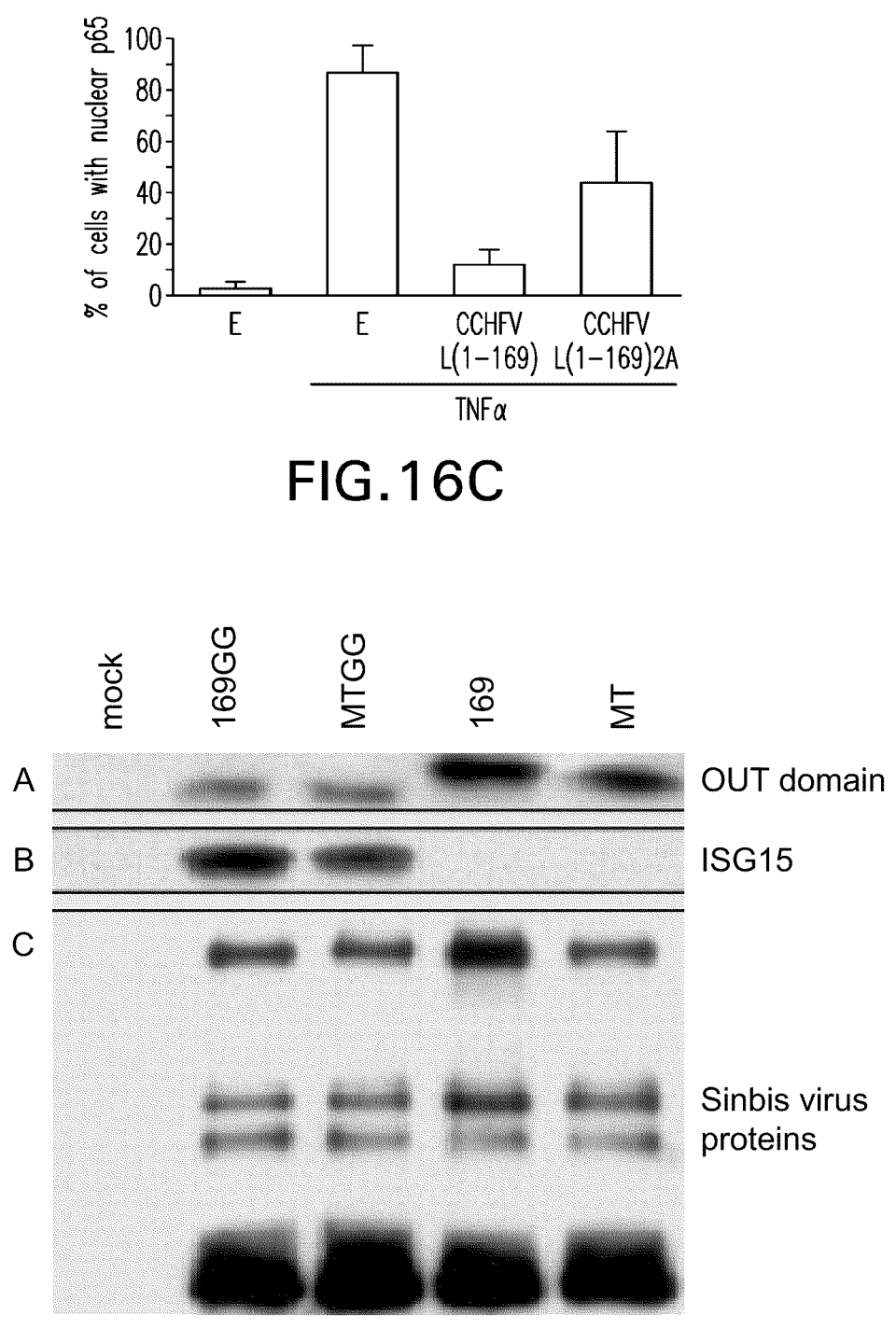

FIG. 17. Expression of OTU domain and ISG15 from recombinant Sindbis viruses. BHK-21 cells were infected at an MOI of 10 with the indicated viruses and cell lysates were immunoblotted for CCHFV-L OTU domain expression (panel A), ISG15 expression (panel B) and expression of Sindbis viral proteins (panel C). Polyclonal antibody against Sindbis virus was provided by Dianne Griffin (Johns Hopkins University, Baltimore, Md.; Levine et al., 1996)

Figure 18:
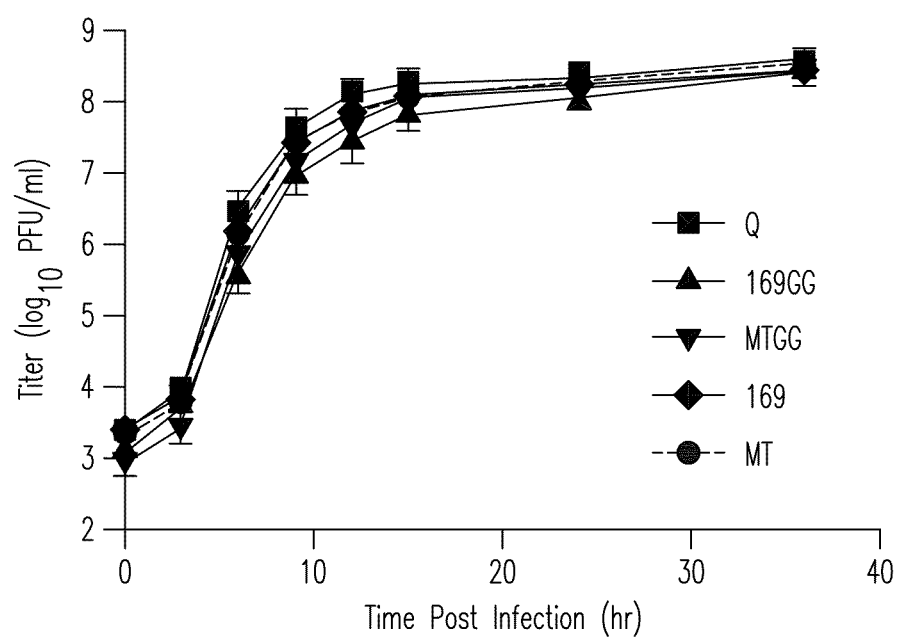

FIG. 18. Single step growth curve of recombinant Sindbis viruses. Single-step growth curves were performed in BHK-21 cells at MOI of 5 as described (Heise et al., 2000). Data is represented as mean+/− SEM for three (dsTE12Q) or six replicates (recombinant viruses). Q refers to parental dsTE12Q virus. There were no significant differences among the viruses (P=0.9910).

Figure 19A:
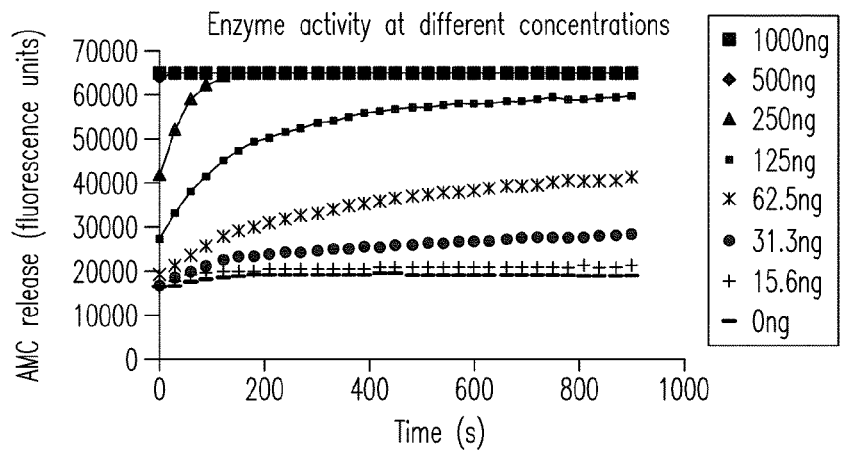
Figure 19B:
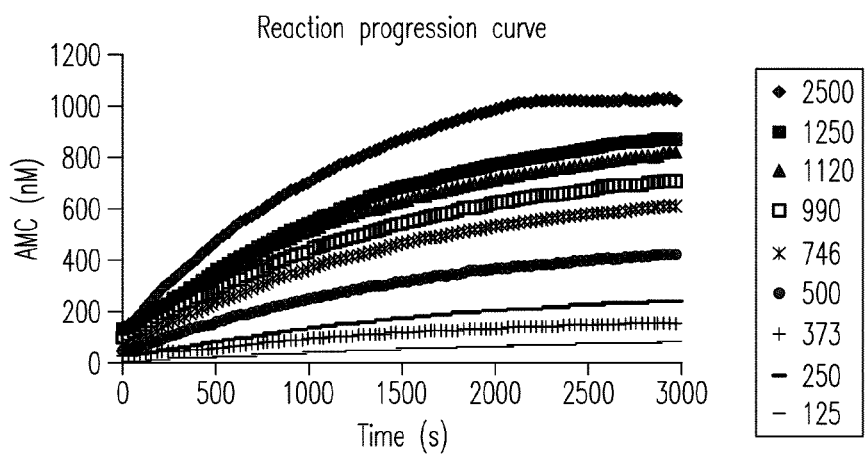
Figure 19C:
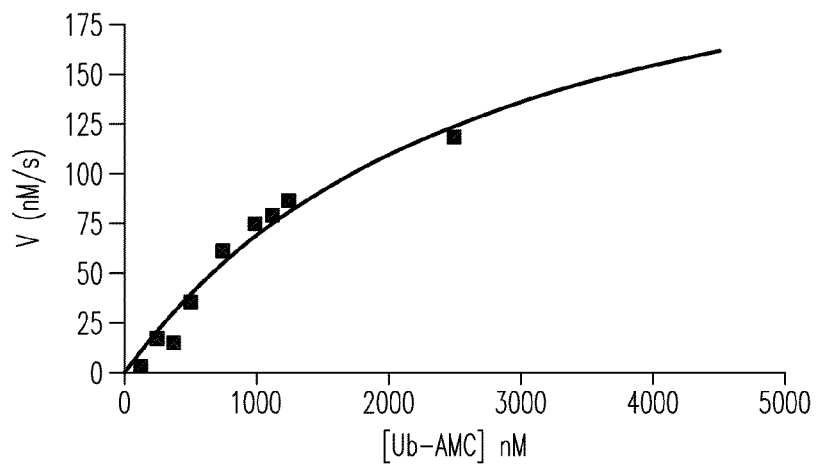

FIG. 19: (A) CCHFV-L OTU activity was established by adding increasing amounts of enzyme (indicated in the box at the right) and measuring fluorescence every 30 seconds for 10 minutes; (B) Representative reaction progress curves at nine UB-AMC substrate concentrations (indicated in the box at the right). Background fluorescence is measured using 40 nM Ub-AMC and no enzyme; (C) The $V_0$ is then plotted against Ub-AMC substrate concentration through Michaelis-Menten enzyme analysis to calculate Km=Vmax/2.

5. DETAILED DESCRIPTION OF THE INVENTION

5.1 Viral OTU Domain-Containing Proteins

The present invention is based, in part, on the identification of viral proteins comprising an OTU domain that have deIS-Gylation activity. As used herein, "a viral OTU domain-containing protein" is a viral protein comprising an OTU domain which, unless explained otherwise or is clear from the context, has deISGylation activity. As used herein, the phrase "an OTU domain-containing protein," when used in the context of viruses, also refers to a viral protein comprising an OTU domain which has deISGylation activity, unless explained otherwise. In a specific embodiment, the viral OTU domain-containing protein deISGylates about 10%, preferably about 15%, 20%, 25%, 30%, 35%, 40% or more of ISG15 conjugated protein as determined using an in vitro assay known to one of skill in the art. In a more specific embodiment, the viral OTU domain-containing protein deISGylates about 10%, preferably about 15%, 20%, 25%, 30%, 35% or 40% or more of ISG15 conjugated protein as determined using an in vitro assay described herein. In a specific embodiment, the viral OTU domain-containing protein does not discriminate among ISGylated proteins and deISGylates the majority (75%, preferably 85%, 90%, 95%, 98% or more) of the types of ISGylated proteins found in a mammalian cell. In certain embodiments, the viral OTU domain-containing protein deconjugates ubiquitin and ubiquitin-like molecules from a target protein. In accordance with this embodiment, the ability of the viral OTU domain-containing protein to deconjugate ubiquitin and/or ubiquitin-like molecules can be determined using an assay known to one of skill in the art. In a specific embodiment, the viral OTU domain-containing protein deconjugates ubiquitin but not SUMO from a target protein. In a specific embodiment, the viral OTU domain-containing protein has interferon antagonist activity.

In some embodiments, a viral OTU domain-containing protein not only has deISGylation activity but also deubiquitination activity. In a specific embodiment, the viral OTU domain-containing protein deubiquitinates about 10%, preferably about 15%, 20%, 25%, 30%, 35%, 40% or more of ubiquitin conjugated protein as determined using an in vitro assay known to one of skill in the art. In a more specific embodiment, the viral OTU domain-containing protein deubiquitinates about 10%, preferably about 15%, 20%, 25%, 30%, 35% or 40% or more of ubiquitin conjugated protein as determined using an in vitro assay described herein. In a specific embodiment, the viral OTU domain-containing protein does not discriminate among ubiquitinated proteins and deubiquitinates the majority (75%, preferably 85%, 90%, 95%, 98% or more) of the types of ubiquitinated proteins found in a mammalian cell. In certain embodiments, a viral OTU domain-containing protein does not have deubiquitination activity as determined using an in vitro assay described herein.

In some embodiments, a viral OTU domain-containing protein not only has deISGylation activity but also deSUMOylation activity. In a specific embodiment, the viral OTU domain-containing protein deSUMOylates about 10%, preferably about 15%, 20%, 25%, 30%, 35%, 40% or more of SUMO conjugated protein as determined using an in vitro assay known to one of skill in the art. In a more specific embodiment, the viral OTU domain-containing protein deSUMOylates about 10%, preferably about 15%, 20%, 25%, 30%, 35% or 40% or more of SUMO conjugated protein as determined using an in vitro assay described herein. In a specific embodiment, the viral OTU domain-containing protein does not discriminate among SUMOylated proteins and deuSUMOylates the majority (75%, preferably 85%, 90%, 95%, 98% or more) of the types of SUMOylated proteins found in a mammalian cell. In certain embodiments, a viral OTU domain-containing protein does not have deSUMOylation activity as determined using an in vitro assay described herein.

In some embodiments, a viral OTU domain-containing protein not only has deISGylation activity but also deNeddylation activity. In a specific embodiment, the viral OTU domain-containing protein deNeddylates about 10%, preferably about 15%, 20%, 25%, 30%, 35%, 40% or more of Nedd8 conjugated protein as determined using an in vitro assay known to one of skill in the art. In a specific embodiment, the viral OTU domain-containing protein does not discriminate among Neddylated proteins and deNeddylates the majority (75%, preferably 85%, 90%, 95%, 98% or more) of the types of Neddylated proteins found in a mammalian cell. In certain embodiments, a viral OTU domain-containing protein does not have deNeddylation activity as determined using an in vitro assay described herein.

In some embodiments, a viral OTU domain-containing protein has deISGylation activity and deubiquitination activity and deNeddylation activity. In a specific embodiment, the viral OTU domain-containing protein deISGylates, deubiquitinates, and deNeddylates about 10%, preferably about 15%, 20%, 25%, 30%, 35%, 40% or more of ISG15, Nedd8, and/or ubiquitin conjugated protein as determined using an in vitro assay known to one of skill in the art. In a specific embodiment, the viral OTU domain-containing protein does not discriminate among ISGylated, Neddylated, and ubiquitinated proteins and deconjugates the majority (75%, preferably 85%, 90%, 95%, 98% or more) of the types of ISGylated, ubiquitinated and/or Neddylated proteins found in a mammalian cell. In certain embodiments, the viral OTU domain-containing protein has deISGylation, deubiquitination, and deNeddylation activity but does not have deSUMOylation activity. In certain embodiments, the viral OTU domain-containing protein has been mutated so that it has lost one or more of its activities of deISGylation, deubiquitination, or deNeddylation.

Viruses comprising a viral OTU domain-containing protein include, but are not limited to, positive- and negative-sense single-stranded RNA viruses and double-stranded DNA and RNA viruses. Viral OTU domain-containing proteins are found in a number of known viral pathogens of humans and other mammals (see, e.g., FIGS. 5 and 9 and Table 2, infra). Non-limiting examples of viruses comprising a viral OTU domain-containing protein include: viruses of the Bunyaviridae family (e.g., viruses of nairovirus genus such as Crimean Congo Hemorrhagic Fever Virus (CCHFV), Dugbe Virus (DUGV), Hazara virus, Hughes virus, Soldado virus, Nairobi Sheep Disease virus, Dera Ghazi Khan virus, Abu Hammad virus, Abu Mina virus, Farallon virus, Punta Salinas virus, Raza virus, Qalyub virus, Bandia virus, Sakhalin virus, Tillamook virus, Thiafora virus, Erve virus), viruses of the arterivirus family (e.g., Equine arteritis virus (EAV), lactate-dehydrogenase elevating virus (LDV), and porcine reproductive and respiratory syndrome virus (PRRSV), including Lelystad virus (LELV)), and herpes viruses (e.g., murine gamma herpesvirus, Epstein-Barr Virus (EBV), bovine herpes virus (BHV4), porcine, lymphotropic herpes virus, and the Squirrel monkey herpesvirus protein *Saimiri* 34). See Table 2, infra, for list of viruses comprising a viral OTU domain-containing protein as well as other information regarding the virus.

TABLE 2

Viruses comprising a viral OTU domain-containing protein and other information about the viruses

| Virus | Subjects(s) and Host(s); Disease(s) | Family/ Genus | Genome organization | OTU domain-containing protein (exemplary OTU domain location in amino acids) (GenBank Accession No.) | Predicted catalytic residues of OTU domain (exemplary) | Other predicted functions of OTU domain-containing protein |
|---|---|---|---|---|---|---|
| Crimean Congo Hemorrhagic Fever Virus (CCHFV) | human (30% mortality), ostriches, some other birds, ticks, small vertebrates (e.g., experimental mouse model), livestock, e.g., cattle, sheep, goats; tick-borne hemorrhagic fever (category A select biological agent/BSL 4 pathogen) | Bunyaviridae/ Nairovirus | tripartite, segmented, negative-strand, single-stranded RNA | viral polymerase L (30-159) (AAQ98866) | Asp37, Cys40, His151 | RNA-dependent RNA polymerase (RdRP); cytoskeleton interactions; helicase, gyrase, topoisomerase; transcription factor |
| Dugbe virus (DUGV) | cattle, human, experimental mice; tick-borne hemorrhagic fever | Bunyaviridae/ Nairovirus | tripartite, segmented, negative-strand, single-stranded RNA | viral polymerase L (30-159) (Q66431) | Asp37, Cys40, His151 | RNA-dependent RNA polymerase; cytoskeleton interactions; helicase, gyrase, topoisomerase; transcription factor |
| Nairobi sheep disease virus (NSDV) | tick, sheep, goat infrequently humans; fever, hemorrhagic gastroenteritis, abortion; high mortality | Bunyaviridae/ Nairovirus | tripartite, segmented, negative-strand, single-stranded RNA | viral polymerase L (within amino terminal aa 34-152) (AY359525) | Dx, Cx + 3 | RNA-dependent RNA polymerase; topoisomerase |
| Equine arteritis virus (EAV) | horse, donkey; fever, depression, edema, conjunctivitis, nasal discharge, abortion, death in young foals | Arteriviridae/ Arterivirus | non-segmented, positive-strand, single-stranded RNA | part of nsp polypeptide; nsp2 mature protein, in some cell types, nsp2 is further processed into nsp2N, which has OTU domain and activity (Nsp2 260-338) (P19811) | Asp267, Cys270, His332 | nsp1 and nsp2 are part of the replicase, needed for genome replication; nsp2 is a co-factor with nsp4 protease in polyprotein processing; nsp2 and nsp3 function in modification of cell membranes during replication non-structural protein (gene 1ab; EAVgp1) is proteolytically matured into 11 proteins: nsp1, papain-like cysteine proteinase 1b; nsp2, cysteine proteinase 2; nsp3 hydrophobic domain; nsp4, 3C-like serine proteinase; nsp5 hydrophobic domain; nsp6-8; nsp9, RdRP; nsp10, metal-binding and NTPase/helicase domains; nsp11; nsp12 |
| Porcine reproductive and respiratory syndrome virus (PRRSV) | swine; reproductive failure, post-weaning respiratory disease; significant problem among nursery pigs | Arteriviridae/ Arterivirus | non-segmented, positive-strand, single-stranded RNA | polypeptide nsp, nsp2 mature protein (strain 16244B: Acc. Q9YN02) | Cys437, His507 | non-structural protein encoded by ORF1; genome replication |
| Lelystad virus (LELV) strain of PRRSV | swine | Arteriviridae/ Arterivirus | non-segmented, positive-strand, single-stranded RNA | polypeptide nsp, nsp2 mature protein (Nsp2 419-504) (Q04561) | Asp426, Cys429, His498 | non-structural protein, genome replication |
| Lactate dehydrogenase elevating virus (LDV) | mouse | Arteriviridae/ Arterivirus | non-segmented, positive-strand, single-stranded RNA | polypeptide nsp, nsp2 mature protein (Nsp2 380-462) (AAA85663) | Asp387, Cys390, His456 | non-structural protein |
| Epstein-Barr Virus (EBV) (human herpesvirus 4) | human | Herpesviridae; Gammaherpesvirinae/ Lymphocryptovirus | double-stranded DNA | BGLF3 (within aa 141 to end) | Cys165, | tegument |
| Porcine lymphotropic | cow; sheep; goat; pig | Herpesviridae; Gammaherpesvirinae/ | double-stranded DNA | PLHV3 Conserved | Asp168, Cys171 | |

TABLE 2-continued

Viruses comprising a viral OTU domain-containing protein and other information about the viruses

| Virus | Subjects(s) and Host(s); Disease(s) | Family/ Genus | Genome organization | OTU domain-containing protein (exemplary OTU domain location in amino acids) (GenBank Accession No.) | Predicted catalytic residues of OTU domain (exemplary) | Other predicted functions of OTU domain-containing protein |
|---|---|---|---|---|---|---|
| herpesvirus 3 (PLHV3) and other lymphotropic herpesviruses | | Rhadinovirus | | ORF 34 (AAO12337) | | |
| murine gamma herpesvirus type 68 (GHV) (Murid herpesvirus 4) | mouse | Herpesviridae; Gammaherpesvirinae/ Rhadinovirus | double-stranded DNA | gHV68 within aa 141 to end | Glu172, Cys175 | |
| Bovine Herpesvirus 4 (BHV4) | cow | Herpesviridae; Gammaherpesvirinae/ Rhadinovirus | double-stranded DNA | BHV4 (within aa 140 to end) | Cys173 | |
| Squirrel monkey herpesvirus (Saimiriine herpesvirus 1; Squirrel monkey herpesvirus 1; Herpesvirus saimiri 1; Marmoset herpesvirus; herpesvirus M; Herpesvirus tamarinus; Herpesvirus saimiri; Squirrel monkey alphaherpesvirus type 1) | squirrel monkey | Herpesviridae; Alphaherpesvirinae/ Simplexvirus | double-stranded DNA | Saimiri (within aa 140 to end) | Cys166 | |

In a specific embodiment, the viral OTU domain-containing protein is the RNA-dependent RNA polymerase (encoded by the L gene) of CCHFV. Non-limiting examples of strains and isolates of CCHFV include the prototype CCHFV strain IbAr10200; isolate C68031; China reference strain 66019; the Chinese isolates YT05099; ZAM57/06; CTF-Hu10/06; CTF-Hu15/06; CTF-Hu27/06; CTF-Hu30/06; CTF-Hu7/06; strain BA88166; strain China; Hazara virus (isolate JC280). Non-limiting examples of CCHFV strains and the L segments therein (Accession number in parentheses) which encode an OTU domain-containing protein include strain IbAr10200 (USAMRIID; AY947891; AAQ98866; AY389508; AY389361; AAY24690; AY422209); strain Congo 3010 (DQ099335); strain UG3010 (DQ211624); strain Turkey 200310849 (DQ211623); strain SPU415/85 (DQ211622); strain SPU103/87 (DQ211621); strain SPU97/85 (DQ211620); strain Oman (DQ211619); strain Kashmanov segment L (DQ211618); strain Drosdov (DQ211617.1); strain C-68031 (Q211616); strain ArD39554 (DQ211615); strain ArD15786 (DQ211614); strain ArD8194 (DQ211613); strain AP92 (DQ211612); strain VLV-100 (AY995166); strain Baghdad-12 (AY947890); strain TADJ/HU8966 (AY720893); strain 30908 (AY675240); and strain Matin (AY422208 Soldado; and Hughes). In a specific embodiment, the nairovirus is Dera Ghazi Khan virus, Abu Hammad virus, Abu Mina virus, Farallon virus, Punta Salinas virus, Raza virus, Qalyub virus, Bandia virus, Sakhalin virus, Tillamook virus, Thiafora virus or Erve virus.

In a specific embodiment, the viral OTU domain-containing protein is the RNA-dependent RNA polymerase (encoded by the L gene) of DUGV. Non-limiting examples of strains and isolates of DUGV are ArD44313; KT281/75; 16Ar1792; IbH11480; ArD16095; and ArD16769. In a specific embodiment, the viral OTU domain-containing protein is the RNA-dependent RNA polymerase (encoded by the L gene) of Nairobi sheep disease virus (NSDV). Non-limiting examples of NSDV strains and the L segments therein (Accession number in parentheses) which encode an OTU domain-containing protein include RV082 (AY359525) and Ganjam IG619 (AY359526).

In a specific embodiment, the viral OTU domain-containing protein is the nsp2 protein of EAV. Non-limiting examples of EAV strains with OTU domain-containing proteins are Bucyrus strain; isolate CW01 (GenBank Acc. No. AY349168); isolate CW96 (GenBank Acc. No. AY349167); and Sequence 1 from International Patent Application Publication No. WO 9519438, which is incorporated by reference herein.

In a specific embodiment, the viral OTU domain-containing protein is the nsp2 protein of PRRSV. Non-limiting examples of PRRSV strains or isolates (GenBank Accession No. in parentheses) useful in the practice of the invention are the pathogenic pig isolate 16244B, 2/18/97 (Nebraska) (Q9YNO2); the cell culture-adapted Lelystad virus LV4.2.1 (AY588319 or M96262); European prototype Lelystad virus; isolate China HB-1(sh)/2002 (AY150312); China HB-2(sh)/

2002 (AY262352); isolate HN1 (AY457635); the North American prototype isolate VR-2332 (AY150564 or PRU87392); isolate CC-1 (EF153486); strain HEB1 (EF112447); strain HUB2 (EF112446); strain JXA1 (EF112445); strain HUB1 (EF075945); isolate Ingelvac ATP (DQ988080); strain 01CB1 (DQ864705); strain Prime Pac (DQ779791); strain SD01-08 (DQ489311); the moderately virulent type I isolate of SD01-08; isolate LMY (DQ473474); isolate S1 (DQ459471); strain VR-2332 clone pVR-V7 (DQ217415); clone VR-2332 V7 (DQ176021); isolate MN184B (DQ176020); isolate MN184A (DQ176019); virulent MN184 isolate RFLP184; RespPRRS MLV (AF066183); strain 01NP1.2 (DQ056373); strain PL97-1/LP1 (AY612613); strain PL97-1 (AY585241); strain NVSL 97-7895 (AY545985); strain JA142 (AY424271); Euro-PRRSV (AY366525); isolate PA8 (AF176348); isolate P129 (20271246); strain CH-1a (AY032626); isolate NVSL 97-7985 IA 1-4-2 (AF325691); BJ-4 (AF331831); VR-2332, complete genome; RespPRRS/Repro (AF159149); the vaccine strain SP (AF184212); Lelystad Agent-specific nucleotide sequence from International Patent Application Publication No. WO 9221375; and Lelystad virus sequences from International Patent Application Publication No. WO 02072802, both of which are incorporated by reference herein.

In a specific embodiment, the viral OTU domain-containing protein is the nsp2 protein of LDV. Non-limiting examples of LDV strains or isolates (GenBank Accession No. in parentheses) with OTU domain-containing proteins are the strain Plagemann (NC_001639) and the neuro-virulent type C stain (L13298).

In a specific embodiment, the viral OTU domain-containing protein is a protein of a herpes virus. Non-limiting examples of herpes virus species, strains, or isolates (GenBank Accession No. in parentheses) with OTU domain-containing proteins are the Epstein-Barr viruses Cynomolgus Epstein-Barr Virus A4; Cynomolgus Epstein-Barr Virus Si-IIA; Cynomolgus Epstein-Barr Virus TsB-B6; Epstein-barr virus strain ag876; Epstein-barr virus strain p3hr-1; Human herpesvirus 4 (strain B95-8) (Epstein-Barr virus (strain B95-8)); Human herpesvirus 4 (strain CAO) (Epstein-Barr virus (strain CAO)); Human herpesvirus 4 (strain RAJI) (Epstein-Barr virus (strain RAJI)); Human herpesvirus 4 type 1 (Epstein-Barr virus type 1); Human herpesvirus 4 type 2 (Epstein-Barr virus type 2); B95-8 (V01555) and Raji (M35547) strains (see, e.g., NC_007605); EBV strain GD1 (AY961628); EBV strain AG876 (DQ279927); and Epstein-Barr virus, artifactual joining of B95-8 complete genome and the sequences from Raji of the large deletion found in B95-8 (M80517). Other herpesviruses with OTU domain-containing proteins embodied in this invention are the herpesvirus lymphotropic Ovine herpesvirus 2 (OvHV-2), strain BJ1035, isolated from *Bos bovis* (cow) T cell (AY839756); OvHV-2 strain BJ1035 isolated from *Ovis aries* (sheep) nasal secretions (DQ198083.1); Caprine herpesvirus 2 (CpHV-2); a GHV strain encoded by NC_001826; GHV strain WUMS (U97553); GHV strain g2.4 from *Clethrionomys glareolus* (AF105037); strain 72; strain 4556; the BHV4 *Babyrousa babyrussa* rhadinovirus 1; BHV4 isolate DN-599; BHV4 *Diceros bicornis* rhadinovirus 1; BHV4 *Phacochoerus africanus* rhadinovirus 1; BHV4 *Sus barbatus* rhadinovirus 1 (exemplary genome with GenBank accession no. NC 002665); the *Saimiriine* herpesvirus 1, *Saimiri* alpha-herpesvirus (isolated from *Saimiri sciureus*); the *Saimiriine* herpesvirus 1 type 1/strain mv-5-4-ps1; and porcine lymphotropic herpesvirus 3 (AAO12337).

5.1.1 Methods of Identifying Viral OTU Domain-Containing Proteins with DeISGylation Activity The present invention provides methods for identifying a viral OTU domain-containing protein, the methods comprising: (a) contacting a viral protein having an OTU domain or an OTU domain-containing fragment thereof with a composition comprising ISG15 conjugated protein; and (b) measuring the amount of ISG15 conjugated protein, wherein a decrease in the amount of ISG15 conjugated protein relative to a negative control (e.g., a composition comprising ISG15 conjugated protein not contacted with the viral protein) or a predetermined reference range indicates that the viral protein is a viral OTU domain-containing protein. In certain embodiments, a positive control, such as a known viral OTU domain-containing protein or a known cellular deISGylating protein (e.g., UBP43) is included in the assay. In accordance with this embodiment, the deISGylation activity of a suspected viral OTU domain-containing protein can be compared to a known viral OTU domain-containing protein or a known cellular deISGylating protein. In some embodiments, the decrease in ISG15 conjugates is proportional to the amount of viral OTU domain-containing protein or an OTU domain-containing fragment thereof added to the reaction.

Viral OTU domain-containing proteins can be determined using a cell-based assay. In a specific embodiment, the invention provides a method for identifying a viral OTU domain-containing protein, the method comprising: (a) engineering a cell to express a viral protein having an OTU domain or an OTU domain-containing fragment thereof and ISG15; and (b) measuring the amount of ISG15 conjugated protein, wherein a decrease in the amount of ISG15 conjugated protein relative to a negative control (e.g., a cell engineered to express ISG15 which does not express the viral protein) or predetermined reference range indicates that the viral protein is a viral OTU domain-containing protein. In another embodiment, the invention provides a method for identifying a viral OTU domain-containing protein, the method comprising: (a) contacting a cell expressing ISG15 with a viral protein having an OTU domain or an OTU domain-containing fragment thereof; and (b) measuring the amount of ISG15 conjugated protein, wherein a decrease in the amount of ISG15 conjugated protein relative to a negative control (e.g., a cell expressing ISG15 not contacted with the viral protein) or a predetermined reference range indicates that the viral protein is a viral OTU domain-containing protein. In some embodiments, the cell is engineered to express ISG15 or overexpress ISG15. In some embodiments, an affinity peptide tag such as poly-histidine, biotin, hemagglutinin (HA), glutathione S-transferase (GST), mannose binding protein (MBP), or FLAG is conjugated to ISG15. In other embodiments, ISG15 is expressed together with other proteins of the ISGylation cascade. In a particular embodiment, tagged ISG15 is overexpressed with proteins of the ISGylation cascade. In a specific embodiment, the proteins of the ISG15 cascade are UBE1L and UbcM8. In some embodiments, the cell is engineered to express ISG15 by contacting the cell with interferon (e.g., IFN-β).

In a specific embodiment, the invention provides a method for identifying a viral OTU domain-containing protein, the method comprising: (a) infecting a cell expressing ISG15 with a virus comprising a protein having an OTU domain; and (b) measuring the amount of ISG15 conjugated protein, wherein a decrease in the amount of ISG15 conjugated protein relative to a negative control (e.g., a cell not infected with the virus) or a predetermined reference range indicates that the viral protein is a viral OTU domain-containing protein. In some embodiments, the cell is engineered to express or overexpress ISG15. In a specific embodiment, the virus naturally encodes such viral OTU domain-containing protein. In another embodiment, the virus comprises a heterologous viral OTU domain-containing protein or OTU domain-containing fragment thereof. In some embodiments, Sindbis virus is used to infect the cell. In a particular embodiment, the dsTE12Q double subgenomic Sindbis virus contains a heterologous viral OTU domain-containing protein or an OTU domain-containing fragment thereof.

In some embodiments, the cell used in the methods described in the preceding two paragraphs is a eukaryotic cell or a prokaryotic cell. In a specific embodiment, the cell used is a mammalian cell. In another embodiment, the cell used is yeast cell. In another embodiment, the cell used is a human cell. In a specific embodiment, the cell is deficient in the interferon response. In another embodiment, the cell is deficient in deISGylation. In some embodiments, the cell engineered to express ISG15 is UBP43−/−. In a specific embodiment, the cell extract is from IFNβ-treated murine embryonic fibroblasts (MEFs) derived from Ubp43−/− mice.

Viral OTU domain-containing proteins can be determined using a cell-free assay. In a specific embodiment, the invention provides a method for identifying a viral OTU domain-containing protein, the method comprising: (a) contacting a cell extract with a viral protein having an OTU domain; and (b) measuring the amount of ISG15 conjugated protein, wherein a decrease in the amount of ISG15 conjugated protein relative to a negative control (e.g., a cell extract not contacted with the viral protein) or predetermined reference range indicates that the viral protein is a viral OTU domain-containing protein. In some embodiments, the cell extract is from a cell engineered to express ISG15 or overexpress ISG15. In some embodiments, an affinity peptide tag such as poly-histidine, biotin, hemagglutinin (HA), glutathione S-transferase (GST), mannose binding protein (MBP), or FLAG) is conjugated to ISG15. In other embodiments, the cell extract is from a cell engineered to express ISG15 and other proteins of the ISGylation cascade. In a particular embodiment, tagged ISG15 is overexpressed with proteins of the ISGylation cascade. In a specific embodiment, the proteins of the ISG15 cascade are UBE1L and UbcM8. In some embodiments, the cell extract is from a cell engineered to express ISG15 by contacting the cell with interferon (e.g., IFN-β).

In a specific embodiment, ISG15 conjugates are enriched before they are contacted with the OTU domain-containing viral protein or OTU domain-containing fragment thereof. In one embodiment, ISG15 conjugates in a cell extract are enriched, e.g., by chromatography. In another embodiment, ISG15 conjugates are enriched by affinity chromatography using an antibody specific to ISG15 or to the ISGylated protein. In another embodiment, the ISGylated protein source is enriched by affinity chromatography using a tag. In some embodiments, the protein target is tagged. In other embodiments, ISG15 is tagged. The tag can be any affinity tag known to those of skill in the art, including but not limited to poly-histidine, biotin, hemagglutinin (HA), glutathione S-transferase (GST), and mannose binding protein (MBP).

In some embodiments, the cell extract used in the methods described in the preceding two paragraphs is a eukaryotic cell extract or a prokaryotic cell extract. In a specific embodiment, the cell extract used is a mammalian cell extract. In another embodiment, the cell extract used is yeast cell extract. In another embodiment, the cell extract used is a human cell extract. In a specific embodiment, the cell extract is from a cell deficient in the interferon response. In another embodiment, the cell extract is from a cell deficient in deISGylation. In some embodiments, the cell extract is from a UBP43−/− cell. In a specific embodiment, the cell extract is from IFN-β-treated murine embryonic fibroblasts (MEFs) derived from Ubp43−/− mice.

The amount of ISG15 conjugated protein can be measured using any assay known to one of skill in the art for measuring ISGylation and/or deISGylation, including but not limited to an immunoassay, such as a Western blot or an ELISA, or a colorimetric assay. For example, the amount of ISG15 conjugated protein can be detected by lysing the cells and performing a Western blot or ELISA using an anti-ISG15 antibody (such as anti-ISG15 monoclonal antibody 3C2 described in Lenschow et al., 2005, J. Virol. 79: 13974-13983) or an anti-affinity peptide antibody (e.g., an anti-His antibody) if the ISG15 is affinity peptide-tagged ISG15.

In an exemplary embodiment, expression plasmids or empty plasmids are co-transfected into mammalian cells with a plasmid containing ISG15. In one embodiment, ISG15 is tagged. In a specific embodiment, the tag is an HA tag. In one embodiment, the cells are co-transfected with ISG15, UBE1L and UbcM8. Total levels of ISGylated proteins are detected by Western blotting. If the ISGylation signal decreases in the presence of the viral OTU domain-containing protein or OTU domain-containing fragment thereof, that protein contains deISGylation activity or inhibits ISGylation. In one embodiment, the decrease in total ISGylation is comparable to the effect of the deISGylation enzyme UBP43.

In an exemplary assay, His-tagged ISG15, UBE1L and UbcM8 are overexpressed in 293T cells and the ISG15 conjugates are enriched using Ni-NTA affinity columns. Enriched ISG15 conjugates are next incubated with recombinant OTU domain-containing viral protein and the total level of ISGylated proteins is detected by Western blot. If the signal of ISG15 conjugates decreases, it is confirmed that the recombinant viral OTU domain-containing protein or OTU domain-containing fragment thereof can deconjugate ISGylated proteins. In some embodiments, the viral OTU domain-containing protein deconjugates ISGylated proteins in a concentration dependent manner. In some embodiments, no other cellular proteins are involved in the observed deISGylation.

The amount of ISG conjugated protein can also be measured by a fluorescence-based assay, such as an assay to detect deISGylation of a fluorescent artificial substrate that mimics the ISG15 cleavage in which the flurophore becomes active after it is cleaved off ISG15.

In one embodiment, the invention provides methods for identifying a viral OTU domain-containing protein, the methods comprising: (a) contacting a composition comprising an artificial substrate that mimics the ISG15 cleavage and an OTU domain-containing viral protein or OTU domain-containing fragment thereof; and (b) measuring the amount of cleavage of the artificial substrate, wherein an increase in the cleavage of the artificial substrate relative to a negative control (e.g., the composition comprising an artificial substrate that mimics the ISG15 cleavage without the OTU domain-containing viral protein or OTU domain-containing fragment thereof) or a predetermined reference range indicates that the viral protein is a viral OTU domain-containing protein. In certain embodiments, the artificial substrate is a small synthetic fluorogenic substrate, such as AMC or AFC, that incorporates the C-terminal four (or six) residues found in Ub and ISG15 (LRGG) or (LRLRGG) (SEQ ID NO:1). (Lindner, H et al. J Virol. December 2005 Vol 79 p 15199-15208), (Blakirev, M et al, J Virol, June 2002, Vol 76 p 6323-6331). In other embodiments, the artificial substrate has DABCYL and EDANS moieties on opposite ends of a 12-(or other) mer peptide that can be detected by FRET (as used in: Barretto et al, J Virol, December 2005, Vol 79 p 15189-15198), in which such peptide has the cleavage site of interest (e.g., LRLRGG) (SEQ ID NO:1).

In another embodiment, the invention provides methods for identifying a viral OTU domain-containing protein, the methods comprising: (a) contacting an ISG15-fluorogenic substrate (such as, e.g., ISG15-AMC or ISG15-AFC available from Boston Biochem, Inc., Cambridge, Mass.) with an OTU domain-containing viral protein or an OTU domain-containing fragment thereof; and (b) measuring the fluorescence of the mixture, wherein an increase in the fluorescence relative to a negative control (e.g., the composition comprising an ISG15-fluorogenic substrate without the OTU domain-containing viral protein or OTU domain-containing fragment thereof) or a predetermined reference range indicates that the viral protein is a viral OTU domain-containing protein. In certain embodiments, the fluorescence is measured using a spectrofluorometer at, e.g., an excitation wavelength of 380 nm and emission is measured at, e.g., 440 nm.

5.1.2 Methods for Identifying Viral OTU Domain-Containing Proteins with Deubiquitination Activity The present invention provides methods for identifying a viral OTU domain-containing protein with deubiquitination activity, the methods comprising: (a) contacting a viral OTU domain-containing protein or an OTU domain-containing fragment thereof with a composition comprising ubiquitinated protein, and (b) measuring the amount of ubiquitinated protein, wherein a decrease in the amount of ubiquitinated protein relative to a negative control (e.g., a composition comprising ubiquitinated protein not contacted with the viral protein) or a predetermined reference range indicates that the viral protein or fragment thereof has deubiquitinating activity. In certain embodiments, a positive control, such as a known viral OTU domain-containing protein with deubiquitination activity or a known cellular deubiquitinating protein is included in the assay. In accordance with this embodiment, the deubiquitination activity of a viral OTU domain-containing protein can be compared to a known viral OTU domain-containing protein with deubiquitination activity or a known cellular deubiquitinating protein. In some embodiments, the decrease in ubiquitinated protein is proportional to the amount of viral OTU domain-containing protein or an OTU domain-containing fragment thereof added to the reaction.

The deubiquitinating activity of viral OTU domain-containing proteins can be determined using a cell-based assay. In a specific embodiment, the invention provides a method for identifying a viral OTU domain-containing protein with deubiquitinating activity, the method comprising: (a) engineering a cell to express a viral OTU domain-containing protein or an OTU domain-containing fragment thereof and ubiquitin; and (b) measuring the amount of ubiquitinated protein, wherein a decrease in the amount of ubiquitinated protein relative to a negative control (e.g., a cell engineered to express ubiquitinated protein which does not express the viral protein) or predetermined reference range indicates that the viral protein or fragment thereof has deubiquitination activity. In another embodiment, the invention provides methods for identifying a viral OTU domain-containing protein with deubiquitination activity, the method comprising: (a) contacting a cell expressing ubiquitin with a viral OTU domain-containing protein or an OTU domain-containing fragment thereof; and (b) measuring the amount of ubiquitinated protein, wherein a decrease in the amount of ubiquitinated protein relative to a negative control (e.g., a cell expressing ubiquitin not contacted with the viral protein) or a predetermined reference range indicates that the viral protein or fragment thereof has deubiquitinating activity. In some embodiments, the cell is engineered to express or overexpress ubiquitin. In some embodiments, an affinity peptide tag such as poly-histidine, biotin, hemagglutinin (HA), glutathione S-transferase (GST), mannose binding protein (MBP), or FLAG) is conjugated to the ubiquitin. In other embodiments, ubiquitin is expressed together with other proteins of the ubiquitination cascade. In a particular embodiment, tagged ubiquitin is overexpressed with proteins of the ubiquitination cascade.

In a specific embodiment, the invention provides a method for identifying a viral OTU domain-containing protein with deubiquitinating activity, the method comprising: (a) infecting a cell expressing ubiquitin with a virus comprising a viral OTU domain-containing protein or an OTU domain-containing fragment thereof; and (b) measuring the amount of ubiquitinated protein, wherein a decrease in the amount of ubiquitinated protein relative to a negative control (e.g., a cell not infected with the virus) or a predetermined reference range indicates that the viral protein or a fragment thereof has deubiquitination activity. In some embodiments, the cell is engineered to express or overexpress ubiquitin. In a specific embodiment, the virus naturally encodes such viral OTU domain-containing protein. In another embodiment, the virus comprises a heterologous viral OTU domain-containing protein or OTU domain-containing fragment thereof. In some embodiments, Sindbis virus is used to infect the cell. In a particular embodiment, the dsTE12Q double subgenomic Sindbis virus contains a heterologous viral OTU domain-containing protein or an OTU domain-containing fragment thereof.

In some embodiments, the cell used in the methods described in the preceding two paragraphs is a eukaryotic cell or a prokaryotic cell. In a specific embodiment, the cell used is a mammalian cell. In another embodiment, the cell used is yeast cell. In another embodiment, the cell used is a human cell. In a specific embodiment, the cell is deficient in one or more components of the deubiquitination pathway.

The deubiquitination activity of a viral OTU domain-containing proteins can be determined using a cell-free assay. In a specific embodiment, the invention provides a method for identifying a viral OTU domain-containing protein with deubiquitinating activity, the method comprising: (a) contacting poly-ubiquitin chains with a viral OTU domain-containing protein or an OTU domain-containing fragment thereof and (b) measuring the amount of poly-ubiquitin chains, wherein a decrease in the amount of polyubiquitin chains relative to a negative control (e.g., poly-ubiquitin chains not contacted with the viral protein) or predetermined reference range indicates that the viral protein or fragment thereof has deubiquitination activity. In some embodiments, commercially available poly-ubiquitin chains are used in accordance with the methods. In one embodiment, K48 and K63-linked ubiquitin chains are used in accordance with the invention.

In a specific embodiment, the invention provides a method for identifying a viral OTU domain-containing protein with deubiquitination activity, the method comprising: (a) contacting a cell extract with a viral OTU domain-containing protein or an OTU domain-containing fragment thereof and (b) measuring the amount of ubiquitinated protein, wherein a decrease in the amount of ubiquitinated protein relative to a negative control (e.g., a cell extract not contacted with the viral protein) or predetermined reference range indicates that the viral protein or fragment thereof has deubiquitination activity. In some embodiments, the cell extract is from a cell engineered to express or overexpress ubiquitin. In some embodiments, an affinity peptide tag such as poly-histidine, biotin, hemagglutinin (HA), glutathione S-transferase (GST), mannose binding protein (MBP), or FLAG) is conjugated to the ubiquitin. In other embodiments, cell extract is from a cell engineered to express ubiquitin and other proteins of the ubiquitination cascade. In a particular embodiment, tagged ubiquitin is overexpressed with proteins of the ubiquitination cascade.

In a specific embodiment, ubiquitinated proteins are enriched before they are contacted with the viral OTU domain-containing protein or OTU domain-containing fragment thereof. In one embodiment, ubiquitinated proteins in a cell extract are enriched, e.g., by chromatography. In another embodiment, ubiquitinated proteins are enriched by affinity chromatography using an antibody specific to ubiquitin or to the ubiquitinated protein. In another embodiment, the ubiquitinated protein is enriched by affinity chromatography using a tag. In some embodiments, the protein target is tagged. In other embodiments, ubiquitin is tagged. The tag can be any affinity tag known to those of skill in the art, including but not limited to poly-histidine, biotin, hemagglutinin (HA), glutathione S-transferase (GST), and mannose binding protein (MBP).

In some embodiments, the cell extract used in the methods described in the preceding two paragraphs is a eukaryotic cell extract or a prokaryotic cell extract. In a specific embodiment, the cell extract used is a mammalian cell extract. In another embodiment, the cell extract used is yeast cell extract. In another embodiment, the cell extract used is a human cell extract. In a specific embodiment, the cell extract is from a cell deficient in one or more components of the deubiquitination pathway.

The amount of ubiquitinated protein can be measured using any assay known to one of skill in the art for measuring ubiquitination and/or deubiquitination, including but not limited to an immunoassay, such as a Western blot or an ELISA, SDS-PAGE and Coomassie staining, or a colorimetric assay. For example, the amount of ubiquitinated protein can be detected by lysing the cells and performing a Western blot or ELISA using an anti-ubiquitin antibody or an anti-affinity peptide antibody (e.g., an anti-His antibody) if the ubiquitin is affinity peptide-tagged.

The amount of ubiquitinated protein can also be measured by a fluorescence-based assay, such as an assay to detect deubiquitination of a fluorescent artificial substrate that mimics the ubiquitin cleavage in which the fluorophore becomes active after it is cleaved off ubiquitin.

In one embodiment, the invention provides methods for identifying a viral OTU domain-containing protein with deubiquitinating activity, the methods comprising: (a) contacting a composition comprising an artificial substrate that mimics the ubiquitin cleavage with a viral OTU domain-containing protein or OTU domain-containing fragment thereof; and (b) measuring the amount of cleavage of the artificial substrate, wherein an increase in the cleavage of the artificial substrate relative to a negative control (e.g., the composition comprising an artificial substrate that mimics the ubiquitin cleavage without the viral OTU domain-containing protein or OTU domain-containing fragment thereof) or a predetermined reference range indicates that the viral OTU domain-containing protein or OTU domain-containing fragment thereof has deubiquitination activity. In a specific embodiment, the viral OTU domain-containing protein has deISGylation and deubiquitination activity. In certain embodiments, the artificial substrate is a small synthetic fluorogenic substrate, such as AMC or AFC, that incorporates the C-terminal four (or six) residues found in Ub and ISG15 (LRGG) or (LRLRGG) (SEQ ID NO:1). (Lindner, H et al. J Virol. December 2005 Vol 79 p 15199-15208), (Blakirev, M et al, J Virol, June 2002, Vol 76 p 6323-6331). In other embodiments, the artificial substrate has DABCYL and EDANS moieties on opposite ends of a 12-(or other) mer peptide that can be detected by FRET (as used in: Barretto et al, J Virol, December 2005, Vol 79 p 15189-15198), in which such peptide has the cleavage site of interest (e.g., LRLRGG (SEQ ID NO:1)).

In another embodiment, the invention provides methods for identifying a viral OTU domain-containing protein with deubiquitination activity, the methods comprising: (a) contacting a ubiquitin-fluorogenic substrate (such as, e.g., ubiquitin-AMC or ubiquitin-AFC available from Boston Biochem, Inc., Cambridge, Mass.), with a viral OTU domain-containing protein or an OTU domain-containing fragment thereof; and (b) measuring the fluorescence of the mixture, wherein an increase in the fluorescence relative to a negative control (e.g., the composition comprising a ubiquitin-fluorogenic substrate without the viral OTU domain-containing protein or OTU domain-containing fragment thereof) or a predetermined reference range indicates that the viral OTU domain-containing protein or OTU domain-containing fragment thereof has deubiquitination activity. In certain embodiments, the fluorescence is measured using a spectrofluorometer.

5.1.3 Methods for Identifying Viral OTU Domain-Containing Proteins With DeSUMOylation Activity The present invention provides methods for identifying a viral OTU domain-containing protein with deSUMOylation activity, the methods comprising: (a) contacting a viral OTU domain-containing protein or an OTU domain-containing fragment thereof with a composition comprising SUMOylated protein; and (b) measuring the amount of SUMOylated protein, wherein a decrease in the amount of SUMOylated protein relative to a negative control (e.g., a composition comprising SUMOylated protein not contacted with the viral protein) or a predetermined reference range indicates that the viral protein or fragment thereof has deSUMOylating activity. In certain embodiments, a positive control, such as a known viral OTU domain-containing protein with deSUMOylating activity or a known cellular deSUMOylating protein is included in the assay. In accordance with this embodiment, the deSUMOylation activity of a viral OTU domain-containing protein can be compared to a known viral OTU domain-containing protein with deSUMOylation activity or a known cellular deSUMOylating protein. In some embodiments, the decrease in SUMOylated protein is proportional to the amount of viral OTU domain-containing protein or an OTU domain-containing fragment thereof added to the reaction.

The deSUMOylating activity of viral OTU domain-containing proteins can be determined using a cell-based assay. In a specific embodiment, the invention provides a method for identifying a viral OTU domain-containing protein with deSUMOylation activity, the method comprising: (a) engineering a cell to express a viral OTU domain-containing protein or an OTU domain-containing fragment thereof and SUMO; and (b) measuring the amount of SUMOylated protein, wherein a decrease in the amount of SUMOylated protein relative to a negative control (e.g., a cell engineered to express SUMOylated protein which does not express the viral protein) or predetermined reference range indicates that the viral protein or fragment thereof has deSUMOylation activity. In another embodiment, the invention provides a method for identifying a viral OTU domain-containing protein with deSUMOylation activity, the method comprising: (a) contacting a cell expressing SUMO with a viral OTU domain-containing protein or an OTU domain-containing fragment thereof; and (b) measuring the amount of SUMOylated protein, wherein a decrease in the amount of SUMOylated protein relative to a negative control (e.g., a cell expressing SUMO not contacted with the viral protein) or a predetermined reference range indicates that the viral protein or fragment thereof has deSUMOylation activity. In some embodiments, the cell is engineered to express or overexpress SUMO. In some embodiments, an affinity peptide tag such as poly-histidine, biotin, hemagglutinin (HA), glutathione S-transferase (GST), mannose binding protein (MBP), or FLAG) is conjugated to SUMO. In other embodiments, SUMO is expressed together with other proteins of the SUMOylation cascade. In a particular embodiment, tagged SUMO is overexpressed with proteins of the SUMOylation cascade.

In a specific embodiment, the invention provides a method for identifying a viral OTU domain-containing protein with deSUMOylating activity, the method comprising: (a) infecting a cell expressing SUMO with a virus comprising a viral OTU domain-containing protein or an OTU domain-containing fragment thereof; and (b) measuring the amount of SUMOylated protein, wherein a decrease in the amount of SUMOylated protein relative to a negative control (e.g., a cell not infected with the virus) or a predetermined reference range indicates that the viral protein or a fragment thereof has deSUMOylation activity. In some embodiments, the cell is engineered to express or overexpress SUMO. In a specific embodiment, the virus naturally encodes such viral OTU domain-containing protein. In another embodiment, the virus comprises a heterologous viral OTU domain-containing protein or OTU domain-containing fragment thereof. In some embodiments, Sindbis virus is used to infect the cell. In a particular embodiment, the dsTE12Q double subgenomic Sindbis virus contains a heterologous viral OTU domain-containing protein or an OTU domain-containing fragment thereof.

In some embodiments, the cell used in the methods described in the preceding two paragraphs is a eukaryotic cell or a prokaryotic cell. In a specific embodiment, the cell used is a mammalian cell. In another embodiment, the cell used is yeast cell. In another embodiment, the cell used is a human cell. In a specific embodiment, the cell is deficient in one or more components of the deSUMOylation pathway.

The deSUMOylation activity of a viral OTU domain-containing protein can be determined using a cell-free assay. In a specific embodiment, the invention provides a method for identifying a viral OTU domain-containing protein with deSUMOylation activity, the method comprising: (a) contacting poly-SUMO chains (e.g., poly-SUMO-2 chains or poly-SUMO-3 chains) with a viral OTU domain-containing viral protein or an OTU domain-containing fragment thereof and (b) measuring the amount of poly-SUMO chains, wherein a decrease in the amount of poly-SUMO chains relative to a negative control (e.g., poly-SUMO chains not contacted with the viral protein) or predetermined reference range indicates that the viral protein or fragment thereof has deSUMOylation activity. In some embodiments, commercially available poly-SUMO chains are used in accordance with the methods.

In a specific embodiment, the invention provides a method for identifying a viral OTU domain-containing protein with deSUMOylation activity, the method comprising: (a) contacting a cell extract with a viral OTU domain-containing protein or an OTU domain-containing fragment thereof and (b) measuring the amount of SUMOylated protein, wherein a decrease in the amount of SUMOylated protein relative to a negative control (e.g., a cell extract not contacted with the viral protein) or predetermined reference range indicates that the viral protein or fragment thereof has deSUMOylation activity. The cell extract is from a cell engineered to express or overexpress SUMO. In some embodiments, an affinity peptide tag such as poly-histidine, biotin, hemagglutinin (HA), glutathione S-transferase (GST), mannose binding protein (MBP), or FLAG) is conjugated to SUMO. In other embodiments, the cell extract is from a cell engineered to express SUMO and other proteins of the SUMOylation cascade. In a particular embodiment, tagged SUMO is overexpressed with proteins of the SUMOylation cascade.

In a specific embodiment, SUMOylated proteins are enriched before they are contacted with the viral OTU domain-containing protein or OTU domain-containing fragment thereof. In one embodiment, SUMOylated proteins in a cell extract are enriched, e.g., by chromatography. In another embodiment, SUMOylated proteins are enriched by affinity chromatography using an antibody specific to SUMO or to the SUMOylated protein. In another embodiment, the SUMOylated protein is enriched by affinity chromatography using a tag. In some embodiments, the protein target is tagged. In other embodiments, SUMO is tagged. The tag can be any affinity tag known to those of skill in the art, including but not limited to poly-histidine, biotin, hemagglutinin (HA), glutathione S-transferase (GST), and mannose binding protein (MBP).

In some embodiments, the cell extract used in the methods described in the preceding two paragraphs is a eukaryotic cell extract or a prokaryotic cell extract. In a specific embodiment, the cell extract used is a mammalian cell extract. In another embodiment, the cell extract used is yeast cell extract. In another embodiment, the cell extract used is a human cell extract. In a specific embodiment, the cell extract is from a cell deficient in one or more components of the deSUMOylation pathway. The amount of SUMOylated protein can be measured using any assay known to one of skill in the art for measuring SUMOylation and/or deSUMOylation, including but not limited to SDS-PAGE and Coomassie staining, an immunoassay, such as a Western blot or an ELISA, or a colorimetric assay. For example, the amount of SUMOylated protein can be detected by lysing the cells and performing a Western blot or ELISA using an anti-SUMO antibody or an anti-affinity peptide antibody (e.g., an anti-His antibody) if the SUMO is affinity peptide-tagged.

The amount of SUMOylated protein can also be measured by a fluorescence-based assay, such as an assay to detect deSUMOylation of a fluorescent artificial substrate that mimics the SUMO cleavage in which the fluorophore becomes active after it is cleaved off SUMO.

In one embodiment, the invention provides methods for identifying a viral OTU domain-containing protein with deSUMOylation activity, the methods comprising: (a) contacting a composition comprising an artificial substrate that mimics the SUMO cleavage with a viral OTU domain-containing protein or OTU domain-containing fragment thereof; and (b) measuring the amount of cleavage of the artificial substrate, wherein an increase in the cleavage of the artificial substrate relative to a negative control (e.g., the composition comprising an artificial substrate that mimics the SUMO cleavage without the viral OTU domain-containing protein or OTU domain-containing fragment thereof) or a predetermined reference range indicates that the viral OTU domain-containing protein or OTU domain-containing fragment thereof has deSUMOylation activity. In some embodiments the artificial substrate has DABCYL and EDANS moieties on opposite ends of a 12-(or other) mer peptide that can be detected by FRET (as used in: Barretto et al, J Virol, December 2005, Vol 79 p 15189-15198), in which such peptide has the cleavage site of interest.

In another embodiment, the invention provides methods for identifying a viral OTU domain-containing protein that has deSUMOylation activity, the methods comprising: (a) contacting a composition with a SUMO-fluorogenic substrate (such as, e.g., SUMO-1-AMC or SUMO-1-AFC available from Boston Biochem, Inc., Cambridge, Mass.) with a viral OTU domain-containing protein or an OTU domain-containing fragment thereof; and (b) measuring the fluorescence of the mixture, wherein an increase in the fluorescence relative to a negative control (e.g., the composition comprising an SUMO-fluorogenic substrate without the viral OTU domain-containing protein or OTU domain-containing fragment thereof) or a predetermined reference range indicates that the viral OTU domain-containing protein or OTU domain-containing fragment thereof has deSUMOylation activity. In certain embodiments, the fluorescence is measured using a spectrofluorometer.

5.1.4 Methods for Identifying Viral OTU Domain-Containing Proteins With DeNeddylation Activity The present invention provides methods for identifying a viral OTU domain-containing protein with deNeddylation activity, the methods comprising: (a) contacting a viral OTU domain-containing protein or an OTU domain-containing fragment thereof with a composition comprising Neddylated protein, and (b) measuring the amount of Neddylated protein, wherein a decrease in the amount of Neddylated protein relative to a negative control (e.g., a composition comprising Neddylated protein not contacted with the viral protein) or a predetermined reference range indicates that the viral protein or fragment thereof has deNeddylation activity. In certain embodiments, a positive control, such as a known viral OTU domain-containing protein with deNeddylation activity or a known cellular deNeddylating protein is included in the assay. In accordance with this embodiment, the deNeddylation activity of a viral OTU domain-containing protein can be compared to a known viral OTU domain-containing protein with deNeddylation activity or a known cellular deNeddylating protein. In some embodiments, the decrease in Neddylated protein is proportional to the amount of viral OTU domain-containing protein or an OTU domain-containing fragment thereof added to the reaction.

The deNeddylating activity of viral OTU domain-containing proteins can be determined using a cell-based assay. In a specific embodiment, the invention provides a method for identifying a viral OTU domain-containing protein with deNeddylation activity, the method comprising: (a) engineering a cell to express a viral OTU domain-containing protein or an OTU domain-containing fragment thereof and Nedd8; and (b) measuring the amount of Neddylated protein, wherein a decrease in the amount of Neddylated protein relative to a negative control (e.g., a cell engineered to express Neddylated protein which does not express the viral protein) or predetermined reference range indicates that the viral protein or fragment thereof has deNeddylation activity. In another embodiment, the invention provides a method for identifying a viral OTU domain-containing protein with deNeddylation activity, the method comprising: (a) contacting a cell expressing Nedd8 with a viral OTU domain-containing protein or an OTU domain-containing fragment thereof; and (b) measuring the amount of Neddylated protein, wherein a decrease in the amount of Neddylated protein relative to a negative control (e.g., a cell expressing Nedd8 not contacted with the viral protein) or a predetermined reference range indicates that the viral protein or fragment thereof has deNeddylation activity. In some embodiments, the cell is engineered to express or overexpress Nedd8. In some embodiments, an affinity peptide tag such as poly-histidine, biotin, hemagglutinin (HA), glutathione S-transferase (GST), mannose binding protein (MBP), or FLAG) is conjugated to Nedd8. In other embodiments, Nedd8 is expressed together with other proteins of the Neddylation cascade. In a particular embodiment, tagged Nedd8 is overexpressed with proteins of the Neddylation cascade.

In a specific embodiment, the invention provides a method for identifying a viral OTU domain-containing protein with deNeddylating activity, the method comprising: (a) infecting a cell expressing Nedd8 with a virus comprising an OTU domain-containing protein or an OTU domain-containing fragment thereof and (b) measuring the amount of Neddylated protein, wherein a decrease in the amount of Neddylated protein relative to a negative control (e.g., a cell not infected with the virus) or a predetermined reference range indicates that the viral protein or a fragment thereof has deNeddylation activity. In some embodiments, the cell is engineered to express or overexpress Nedd8. In a specific embodiment, the virus naturally encodes such viral OTU domain-containing protein. In another embodiment, the virus comprises a heterologous viral OTU domain-containing protein or OTU domain-containing fragment thereof. In some embodiments, the cell is infected with a Sindbis virus. In a particular embodiment, the dsTE12Q double subgenomic Sindbis virus contains a heterologous viral OTU domain-containing protein or an OTU domain-containing fragment thereof.

In some embodiments, the cell used in the methods described in the preceding two paragraphs is a eukaryotic cell or a prokaryotic cell. In a specific embodiment, the cell used is a mammalian cell. In another embodiment, the cell used is yeast cell. In another embodiment, the cell used is a human cell. In a specific embodiment, the cell is deficient in one or more components of the deNeddylation pathway.

The deNeddylation activity of a viral OTU domain-containing protein can be determined using a cell-free assay. In a specific embodiment, the invention provides a method for identifying a viral OTU domain-containing protein with deNeddylation activity, the method comprising: (a) contacting pro-Nedd8 with a viral OTU domain-containing viral protein or an OTU domain-containing fragment thereof and (b) measuring the amount of pro-Nedd8, wherein a decrease in the amount of pro-Nedd8 relative to a negative control (e.g., pro-Nedd8 not contacted with the viral protein) or predetermined reference range indicates that the viral protein or fragment thereof has deNeddylation activity. In some embodiments, commercially available pro-Nedd8 is used in accordance with the methods.

In a specific embodiment, the invention provides a method for identifying a viral OTU domain-containing protein with deNeddylation activity, the method comprising: (a) contacting a cell extract with a viral OTU domain-containing protein or an OTU domain-containing fragment thereof and (b) measuring the amount of Neddylated protein, wherein a decrease in the amount of Neddylated protein relative to a negative control (e.g., a cell extract not contacted with the viral protein) or predetermined reference range indicates that the viral protein or fragment thereof has deNeddylation activity. In some embodiments, the cell extract is from a cell engineered to express or overexpress Nedd8. In some embodiments, an affinity peptide tag such as poly-histidine, biotin, hemagglutinin (HA), glutathione S-transferase (GST), mannose binding protein (MBP), or FLAG) is conjugated to Nedd8. In other embodiments, the cell extract is from a cell engineered to express Nedd8 and other proteins of the Neddylation cascade. In a particular embodiment, tagged Nedd8 is overexpressed with proteins of the Neddylation cascade.

In a specific embodiment, Neddylated proteins are enriched before they are contacted with the viral OTU domain-containing protein or OTU domain-containing fragment thereof. In one embodiment, Neddylated proteins in a cell extract are enriched, e.g., by chromatography. In another embodiment, Neddylated proteins are enriched by affinity chromatography using an antibody specific to Nedd8 or to the Neddylated protein. In another embodiment, the Neddylated protein is enriched by affinity chromatography using a tag. In some embodiments, the protein target is tagged. In other embodiments, Nedd8 is tagged. The tag can be any affinity tag known to those of skill in the art, including but not limited to poly-histidine, biotin, hemagglutinin (HA), glutathione S-transferase (GST), and mannose binding protein (MBP).

In some embodiments, the cell extract used in the methods described in the preceding two paragraphs is a eukaryotic cell extract or a prokaryotic cell extract. In a specific embodiment, the cell extract used is a mammalian cell extract. In another embodiment, the cell extract used is yeast cell extract. In another embodiment, the cell extract used is a human cell extract. In a specific embodiment, the cell extract is from a cell deficient in one or more components of the deNeddylation pathway.

The amount of Neddylated protein can be measured using any assay known to one of skill in the art for measuring Neddylation and/or deNeddylation, including but not limited to SDS-PAGE and Coomassie staining, an immunoassay, such as a Western blot or an ELISA, or a colorimetric assay. For example, the amount of Neddylated protein can be detected by lysing the cells and performing a Western blot or ELISA using an anti-Nedd8 antibody or an anti-affinity peptide antibody (e.g., an anti-His antibody) if the Nedd8 is affinity peptide-tagged.

The amount of Neddylated protein can also be measured by a fluorescence-based assay, such as an assay to detect deNeddylation of a fluorescent artificial substrate that mimics the Nedd8 cleavage in which the fluorophore becomes active after it is cleaved off Nedd8.

In one embodiment, the invention provides methods for identifying a viral OTU domain-containing protein with deNeddylation activity, the methods comprising: (a) contacting a composition comprising an artificial substrate that mimics the Nedd8 cleavage with a viral OTU domain-containing protein or OTU domain-containing fragment thereof; and (b) measuring the amount of cleavage of the artificial substrate, wherein an increase in the cleavage of the artificial substrate relative to a negative control (e.g., the composition comprising an artificial substrate that mimics the Nedd8 cleavage without the viral OTU domain-containing protein or OTU domain-containing fragment thereof) or a predetermined reference range indicates that the viral OTU domain-containing protein or OTU domain-containing fragment thereof has deNeddylation activity. In some embodiments the artificial substrate has DABCYL and EDANS moieties on opposite ends of a 12-(or other) mer peptide that can be detected by FRET (as used in: Barretto et al, J Virol, December 2005, Vol 79 p 15189-15198), in which such peptide has the cleavage site of interest.

In another embodiment, the invention provides methods for identifying a viral OTU domain-containing protein that has deNeddylation activity, the methods comprising: (a) contacting a composition with a Nedd8-fluorogenic substrate with a viral OTU domain-containing protein or an OTU domain-containing fragment thereof; and (b) measuring the fluorescence of the mixture, wherein an increase in the fluorescence relative to a negative control (e.g., the composition comprising an Nedd8-fluorogenic substrate without the viral OTU domain-containing protein or OTU domain-containing fragment thereof) or a predetermined reference range indicates that the viral OTU domain-containing protein or OTU domain-containing fragment thereof has deNeddylation activity. In certain embodiments, the fluorescence is measured using a spectrofluorometer.

5.1.5 In Vivo Assays for Viral DeISGylation and Its Effect on Virulence

The invention provides methods for determining the effect of a viral OTU domain-containing protein or an OTU domain-containing fragment thereof on virulence of a virus, the methods comprising: (a) infecting a cell with a virus comprising a viral OTU domain-containing protein or an OTU domain-containing fragment thereof; and (b) measuring the titer of the virus, wherein an increase in the viral titer relative to the viral titer of a cell infected with a virus of the same species deficient in deISGylation activity indicates that the viral OTU domain-containing protein or an OTU domain-containing fragment thereof increases the virulence of the virus. In a specific embodiment, the invention provides methods for determining the effect of a viral OTU domain-containing protein or an OTU domain-containing fragment thereof on virulence of a virus, the methods comprising: (a) infecting a subject with a virus comprising a viral OTU domain-containing protein or an OTU domain-containing fragment thereof; and (b) measuring the titer of the virus, wherein an increase in the viral titer relative to the viral titer in a subject infected with a virus of the same species deficient or impaired in deISGylation activity indicates that the viral OTU domain-containing protein or an OTU domain-containing fragment thereof increases the virulence of the virus. Techniques known to one of skill in the art can be used to measure virus titer.

The invention provides methods for determining the effect of a viral OTU domain-containing protein or an OTU domain-containing fragment thereof on virulence of a virus, the methods comprising: (a) infecting a subject with a virus comprising a viral OTU domain-containing protein or an OTU domain-containing fragment thereof; and (b) measuring the survival of the subject, wherein a decrease in the survival of the subject relative to the survival of a subject infected with a virus of the same species deficient or impaired in deISGylation activity indicates that the viral OTU domain-containing protein or an OTU domain-containing fragment thereof increases the virulence of the virus. The invention also provides methods for determining the effect of a viral OTU domain-containing protein or an OTU domain-containing fragment thereof on virulence of a virus, the methods comprising: (a) infecting a subject with a virus comprising a viral OTU domain-containing protein or an OTU domain-containing fragment thereof; and (b) measuring the immune response induced in the subject, wherein a decline in the immune response in the subject relative to the immune response in a subject infected with a virus of the same species deficient or impaired in deISGylation activity indicates that the viral OTU domain-containing protein or an OTU domain-containing fragment thereof increases the virulence of the virus.

The invention also provides methods for determining the effect of a viral OTU domain-containing protein or an OTU domain-containing fragment thereof on virulence of a virus, the methods comprising: (a) infecting a subject with a virus comprising a viral OTU domain-containing protein or an OTU domain-containing fragment thereof; and (b) measuring the symptoms manifested by the subject, wherein an increase in the number, duration and/or severity of one or more symptoms in the subject relative to the number, duration and/or severity of the same symptoms in a subject infected with a virus of the same species deficient or impaired in deISGylation activity indicates that the viral OTU domain-containing protein or an OTU domain-containing fragment thereof increases the virulence of the virus. The invention further provides methods for determining the effect of a viral OTU domain-containing protein or an OTU domain-containing fragment thereof on virulence of a virus, the methods comprising: (a) infecting a subject with a virus comprising a viral OTU domain-containing protein or an OTU domain-containing fragment thereof; and (b) measuring the time before onset of one or more symptoms in the subject, wherein a decrease in the delay before onset of one or more symptoms in the subject relative to the delay before onset of the same symptoms in a subject infected with a virus of the same species deficient or impaired in deISGylation activity indicates that the viral OTU domain-containing protein or an OTU domain-containing fragment thereof increases the virulence of the virus.

In a specific embodiment, the virus naturally encodes such viral OTU domain-containing protein. In another embodiment, the virus comprises a heterologous viral OTU domain-containing protein or OTU domain-containing fragment thereof. In some embodiments, Sindbis virus is used to infect the cell. In a particular embodiment, the dsTE12Q double subgenomic Sindbis virus contains a heterologous viral OTU domain-containing protein or an OTU domain-containing fragment thereof. In a specific embodiment, the control virus is deficient in deISGylation activity as a result of a mutation in the viral OTU domain-containing protein.

In some embodiments, the subject to be infected is transgenic. In some embodiments, the subject to be infected is a mutant. In some embodiments, the subject to be infected has an impaired interferon response. In other embodiments, the subject to be infected lacks ISGylation activity and/or lacks deISGylation activity.

In a specific embodiment, the invention provides a method for determining the effect of a viral OTU domain-containing protein or an OTU domain-containing fragment thereof on virulence of a virus, the methods comprising: (a) infecting Ifnar−/− mice with a Sindbis virus expressing ISG15 from dsTE12Q and a viral OTU domain-containing protein or an OTU domain-containing fragment thereof (e.g., by separating ISG15 from the OTU domain-containing insert with an IRES sequence); and (b) measuring the survival of the mice, wherein a decrease in the survival of mice relative to the survival of mice infected with a Sindbis virus expressing ISG15 from dsTE12Q but not expressing the viral protein or fragment thereof indicates the viral OTU domain-containing protein or fragment thereof contributes to the virulence of the virus. In another specific embodiment, the invention provides a method for determining the effect of a viral OTU domain-containing protein or an OTU domain-containing fragment thereof on virulence of a virus, the methods comprising: (a) infecting Ifnar−/− mice with a Sindbis virus expressing ISG15 from dsTE12Q and a viral OTU domain-containing protein or an OTU domain-containing fragment thereof (e.g., by separating ISG15 from the OTU domain-containing insert with an IRES sequence); and (b) measuring the survival of the mice, wherein a decrease in the survival of mice relative to the survival of mice infected with a Sindbis virus expressing ISG15 from dsTE12Q and the same viral OTU domain-containing protein or fragment, except that the OTU domain is nonfunctional for deISGylation, indicates the OTU domain-containing viral protein or fragment thereof contributes to the virulence of the virus. In another embodiment, the invention provides a method for determining the effect of a viral OTU domain-containing protein or an OTU domain-containing fragment thereof on virulence of a virus, the methods comprising: (a) infecting Ifnar−/− mice with a Sindbis virus expressing ISG15 from dsTE12Q and a viral OTU domain-containing protein or an OTU domain-containing fragment thereof (e.g., by separating ISG15 from the OTU domain-containing insert with an IRES sequence); and (b) measuring the titer of virus in the mice, wherein an increase in the virus titer in mice relative to the virus titer in mice infected with a Sindbis virus expressing ISG15 from dsTE12Q but not expressing the viral protein or fragment thereof indicates the OTU domain-containing viral protein or fragment thereof contributes to the virulence of the virus. In another specific embodiment the invention provides a method for determining the effect of a viral OTU domain-containing protein or an OTU domain-containing fragment thereof on virulence of a virus, the methods comprising: (a) infecting Ifnar−/− mice with a Sindbis virus expressing ISG15 from dsTE12Q and a viral OTU domain-containing protein or an OTU domain-containing fragment thereof (e.g., by separating ISG15 from the OTU domain-containing insert with an IRES sequence); and (b) measuring the titer of virus in the mice, wherein an increase in the virus titer in mice relative to the virus titer in mice infected with a Sindbis virus expressing ISG15 from dsTE12Q and the same viral OTU domain-containing protein or fragment, except that OTU domain is nonfunctional for deISGylation, indicates the viral OTU domain-containing protein or fragment thereof contributes to the virulence of the virus.

In one embodiment, ISG15-expressing, Ifnar−/− mice are infected s.c. with approximately $1 \times 10^4$ to approximately $1 \times 10^9$ PFU of recombinant Sindbis virus that comprises a viral OTU domain or OTU domain-containing protein and survival is monitored over 10 days, preferably over 15 days, more preferably over 20 days, and most preferably over 25 days. In one embodiment, ISG15-expressing, Ifnar−/− mice are infected s.c. with approximately $1 \times 10^4$ PFU, approximately $5 \times 10^4$ PFU, approximately $1 \times 10^6$ PFU, approximately $5 \times 10^6$ PFU, approximately $1 \times 10^7$ PFU, approximately $5 \times 10^7$ PFU, approximately $1 \times 10^8$ PFU, approximately $5 \times 10^8$ PFU, or approximately $1 \times 10^9$ PFU of recombinant Sindbis that comprises a viral OTU domain or OTU domain-containing protein virus and survival is monitored over 10 days, preferably over 15 days, 20 days, 25 days, 30 days, or more.

In one embodiment of this invention, the deISGylation activity of a virus is due to a viral OTU domain-containing protein and not a protein that does not have an OTU domain. In one embodiment, the deISGylation activity of a virus is due to a viral OTU domain-containing protein and not the activity of another protease domain, such as UCH, USP, MJD, OTU domain of a cellular protein, or JAMM. In some embodiments, the deISGylation activity is not through the SARS-CoV PLpro USP domain, herpesvirus UL36USP, or the adenovirus adenain ULP domain.

5.2 Methods for Identifying Mutants of the Viral OTU Domain-Containing Protein

The present invention provides methods for identifying mutants of a viral OTU domain-containing protein with altered deISGylation activity, the methods comprising: (a) contacting a mutated viral OTU domain-containing protein or an OTU domain-containing fragment thereof with a composition comprising ISG15 conjugated protein, and (b) measuring the amount of ISG15 conjugated protein, wherein an alteration in the amount of ISG15 conjugated protein relative to a control (e.g., a composition comprising ISG15 conjugated protein contacted with the wild-type viral OTU domain-containing protein) or a predetermined reference range indicates that the mutated viral OTU domain-containing protein or OTU domain-containing fragment thereof has altered deISGylation activity. In particular, the present invention provides methods for identifying mutants of a viral OTU domain-containing protein with reduced deISGylation activity, the methods comprising: (a) contacting a mutated viral OTU domain-containing protein or an OTU domain-containing fragment thereof with a composition comprising ISG15 conjugated protein, and (b) measuring the amount of ISG15 conjugated protein, wherein an increase in the amount of ISG15 conjugated protein relative to a control (e.g., a composition comprising ISG15 conjugated protein contacted with the wild-type viral OTU domain-containing protein) or a predetermined reference range indicates that the mutated viral OTU domain-containing protein or OTU domain-containing fragment thereof has reduced deISGylation activity.

In a specific embodiment, the invention provides a method for identifying mutants of a viral OTU domain-containing protein with reduced deISGylation activity, the method comprising: (a) engineering a cell to express a mutated viral OTU domain-containing protein or an OTU domain-containing fragment thereof and ISG15; and (b) measuring the amount of ISG15 conjugated protein, wherein an increase in the amount of ISG15 conjugated protein relative to a control (e.g., a cell engineered to express ISG15 and the wild-type viral OTU domain-containing protein) or predetermined reference range indicates that the mutated viral OTU domain-containing viral protein or OTU domain-containing fragment thereof has reduced deISGylation activity. In another embodiment, the invention provides a method for identifying a viral OTU domain-containing protein with reduced deISGylation activity, the method comprising: (a) contacting a cell expressing ISG15 with a mutated viral OTU domain-containing protein or an OTU domain-containing fragment thereof; and (b) measuring the amount of ISG15 conjugated protein, wherein an increase in the amount of ISG15 conjugated protein relative to a control (e.g., a cell expressing ISG15 contacted with the wild-type viral OTU domain-containing protein) or a predetermined reference range indicates that the mutated viral OTU domain-containing protein or OTU domain-containing fragment thereof has reduced deISGylation activity. In some embodiments, the cell is engineered to express or overexpress ISG15. In some embodiments, an affinity peptide tag such as poly-histidine, biotin, hemagglutinin (HA), glutathione S-transferase (GST), mannose binding protein (MBP), or FLAG) is conjugated to ISG15. In other embodiments, ISG15 is expressed together with other proteins of the ISGylation cascade. In a particular embodiment, tagged ISG15 is overexpressed with proteins of the ISGylation cascade. In a specific embodiment, the proteins of the ISG15 cascade are UBE1L and UbcM8. In some embodiments, the cell is engineered to express ISG15 by contacting the cell with interferon (e.g., IFN-β).

In a specific embodiment, the invention provides a method for identifying mutants of a viral OTU domain-containing protein with reduced deISGylation activity, the method comprising: (a) infecting a cell expressing ISG15 with a virus comprising a mutated viral OTU domain-containing protein or an OTU domain-containing fragment thereof; and (b) measuring the amount of ISG15 conjugated protein, wherein an increase in the amount of ISG15 conjugated protein relative to a control (e.g., a cell infected with a virus of the same species expressing wild-type viral OTU domain-containing protein) or a predetermined reference range indicates that the mutated viral OTU domain-containing protein or OTU domain-containing fragment thereof has reduced deISGylation activity. In some embodiments, the cell is engineered to express or overexpress ISG15. In a specific embodiment, the virus naturally encodes such a viral OTU domain-containing protein. In another embodiment, the virus comprises a heterologous viral OTU domain-containing protein or OTU domain-containing fragment thereof. In some embodiments, Sindbis virus is used to infect the cell.

In some embodiments, the cell or cell extract used in the methods described in the preceding two paragraphs is a eukaryotic cell or a prokaryotic cell. In a specific embodiment, the cell or extract is a mammalian cell. In another embodiment, the cell used is a yeast cell. In another embodiment, the cell used is a human cell. In a specific embodiment, the cell is deficient in the interferon response. In another embodiment, the cell is deficient in deISGylation. In some embodiments, the cell engineered to express ISG15 is UBP43−/−. In a specific embodiment, the cell is IFN-β-treated murine embryonic fibroblasts (MEFs) derived from Ubp43−/− mice.

In a specific embodiment, the invention provides a method for identifying mutants of a viral OTU domain-containing protein with reduced deISGylation activity, the method comprising: (a) contacting a cell extract with a mutated viral OTU domain-containing protein or an OTU domain-containing fragment thereof and (b) measuring the amount of ISG15 conjugated protein, wherein an increase in the amount of ISG15 conjugated protein relative to a control (e.g., a cell extract contacted with the wild-type viral OTU domain-containing protein) or predetermined reference range indicates that the mutated viral OTU domain-containing protein or OTU domain-containing fragment thereof has reduced deISGylation activity. In some embodiments, the cell extract is from a cell engineered to express or overexpress ISG15. In some embodiments, an affinity peptide tag such as poly-histidine, biotin, hemagglutinin (HA), glutathione S-transferase (GST), mannose binding protein (MBP), or FLAG is conjugated to ISG15. In other embodiments, the cell extract is from a cell engineered to express ISG15 and other proteins of the ISGylation cascade. In a particular embodiment, tagged ISG15 is overexpressed with proteins of the ISGylation cascade. In a specific embodiment, the proteins of the ISG15 cascade are UBE1L and UbcM8. In some embodiments, the cell extract is from a cell engineered to express ISG15 by contacting the cell with interferon (e.g., IFN-β).

In a specific embodiment, ISG15 conjugates are enriched before they are contacted with the viral OTU domain-containing protein or OTU domain-containing fragment thereof. In one embodiment, ISG15 conjugates in a cell extract are enriched, e.g., by chromatography. In another embodiment, ISG15 conjugates are enriched by affinity chromatography using an antibody specific to ISG15 or to the ISGylated protein. In another embodiment, the ISGylated protein source is enriched by affinity chromatography using a tag. In some embodiments, the protein target is tagged. In other embodiments, ISG15 is tagged. The tag can be any affinity tag known to those of skill in the art, including but not limited to poly-histidine, biotin, hemagglutinin (HA), glutathione S-transferase (GST), and mannose binding protein (MBP).

In some embodiments, the cell extract used in the methods described in the preceding two paragraphs is a eukaryotic cell extract or a prokaryotic cell extract. In a specific embodiment, the cell extract used is a mammalian cell extract. In another embodiment, the cell extract used is yeast cell extract. In another embodiment, the cell extract used is a human cell extract. In a specific embodiment, the cell extract is from a cell deficient in the interferon response. In another embodiment, the cell extract is from a cell deficient in deISGylation. In some embodiments, the cell extract is from a UBP43−/− cell. In a specific embodiment, the cell extract is from IFN-β-treated murine embryonic fibroblasts (MEFs) derived from Ubp43−/− mice.

The amount of ISG15 conjugated protein can be measured using any assay known to one of skill in the art for measuring ISGylation and/or deISGylation, including but not limited to an immunoassay, such as a Western blot or an ELISA, or a colorimetric assay. For example, the amount of ISG15 conjugated protein can be detected by lysing the cells and performing a Western blot or ELISA using an anti-ISG15 antibody (such as anti-ISG15 monoclonal antibody 3C2 described in Lenschow et al., 2005, J. Virol. 79: 13974-13983) or an anti-affinity peptide antibody (e.g., an anti-His antibody) if the ISG15 is affinity peptide-tagged ISG15.

In another example, the amount of ISG conjugated protein can be measured by a fluorescence-based assay, such as an assay to detect deISGylation of a fluorescent artificial substrate that mimics the ISG15 cleavage in which the fluorophore becomes active after they are cleaved off ISG15.

In one embodiment, the invention provides methods for identifying mutants of a viral OTU domain-containing protein with reduced deISGylation activity, the methods comprising: (a) contacting a composition comprising an artificial substrate that mimics the ISG15 cleavage and a mutated viral OTU domain-containing protein or OTU domain-containing fragment thereof; and (b) measuring the amount of cleavage of the artificial substrate, wherein a decrease in the cleavage of the artificial substrate relative to a negative control (e.g., the composition comprising an artificial substrate that mimics the ISG15 cleavage contacted with the wild-type viral OTU domain-containing protein or OTU domain-containing fragment thereof) or a predetermined reference range indicates that the mutated viral OTU domain-containing protein or OTU domain-containing fragment has reduced deISGylation activity. In certain embodiments, the artificial substrate is a small synthetic fluorogenic substrate, such as AMC or AFC, that incorporates the C-terminal four (or six) residues found in Ub and ISG15 (LRGG) or (LRLRGG) (SEQ ID NO:1). (Lindner, H et al. J Virol. December 2005 Vol 79 p 15199-15208), (Blakirev, M et al, J Virol, June 2002, Vol 76 p 6323-6331). In other embodiments, the artificial substrate has DABCYL and EDANS moieties on opposite ends of a 12-(or other) mer peptide that can be detected by FRET (as used in: Barretto et al, J Virol, December 2005, Vol 79 p 15189-15198), in which such peptide has the cleavage site of interest (e.g., LRLRGG (SEQ ID NO:1)).

In another embodiment, the invention provides methods for identifying mutants of a viral OTU domain-containing protein with reduced desISGylation activity, the methods comprising: (a) contacting an ISG15-fluorogenic substrate (such as, e.g., ISG15-AMC or ISG15-AFC available from Boston Biochem, Inc., Cambridge, Mass.) with a mutated viral OTU domain-containing protein or an OTU domain-containing fragment thereof; and (b) measuring the fluorescence of the mixture, wherein a decrease in the fluorescence relative to a negative control (e.g., the composition comprising an ISG15-fluorogenic substrate contacted with the wild-type OTU domain-containing viral protein or OTU domain-containing fragment thereof) or a predetermined reference range indicates that the mutated viral OTU domain-containing protein or OTU domain-containing fragment thereof has reduced deISGylation activity.

The assays described in Section 5.1.1, supra, can be modified and used to assess the effect of mutation in the viral OTU domain-containing protein on its deISGylation activity.

In some embodiments, the mutation in the viral OTU domain-containing protein or an OTU domain-containing fragment thereof is introduced using chemical mutagenesis. In other embodiments, the mutation in the viral OTU domain-containing viral protein or an OTU domain-containing fragment thereof is introduced using genetic engineering. In other embodiments, the mutation in the viral OTU domain-containing protein or an OTU domain-containing fragment thereof is naturally occurring. In some embodiments, the mutation in the viral OTU domain-containing viral protein or an OTU domain-containing fragment thereof is a single amino acid substitution. In other embodiments, the mutation in the viral OTU domain-containing protein or an OTU domain-containing fragment thereof is a substitution of more than one amino acid (i.e., 2, 3, 4, 5, 6, 7, 8, 9, 10 or more amino acids). In yet other embodiments, the mutation in the viral OTU domain-containing protein or an OTU domain-containing fragment thereof is an amino acid addition or deletion.

In some embodiments of this invention, the OTU domain of the viral OTU domain-containing protein is mutated in its catalytic cysteine, histidine, and/or aspartic acid. In one embodiment, the catalytic cysteine is mutated. In a specific embodiment, the mutation is in the catalytic cysteine of the OTU domain of CCHFV or DUGV L. In another embodiment, the cysteine and histidine are mutated. In some embodiments, the cysteine and histidine of CCHFV or DUGV L are mutated. In some embodiments, the cysteine and or histidine are mutated to alanine.

In a specific embodiment, a mutation in a viral OTU domain-containing protein reduces the deISGylation activity of the viral protein by approximately 5 to 25%, approximately 10 to 30%, approximately 25 to 60%, approximately 25 to 75%, approximately 30 to 95%, or approximately 40 to 99% as measured using an in vitro assay described herein. In another embodiment, a mutation in a viral OTU domain-containing protein reduces the deISGylation activity of the viral protein by about 10% or more, preferably about 15% or more, about 25% or more, about 30% or more, about 40% or more, about 45% or more, about 50% or more, about 55% or more, about 60% or more, about 75% or more, about 80% or more, about 85% or more, about 90% or more, or about 95% or more.

In addition to providing methods for assessing the effect of mutations in a viral OTU domain-containing protein on its deISGylation activity, methods to assess the effect of such mutations on the ability of the viral OTU domain-containing protein to deconjugate ubiquitin and/or ubiquitin-like molecules from a target protein are also provided herein.

The present invention provides methods for identifying mutants of a viral OTU domain-containing protein with altered deubiquitination activity, the methods comprising: (a) contacting a mutated viral OTU domain-containing protein or an OTU domain-containing fragment thereof with a composition comprising ubiquitinated protein, and (b) measuring the amount of ubiquitinated protein, wherein an alteration in the amount of ubiquitinated protein relative to a control (e.g., a composition comprising ubiquitinated protein contacted with the wild-type viral OTU domain-containing protein) or a predetermined reference range indicates that the mutated viral OTU domain-containing protein or OTU domain-containing fragment thereof has altered deubiquitination activity. In particular, the present invention provides methods for identifying mutants of a viral OTU domain-containing protein with reduced deubiquitination activity, the methods comprising: (a) contacting a mutated viral OTU domain-containing protein or an OTU domain-containing fragment thereof with a composition comprising ubiquitinated protein, and (b) measuring the amount of ubiquitinated protein, wherein an increase in the amount of ubiquitinated protein relative to a control (e.g., a composition comprising ubiquitinated protein contacted with the wild-type viral OTU domain-containing protein) or a predetermined reference range indicates that the mutated viral OTU domain-containing protein or OTU domain-containing fragment thereof has reduced deubiquitination activity. The assays described in Section 5.1.2, supra, can be modified and used to assess the effect of mutation in the viral OTU domain-containing protein on its deubiquitination activity.

In a specific embodiment, a mutation in a viral OTU domain-containing protein reduces the deubiquitination activity of the viral protein by approximately 5 to 25%, approximately 10 to 30%, approximately 25 to 60%, approximately 25 to 75%, approximately 30 to 95%, or approximately 40 to 99% as measured using an in vitro assay described herein. In another embodiment, a mutation in a viral OTU domain-containing protein reduces the deubiquitination activity of the viral protein by about 10% or more, preferably about 15% or more, about 25% or more, about 30% or more, about 40% or more, about 45% or more, about 50% or more, about 55% or more, about 60% or more, about 75% or more, about 80% or more, about 85% or more, about 90% or more, or about 95% or more.

The present invention provides methods for identifying mutants of a viral OTU domain-containing protein with altered deNeddylation activity, the methods comprising: (a) contacting a mutated viral OTU domain-containing protein or an OTU domain-containing fragment thereof with a composition comprising Neddylated protein, and (b) measuring the amount of Neddylated protein, wherein an alteration in the amount of Neddylated protein relative to a control (e.g., a composition comprising Neddylated protein contacted with the wild-type viral OTU domain-containing protein) or a predetermined reference range indicates that the mutated viral OTU domain-containing protein or OTU domain-containing fragment thereof has altered deNeddylation activity. In particular, the present invention provides methods for identifying mutants of a viral OTU domain-containing protein with reduced deNeddylation activity, the methods comprising: (a) contacting a mutated viral OTU domain-containing protein or an OTU domain-containing fragment thereof with a composition comprising Neddylated protein, and (b) measuring the amount of Neddylated protein, wherein an increase in the amount of Neddylated protein relative to a control (e.g., a composition comprising Neddylated protein contacted with the wild-type viral OTU domain-containing protein) or a predetermined reference range indicates that the mutated viral OTU domain-containing protein or OTU domain-containing fragment thereof has reduced deNeddylation activity. The assays described in Section 5.1.4, supra, can be modified and used to assess the effect of mutation in the viral OTU domain-containing protein on its deNeddylation activity.

In a specific embodiment, a mutation in a viral OTU domain-containing protein reduces the deNeddylation activity of the viral protein by approximately 5 to 25%, approximately 10 to 30%, approximately 25 to 60%, approximately 25 to 75%, approximately 30 to 95%, or approximately 40 to 99% as measured using an in vitro assay described herein. In another embodiment, a mutation in a viral OTU domain-containing protein reduces the deNeddylation activity of the viral protein by about 10% or more, preferably about 15% or more, about 25% or more, about 30% or more, about 40% or more, about 45% or more, about 50% or more, about 55% or more, about 60% or more, about 75% or more, about 80% or more, about 85% or more, about 90% or more, or about 95% or more.

5.3 Viral Mutants

The present invention provides viruses having an impaired ability to deISGylate ISG15 conjugates. In particular, the present invention provides viral mutants comprising a mutation (i.e., an addition, substitution and/or deletion) in the viral genome that reduces or eliminates the ability of the viral OTU domain-containing protein encoded by the viral genome to deISGylate ISG15 conjugates. In certain aspects, the reduced or impaired ability of the virus to deISGylate ISG15 conjugates reduces the virus' ability to antagonize the cellular interferon response. In one embodiment, such mutant viruses encode an OTU domain-containing protein with reduced interferon antagonist activity and the mutant viruses have an IFN inducing phenotype. Accordingly, the virus is less virulent and is useful in immunogenic compositions to induce an immune response to the virus and/or a heterologous antigen encoded by the viral genome.

The present invention provides mutants of viruses comprising an OTU domain-containing protein, wherein the mutants comprise a mutation in the viral gene encoding the OTU domain-containing protein that reduces or inhibits the deISGylation activity of the OTU domain-containing protein. The present invention also provides viruses comprising an OTU domain-containing protein, wherein the mutants comprise a mutation in the viral gene encoding the OTU domain-containing protein that reduces or inhibits the deubiquitination activity of the OTU domain-containing protein. The present invention further provides viruses comprising an OTU domain-containing protein, wherein the mutants comprise a mutation in the viral gene encoding the OTU domain-containing protein that reduces or inhibits the deISGylation activity and deubiquitination activity of the OTU domain-containing protein. In a preferred embodiment, the viral mutants are attenuated.

In a specific embodiment, the mutation in the gene encoding the OTU domain-containing protein reduces the deISGylation activity of the viral OTU domain-containing protein by about 5% to about 25%, about 10% to about 30%, about 10% to about 50%, about 25% to about 50%, about 25% to about 75%, or about 30% to about 90% as measured in an assay known to one of skill in the art. In another embodiment, the mutation in the gene encoding the OTU domain-containing protein reduces the deISGylation activity of the viral OTU domain-containing protein by about 5 to about 25%, about 10% to about 30%, about 10% to about 50%, about 25% to about 50%, about 25% to about 75%, or about 30% to about 90% as measured in an in vitro assay described herein. In another embodiment, the mutation in the gene encoding the OTU domain-containing protein reduces the deISGylation activity of the viral OTU domain-containing protein by at least 10%, preferably at least 15%, at least 25%, at least 40%, at least 50%, at least 75%, at least 85%, at least 90%, or at least 95% as measured in an assay known to one of skill in the art. In yet another embodiment, the mutation in the gene encoding the OTU domain-containing protein reduces the deISGylation activity of the viral OTU domain-containing protein by at least 10%, preferably at least 15%, at least 25%, at least 40%, at least 50%, at least 75%, at least 85%, at least 90%, or at least 95% as measured in an in vitro assay described herein.

In a specific embodiment, the mutation in the gene encoding the OTU domain-containing protein reduces the deubiquitination activity of the viral OTU domain-containing protein by about 5% to about 25%, about 10% to about 30%, about 10% to about 50%, about 25% to about 50%, about 25% to about 75%, or about 30% to about 90% as measured in an assay known to one of skill in the art. In another embodiment, the mutation in the gene encoding the OTU domain-containing protein reduces the deubiquitination activity of the viral OTU domain-containing protein by about 5% to about 25%, about 10% to about 30%, about 10% to about 50%, about 25% to about 50%, about 25% to about 75%, or about 30% to about 90% as measured in an in vitro assay described herein. In another embodiment, the mutation in the gene encoding the OTU domain-containing protein reduces the deubiquitination activity of the viral OTU domain-containing protein by at least 10%, preferably at least 15%, at least 25%, at least 40%, at least 50%, at least 75%, at least 85%, at least 90%, or at least 95% as measured in an assay known to one of skill in the art. In yet another embodiment, the mutation in the gene encoding the OTU domain-containing protein reduces the deubiquitination activity of the viral OTU domain-containing protein by at least 10%, preferably at least 15%, at least 25%, at least 40%, at least 50%, at least 75%, at least 85%, at least 90%, or at least 95% as measured in an in vitro assay described herein.

In a specific embodiment, the mutation in the gene encoding the OTU domain-containing protein reduces the deNeddylation activity of the viral OTU domain-containing protein by about 5% to about 25%, about 10% to about 30%, about 10% to about 50%, about 25% to about 50%, about 25% to about 75%, or about 30% to about 90% as measured in an assay known to one of skill in the art. In another embodiment, the mutation in the gene encoding the OTU domain-containing protein reduces the deNeddylation activity of the viral OTU domain-containing protein by about 5% to about 25%, about 10% to about 30%, about 10% to about 50%, about 25% to about 50%, about 25% to about 75%, or about 30% to about 90% as measured in an in vitro assay described herein. In another embodiment, the mutation in the gene encoding the OTU domain-containing protein reduces the deNeddylation activity of the viral OTU domain-containing protein by at least 10%, preferably at least 15%, at least 25%, at least 40%, at least 50%, at least 75%, at least 85%, at least 90%, or at least 95% as measured in an assay known to one of skill in the art. In yet another embodiment, the mutation in the gene encoding the OTU domain-containing protein reduces the deNeddylation activity of the viral OTU domain-containing protein by at least 10%, preferably at least 15%, at least 25%, at least 40%, at least 50%, at least 75%, at least 85%, at least 90%, or at least 95% as measured in an in vitro assay described herein.

Any mutation that results in the desired phenotype (i.e., an impaired deISGylation activity) can be introduced into the virus gene encoding the OTU domain-containing protein or into a gene that affects the function of the OTU domain-containing protein. In one embodiment, the desired phenotype is impaired deISGylation and impaired deubiquitination. In one embodiment, the desired phenotype is impaired deISGylation and impaired deNeddylation. In one embodiment, the desired phenotype is impaired deISGylation, impaired deubiquitination and impaired deNeddylation. Examples of the types of mutations that can be included in or introduced into the gene include, but are not limited to, deletions, substitutions, insertions and combinations thereof. One or more mutations can be located anywhere throughout the coding region, non-coding region, and/or the regulatory element. The mutation in the viral gene encoding an OTU domain-containing protein may be in the open reading frame of the nucleotide sequence encoding the OTU domain-containing protein. The mutation in the viral gene encoding an OTU domain-containing protein may also be in the non-coding region of the gene. Further, the mutation in the viral gene encoding an OTU domain-containing protein may be in the region of the gene regulating the expression of the OTU domain-containing protein. In a specific embodiment, the mutation in the viral gene encoding an OTU domain-containing protein is in the open reading frame. In another embodiment, the mutation in the viral gene encoding an OTU domain-containing protein is in the non-coding region of the gene. In another embodiment, the mutation in the viral gene encoding an OTU domain-containing protein is in the open reading frame and non-coding region of the gene. In yet another embodiment, the mutation in the viral gene encoding an OTU domain-containing protein is in the open reading frame and regulatory region of the gene. The viral gene encoding an OTU domain-containing protein may have multiple mutations (e.g., 2, 3, 4, 5 or more mutations).

In one embodiment, the mutation in the viral gene encoding an OTU domain-containing protein is in the region of the gene encoding the catalytic region of the OTU domain. In a specific embodiment, the mutation in the viral gene encoding an OTU domain-containing protein results in the substitution or deletion of the catalytic cysteine, histidine, and/or aspartic acid residues. In a more specific embodiment, the mutation in the viral gene encoding an OTU domain-containing protein results in the substitution of the catalytic cysteine, histidine, and/or aspartic acid residues for alanine residues. In another embodiment, the mutation in the viral gene encoding the OTU domain-containing protein is a deletion of the catalytic region of the OTU domain or a fragment thereof.

In one embodiment, the viral OTU domain-containing protein is the nsp2 protein of an arterivirus, such as equine arteritis virus, porcine reproductive and respiratory syndrome virus, such as Lelystad virus, or lactate dehydrogenase elevating virus. In another embodiment, the viral OTU domain-containing protein is the L protein (the RNA dependent RNA polymerase) of CCHFV. In another embodiment, the viral OTU domain-containing protein is the L protein (the RNA dependent RNA polymerase) of DUGV. In accordance with these embodiments, a mutation to the nsp2 protein of an arterivirus or L protein of CCHFV or DUGV is, in some embodiments, in the catalytic cysteine, histidine and/or aspartic acid of the L protein. In a specific embodiment, the catalytic cysteine (Cys40) of CCHFV L is mutated. In another embodiment, the catalytic His151 is mutated. In another embodiment, the predicted catalytic Asp37 is mutated. In some embodiments, the CCHFV L domain has one or a combination of these mutations. In another specific embodiment, the catalytic cysteine (Cys40) of DUGV L is mutated. In another embodiment, the catalytic His151 is mutated. In another embodiment, the predicted catalytic Asp37 is mutated. In some embodiments, the DUGV L domain has one or a combination of these mutations.

In a specific embodiment, a mutation in the viral gene encoding an OTU domain-containing protein does not reduce or does not significantly reduce one or more activities of the OTU domain-containing protein (see Table 2, infra) other than the deISGylation activity (and in some embodiments, the deubiquitination, deNeddylation and/or deSUMOylation activities) as assessed by an assay known to one of skill. In another embodiment, a mutation in the viral gene encoding an OTU domain-containing protein reduces the one or more activities other than the deISGylation activity (and in some embodiments, the deubiquitination, deNeddylation and/or deSUMOylation activities) of the OTU domain-containing protein by no more than about 75%, preferably no more than about 50%, 45%, 40%, 35%, 30%, or 25% as assessed by an assay known to one of skill in the art. In a particular embodiment, a mutation in the L protein of CCFHV or DUGV does not reduce the activity or does not significantly reduce of the RNA dependent RNA polymerase of the protein as assessed by an assay known to one of skill in the art. In one embodiment, the RNA dependent RNA polymerase is tested for its ability to support virus replication in cells. In another embodiment, the activity of the RNA dependent RNA polymerase is tested using a mini-replicon or mini-genome assay, see, e.g., U.S. Pat. No. 5,840,520 which describes mini-replicon and mini-genome assays. In a specific embodiment, the virus is tested for its ability to replicate in ISG15 deficient cells. In specific embodiments, activity of the RNA dependent RNA polymerase is assessed by a plaque assay for propagation of the virus in tissue culture, e.g., in SW13 cells or Vero cells, or in ISG15 deficient cells.

In another embodiment, RNA dependent RNA polymerase activity is tested by assessing virulence of the virus in vivo, e.g., by infecting an ISG15-deficient mouse or cells derived from such mouse and assessing survival of the mouse or mouse cells. In another embodiment, a mutation in the L protein of CCFHV or DUGV does not reduce of the RNA dependent RNA polymerase activity of the protein by more than about 75%, preferably no more than about 50%, 45%, 40%, 35%, 30%, or 25% as assessed by an assay known to one of skill in the art. In one embodiment, the RNA dependent RNA polymerase is tested for its ability to support virus replication in cells. In a specific embodiment, the virus is tested for its ability to replicate in ISG15 deficient cells. In specific embodiments, activity of the RNA dependent RNA polymerase is assessed by a plaque assay for propagation of the virus in tissue culture, e.g., in SW13 cells or Vero cells, or in ISG15 deficient cells. In another embodiment, RNA dependent RNA polymerase activity is tested by assessing virulence of the virus in vivo, e.g., by infecting an ISG15-deficient mouse or cells derived from such mouse and assessing survival of the mouse or mouse cells.

In another embodiment, a mutation in the nsp2 protein of EAV, PRRSV, LELV, or LDV does not reduce or does not significantly reduce the activity of the nsp2 protein, other than its deISGylation activity (and in some embodiments, the deubiquitination, deNeddylation and/or deSUMOylation activities), as assessed by an assay known to one of skill in the art. In another embodiment, a mutation in the nsp2 protein of EAV, PRRSV, LELV, or LDV does not reduce or does not significantly reduce the activity of the polyprotein precursor that contains the nsp2 protein, other than the deISGylation activity (and in some embodiments, the deubiquitination, deNeddylation and/or deSUMOylation activities), as assessed by an assay known to one of skill in the art. In one embodiment, the replicase function of nsp2 is tested. In one such embodiment, in vitro generated viral RNA transcripts are introduced into cells and RNA replication is assessed. In another embodiment, viral RNA replication is tested with the use of DNA launch plasmids. In another embodiment, a GFP tag is inserted between the nsp1 and nsp2 sequences of the polyprotein, and viral genome replication is assessed by monitoring the fluorescence of the cells. In some embodiments, replicase function is assessed in ISG15-deficient cells. In another embodiment, a mutation in the nsp2 protein of EAV, PRRSV, LELV, or LDV does not reduce replicase activity by more than about 75%, preferably no more than about 50%, 45%, 40%, 35%, 30%, or 25% as assessed by an assay known to one of skill in the art. In one embodiment, the replicase function of nsp2 is tested. In one such embodiment, in vitro generated viral RNA transcripts are introduced into cells and viral RNA replication is assessed. In another embodiment, viral RNA replication is tested with the use of DNA launch plasmids. In another embodiment, a GFP tag is inserted between the nsp1 and nsp2 sequences of the polyprotein, and viral genome replication is assessed by monitoring the fluorescence of the cells. In some embodiments, replicase function is assessed in ISG15-deficient cells.

In some embodiments, a mutation that abrogates deISGylation function of the OTU domain-containing viral protein also abrogates the other functions of the protein.

In a specific embodiment, the viral mutants described herein are attenuated. In a preferred embodiment, the viral mutants described herein replicate in vivo to provide subclinical levels of infection and are not pathogenic. Such viruses are ideal candidates for live viral vaccines.

In one embodiment, a mutation in the viral gene encoding the OTU domain-containing protein reduces the ability of the OTU domain-containing protein to deISGylate ISG15 conjugates (and, in some embodiments, also reduces the ability of the OTU domain-containing protein to deconjugate Nedd8 and/or Ub conjugates), and permits the virus, at a multiplicity of infection (MOI) of between 0.0005 and 0.001, 0.001 and 0.01, 0.01 and 0.1, or 0.1 and 1, or a MOI of 0.0005, 0.0007, 0.001, 0.005, 0.01, 0.05, 0.1, 0.5, 1.0, 1.5, 2.0, 2.5, 3.0, 3.5, 4.0, 4.5, 5.0, 5.5, or 6.0, to grow to titers between approximately 1 to approximately 100 fold, approximately 5 to approximately 80 fold, approximately 20 to approximately 80 fold, or approximately 40 to approximately 80 fold, approximately 1 to approximately 10 fold, approximately 1 to approximately 5 fold, approximately 1 to approximately 4 fold, approximately 1 to approximately 3 fold, approximately 1 to approximately 2 fold, or approximately 1, 2, 3, 4, 5, 6, 7, 8, 10, 15, 20, 25, 30, 35, 40, 45, 50, 55, 60, 65, 70, 75, 80, 85, 90, 95 or 100 fold lower than the wild-type virus in cells (e.g., cells of a human, pig, cow, horse, goat, sheep, mouse, chicken, rat, birds, or pig), as determined approximately 2 to 10 days, 3 to 7 days, 3 to 5 days, or 2, 3, 4, 5, 6, 7, 8, 9, 10 days post-infection when propagated under the same conditions. The titers of attenuated and wild-type viruses can be determined utilizing any technique well-known in the art or described herein, (e.g., plaque assays, tissue culture infectious doses (TCID50), etc.) and the viruses can be propagated under conditions described herein or well-known in the art. In one embodiment, the growth of an virus of the invention is compared to a particular standard or reference, e.g., wild-type CCHFV or DUGV.

The invention provides attenuated viruses comprising a genome comprising at least two, at least three, at least four or more mutations in two, three, four or more virus genes, wherein at least one of the mutations is in a viral gene encoding an OTU domain-containing protein or has an effect on the activity of the viral OTU domain-containing protein and contributes to or is responsible for the reduced ability of the virus to deISGylate ISG15 conjugates (and, in some embodiments, also contributes to or reduces the ability of the OTU domain-containing protein to deconjugate Nedd8 and/or Ub conjugates) and, in some embodiments, contributes to or is responsible (directly or indirectly) for the attenuation of the virus. In a specific embodiment, an attenuated virus of the invention comprises a genome comprising at least two, at least three, at least four or more mutations in two, three, four or more virus genes, wherein at least one of the mutations is in the viral gene encoding an OTU domain-containing protein and contributes to or is responsible for the reduced ability of the virus to deISGylate ISG15 conjugates (and, in some embodiments, also contributes to or reduces the ability of the OTU domain-containing protein to deconjugate Nedd8 and/or Ub conjugates), and permits the attenuated virus, at a MOI of between 0.0005 and 0.001, 0.001 and 0.01, 0.01 and 0.1, or 0.1 and 1, or MOI of 0.0005, 0.0007, 0.001, 0.005, 0.01, 0.05, 0.1, 0.5, 1.0, 1.5, 2.0, 2.5, 3.0, 3.5, 4.0, 4.5, 5.0, 5.5, or 6.0, to grow to titers between approximately 1 to approximately 100 fold, approximately 5 to approximately 80 fold, approximately 20 to approximately 80 fold, or approximately 40 to approximately 80 fold, approximately 1 to approximately 10 fold, approximately 1 to approximately 5 fold, approximately 1 to approximately 4 fold, approximately 1 to approximately 3 fold, approximately 1 to approximately 2 fold, or approximately 1, 2, 3, 4, 5, 6, 7, 8, 10, 15, 20, 25, 30, 35, 40, 45, 50, 55, 60, 65, 70, 75, 80, 85, 90, 95 or 100 fold lower than the wild-type virus, as determined by assays provided herein, approximately 2 to 10 days, 3 to 7 days, or 2, 3, 5, 6, 7, 8, 9, 10 days post-infection when the viruses are propagated under the same conditions. In another embodiment, an attenuated virus of the invention comprises a genome comprising at least two, three, four or more mutations in two, three, four or more virus genes, wherein at least one of the mutations is in the viral gene encoding an OTU domain-containing protein and contributes to or is responsible for the reduced ability of the virus to deISGylate ISG15 conjugates (and, in some embodiments, also contributes to or reduces the ability of the OTU domain-containing protein to deconjugate Nedd8 and/or Ub conjugates), and permits the attenuated virus, at a MOI of between 0.0005 and 0.001, 0.001 and 0.01, 0.01 and 0.1, or 0.1 and 1, or a MOI of 0.0005, 0.0007, 0.001, 0.005, 0.01, 0.05, 0.1, 0.5, 1.0, 1.5, 2.0, 2.5, 3.0, 3.5, 4.0, 4.5, 5.0, 5.5, or 6.0, to grow to titers between approximately 1 to approximately 100 fold, approximately 5 to approximately 80 fold, approximately 20 to approximately 80 fold, or approximately 40 to approximately 80 fold, approximately 1 to approximately 10 fold, approximately 1 to approximately 5 fold, approximately 1 to approximately 4 fold, approximately 1 to approximately 3 fold, approximately 1 to approximately 2 fold, or approximately 1, 2, 3, 4, 5, 6, 7, 8, 10, 15, 20, 25, 30, 35, 40, 45, 50, 55, 60, 65, 70, 75, 80, 85, 90, 95 or 100 fold lower than a wild-type virus in cells, as determined by assays described herein, approximately 2 to 10 days, 3 to 7 days, 3 to 5 days, or 2, 3, 5, 6, 7, 8, 9, 10 days post-infection when the viruses are propagated under the same conditions.

An attenuated virus having the desired phenotype can itself be used as the active ingredient in an immunogenic composition (e.g., a vaccine) or a pharmaceutical composition. Alternatively, the virus can be used as the vector or "backbone" of recombinantly produced immunogenic compositions. To this end, the "reverse genetics" technique can be used to engineer mutations or introduce heterologous sequences, such as foreign epitopes into the attenuated virus, which would serve as the "parental" strain. In this way, vaccines can be designed for immunization against strain variants, or in the alternative, against completely different infectious agents or disease antigens (e.g., tumor-associated antigens or bacteria). For example, the attenuated virus can be engineered to express neutralizing epitopes of other preselected strains. Alternatively, epitopes of other viruses can be built into the attenuated virus. Alternatively, epitopes of non-viral infectious pathogens (e.g., parasites, bacteria, fungi) can be engineered into the attenuated virus. Further, tumor-associated antigens can be built into the attenuated virus. Preferably, the virus sequences (including the heterologous sequences) do not include a nucleic acid sequence that alters the attenuated phenotype of the virus. Accordingly, nucleic acid sequences encoding proteins, polypeptides or peptides with deISGylating activity are preferably not engineered into the virus.

The virus of the present invention may be a chimeric virus that expresses a heterologous sequence, e.g., antigens of other vaccine strains (e.g., using reverse genetics, reassortment or helper-free plasmid technology). The attenuated viruses may be engineered, using reverse genetics, reassortment or helper-free plasmid technology with genetically engineered viruses, to express completely foreign epitopes, e.g., antigens of other infectious pathogens, tumor-associated antigens, or targeting antigens. In certain embodiments, the attenuated viruses express a heterologous sequence derived from other agents that infect the same host species, infectious agents that do not infect the same host species, or tumor-associated antigens (e.g., carcinoembryonic antigen (CEA), breast cancer antigen such as EGFR (epidermal growth factor receptor), HER2 antigen (p185HER2), HER2 neu epitope, cancer antigen-50 (CA-50), cancer antigen 15-3 (CA15-3) associated with breast cancer, carcinoma associated antigen (CAA), melanoma antigen, and melanoma associated antigens 100, 25, and 150). In other embodiments, the attenuated virus of the present invention may contain a segment derived from another virus. In some embodiments, epitopes which alter the tropism of the virus in vivo can be engineered into the chimeric attenuated viruses of the invention.

5.3.1 Generation of Mutants with Altered DeISGylation Activity

Any mutant virus or strain that has a mutation in the viral genome which reduces the deISGylation activity (and, in some embodiments, also reduces the deubiquitination and/or deNeddylation activity) of the viral OTU domain-containing protein encoded by the viral genome can be selected and used in accordance with the invention. In one embodiment, naturally occurring mutants or variants, or spontaneous virus mutants are selected that are impaired in their ability to decrease the number of ISG15 conjugates. In one embodiment, virus mutants are selected that are impaired in their ability to decrease the number of ISG15 conjugates and also are impaired in their ability to decrease the number of Ub and/or Nedd8 conjugates. In another embodiment, mutant viruses are generated by exposing the virus to mutagens, such as ultraviolet irradiation or chemical mutagens, or by multiple passages and/or passage in nonpermissive hosts. Screening for the ability to deISGylate ISG15 conjugates in an in vitro assay can be used to select for those mutants having impaired deISGylation function. In one embodiment, mutants are selected that also have impaired deubiquitination and/or deNeddylation function. In the case of viruses with a segmented genome, such as the nairoviruses, the attenuated phenotype can be transferred to another strain having a desired antigen by reassortment, i.e., by co-infection of the attenuated virus and the desired strain, and selection for reassortants displaying both phenotypes. In a specific embodiment, the viruses of the invention are not naturally occurring viruses. In another specific embodiment, the viruses of the invention are genetically engineered viruses. In some embodiments, a virus with a naturally occurring defect in deISGylation is not encompassed by the invention. In some specific embodiments, known viruses that lack or are abrogated for deISGylation function are not encompassed by the invention.

Mutations can be engineered into a virus of the invention using genetic engineering techniques known to one of skill in the art. In the case of negative-sense RNA viruses, mutations can be engineered into the virus by "reverse genetics" approaches. In this way, natural or other mutations which confer the attenuated phenotype can be engineered into vaccine strains. For example, deletions, insertions, or substitutions of the coding region of the viral gene that encodes the viral OTU domain-containing viral protein can be engineered. Deletions, substitutions or insertions in the non-coding region of the virus gene encoding the viral OTU domain-containing protein are also contemplated. To this end, mutations in the signals responsible for the transcription, replication, polyadenylation and/or packaging of the gene encoding the viral OTU domain-containing protein can be engineered. Such mutations, for example to the promoter, could downregulate the expression of the virus gene encoding the viral OTU domain-containing protein. In some embodiments, expression is not downregulated enough to prevent replication. Mutations in the promoter can be made, for example, by promoter shuffling, or in the noncoding regions of the viral gene encoding the viral OTU domain-containing protein. Mutations in virus genes which may regulate the expression of the virus gene encoding the viral OTU domain-containing protein are also within the scope of viruses that can be used in accordance with the invention.

The reverse genetics technique involves the preparation of synthetic recombinant viral RNAs that contain the non-coding regions of the virus RNA which are essential for the recognition by viral polymerases and for packaging signals necessary to generate a mature virion. The recombinant RNAs are synthesized from a recombinant DNA template and reconstituted in vitro with purified viral polymerase complex to form recombinant ribonucleoproteins (RNPs) which can be used to transfect cells. A more efficient transfection is achieved if the viral polymerase proteins are present during transcription of the synthetic RNAs either in vitro or in vivo. The synthetic recombinant RNPs can be rescued into infectious virus particles. The foregoing techniques are described in U.S. Pat. No. 5,166,057 issued Nov. 24, 1992; in U.S. Pat. No. 5,854,037 issued Dec. 29, 1998; in European Patent Publication EP 0702085A1, published Feb. 20, 1996; in U.S. patent application Ser. No. 09/152,845; in International Patent Publications PCT WO 97/12032 published Apr. 3, 1997; WO 96/34625 published Nov. 7, 1996; in European Patent Publication EP A780475; WO 99/02657 published Jan. 21, 1999; WO 98/53078 published Nov. 26, 1998; WO 98/02530 published Jan. 22, 1998; WO 99/15672 published Apr. 1, 1999; WO 98/13501 published Apr. 2, 1998; WO 97/06270 published Feb. 20, 1997; and EPO 780 475A1 published Jun. 25, 1997, each of which is incorporated by reference herein in its entirety.

The helper free plasmid technology can also be utilized to engineer an attenuated virus comprising a mutation in the viral OTU domain-containing protein that reduces its deISGylation activity. For a description of helper-free plasmid technology see, e.g., International Publication No. WO 01/04333; U.S. Pat. No. 6,649,372; Fodor et al., 1999, J. Virol. 73:9679-9682; Hoffmann et al., 2000, Proc. Natl. Acad. Sci. USA 97:6108-6113; and Neumann et al., 1999, Proc. Natl. Acad. Sci. USA 96:9345-9350, which are incorporated herein by reference in their entireties.

Attenuated viruses generated by a genetic engineering approach, such as a reverse genetics approach or helper-free plasmid technology, can be used in the immunogenic compositions and pharmaceutical compositions described herein. Genetic engineering approaches, such as a reverse genetics approach or helper-free plasmid technology, can also be used to engineer additional mutations to other viral genes important for immunogenic composition and pharmaceutical composition production—e.g., the epitopes of useful vaccine strain variants can be engineered into the attenuated virus.

5.3.2 Selection of Attenuated Viruses

The invention provides methods for identifying viral mutants with reduced deISGylation activity, the method comprising: (a) infecting a cell expressing ISG15 with a virus mutant; and (b) measuring the amount of ISG15 conjugated protein, wherein an increase in the amount of ISG15 conjugated protein relative to a control (e.g., a cell infected with the wild-type virus or parental strain from which the mutant virus is derived under the same conditions) or a predetermined reference range indicates that the virus mutant has reduced deISGylation activity. In some embodiments, the cell is engineered to express or overexpress ISG15. In a specific embodiment, the virus naturally encodes a viral OTU domain-containing protein. In another embodiment, the virus comprises a heterologous viral OTU domain-containing protein or OTU domain-containing fragment thereof. In some embodiments, Sindbis virus is used to infect the cell. In a particular embodiment, the dsTE12Q double subgenomic Sindbis virus contains a heterologous viral OTU domain-containing protein or an OTU domain-containing fragment thereof.

In a specific embodiment, the invention provides a method for identifying viral mutants with reduced deubiquitinating activity, the method comprising: (a) infecting a cell expressing ubiquitin with a virus mutant; and (b) measuring the amount of ubiquitinated protein, wherein an increase in the amount of ubiquitinated protein relative to a control (e.g., a cell infected with the wild-type virus or parental strain from which the mutant virus is derived under the same conditions) or a predetermined reference range indicates that the virus mutant has reduced deubiquitinating activity. In some embodiments, the cell is engineered to express or overexpress ubiquitin. In a specific embodiment, the virus naturally encodes a viral OTU domain-containing protein. In another embodiment, the virus comprises a heterologous viral OTU domain-containing protein or OTU domain-containing fragment thereof. In some embodiments, Sindbis virus is used to infect the cell. In a particular embodiment, the dsTE12Q double subgenomic Sindbis virus contains a heterologous viral OTU domain-containing protein or an OTU domain-containing fragment thereof.

In a specific embodiment, the invention provides a method for identifying viral mutants with reduced deNeddylation activity, the method comprising: (a) infecting a cell expressing Nedd8 with a virus mutant; and (b) measuring the amount of Neddylated protein, wherein an increase in the amount of Neddylated protein relative to a control (e.g., a cell infected with the wild-type virus or parental strain from which the mutant virus is derived under the same conditions) or a predetermined reference range indicates that the virus mutant has reduced deNeddylation activity. In some embodiments, the cell is engineered to express or overexpress Nedd8. In a specific embodiment, the virus naturally encodes a viral OTU domain-containing protein. In another embodiment, the virus comprises a heterologous viral OTU domain-containing protein or OTU domain-containing fragment thereof. In some embodiments, Sindbis virus is used to infect the cell. In a particular embodiment, the dsTE12Q double subgenomic Sindbis virus contains a heterologous viral OTU domain-containing protein or an OTU domain-containing fragment thereof.

In some embodiments, the cell used in the methods described in the preceding three paragraphs is a eukaryotic cell or a prokaryotic cell. In a specific embodiment, the cell used is a mammalian cell. In another embodiment, the cell used is yeast cell. In another embodiment, the cell used is a human cell. In a specific embodiment, the cell is deficient in the interferon response. In another embodiment, the cell is deficient in deISGylation. In some embodiments, the cell engineered to express ISG15 is UBP43−/−. In a specific embodiment, the cell is IFN-β-treated murine embryonic fibroblasts (MEFs) derived from Ubp43−/− mice.

The amount of ISG15 conjugated protein, ubiquitinated protein, or Nedd8 conjugated protein can be measured using any assay known to one of skill in the art for measuring ISGylation/deISGylation, ubiquitination/deubiquitination, or Neddylation/deNeddylation, respectively, including but not limited to SDS-PAGE and Coomassie staining, an immunoassay, such as a Western blot or an ELISA, or a colorimetric assay. For example, the amount of ISG15 conjugated protein can be detected by lysing the cells and performing a Western blot or ELISA using an anti-ISG15 antibody (such as anti-ISG15 monoclonal antibody 3C2 described in Lenschow et al., 2005, J. Virol. 79: 13974-13983) or an anti-affinity peptide antibody (e.g., an anti-His antibody) if the ISG15 is affinity peptide-tagged ISG15.

The invention provides methods for identifying attenuated viral mutants, the methods comprising: (a) infecting a cell with a virus mutant; and (b) measuring the titer of the virus, wherein a decrease in the viral titer relative to the viral titer of a cell infected with the wild-type virus or parental strain from which the mutant virus is derived under the same conditions indicates that the virus mutant is attenuated. Techniques known to one of skill in the art can be used to measure virus titer.

The pathogenesis of mutant viruses of the invention can also be assessed in subjects or hosts in vivo. Any assay known to one of skill in the art can be used to assess the pathogenesis of the mutant viruses. The invention provides methods for identifying attenuated virus mutants, the methods comprising: (a) infecting a subject with a mutant virus; and (b) measuring the survival of the subject, wherein an increase in the survival of the subject relative to the survival of a subject infected with the wild-type virus or parental strain from which the mutant virus is derived under the same conditions indicates that the virus mutant is attenuated. The invention also provides methods for identifying attenuated virus mutants, the methods comprising: (a) infecting a subject with a mutant virus; and (b) measuring the immune response induced in the subject, wherein an improvement in the immune response in the subject relative to the immune response in a subject infected with the wild-type virus or parental strain from which the mutant virus is derived under the same conditions indicates that the virus mutant is attenuated.

The invention also provides methods for identifying attenuated virus mutants, the methods comprising: (a) infecting a subject with a mutant virus; and (b) measuring the symptoms manifested by the subject, wherein a decrease in the number, duration and/or severity of one or more symptoms in the subject relative to the number, duration and/or severity of the same symptoms in a subject infected with the wild-type virus or parental strain from which the mutant virus is derived under the same conditions indicates that the virus mutant is attenuated. The invention further provides methods for identifying attenuated virus mutants, the methods comprising: (a) infecting a subject with a mutant virus; and (b) measuring the time before onset of one or more symptoms in the subject, wherein a increase in the delay before onset of one or more symptoms in the subject relative to the delay before onset of the same symptoms in a subject infected with the wild-type virus or parental strain from which the mutant virus is derived under the same conditions indicates that the virus mutant is attenuated.

The efficacy of the attenuated viruses as immunogenic compositions can be determined using any technique known to one of skill in the art. For example, the ability of the attenuated virus mutants to prevent infection can be assessed in an in vitro assay or an animal model before use in humans. See, e.g., the assays described in Sections 5.5.1 and 5.5.4 below.

5.3.3 Propagation of Attenuated Virus

The present invention provides methods for propagating mutant viruses (e.g., attenuated viruses) in cells, embryonated eggs, and animals. The attenuated viruses of the present invention can be propagated in any substrate that allows the virus to grow to titers that permit a use of the attenuated virus described herein. In a specific embodiment, the attenuated viruses of the present invention are propagated in any substrate that allows the virus to grow to titers comparable to those determined for wild type virus strains in ISGylation-competent substrates. In another embodiment, the attenuated viruses of the invention are propagated in ISGylation-deficient substrates. Substrates which are useful for selection of the attenuated viruses of the invention do not have to be (but may be) used for propagation and vice versa.

In accordance with the methods of the present invention, the mutant viruses (e.g., attenuated viruses) that may be grown in cells, embryonated eggs, and animals are selected from naturally occurring strains, variants or mutants, mutagenized virus, reassortants and/or genetically engineered viruses. The methods of the present invention encompass growing the mutant viruses (e.g., attenuated viruses), preferably using appropriate growth conditions, and collecting the progeny virus.

In a specific embodiment, the mutant viruses (e.g., attenuated viruses) of the invention are propagated in mammalian cells. In accordance with this embodiment, the cells may or may not be ISGylation-deficient or have reduced ISG15 activity. Non-limiting examples of cells include mouse cells, human cells, pig cells, pig cell lines, human cell lines, mouse cell lines, and MEFs. Representative cells include, but are not limited to, Daudi cells, cancer cell lines such as A549, murine fibroblast cell lines such as L929 or HCT116, HeLa cells, COS-7 cells, RAW 264.7 cells, NIH3T3 cells, 2fTGH cells, A431 cells and KT-1 cells. Other cells that may be used in the practice of the invention include primary cells or organ culture derived from the, e.g., liver, lung, heart, kidney, thymus, macrophages, bone marrow, spleen, or brain of mice, e.g, suckling mouse brain. In another embodiment, MEFs are used. Consistent with these embodiments, the cells may be treated with interferon. In other embodiments, the cells are IFN-deficient. Additional cells that can be used to propagate the viruses of the invention are BS-C-1 cells, MDCK-1 cells, Sw13 cells, Vero cells, or BHK-21 cells. In certain embodiments, the cells are treated with IFN, e.g., IFN-β. In some embodiments, the cells are IFN-deficient or impaired for their interferon response. In other embodiments, the cells are engineered to express ISG15. In other embodiments, the cells are engineered to be deficient in ISG15 or deficient in ISGylation and/or deISGylation (e.g., ISG15-deficient, or UBP43−/−, respectively). In some embodiments, the cells are deficient in one or more components of the ubiquitination and/or deubiquitination pathway. In other embodiments, the cells are deficient in one or more components of the SUMOylation and/or deSUMOylation pathway. In some embodiments, the cells are deficient in one or more components of the Neddylation and/or deNeddylation pathway.

In certain embodiments, the invention provides methods of propagating the mutant viruses (e.g., attenuated viruses) of the invention in embryonated eggs, e.g., from 6 to 14 days old. In some embodiments, 10 to 12 day old embryonated eggs are used to propagate mutant viruses (e.g., attenuated viruses) of the invention. In other embodiments, young or immature embryonated eggs can be used to propagate mutant viruses (e.g., attenuated viruses) of the invention. In accordance with the present invention, immature embryonated eggs encompass eggs which are less than ten day old eggs, preferably six to nine day old eggs, six to eight day old, six to seven day old eggs or six days old eggs. Immature embryonated eggs of the present invention also encompass eggs which artificially mimic immature eggs up to, but less than ten day old, as a result of alterations to the growth conditions, e.g., changes in incubation temperatures; treating with drugs; or any other alteration which results in an egg with a retarded development, such that the IFN system is not fully developed as compared with ten to twelve day old eggs. The mutant viruses (e.g., attenuated viruses) can be propagated in different locations of the embryonated egg, e.g., the allantoic cavity. In certain embodiments, the embryonated eggs are chick eggs.

The invention also encompasses methods and IFN deficient substrates for the growth and isolation of mutant viruses (e.g., attenuated viruses) of the present invention. See, e.g., U.S. Pat. No. 6,573,079, which is expressly incorporated by reference in its entirety. IFN-deficient substrates which can be used to support the growth of the attenuated viruses include, but are not limited to, naturally occurring cells, cell lines, embryonated eggs, and IFN-deficient systems, e.g., Vero cells, young embryonated eggs; recombinant cells or cell lines that are engineered to be IFN deficient, e.g., IFN deficient cell lines derived from STAT1 knockouts, IRF3 knockouts, IRF7 knockouts, PKR knockouts, etc.; embryonated eggs obtained from IFN deficient birds, especially fowl (e.g., chickens, ducks, turkeys) including flocks that are bred to be IFN deficient or transgenic birds (e.g., STAT1 knockouts). In certain embodiments, the IFN-deficient substrate is not Vero cells and/or not a STAT1 deficient cell line.

The host system, cells, cell lines, eggs or animals can be genetically engineered to express transgenes encoding inhibitors of the IFN system, e.g., dominant negative mutants, such as STAT1 lacking the DNA binding domain, antisense RNA, ribozymes, inhibitors of IFN production, inhibitors of IFN signaling, and/or inhibitors of antiviral genes induced by IFN. It should be recognized that animals that are bred or genetically engineered to be IFN deficient will be somewhat immunocompromised, and should be maintained in a controlled, disease free environment. Thus, appropriate measures (including the use of dietary antibiotics) should be taken to limit the risk of exposure to infectious agents of transgenic IFN-deficient animals, such as mice, flocks of breeding hens, ducks, turkeys etc. Alternatively, the host system, e.g., cells, cell lines, eggs or animals can be treated with a compound which inhibits IFN production and/or the IFN pathway e.g., drugs, antibodies, antisense molecules, ribozyme molecules targeting the STAT1 gene, and/or antiviral genes induced by IFN.

The present invention encompasses methods of growing and isolating virus mutants in cells and cell lines which naturally do not have an IFN pathway or have a deficient IFN pathway or have a deficiency in the IFN system e.g., low levels of IFN expression as compared to wild type cells. In a particular embodiment, the present invention encompasses methods of growing the mutant viruses (e.g., attenuated viruses) of the invention in chicken embryo fibroblasts derived from 6-day-old embryonated eggs, Vero cells, or IFN-compromised embryonated eggs (e.g., immature embryonated eggs such as 6-, 7- or 8-day old embryonated eggs). In another embodiment, the present invention encompasses methods of growing the mutant viruses (e.g., attenuated viruses) of the invention in cells where the cells are not Vero cells.

The present invention provides methods of growing and isolating the mutant viruses of the invention from a genetically engineered IFN-deficient substrate. The present invention encompasses transgenic pigs and avians in which a gene essential to the IFN system is mutated, e.g., STAT1, which would lay eggs that are IFN-deficient. The present invention further encompasses avian transgenics which express dominant negative transcription factors, e.g., STAT1 lacking the DNA binding domain, ribozymes, antisense RNA, inhibitors of IFN production, inhibitors of IFN signaling, and inhibitors of antiviral genes induced in response to IFN.

The invention provides recombinant cell lines or animals in which one or more genes essential for IFN synthesis, the IFN pathway, and/or an antiviral gene induced by IFN, e.g. interferon receptor, ISG, STAT1, PKR, IRF3, IRF7, etc. has been mutated (e.g., disrupted, i.e., is a "knockout"). The recombinant animal can be any animal (such as a mouse, a pig or an avian, e.g., chicken, turkey, hen, duck, etc. (see, e.g., Sang, 1994, Trends Biotechnol. 12:415; Perry, et al., 1993, Transgenic Res. 2:125; Stern, C. D., 1996, Curr Top Microbiol Immunol 212:195 206; and Shuman, 1991, Experientia 47:897 for reviews regarding the production of avian transgenics each of which is incorporated by reference herein in its entirety). Such a cell line or animal can be generated by any method known in the art for disrupting a gene on the chromosome of the cell or animal. Such techniques include, but are not limited to pronuclear microinjection (Hoppe & Wagner, 1989, U.S. Pat. No. 4,873,191); retrovirus mediated gene transfer into germ lines (Van der Putten et al., 1985, Proc. Natl. Acad. Sci., USA 82:6148 6152); gene targeting in embryonic stem cells (Thompson et al., 1989, Cell 56:313); electroporation of embryos (Lo, 1983, Mol Cell. Biol. 3:1803); and sperm mediated gene transfer (Lavitrano et al., 1989, Cell 57:717); etc. For a review of such techniques, see Gordon, 1989, Transgenic Animals, Intl. Rev. Cytol. 115:171, which is incorporated by reference herein in its entirety.

By way of non-limiting example, a STAT1 knockout animal can be produced by promoting homologous recombination between a STAT1 gene in its chromosome and an exogenous STAT1 gene that has been rendered biologically inactive (preferably by insertion of a heterologous sequence, e.g., an antibiotic resistance gene). Homologous recombination methods for disrupting genes in the mouse genome are described, for example, in Capecchi (1989, Science 244:1288) and Mansour et al. (1988, Nature 336:348 352).

Briefly, all or a portion of a STAT1 genomic clone is isolated from genomic DNA from the same species as the knock out cell or animal. The STAT1 genomic clone can be isolated by any method known in the art for isolation of genomic clones (e.g. by probing a genomic library with a probe derived from a STAT1 sequence. Once the genomic clone is isolated, all or a portion of the clone is introduced into a recombinant vector. Preferably, the portion of the clone introduced into the vector contains at least a portion of an exon of the STAT1 gene, i.e., contains a STAT1 protein coding sequence. A sequence not homologous to the STAT1 sequence, preferably a positive selectable marker, such as a gene encoding an antibiotic resistance gene, is then introduced into the STAT1 gene exon. The selectable marker is preferably operably linked to a promoter, more preferably a constitutive promoter. The non-homologous sequence is introduced anywhere in the STAT1 coding sequence that will disrupt STAT1 activity, e.g., at a position where point mutations or other mutations have been demonstrated to inactivate STAT1 protein function. For example, but not by way of limitation, the non homologous sequence can be inserted into the coding sequence for the portion of the STAT1 protein containing all or a portion of the kinase domain (e.g., the nucleotide sequence coding for at least 50, 100, 150, 200 or 250 amino acids of the kinase domain).

The positive selectable marker is preferably a neomycin resistance gene (neo gene) or a hygromycin resistance gene (hygro gene). The promoter may be any promoter known in the art; by way of example the promoter may be the phosphoglycerate kinase (PGK) promoter (Adra et al., 1987, Gene 60:65 74), the Pol II promoter (Soriano et al., 1991, Cell 64:693 701), or the MC1 promoter, which is a synthetic promoter designed for expression in embryo derived stem cells (Thomas & Capecchi, 1987, Cell 51:503 512). Use of a selectable marker, such as an antibiotic resistance gene, allows for the selection of cells that have incorporated the targeting vector (for example, the expression of the neo gene product confers resistance to G418, and expression of the hygro gene product confers resistance to hygromycin).

In a preferred embodiment, a negative selectable marker for a counter-selection step for homologous, as opposed to non homologous, recombination of the vector is inserted outside of the STAT1 genomic clone insert. For example, such a negative selectable marker is the HSV thymidine kinase gene (HSV tk), the expression of which makes cells sensitive to ganciclovir. The negative selectable marker is preferably under the control of a promoter such as, but not limited to the PGK promoter, the Pol II promoter or the MC1 promoter.

When homologous recombination occurs, the portions of the vector that are homologous to the STAT1 gene, as well as the non homologous insert within the STAT1 gene sequences, are incorporated into the STAT1 gene in the chromosome, and the remainder of the vector is lost. Thus, since the negative selectable marker is outside the region of homology with the STAT1 gene, cells in which homologous recombination has occurred (or their progeny), will not contain the negative selectable marker. For example, if the negative selectable marker is the HSV tk gene, the cells in which homologous recombination has occurred will not express thymidine kinase and will survive exposure to ganciclovir. This procedure permits the selection of cells in which homologous recombination has occurred, as compared to non homologous recombination in which it is likely that the negative selectable marker is also incorporated into the genome along with the STAT1 sequences and the positive selectable marker. Thus, cells in which non homologous recombination has occurred would most likely express thymidine kinase and be sensitive to ganciclovir.

Once the targeting vector is prepared, it is linearized with a restriction enzyme for which there is a unique site in the targeting vector, and the linearized vector is introduced into embryo derived stem (ES) cells (Gossler et al., 1986, Proc. Natl. Acad. Sci. USA 83:9065 9069) by any method known in the art, for example by electroporation. If the targeting vector includes a positive selectable marker and a negative, counter-selectable marker, the ES cells in which homologous recombination has occurred can be selected by incubation in selective media. For example, if the selectable markers are the neo resistance gene and the HSV tk gene, the cells are exposed to G418 (e.g., approximately 300 μg/ml) and ganciclovir (e.g., approximately 2 μM).

Any technique known in the art for genotyping, for example but not limited to Southern blot analysis or the polymerase chain reaction, can be used to confirm that the disrupted STAT1 sequences have homologously recombined into the STAT1 gene in the genome of the ES cells. Because the restriction map of the STAT1 genomic clone is known and the sequence of the STAT1 coding sequence is known (see Meraz et al. 1996, Cell 84:431, Durbin et al. 1996, Cell 84:443 450, all references cited therein), the size of a particular restriction fragment or a PCR amplification product generated from DNA from both the disrupted and non disrupted alleles can be determined. Thus, by assaying for a restriction fragment or PCR product, the size of which differs between the disrupted and non disrupted STAT1 gene, one can determine whether homologous recombination has occurred to disrupt the STAT1 gene.

The ES cells with the disrupted STAT1 locus can then be introduced into blastocysts by microinjection and then the blastocysts can be implanted into the uteri of pseudopregnant mice using routine techniques. The animal that develop from the implanted blastocysts are chimeric for the disrupted allele. The chimeric males can be crossed to females, and this cross can be designed such that germline transmission of the allele is linked to transmission of a certain coat color. The germline transmission of the allele can be confirmed by Southern blotting or PCR analysis, as described above, of genomic DNA isolated from tissue samples.

Any gene whose product is important for interferon regulation can be used. Other mutations in the interferon pathway which may be used in accordance with the present invention include kinase deficient versions of Jak1, TyK2 or transcription factors lacking DNA binding domains STAT1, and STAT2 (see, e.g., Krishnan et al., 1997, Eur. J. Biochem 247: 298 305).

For virus purification, the mutant virus is removed from cell culture and separated from cellular components, typically by well known clarification procedures, e.g., such as gradient centrifugation and column chromatography, and may be further isolated as desired using procedures well known to those skilled in the art, e.g., plaque assays.

5.4 Screening Assays for Compounds that Modulate DeISGylation Activity and/or Deubiquitination Activity of Viral OTU Domain-Containing Proteins The present invention provides methods of identifying novel anti-viral compounds. In particular, the methods of the invention identify compounds that reduce or inhibit the deISGylation activity of a viral OTU domain-containing protein. The invention also provides methods for identifying compounds that reduce or inhibit the deubiquitination activity of a viral OTU domain-containing protein. Further, the invention provides methods for identifying compounds that reduce or inhibit the deconjugation of ubiquitin-like molecules (e.g., Nedd8 and SUMO) from target proteins. The methods for identifying such compounds can be performed using assays analogous to those described in Sections 5.4.1, 5.4.2, and 5.4.3, infra, for compounds that modulate the deISGylation activity, deubiquitination, and/or deNeddylation activity, respectively, of a viral OTU domain-containing protein. In certain embodiments, the compound is an attenuated virus mutant.

Compounds identified as inhibitors of the deISGylation activity, or the deISGylation activity and deubiquitination activity and/or the deISGylation activity and deNeddylation activity of a viral OTU domain-containing protein are further screened in a series of secondary assays designed to select for the ability to specifically inhibit viral replication. The methods of the invention further provide for the synthesis of novel compounds based on the identified inhibitors. The novel compounds are designed using structure activity relationship analyses combined with molecular modeling approaches. The novel compounds represent compounds optimized for their ability to inhibit viral replication while maintaining low toxicity with respect to eukaryotic cells, preferably mammalian cells.

In some embodiments, a compound is identified that reduces or inhibits the deISGylation activity and/or deubiquitination activity of a viral OTU domain-containing protein but not the deubiquitination activity of a cellular OTU domain-containing protein. Cellular OTU domain-containing proteins that can be tested in such embodiments include Otubain 1, Otubain 2, Cezanne, VCIP135, and A20.

Various in vitro assays can be used to identify and verify compounds having the desired anti-viral activity. Such assays include, for example, assays which measure the ability of a compound to inhibit deISGylation activity, inhibit viral protein synthesis, or inhibit viral replication. Multiple in vitro assays can be performed simultaneously or sequentially to assess the anti-viral activity of a compound or a pool of compounds. In a specific embodiment, the in vitro assays described herein are performed in a high-throughput assay format.

5.4.1 Methods for Identifying Compounds that Modulate the DeISGylation Activity of a Viral OTU Domain-Containing Protein The present invention provides methods for identifying a compound that modulates the deISGylation activity of a viral OTU domain-containing protein, the methods comprising: (a) contacting a compound with a composition comprising ISG15 conjugated protein and a viral OTU domain-containing protein or an OTU domain-containing fragment thereof; and (b) measuring the amount of ISG15 conjugated protein, wherein an alteration in the amount of ISG15 conjugated protein relative to a negative control (e.g., a composition comprising ISG15 conjugated protein and a viral OTU domain-containing protein or an OTU domain-containing fragment thereof not contacted with the compound) or a predetermined reference range indicates that the compound modulates the deISGylation activity of the viral OTU domain-containing protein. In a specific embodiment, the invention provides methods for identifying a compound that reduces the deISGylation activity of a viral OTU domain-containing protein, the methods comprising: (a) contacting a compound with a composition comprising ISG15 conjugated protein and a viral OTU domain-containing protein or an OTU domain-containing fragment thereof; and (b) measuring the amount of ISG15 conjugated protein, wherein an increase in the amount of ISG15 conjugated protein relative to a negative control (e.g., a composition comprising ISG15 conjugated protein and a viral OTU domain-containing protein or an OTU domain-containing fragment thereof not contacted with the compound) or a predetermined reference range indicates that the compound reduces the deISGylation activity of the viral OTU domain-containing protein.

Compounds that modulate the deISGylation activity of a viral OTU domain-containing protein can be identified using a cell-based assay. The invention provides a method for identifying a compound that modulates the deISGylation activity of a viral OTU domain-containing protein, the method comprising: (a) contacting a compound with a cell engineered to express a viral OTU domain-containing protein or an OTU domain-containing fragment thereof and ISG15; and (b) measuring the amount of ISG15 conjugated protein, wherein an alteration in the amount of ISG15 conjugated protein relative to a negative control (e.g., a cell engineered to express ISG15 and the viral OTU domain-containing protein which is not contacted with the compound) or predetermined reference range indicates that the compound modulates the deISGylation activity of the viral OTU domain-containing protein. The invention provides a method for identifying a compound that modulates the deISGylation activity of a viral OTU domain-containing protein, the method comprising: (a) contacting a compound with a viral OTU domain-containing protein or an OTU domain-containing fragment thereof and a cell expressing ISG15; and (b) measuring the amount of ISG15 conjugated protein, wherein an alteration in the amount of ISG15 conjugated protein relative to a negative control (e.g., the viral OTU domain-containing protein or fragment thereof and a cell expressing ISG15 not contacted with the compound) or a predetermined reference range indicates that the compound modulates the deISGylation activity of the viral OTU domain-containing protein.

In a specific embodiment, the invention provides a method for identifying a compound that reduces the deISGylation activity of a viral OTU domain-containing protein, the method comprising: (a) contacting a compound with a cell engineered to express a viral OTU domain-containing protein or an OTU domain-containing fragment thereof and ISG15; and (b) measuring the amount of ISG15 conjugated protein, wherein an increase in the amount of ISG15 conjugated protein relative to a negative control (e.g., a cell engineered to express ISG15 and the viral OTU domain-containing protein which is not contacted with the compound) or predetermined reference range indicates that the compound reduces the deISGylation activity of the viral OTU domain-containing protein. In another embodiment, the invention provides a method for identifying a compound that reduces the deISGylation activity of a viral OTU domain-containing protein, the method comprising: (a) contacting a compound with a viral OTU domain-containing protein or an OTU domain-containing fragment thereof and a cell expressing ISG15; and (b) measuring the amount of ISG15 conjugated protein, wherein an increase in the amount of ISG15 conjugated protein relative to a negative control (e.g., the viral OTU domain-containing protein or fragment thereof and a cell expressing ISG15 not contacted with the compound) or a predetermined reference range indicates that the compound reduces the deISGylation activity of the viral OTU domain-containing protein.

The invention provides a method for identifying a compound that modulates the deISGylation activity of a viral OTU domain-containing protein, the method comprising: (a) contacting a compound with an ISG15-expressing cell infected with a virus comprising a viral OTU domain-containing protein; and (b) measuring the amount of ISG15 conjugated protein, wherein an alteration in the amount of ISG15 conjugated protein relative to a negative control (e.g., an ISG15-expressing cell infected with the virus comprising a viral OTU domain-containing protein which is not contacted with the compound) or a predetermined reference range indicates that the compound modulates the deISGylation activity of the viral OTU domain-containing protein. In a specific embodiment, the invention provides a method for identifying a compound that reduces the deISGylation activity of a viral OTU domain-containing protein, the method comprising: (a) contacting a compound with an ISG15 expressing cell infected with a virus comprising a viral OTU domain-containing protein; and (b) measuring the amount of ISG15 conjugated protein, wherein an increase in the amount of ISG15 conjugated protein relative to a negative control (e.g., an ISG15 expressing cell infected with the virus comprising a viral OTU domain-containing protein which is not contacted with the compound) or a predetermined reference range indicates that the compound reduces the deISGylation activity of the viral OTU domain-containing protein.

In one embodiment, the virus naturally encodes such viral OTU domain-containing protein. In another embodiment, the virus comprises a heterologous viral OTU domain-containing protein or OTU domain-containing fragment thereof In some embodiments, Sindbis virus is used to infect the cell. In a particular embodiment, the dsTE12Q double subgenomic Sindbis virus contains a heterologous viral OTU domain-containing protein or an OTU domain-containing fragment thereof.

In some embodiments, the cell is engineered to express or overexpress ISG15. In one embodiment, the virus naturally encodes such viral OTU domain-containing protein. In another embodiment, the virus comprises a heterologous viral OTU domain-containing protein or OTU domain-containing fragment thereof In some embodiments, Sindbis virus is used to infect the cell. In a particular embodiment, the dsTE12Q double subgenomic Sindbis virus contains a heterologous viral OTU domain-containing protein or an OTU domain-containing fragment thereof.

In some embodiments, the cell used in the methods described above is a eukaryotic cell or a prokaryotic cell. In a specific embodiment, the cell used is a mammalian cell. In another embodiment, the cell used is yeast cell. In another embodiment, the cell used is a human cell. In a specific embodiment, the cell is deficient in the interferon response. In another embodiment, the cell is deficient in deISGylation. In some embodiments, the cell engineered to express ISG15 is UBP43−/−. In a specific embodiment, the cell extract is from IFNβ-treated murine embryonic fibroblasts (MEFs) derived from Ubp43−/− mice.

In some embodiments, the cell is engineered to express ISG15 or overexpress ISG15. In some embodiments, an affinity peptide tag such as poly-histidine, biotin, hemagglutinin (HA), glutathione S-transferase (GST), mannose binding protein (MBP), or FLAG) is conjugated to ISG15. In other embodiments, ISG15 is expressed together with other proteins of the ISGylation cascade. In a particular embodiment, tagged ISG15 is overexpressed with proteins of the ISGylation cascade. In a specific embodiment, the proteins of the ISG15 cascade are UBE1L and UbcM8. In some embodiments, the cell is engineered to express ISG15 by contacting the cell with interferon (e.g., IFN-β).

Compounds that modulate the deISGylation activity of a viral OTU domain-containing proteins can be determined using a cell-free assay. The invention provides a method for identifying a compound that modulates the deISGylation activity of a viral OTU domain-containing protein, the method comprising: (a) contacting a compound with a cell extract and a viral OTU domain-containing protein; and (b) measuring the amount of ISG15 conjugated protein, wherein an alteration in the amount of ISG15 conjugated protein relative to a negative control (e.g., a cell extract contacted with the viral OTU domain-containing protein but not the compound) or predetermined reference range indicates that the compound modulates the deISGylation activity of the viral OTU domain-containing protein. In a specific embodiment, the invention provides a method for identifying a compound that reduces the deISGylation activity of a viral OTU domain-containing protein, the method comprising: (a) contacting a compound with a cell extract and a viral OTU domain-containing protein, and (b) measuring the amount of ISG15 conjugated protein, wherein an increase in the amount of ISG15 conjugated protein relative to a negative control (e.g., a cell extract contacted with the viral protein but not the compound) or predetermined reference range indicates that the compounds reduces the deISGylation activity of the viral OTU domain-containing protein.

In some embodiments, the cell extract is from a cell engineered to express ISG15 or overexpress ISG15. In some embodiments, an affinity peptide tag such as poly-histidine, biotin, hemagglutinin (HA), glutathione S-transferase (GST), mannose binding protein (MBP), or FLAG) is conjugated to ISG15. In other embodiments, the cell extract is from a cell engineered to express ISG15 and other proteins of the ISGylation cascade. In a particular embodiment, tagged ISG15 is overexpressed with proteins of the ISGylation cascade. In a specific embodiment, the proteins of the ISG15 cascade are UBE1L and UbcM8. In some embodiments, the cell extract is from a cell engineered to express ISG15 by contacting the cell with interferon (e.g., IFN-β).

In a specific embodiment, ISG15 conjugates are enriched before they are contacted with the viral OTU domain-containing protein or OTU domain-containing fragment thereof. In one embodiment, ISG15 conjugates in a cell extract are enriched, e.g., by chromatography. In another embodiment, ISG15 conjugates are enriched by affinity chromatography using an antibody specific to ISG15 or to the ISGylated protein. In another embodiment, the ISGylated protein source is enriched by affinity chromatography using a tag. In some embodiments, the protein target is tagged. In other embodiments, ISG15 is tagged. The tag can be any affinity tag known to those of skill in the art, including but not limited to poly-histidine, biotin, hemagglutinin (HA), glutathione S-transferase (GST), and mannose binding protein (MBP).

In some embodiments, the cell extract used in the methods described in the preceding three paragraphs is a eukaryotic cell extract or a prokaryotic cell extract. In a specific embodiment, the cell extract used is a mammalian cell extract. In another embodiment, the cell extract used is yeast cell extract. In another embodiment, the cell extract used is a human cell extract. In a specific embodiment, the cell extract is from a cell deficient in the interferon response. In another embodiment, the cell extract is from a cell deficient in deISGylation. In some embodiments, the cell extract is from a UBP43−/− cell. In a specific embodiment, the cell extract is from IFN-β-treated murine embryonic fibroblasts (MEFs) derived from Ubp43−/− mice.

The amount of ISG15 conjugated protein can be measured using any assay known to one of skill in the art for measuring ISGylation and/or deISGylation, including but not limited to an immunoassay, such as a Western blot or an ELISA, or a colorimetric assay. For example, the amount of ISG15 conjugated protein can be detected by lysing the cells and performing a Western blot or ELISA using an anti-ISG15 antibody (such as anti-ISG15 monoclonal antibody 3C2 described in Lenschow et al., 2005, J. Virol. 79: 13974-13983) or an anti-affinity peptide antibody (e.g., an anti-His antibody) if the ISG15 is affinity peptide-tagged ISG15.

In one embodiment, the invention provides methods for identifying a compound that modulates the deISGylation activity of a viral OTU domain-containing protein or an OTU domain-containing fragment thereof, the methods comprising: (a) contacting a compound with a composition comprising an artificial substrate that mimics the ISG15 cleavage and a viral OTU domain-containing protein or OTU domain-containing fragment thereof; and (b) measuring the amount of cleavage of the artificial substrate, wherein an alteration in the cleavage of the artificial substrate relative to a negative control (e.g., the composition comprising an artificial substrate that mimics the ISG15 cleavage and the viral OTU domain-containing protein or OTU domain-containing fragment thereof not contacted with the compound) or a predetermined reference range indicates that the compound modulates the deISGylation activity of the viral OTU domain-containing protein or OTU domain-containing fragment thereof. In certain embodiments, the artificial substrate is a small synthetic AMC of AFC substrate that incorporates the C-terminal four (or six) residues found in Ub and ISG15 (LRGG) or (LRLRGG) (SEQ ID NO:1). (Lindner, H et al. J Virol. December 2005 Vol 79 p 15199-15208), (Blakirev, M et al, J Virol, June 2002, Vol 76 p 6323-6331). In other embodiments the artificial substrate has DABCYL and EDANS moieties on opposite ends of a 12-(or other) mer peptide that can be detected by FRET (as used in: Barretto et al, J Virol, December 2005, Vol 79 p 15189-15198), in which such peptide has the cleavage site of interest (e.g., LRLRGG (SEQ ID NO:1)).

In another embodiment, the invention provides methods for identifying a compound that modulates the deISGylation activity of a viral OTU domain-containing protein or an OTU domain-containing fragment thereof, the methods comprising: (a) contacting a compound with an ISG15 fluorogenic substrate (such as, e.g., ISG15-7-amido-4-methylcoumarin (AMC) or -7-amino-4-methylcoumarin (AFC) available from Boston Biochem, Inc., Cambridge, Mass.), and a viral OTU domain-containing protein or an OTU domain-containing fragment thereof and (b) measuring the fluorescence of the mixture, wherein an alteration in the fluorescence relative to a negative control (e.g., the composition comprising an ISG15 fluorogenic substrate and the viral OTU domain-containing protein or OTU domain-containing fragment thereof not contacted with the compound) or a predetermined reference range indicates that the compound modulates the deISGylation activity of the viral OTU domain-containing protein or OTU domain-containing fragment thereof.

In one embodiment, the invention provides methods for identifying a compound that reduces the deISGylation activity of a viral OTU domain-containing protein or an OTU domain-containing fragment thereof, the methods comprising: (a) contacting a compound with a composition comprising an artificial substrate that mimics the ISG15 cleavage and a viral OTU domain-containing protein or OTU domain-containing fragment thereof and (b) measuring the amount of cleavage of the artificial substrate, wherein a decrease in the cleavage of the artificial substrate relative to a negative control (e.g., the composition comprising an artificial substrate that mimics the ISG15 cleavage and the viral OTU domain-containing protein or OTU domain-containing fragment thereof not contacted with the compound) or a predetermined reference range indicates that the compound reduces or inhibits the deISGylation activity of the viral OTU domain-containing protein or OTU domain-containing fragment thereof. In certain embodiments, the artificial substrate is a small synthetic fluorogenic substrate, such as AMC or AFC, that incorporates the C-terminal four (or six) residues found in Ub and ISG15 (LRGG) or (LRLRGG) (SEQ ID NO:1). (Lindner, H et al. J Virol. December 2005 Vol 79 p 15199-15208), (Blakirev, M et al, J Virol, June 2002, Vol 76 p 6323-6331). In other embodiments the artificial substrate has DABCYL and EDANS moieties on opposite ends of a 12-(or other) mer peptide that can be detected by FRET (as used in: Barretto et al, J Virol, December 2005, Vol 79 p 15189-15198), in which such peptide has the cleavage site of interest (e.g., LRLRGG (SEQ ID NO:1)).

In another embodiment, the invention provides methods for identifying a compound that reduces the deISGylation activity of a viral OTU domain-containing protein or an OTU domain-containing fragment thereof, the methods comprising: (a) contacting a compound with an ISG15-fluorogenic substrate (such as, e.g., ISG15-AMC or ISG15-AFC available from Boston Biochem, Inc., Cambridge, Mass.), and a viral OTU domain-containing protein or an OTU domain-containing fragment thereof; and (b) measuring the fluorescence of the mixture, wherein a decrease in the fluorescence relative to a negative control (e.g., the composition comprising an ISG15-fluorogenic substrate and the viral OTU domain-containing protein or OTU domain-containing fragment thereof not contacted with the compound) or a predetermined reference range indicates that the compound reduces or inhibits the deISGylation activity of the viral OTU domain-containing protein or OTU domain-containing fragment thereof. In certain embodiments, the fluorescence is measured using a spectrofluorometer at, e.g., an excitation wavelength of 380 nm and emission is measured at, e.g., 440 nm.

In a specific embodiment, a compound that decreases the deISGylation activity of a viral OTU domain-containing protein results in an increase in the amount of ISG15 conjugated protein by about 10%, preferably about 15%, 20%, 25%, 30%, 35%, 40% or more relative to a negative control as determined using an in vitro assay known to one of skill in the art. In a more specific embodiment, a compound that decreases the deISGylation activity of a viral OTU domain-containing protein results in an increase in the amount of ISG15 conjugated protein by about 10%, preferably about 15%, 20%, 25%, 30%, 35%, 40% or more relative to a negative control as determined using an in vitro assay described herein.

5.4.2 Methods for Identifying Compounds that Modulate the Deubiquitination Activity of a Viral OTU Domain-Containing Protein The present invention provides methods for identifying a compound that modulates the deubiquitination activity of a viral OTU domain-containing protein, the methods comprising: (a) contacting a compound with a composition comprising ubiquitinated protein and a viral OTU domain-containing protein or an OTU domain-containing fragment thereof; and (b) measuring the amount of ubiquitinated protein, wherein an alteration in the amount of ubiquitinated protein relative to a negative control (e.g., a composition comprising ubiquitinated protein and a viral OTU domain-containing protein or an OTU domain-containing fragment thereof not contacted with the compound) or a predetermined reference range indicates that the compound modulates the deubiquitination activity of the viral OTU domain-containing protein. In a specific embodiment, the invention provides methods for identifying a compound that reduces the deubiquitination activity of a viral OTU domain-containing protein, the methods comprising: (a) contacting a compound with a composition comprising ubiquitinated protein and a viral OTU domain-containing protein or an OTU domain-containing fragment thereof; and (b) measuring the amount of ubiquitinated protein, wherein an increase in the amount of ubiquitinated protein relative to a negative control (e.g., a composition comprising ubiquitinated protein and a viral OTU domain-containing protein or an OTU domain-containing fragment thereof not contacted with the compound) or a predetermined reference range indicates that the compound reduces the deubiquitination activity of the viral OTU domain-containing protein.

Compounds that modulate the deubiquitination activity of a viral OTU domain-containing protein can be determined using a cell-based assay. The invention provides a method for identifying a compound that modulates the deubiquitination activity of a viral OTU domain-containing protein, the method comprising: (a) contacting a compound with a cell engineered to express a viral OTU domain-containing protein or an OTU domain-containing fragment thereof and ubiquitin; and (b) measuring the amount of ubiquitin conjugated protein, wherein an alteration in the amount of ubiquitinated protein relative to a negative control (e.g., a cell engineered to express ubiquitin and the viral protein which is not contacted with the compound) or predetermined reference range indicates that the compound modulates the deubiquitination activity of the viral OTU domain-containing protein. The invention provides a method for identifying a compound that modulates the deubiquitination activity of a viral OTU domain-containing protein, the method comprising: (a) contacting a compound with a viral OTU domain-containing protein or an OTU domain-containing fragment thereof and a cell expressing ubiquitin; and (b) measuring the amount of ubiquitinated protein, wherein an alteration in the amount of ubiquitinated protein relative to a negative control (e.g., the viral protein or fragment thereof and a cell expressing ubiquitin not contacted with the compound) or a predetermined reference range indicates that the compound modulates the deubiquitination activity of the viral OTU domain-containing protein.

In a specific embodiment, the invention provides a method for identifying a compound that reduces the deubiquitination activity of a viral OTU domain-containing protein, the method comprising: (a) contacting a compound with a cell engineered to express a viral OTU domain-containing protein or an OTU domain-containing fragment thereof and ubiquitin; and (b) measuring the amount of ubiquitinated protein, wherein an increase in the amount of ubiquitinated protein relative to a negative control (e.g., a cell engineered to express ubiquitin and the viral protein which is not contacted with the compound) or predetermined reference range indicates that the compound reduces the deubiquitination activity of the viral OTU domain-containing protein. In another embodiment, the invention provides a method for identifying a compound that reduces the deubiquitination activity of a viral OTU domain-containing protein, the method comprising: (a) contacting a compound with a viral OTU domain-containing protein or an OTU domain-containing fragment thereof and a cell expressing ubiquitin; and (b) measuring the amount of ubiquitinated protein, wherein an increase in the amount of ubiquitinated protein relative to a negative control (e.g., the viral protein or fragment thereof and a cell expressing ubiquitin not contacted with the compound) or a predetermined reference range indicates that the compound reduces the deubiquitination activity of the viral OTU domain-containing protein.

The invention provides a method for identifying a compound that modulates the deubiquitination activity of a viral OTU domain-containing protein, the method comprising: (a) contacting a compound with a ubiquitin-expressing cell infected with a virus comprising a viral OTU domain-containing protein or an OTU domain-containing fragment thereof; and (b) measuring the amount of ubiquitinated protein, wherein an alteration in the amount of ubiquitinated protein relative to a negative control (e.g., a ubiquitin-expressing cell infected with the virus which is not contacted with the compound) or a predetermined reference range indicates that the compound modulates the deubiquitination activity of the viral OTU domain-containing protein. In a specific embodiment, the invention provides a method for identifying a compound that reduces the deubiquitination activity of a viral OTU domain-containing protein, the method comprising: (a) contacting a compound with a ubiquitin-expressing cell infected with a virus comprising a viral OTU domain-containing protein or an OTU domain-containing fragment thereof; and (b) measuring the amount of ubiquitinated protein, wherein an increase in the amount of ubiquitinated protein relative to a negative control (e.g., a ubiquitin-expressing cell infected with the virus which is not contacted with the compound) or a predetermined reference range indicates that the compound reduces the deubiquitination activity of the viral OTU domain-containing protein.

In one embodiment, the virus naturally encodes such viral OTU domain-containing protein. In another embodiment, the virus comprises a heterologous viral OTU domain-containing protein or OTU domain-containing fragment thereof. In some embodiments, Sindbis virus is used to infect the cell. In a particular embodiment, the dsTE12Q double subgenomic Sindbis virus contains a heterologous viral OTU domain-containing protein or an OTU domain-containing fragment thereof.

In a specific embodiment, the invention provides a method for identifying a compound that reduces the deubiquitination activity of a viral OTU domain-containing protein, the method comprising: (a) contacting a compound with a ubiquitin-expressing cell infected with a virus comprising a viral OTU domain-containing protein or an OTU domain-containing fragment thereof; and (b) measuring the amount of ubiquitinated protein, wherein an increase in the amount of ubiquitin conjugated protein relative to a negative control (e.g., a cell infected with the virus which is not contacted with the compound) or a predetermined reference range indicates that the compound reduces the deubiquitination activity of the viral OTU domain-containing protein. In some embodiments, the cell is engineered to express or overexpress ubiquitin. In a specific embodiment, the virus naturally encodes such viral OTU domain-containing protein. In another embodiment, the virus comprises a heterologous viral OTU domain-containing protein or OTU domain-containing fragment thereof. In some embodiments, Sindbis virus is used to infect the cell. In a particular embodiment, the dsTE12Q double subgenomic Sindbis virus contains a heterologous viral OTU domain-containing protein or an OTU domain-containing fragment thereof.

In some embodiments, the cell used in the methods described above is a eukaryotic cell or a prokaryotic cell. In a specific embodiment, the cell used is a mammalian cell. In another embodiment, the cell used is yeast cell. In another embodiment, the cell used is a human cell. In a specific embodiment, the cell is deficient in the interferon response. In another embodiment, the cell is deficient in one or more components of the cellular deubiquitination pathway.

In some embodiments, the cell is engineered to express or overexpress ubiquitin. In some embodiments, an affinity peptide tag such as poly-histidine, biotin, hemagglutinin (HA), glutathione S-transferase (GST), mannose binding protein (MBP), or FLAG) is conjugated to ubiquitin. In other embodiments, ubiquitin is expressed together with other proteins of the ubiquitination cascade. In a particular embodiment, tagged ubiquitin is overexpressed with proteins of the ubiquitination cascade.

Compounds that modulate the deubiquitination activity of a viral OTU domain-containing protein can be determined using a cell-free assay. The invention provides a method for identifying a compound that modulates the deubiquitination activity of a viral OTU domain-containing protein, the method comprising: (a) contacting a compound with a cell extract and a viral OTU domain-containing protein or an OTU domain-containing fragment thereof; and (b) measuring the amount of ubiquitinated protein, wherein an alteration in the amount of ubiquitinated protein relative to a negative control (e.g., a cell extract contacted with the viral protein but not the compound) or predetermined reference range indicates that the compounds modulates the deubiquitination activity of the viral OTU domain-containing protein. In a specific embodiment, the invention provides a method for identifying a compound that reduces the deubiquitination activity of a viral OTU domain-containing protein, the method comprising: (a) contacting a compound with a cell extract and a viral OTU domain-containing protein or OTU domain-containing fragment thereof; and (b) measuring the amount of ubiquitinated protein, wherein an increase in the amount of ubiquitinated protein relative to a negative control (e.g., a cell extract contacted with the viral protein but not the compound) or predetermined reference range indicates that the compound reduces the deubiquitination activity of the viral OTU domain-containing protein.

In some embodiments, the cell extract is from a cell engineered to express or overexpress ubiquitin. In some embodiments, an affinity peptide tag such as poly-histidine, biotin, hemagglutinin (HA), glutathione S-transferase (GST), mannose binding protein (MBP), or FLAG is conjugated to ubiquitin. In other embodiments, the cell extract is from a cell engineered to express ubiquitin and other proteins of the ubiquitination cascade. In a particular embodiment, tagged ubiquitin is overexpressed with proteins of the ubiquitination cascade.

In a specific embodiment, ubiquitinated conjugates are enriched before they are contacted with the OTU domain-containing viral protein or OTU domain-containing fragment thereof. In one embodiment, ubiquitinated conjugates in a cell extract are enriched, e.g., by chromatography. In another embodiment, ubiquitinated conjugates are enriched by affinity chromatography using an antibody specific to ubiquitin or to the ubiquitinated protein. In another embodiment, the ubiquitinated protein source is enriched by affinity chromatography using a tag. In some embodiments, the protein target is tagged. In other embodiments, ubiquitin is tagged. The tag can be any affinity tag known to those of skill in the art, including but not limited to poly-histidine, biotin, hemagglutinin (HA), glutathione S-transferase (GST), and mannose binding protein (MBP).

In some embodiments, the cell extract used in the methods described in the preceding three paragraphs is a eukaryotic cell extract or a prokaryotic cell extract. In a specific embodiment, the cell extract used is a mammalian cell extract. In another embodiment, the cell extract used is yeast cell extract. In another embodiment, the cell extract used is a human cell extract. In a specific embodiment, the cell extract is from a cell deficient in the interferon response. In another embodiment, the cell extract is from a cell deficient in deubiquitination.

The amount of ubiquitinated protein can be measured using any assay known to one of skill in the art for measuring ubiquitination and/or deubiquitination, including but not limited to an immunoassay, such as a Western blot or an ELISA, SDS-PAGE and Coomassie staining or a colorimetric assay.

In one embodiment, the invention provides methods for identifying a compound that modulates the deubiquitination activity of a viral OTU domain-containing protein or an OTU domain-containing fragment thereof, the methods comprising: (a) contacting a compound with a composition comprising an artificial substrate that mimics the ubiquitin cleavage and a viral OTU domain-containing protein or OTU domain-containing fragment thereof; and (b) measuring the amount of cleavage of the artificial substrate, wherein an alteration in the cleavage of the artificial substrate relative to a negative control (e.g., the composition comprising an artificial substrate that mimics the ubiquitin cleavage and the viral OTU domain-containing protein or OTU domain-containing fragment thereof not contacted with the compound) or a predetermined reference range indicates that the compound modulates the deubiquitination activity of the viral OTU domain-containing protein or OTU domain-containing fragment thereof. In certain embodiments, the artificial substrate is a small synthetic fluorogenic substrate, such as AMC or AFC, that incorporates the C-terminal four (or six) residues found in Ub and ISG15 (LRGG) or (LRLRGG) (SEQ ID NO:1). (Lindner, H et al. J Virol. December 2005 Vol 79 p 15199-15208), (Blakirev, M et al, J Virol, June 2002, Vol 76 p 6323-6331). In other embodiments the artificial substrate has DABCYL and EDANS moieties on opposite ends of a 12-(or other) mer peptide that can be detected by FRET (as used in: Barretto et al, J Virol, December 2005, Vol 79 p 15189-15198), in which such peptide has the cleavage site of interest (e.g., LRLRGG (SEQ ID NO:1)).

In another embodiment, the invention provides methods for identifying a compound that modulates the deubiquitination activity of a viral OTU domain-containing protein or an OTU domain-containing fragment thereof, the methods comprising: (a) contacting a compound with an ubiquitin-fluorogenic substrate (such as, e.g., ubiquitin-AMC or ubiquitin-AFC available from Boston Biochem, Inc., Cambridge, Mass.), and a viral OTU domain-containing protein or an OTU domain-containing fragment thereof; and (b) measuring the fluorescence of the mixture, wherein an alteration in the fluorescence relative to a negative control (e.g., the composition comprising an ubiquitin-fluorogenic substrate and the viral OTU domain-containing protein or OTU domain-containing fragment thereof not contacted with the compound) or a predetermined reference range indicates that the compound modulates the deubiquitination activity of the viral OTU domain-containing protein or OTU domain-containing fragment thereof.

In one embodiment, the invention provides methods for identifying a compound that reduces the deubiquitination activity of a viral OTU domain-containing protein or an OTU domain-containing fragment thereof, the methods comprising: (a) contacting a compound with a composition comprising an artificial substrate that mimics the ubiquitin cleavage and a viral OTU domain-containing protein or OTU domain-containing fragment thereof; and (b) measuring the amount of cleavage of the artificial substrate, wherein a decrease in the cleavage of the artificial substrate relative to a negative control (e.g., the composition comprising an artificial substrate that mimics the ubiquitin cleavage and the viral OTU domain-containing protein or OTU domain-containing fragment thereof not contacted with the compound) or a predetermined reference range indicates that the compound reduces or inhibits the deubiquitination activity of the viral OTU domain-containing protein or OTU domain-containing fragment thereof. In certain embodiments, the artificial substrate is a small synthetic fluorogenic substrate, such as AMC or AFC, that incorporates the C-terminal four (or six) residues found in Ub and ISG15 (LRGG) or (LRLRGG) (SEQ ID NO:1). (Lindner, H et al. J Virol. December 2005 Vol 79 p 15199-15208), (Blakirev, M et al, J Virol, June 2002, Vol 76 p 6323-6331). In other embodiments the artificial substrate has DABCYL and EDANS moieties on opposite ends of a 12-(or other) mer peptide that can be detected by FRET (as used in: Barretto et al, J Virol, December 2005, Vol 79 p 15189-15198), in which such peptide has the cleavage site of interest (e.g., LRLRGG (SEQ ID NO:1)).

In another embodiment, the invention provides methods for identifying a compound that reduces the deubiquitination activity of a viral OTU domain-containing protein or an OTU domain-containing fragment thereof, the methods comprising: (a) contacting a compound with an ubiquitin-fluorogenic substrate (such as, e.g., Ubiquitin AMC available from Boston Biochem, Inc., Cambridge, Mass.), and a viral OTU domain-containing protein or an OTU domain-containing fragment thereof; and (b) measuring the fluorescence of the mixture, wherein a decrease in the fluorescence relative to a negative control (e.g., the composition comprising an ubiquitin-fluorogenic substrate and the viral OTU domain-containing protein or OTU domain-containing fragment thereof not contacted with the compound) or a predetermined reference range indicates that the compound reduces or inhibits the deubiquitination activity of the viral OTU domain-containing protein or OTU domain-containing fragment thereof. In certain embodiments, the fluorescence is measured using a spectrofluorometer.

In some embodiments, a compound that decreases the deubiquitination activity of a viral OTU domain-containing protein results in an increase in the amount of ubiquitinated protein by about 10%, preferably about 15%, 20%, 25%, 30%, 35%, 40% or more relative to a negative control as determined using an assay known to one of skill in the art. In a more specific embodiment, a compound that decreases the deubiquitination activity of a viral OTU domain-containing protein results in an increase in the amount of ubiquitinated protein by about 10%, preferably about 15%, 20%, 25%, 30%, 35%, 40% or more relative to a negative control as determined using an in vitro assay described herein. In certain embodiments, a compound does not affect the deubiquitination activity of a viral OTU domain-containing protein as determined, e.g., using an in vitro assay described herein.

5.4.3 Methods for Identifying Compounds that Modulate the DeNeddylation Activity of a Viral OTU Domain-Containing Protein The present invention provides methods for identifying a compound that modulates the deNeddylation activity of a viral OTU domain-containing protein, the methods comprising: (a) contacting a compound with a composition comprising Neddylated protein and a viral OTU domain-containing protein or an OTU domain-containing fragment thereof; and (b) measuring the amount of Neddylated protein, wherein an alteration in the amount of Neddylated protein relative to a negative control (e.g., a composition comprising Neddylated protein and a viral OTU domain-containing protein or an OTU domain-containing fragment thereof not contacted with the compound) or a predetermined reference range indicates that the compound modulates the deNeddylation activity of the viral OTU domain-containing protein. In a specific embodiment, the invention provides methods for identifying a compound that reduces the deNeddylation activity of a viral OTU domain-containing protein, the methods comprising: (a) contacting a compound with a composition comprising Neddylated protein and a viral OTU domain-containing protein or an OTU domain-containing fragment thereof; and (b) measuring the amount of Neddylated protein, wherein an increase in the amount of Neddylated protein relative to a negative control (e.g., a composition comprising Neddylated protein and a viral OTU domain-containing protein or an OTU domain-containing fragment thereof not contacted with the compound) or a predetermined reference range indicates that the compound reduces the deNeddylation activity of the viral OTU domain-containing protein.

Compounds that modulate the deNeddylation activity of a viral OTU domain-containing protein can be determined using a cell-based assay. The invention provides a method for identifying a compound that modulates the deNeddylation activity of a viral OTU domain-containing protein, the method comprising: (a) contacting a compound with a cell engineered to express a viral OTU domain-containing protein or an OTU domain-containing fragment thereof and Nedd8; and (b) measuring the amount of Nedd8 conjugated protein, wherein an alteration in the amount of Neddylated protein relative to a negative control (e.g., a cell engineered to express Nedd8 and the viral protein which is not contacted with the compound) or predetermined reference range indicates that the compound modulates the deNeddylation activity of the viral OTU domain-containing protein. The invention provides a method for identifying a compound that modulates the deNeddylation activity of a viral OTU domain-containing protein, the method comprising: (a) contacting a compound with a viral OTU domain-containing protein or an OTU domain-containing fragment thereof and a cell expressing Nedd8; and (b) measuring the amount of Neddylated protein, wherein an alteration in the amount of Neddylated protein relative to a negative control (e.g., the viral protein or fragment thereof and a cell expressing Nedd8 not contacted with the compound) or a predetermined reference range indicates that the compound modulates the deNeddylation activity of the viral OTU domain-containing protein.

In a specific embodiment, the invention provides a method for identifying a compound that reduces the deNeddylation activity of a viral OTU domain-containing protein, the method comprising: (a) contacting a compound with a cell engineered to express a viral OTU domain-containing protein or an OTU domain-containing fragment thereof and Nedd8; and (b) measuring the amount of Neddylated protein, wherein an increase in the amount of Neddylated protein relative to a negative control (e.g., a cell engineered to express Nedd8 and the viral protein which is not contacted with the compound) or predetermined reference range indicates that the compound reduces the deNeddylation activity of the viral OTU domain-containing protein. In another embodiment, the invention provides a method for identifying a compound that reduces the deNeddylation activity of a viral OTU domain-containing protein, the method comprising: (a) contacting a compound with a viral OTU domain-containing protein or an OTU domain-containing fragment thereof and a cell expressing Nedd8; and (b) measuring the amount of Neddylated protein, wherein an increase in the amount of Neddylated protein relative to a negative control (e.g., the viral protein or fragment thereof and a cell expressing Nedd8 not contacted with the compound) or a predetermined reference range indicates that the compound reduces the deNeddylation activity of the viral OTU domain-containing protein.

The invention provides a method for identifying a compound that modulates the deNeddylation activity of a viral OTU domain-containing protein, the method comprising: (a) contacting a compound with a Nedd8-expressing cell infected with a virus comprising a viral OTU domain-containing protein or an OTU domain-containing fragment thereof; and (b) measuring the amount of Neddylated protein, wherein an alteration in the amount of Neddylated protein relative to a negative control (e.g., a Nedd8 expressing cell infected with the virus which is not contacted with the compound) or a predetermined reference range indicates that the compound modulates the deNeddylation activity of the viral OTU domain-containing protein. In a specific embodiment, the invention provides a method for identifying a compound that reduces the deNeddylation activity of a viral OTU domain-containing protein, the method comprising: (a) contacting a compound with a Nedd8-expressing cell infected with a virus comprising a viral OTU domain-containing protein or an OTU domain-containing fragment thereof; and (b) measuring the amount of Neddylated protein, wherein an increase in the amount of Neddylated protein relative to a negative control (e.g., a Nedd8-expressing cell infected with the virus which is not contacted with the compound) or a predetermined reference range indicates that the compound reduces the deNeddylation activity of the viral OTU domain-containing protein.

In one embodiment, the virus naturally encodes such viral OTU domain-containing protein. In another embodiment, the virus comprises a heterologous viral OTU domain-containing protein or OTU domain-containing fragment thereof. In some embodiments, Sindbis virus is used to infect the cell. In a particular embodiment, the dsTE12Q double subgenomic Sindbis virus contains a heterologous viral OTU domain-containing protein or an OTU domain-containing fragment thereof.

In a specific embodiment, the invention provides a method for identifying a compound that reduces the deNeddylation activity of a viral OTU domain-containing protein, the method comprising: (a) contacting a compound with a Nedd8-expressing cell infected with a virus comprising a viral OTU domain-containing protein or an OTU domain-containing fragment thereof; and (b) measuring the amount of Neddylated protein, wherein an increase in the amount of Nedd8 conjugated protein relative to a negative control (e.g., a Nedd8-expressing cell infected with the virus which is not contacted with the compound) or a predetermined reference range indicates that the compound reduces the deNeddylation activity of the viral OTU domain-containing protein. In some embodiments, the cell is engineered to express or overexpress Nedd8. In a specific embodiment, the virus naturally encodes such viral OTU domain-containing protein. In another embodiment, the virus comprises a heterologous viral OTU domain-containing protein or OTU domain-containing fragment thereof. In some embodiments, Sindbis virus is used to infect the cell. In a particular embodiment, the dsTE12Q double subgenomic Sindbis virus contains a heterologous viral OTU domain-containing protein or an OTU domain-containing fragment thereof.

In some embodiments, the cell used in the methods described above is a eukaryotic cell or a prokaryotic cell. In a specific embodiment, the cell used is a mammalian cell. In another embodiment, the cell used is yeast cell. In another embodiment, the cell used is a human cell. In a specific embodiment, the cell is deficient in the interferon response. In another embodiment, the cell is deficient in one or more components of the cellular deNeddylation pathway.

In some embodiments, the cell is engineered to express or overexpress Nedd8. In some embodiments, an affinity peptide tag such as poly-histidine, biotin, hemagglutinin (HA), glutathione S-transferase (GST), mannose binding protein (MBP), or FLAG) is conjugated to Nedd8. In other embodiments, Nedd8 is expressed together with other proteins of the Neddylation cascade. In a particular embodiment, tagged Nedd8 is overexpressed with proteins of the Neddylation cascade.

Compounds that modulate the deNeddylation activity of a viral OTU domain-containing protein can be determined using a cell-free assay. The invention provides a method for identifying a compound that modulates the deNeddylation activity of a viral OTU domain-containing protein, the method comprising: (a) contacting a compound with a cell extract and a viral OTU domain-containing protein or an OTU domain-containing fragment thereof; and (b) measuring the amount of Neddylated protein, wherein an alteration in the amount of Neddylated protein relative to a negative control (e.g., a cell extract contacted with the viral protein but not the compound) or predetermined reference range indicates that the compounds modulates the deNeddylation activity of the viral OTU domain-containing protein. In a specific embodiment, the invention provides a method for identifying a compound that reduces the deNeddylation activity of a viral OTU domain-containing protein, the method comprising: (a) contacting a compound with a cell extract and a viral OTU domain-containing protein or OTU domain-containing fragment thereof; and (b) measuring the amount of Neddylated protein, wherein an increase in the amount of Neddylated protein relative to a negative control (e.g., a cell extract contacted with the viral protein but not the compound) or predetermined reference range indicates that the compound reduces the deNeddylation activity of the viral OTU domain-containing protein.

In some embodiments, the cell extract is from a cell engineered to express or overexpress Nedd8. In some embodiments, an affinity peptide tag such as poly-histidine, biotin, hemagglutinin (HA), glutathione S-transferase (GST), mannose binding protein (MBP), or FLAG) is conjugated to Nedd8. In other embodiments, the cell extract is from a cell engineered to express Nedd8 and other proteins of the Neddylation cascade. In a particular embodiment, tagged Nedd8 is overexpressed with proteins of the Neddylation cascade.

In a specific embodiment, Neddylated conjugates are enriched before they are contacted with the OTU domain-containing viral protein or OTU domain-containing fragment thereof. In one embodiment, Neddylated conjugates in a cell extract are enriched, e.g., by chromatography. In another embodiment, Neddylated conjugates are enriched by affinity chromatography using an antibody specific to Nedd8 or to the Neddylated protein. In another embodiment, the Neddylated protein source is enriched by affinity chromatography using a tag. In some embodiments, the protein target is tagged. In other embodiments, Nedd8 is tagged. The tag can be any affinity tag known to those of skill in the art, including but not limited to poly-histidine, biotin, hemagglutinin (HA), glutathione S-transferase (GST), and mannose binding protein (MBP).

In some embodiments, the cell extract used in the methods described in the preceding three paragraphs is a eukaryotic cell extract or a prokaryotic cell extract. In a specific embodiment, the cell extract used is a mammalian cell extract. In another embodiment, the cell extract used is yeast cell extract. In another embodiment, the cell extract used is a human cell extract. In a specific embodiment, the cell extract is from a cell deficient in the interferon response. In another embodiment, the cell extract is from a cell deficient in deNeddylation.

The amount of Neddylated protein can be measured using any assay known to one of skill in the art for measuring Neddylation and/or deNeddylation, including but not limited to an immunoassay, such as a Western blot or an ELISA, SDS-PAGE and Coomassie staining or a colorimetric assay.

In one embodiment, the invention provides methods for identifying a compound that modulates the deNeddylation activity of a viral OTU domain-containing protein or an OTU domain-containing fragment thereof, the methods comprising: (a) contacting a compound with a composition comprising an artificial substrate that mimics the Nedd8 cleavage and a viral OTU domain-containing protein or OTU domain-containing fragment thereof; and (b) measuring the amount of cleavage of the artificial substrate, wherein an alteration in the cleavage of the artificial substrate relative to a negative control (e.g., the composition comprising an artificial substrate that mimics the Nedd8 cleavage and the viral OTU domain-containing protein or OTU domain-containing fragment thereof not contacted with the compound) or a predetermined reference range indicates that the compound modulates the deNeddylation activity of the viral OTU domain-containing protein or OTU domain-containing fragment thereof In certain embodiments, the artificial substrate is a small synthetic substrate.

In another embodiment, the invention provides methods for identifying a compound that modulates the deNeddylation activity of a viral OTU domain-containing protein or an OTU domain-containing fragment thereof, the methods comprising: (a) contacting a compound with an Nedd8-fluorogenic substrate and a viral OTU domain-containing protein or an OTU domain-containing fragment thereof; and (b) measuring the fluorescence of the mixture, wherein an alteration in the fluorescence relative to a negative control (e.g., the composition comprising an Nedd8-fluorogenic substrate and the viral OTU domain-containing protein or OTU domain-containing fragment thereof not contacted with the compound) or a predetermined reference range indicates that the compound modulates the deNeddylation activity of the viral OTU domain-containing protein or OTU domain-containing fragment thereof.

In one embodiment, the invention provides methods for identifying a compound that reduces the deNeddylation activity of a viral OTU domain-containing protein or an OTU domain-containing fragment thereof, the methods comprising: (a) contacting a compound with a composition comprising an artificial substrate that mimics the Nedd8 cleavage and a viral OTU domain-containing protein or OTU domain-containing fragment thereof; and (b) measuring the amount of cleavage of the artificial substrate, wherein a decrease in the cleavage of the artificial substrate relative to a negative control (e.g., the composition comprising an artificial substrate that mimics the Nedd8 cleavage and the viral OTU domain-containing protein or OTU domain-containing fragment thereof not contacted with the compound) or a predetermined reference range indicates that the compound reduces or inhibits the deNeddylation activity of the viral OTU domain-containing protein or OTU domain-containing fragment thereof. In certain embodiments, the artificial substrate is a small synthetic substrate.

In another embodiment, the invention provides methods for identifying a compound that reduces the deNeddylation activity of a viral OTU domain-containing protein or an OTU domain-containing fragment thereof, the methods comprising: (a) contacting a compound with an Nedd8-fluorogenic substrate, and a viral OTU domain-containing protein or an OTU domain-containing fragment thereof; and (b) measuring the fluorescence of the mixture, wherein a decrease in the fluorescence relative to a negative control (e.g., the composition comprising an Nedd8-fluorogenic substrate and the viral OTU domain-containing protein or OTU domain-containing fragment thereof not contacted with the compound) or a predetermined reference range indicates that the compound reduces or inhibits the deNeddylation activity of the viral OTU domain-containing protein or OTU domain-containing fragment thereof. In certain embodiments, the fluorescence is measured using a spectrofluorometer.

In some embodiments, a compound that decreases the deNeddylation activity of a viral OTU domain-containing protein results in an increase in the amount of Neddylated protein by about 10%, preferably about 15%, 20%, 25%, 30%, 35%, 40% or more relative to a negative control as determined using an assay known to one of skill in the art. In a more specific embodiment, a compound that decreases the deNeddylation activity of a viral OTU domain-containing protein results in an increase in the amount of Neddylated protein by about 10%, preferably about 15%, 20%, 25%, 30%, 35%, 40% or more relative to a negative control as determined using an in vitro assay described herein. In certain embodiments, a compound does not affect the deNeddylation activity of a viral OTU domain-containing protein as determined, e.g., using an in vitro assay described herein.

5.4.4 Compounds

The compounds screened and identified by the methods of the invention include, but are not limited to, peptides, proteins, peptoids; random biooligomers; diversomers such as hydantoins, benzodiazepines and dipeptides; vinylogous polypeptides; nonpeptidal peptidomimetics; oligocarbamates; peptidyl phosphonates; nucleic acids (e.g., RNAi and antisense); antibodies; carbohydrates; and small molecules. In some embodiments, the compounds are nucleic acid or peptide molecules. In some embodiments, the compound is an attenuated virus mutant. In other embodiments, the types of compounds include, but are not limited to, peptide analogs including peptides comprising non-naturally occurring amino acids, e.g., D-amino acids, phosphorous analogs of amino acids, such as α-amino phosphoric acids, or amino acids having non-peptide linkages, nucleic acid analogs such as phosphorothioates and PNAs, hormones, antigens, synthetic or naturally occurring drugs, opiates, dopamine, serotonin, catecholamines, thrombin, acetylcholine, prostaglandins, organic molecules, pheromones, adenosine, sucrose, glucose, lactose and galactose. In some embodiments, the compounds are Ub/ISG15-aldehyde or Ub/ISG15-vinyl sulfone.

The compounds screened and identified by the methods of the invention may be from libraries which comprise a variety of types of compounds or may be compounds that have been synthesized de novo. In one embodiment, a library is used for an initial screen of many compounds to identify promising candidate structures for further characterization and optimization. In a specific embodiment, the library is a library of small molecules.

Examples of libraries that can be screened in accordance with the methods of the invention include, but are not limited to: peptoids; random biooligomers; diversomers such as hydantoins, benzodiazepines and dipeptides; vinylogous polypeptides; nonpeptidal peptidomimetics; oligocarbamates; peptidyl phosphonates; peptide nucleic acid libraries; antibody libraries; carbohydrate libraries; and small molecule libraries (preferably, small organic molecule libraries). In some embodiments, the compounds in the libraries screened are nucleic acid or peptide molecules. In a non-limiting example, peptide molecules can exist in a phage display library. In other embodiments, the types of compounds include, but are not limited to, peptide analogs including peptides comprising non-naturally occurring amino acids, e.g., D-amino acids, phosphorous analogs of amino acids, such as α-amino phosphoric acids, or amino acids having non-peptide linkages, nucleic acid analogs such as phosphorothioates and PNAs, hormones, antigens, synthetic or naturally occurring drugs, opiates, dopamine, serotonin, catecholamines, thrombin, acetylcholine, prostaglandins, organic molecules, pheromones, adenosine, sucrose, glucose, lactose and galactose. Libraries of polypeptides or proteins can also be used in the assays of the invention.

In a specific embodiment, compound libraries (including combinatorial libraries) which comprise small organic molecule libraries including, but not limited to, benzodiazepines, isoprenoids, thiazolidinones, metathiazanones, pyrrolidines, morpholino compounds, and benzodiazepines. In another embodiment, the compound libraries comprise peptoids; random bio oligomers; benzodiazepines; diversomers such as hydantoins, benzodiazepines and dipeptides; vinylogous polypeptides; nonpeptidal peptidomimetics; oligocarbamates; peptidyl phosphonates; peptide nucleic acid libraries; antibody libraries; or carbohydrate libraries. Compound libraries are themselves commercially available (see, e.g., ComGenex, Princeton, N.J.; Asinex, Moscow, Russia, Tripos, Inc., St. Louis, Mo.; ChemStar, Ltd., Moscow, Russia; 3D Pharmaceuticals, Exton, Pa.; Martek Biosciences, Columbia, Md.).

In a preferred embodiment, the library is preselected so that the compounds of the library are more amenable for cellular uptake. For example, compounds are selected based on specific parameters such as, but not limited to, size, lipophilicity, hydrophilicity, and hydrogen bonding, which enhance the likelihood of compounds getting into the cells. In another embodiment, the compounds are analyzed by computation of three-dimensional or multi-dimensional metrics and evaluated by computer computation programs.

The compound library for use in accordance with the methods of the present invention may be synthesized. There is a great interest in synthetic methods directed toward the creation of large collections of small organic compounds, or libraries, which could be screened for pharmacological, biological or other activity. The synthetic methods applied to create vast compound libraries are performed in solution or in the solid phase, i.e., on a solid support. Solid phase synthesis makes it easier to conduct multi step reactions and to drive reactions to completion with high yields because excess reagents can be easily added and washed away after each reaction step. Solid phase combinatorial synthesis also tends to improve isolation, purification and screening. However, the more traditional solution phase chemistry supports a wider variety of organic reactions than solid phase chemistry.

Combinatorial compound libraries of the present invention may be synthesized using the apparatus described in U.S. Pat. No. 6,190,619 to Kilcoin et al., which is hereby incorporated by reference in its entirety. U.S. Pat. No. 6,190,619 discloses a synthesis apparatus capable of holding a plurality of reaction vessels for parallel synthesis of multiple discrete compounds or for combinatorial libraries of compounds.

In one embodiment, the combinatorial compound library can be synthesized in solution. The method disclosed in U.S. Pat. No. 6,194,612 to Boger et al., which is hereby incorporated by reference in its entirety, features compounds useful as templates for solution phase synthesis of combinatorial libraries. The template is designed to permit reaction products to be easily purified from unreacted reactants using liquid/liquid or solid/liquid extractions. The compounds produced by combinatorial synthesis using the template will preferably be small organic molecules. Some compounds in the library may mimic the effects of non peptides or peptides. In contrast to solid phase synthesis of combinatorial compound libraries, liquid phase synthesis does not require the use of specialized protocols for monitoring the individual steps of a multistep solid phase synthesis (Egner et al., 1995, J. Org. Chem. 60:2652; Anderson et al., 1995, J. Org. Chem. 60:2650; Fitch et al., 1994, J. Org. Chem. 59:7955; Look et al., 1994, J. Org. Chem. 49:7588; Metzger et al., 1993, Angew. Chem., Int. Ed. Engl. 32:894; Youngquist et al., 1994, Rapid Commun. Mass Spect. 8:77; Chu et al., 1995, J. Am. Chem. Soc. 117:5419; Brummel et al., 1994, Science 264:399; and Stevanovic et al., 1993, Bioorg. Med. Chem. Lett. 3:431).

Combinatorial compound libraries useful for the methods of the present invention can be synthesized on solid supports. In one embodiment, a split synthesis method, a protocol of separating and mixing solid supports during the synthesis, is used to synthesize a library of compounds on solid supports (see e.g., Lam et al., 1997, Chem. Rev. 97:41-448; Ohlmeyer et al., 1993, Proc. Natl. Acad. Sci. USA 90:10922-10926 and references cited therein). Each solid support in the final library has substantially one type of compound attached to its surface. Other methods for synthesizing combinatorial libraries on solid supports, wherein one product is attached to each support, will be known to those of skill in the art (see, e.g., Nefzi et al., 1997, Chem. Rev. 97:449-472).

As used herein, the term "solid support" is not limited to a specific type of solid support. Rather a large number of supports are available and are known to one skilled in the art. Solid supports include silica gels, resins, derivatized plastic films, glass beads, cotton, plastic beads, polystyrene beads, alumina gels, and polysaccharides. A suitable solid support may be selected on the basis of desired end use and suitability for various synthetic protocols. For example, for peptide synthesis, a solid support can be a resin such as p-methylbenzhydrylamine (pMBHA) resin (Peptides International, Louisville, Ky.), polystyrenes (e.g., PAM-resin obtained from Bachem Inc., Peninsula Laboratories), including chloromethylpolystyrene, hydroxymethylpolystyrene and aminomethylpolystyrene, poly (dimethylacrylamide)-grafted styrene co-divinyl-benzene (e.g., POLYHIPE resin, obtained from Aminotech, Canada), polyamide resin (obtained from Peninsula Laboratories), polystyrene resin grafted with polyethylene glycol (e.g., TENTAGEL or ARGOGEL, Bayer, Tubingen, Germany) polydimethylacrylamide resin (obtained from Milligen/Biosearch, California), or Sepharose (Pharmacia, Sweden).

In some embodiments of the present invention, compounds can be attached to solid supports via linkers. Linkers can be integral and part of the solid support, or they may be nonintegral that are either synthesized on the solid support or attached thereto after synthesis. Linkers are useful not only for providing points of compound attachment to the solid support, but also for allowing different groups of molecules to be cleaved from the solid support under different conditions, depending on the nature of the linker. For example, linkers can be, inter alia, electrophilically cleaved, nucleophilically cleaved, photocleavable, enzymatically cleaved, cleaved by metals, cleaved under reductive conditions or cleaved under oxidative conditions. In a specific embodiment, the compounds are cleaved from the solid support prior to high-throughput screening of the compounds.

5.5 Characterization of Compounds 5.5.1 Characterization of Antiviral Activity

The biological activity of the compounds of the invention is measured in various in vitro and in vivo assays as described herein. Preferably, the compounds of the invention exhibit an activity profile that is consistent with their ability to inhibit viral replication and/or proliferation while maintaining low toxicity with respect to eukaryotic cells, preferably mammalian cells.

The effect of a compound on the replication of a virus comprising a viral OTU domain-containing protein can be assessed by any method known in the art or described herein. Viral assays, including those that measure altered viral replication (as determined, e.g., by plaque formation) or the production of viral proteins (as determined, e.g., by Western blot analysis) or viral nucleic acid (as determined, e.g., by RT-PCR, northern blot analysis or southern blot) in cultured cells in vitro using methods which are well known in the art can be used to determine the effect of a compound on viral replication.

In a specific embodiment, the effect of a compound on the replication of a virus comprising a viral OTU domain-containing protein is determined by measuring the viral titer. Viral titer can be determined using any technique known to one of skill in the art. For example, viral titer can be measured by inoculating serial dilutions of the virus into cell cultures or live animals. After incubation of the virus for a specified time in the presence of the compound of interest, the virus is isolated using standard methods. Physical quantitation of the virus titer can be performed using PCR applied to virus supernatants or tissue culture infectious doses (TCID50).

The effect of a compound on the virulence of a virus can also be determined using in vivo assays in which the titer of the virus in an infected subject administered a compound of interest, the length of survival of an infected subject administered a compound of interest, the immune response in an infected subject administered a compound of interest, the number, duration and/or severity of the symptoms in an infected subject administered a compound of interest, and/or the time period before onset of one or more symptoms in an infected subject administered a compound of interest is assessed. Techniques known to one of skill in the art can be used to measure such effects.

In a specific embodiment, a compound reduces the replication of a virus comprising a viral OTU domain-containing protein by approximately 10%, preferably 15%, 25%, 30%, 45%, 50%, 60%, 75%, 95% or more relative to a negative control in an assay described herein or known in the art.

5.5.2 Selectivity of Compounds for Viral OTU Domain-Containing Proteins

Cellular OTU domain-containing proteins (in particular, human and other animals), which may be cloned and expressed using art-recognized techniques, are used for direct comparisons of inhibitor effects between viral and cellular protein to identify inhibitors that are specific for the viral protein. Preferably, the same cloning and expression systems are used to produce both the viral and cellular proteins for use in this assay. In a specific embodiment, compounds are selected which inhibit the deISGylation activity and/or deubiquitination activity of a viral OTU domain-containing protein by at least 2-fold, preferably 5 fold, 10 fold, or 25 fold more than they inhibit the deISGylation activity and/or deubiquitination activity of a cellular protein (e.g., a cellular OTU domain-containing protein) in an assay described herein or known to one of skill in the art. In some other embodiments, compounds are selected which inhibit the deISGylation activity and/or deubiquitination activity of a viral OTU domain-containing protein by at least 10-fold greater, at least 20-fold greater, at least 30-fold greater, at least 40-fold greater, at least 50-fold greater, at least 60-fold greater, at least 70-fold greater, at least 80-fold greater, or at least 90-fold greater than they inhibit of deISGylation activity and/or deubiquitination activity of a cellular protein (e.g., a cellular OTU domain-containing protein) in an assay described herein or an assay known to one skill in the art. In other embodiments, compounds are selected which inhibit the deISGylation activity and/or deubiquitination activity of a viral OTU domain-containing protein 10 to 150 fold, 10-50 fold, 25 to 100 fold, 50 to 100 fold, 75 to 150 fold more than they inhibit the deISGylation activity and/or deubiquitination activity of a cellular protein (e.g., a cellular OTU domain-containing protein) in an assay described herein or an assay known to one of skill in the art. In some embodiments, compounds are selected which inhibit the deISGylation activity and/or deubiquitination activity of a viral OTU domain-containing protein by at least 25%, at least 50%, at least 75% or at least 95% more than the compound inhibits the deISGylation and/or deubiquitination activity of a cellular protein (e.g., a cellular OTU domain-containing protein). The assays described, e.g., in Sections 5.1 or 5.4 can be used to assess the selectively of the compound for viral OTU domain-containing proteins.

In some embodiments, a compound is identified that reduces or inhibits the deubiquitination and/or deISGylation activity of a viral OTU domain-containing protein but not the deubiquitination activity of a cellular OTU domain-containing protein. Cellular OTU domain-containing proteins that can be tested in such embodiments include Otubain 1, Otubain 2, Cezanne, VCIP135, and A20.

The selectivity of the compounds which inhibit deNeddylation and/or deSUMOylation activity can also be assed using the assays described in, e.g., Sections 5.1 and 5.4. In some embodiments, compounds are selected which inhibit the deNeddylation and/or deSUMOylation activity of a viral OTU domain-containing protein by at least 25%, at least 50%, at least 75% or at least 95% or more than they inhibit the deNeddylation and/or deubiquitination activity of a cellular protein (e.g., a cellular OTU domain-containing protein).

5.5.3 Mammalian Cytotoxicity

The compounds of the invention are tested for cytotoxicity in mammalian, preferably human, cell lines. In certain specific embodiments, cytotoxicity is assessed in one or more of the following cell lines: U937, a human monocyte cell line; primary peripheral blood mononuclear cells (PBMC); Huh7, a human hepatoblastoma cell line; 293T, a human embryonic kidney cell line; and THP-1, monocytic cells in which intracellular killing of Mycobacterium is tested.

Many assays well-known in the art can be used to assess viability of a cell or cell line following exposure to a compound of the invention and, thus, determine the cytotoxicity of the compound. For example, cell proliferation can be assayed by measuring Bromodeoxyuridine (BrdU) incorporation (see, e.g., Hoshino et al., 1986, Int. J. Cancer 38, 369; Campana et al., 1988, J. Immunol. Meth. 107:79) or (3H) thymidine incorporation (see, e.g., Chen, J., 1996, Oncogene 13:1395-403; Jeoung, J., 1995, J. Biol. Chem. 270:18367 73), by direct cell count, by detecting changes in transcription, translation or activity of known genes such as proto-oncogenes (e.g., fos, myc) or cell cycle markers (Rb, cdc2, cyclin A, D1, D2, D3, E, etc). The levels of such protein and mRNA and activity can be determined by any method well known in the art. For example, protein can be quantitated by known immunodiagnostic methods such as Western blotting or immunoprecipitation using commercially available antibodies. mRNA can be quantitated using methods that are well known and routine in the art, for example, using northern analysis, RNase protection, or polymerase chain reaction in connection with reverse transcription. Cell viability can be assessed by using trypan-blue staining or other cell death or viability markers known in the art. In a specific embodiment, the level of cellular ATP is measured to determined cell viability.

In specific embodiments, cell viability is measured in three-day and seven-day periods using an assay standard in the art, such as the CellTiter-Glo Assay Kit (Promega) which measures levels of intracellular ATP. A reduction in cellular ATP is indicative of a cytotoxic effect.

5.5.4 Animal Studies

The compounds and compositions of the invention are preferably assayed in vitro and in vivo, for the desired therapeutic or prophylactic activity, prior to use in humans. For example, in vitro assays can be used to determine whether it is preferable to administer the compound, a pharmaceutically acceptable salt thereof, and/or another therapeutic agent. Animal model systems can be used to demonstrate safety and efficacy.

The lead compounds identified in the assays described herein can be tested for biological activity using animal models. Such animal model systems include, but are not limited to, rats, mice, chicken, cows, monkeys, pigs, goats, sheep, dogs, rabbits, etc. In a specific embodiment of the invention, a compound identified in accordance with the methods of the invention is tested in a mouse model system. Such model systems are widely used and well-known to the skilled artisan.

The toxicity and/or efficacy of a compound identified in accordance with the invention can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. A compound identified in accordance with the invention that exhibits large therapeutic indices is preferred. While a compound identified in accordance with the invention that exhibits toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of a compound identified in accordance with the invention for use in humans. The dosage of such agents lies preferably within a range of circulating concentrations that include the ED50 with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels in plasma may be measured, for example, by high-performance liquid chromatography.

5.6 Uses of Mutant Viruses

The mutant viruses of the invention can be used in active immunization in a subject. In one aspect, the mutant viruses of the invention can be used to prevent, manage and or treat one or more diseases. In a specific aspect, the mutant viruses of the invention can be used to prevent, manage and/or treat infections by two infectious agents. See Section 5.7 for a description of immunogenic formulation and uses of those formulations for inducing an immune response in a subject. The mutant viruses of the invention can also be used to produce antibodies which can be used in diagnostic immunoassays, passive immunotherapy, and generation of antiidiotypic antibodies. The generated antibodies may be isolated by standard techniques known in the art (e.g., immunoaffinity chromatography, centrifugation, precipitation, etc.) and used in diagnostic immunoassays, passive immunotherapy and generation of antiidiotypic antibodies. The isolated antibodies before being used in passive immunotherapy may be modified, e.g., the antibodies may be chimerized or humanized. See, e.g., U.S. Pat. Nos. 4,444,887 and 4,716,111; and International Publication Nos. WO 98/46645, WO 98/50433, WO 98/24893, WO98/16654, WO 96/34096, WO 96/33735, and WO 91/10741, each of which is incorporated herein by reference in its entirety, for reviews on the generation of chimeric and humanized antibodies.

For antibodies produced by the mutant viruses for use in passive immunization, the dosage administered to a subject is typically 0.0001 mg/kg to 100 mg/kg of the patient's body weight. Preferably, the dosage administered to a patient is between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the subject's body weight.

The antibodies isolated from subjects administered a mutant virus of the invention may also be used to monitor treatment and/or disease progression. Any immunoassay system known in the art may be used for this purpose including but not limited to competitive and noncompetitive assay systems using techniques such as radioimmunoassays, ELISA (enzyme linked immunosorbent assays), "sandwich" immunoassays, precipitin reactions, gel diffusion precipitin reactions, immunodiffusion assays, agglutination assays, complement fixation assays, immunoradiometric assays, fluorescent immunoassays, protein A immunoassays and immunoelectrophoresis assays, to name but a few.

The antibodies generated by the mutant viruses of the invention can also be used in the production of antiidiotypic antibody. The antiidiotypic antibody can then in turn be used for immunization, in order to produce a subpopulation of antibodies that bind an initial antigen of a mutant virus of the invention or, in the case of viruses encoding sequences from another virus or other pathogen, an antigen of the heterologous species (Jerne, 1974, Ann. Immunol. (Paris) 125c:373; Jerre et al., 1982, EMBO J. 1:234).

In immunization procedures, the amount of immunogen to be used and the immunization schedule will be determined by a physician skilled in the art and will be administered by reference to the immune response and antibody titers of the subject.

The mutant viruses of the invention may also be used in assays, such as those described in Sections 5.1.1 to 5.1.4 to determine whether a protein has deISGylation, deubiquitination, deNeddylation, and/or deSUMOylation activity. The protein may be a viral, human, bacteria, etc.

5.7 Immunogenic Compositions

The invention also encompasses the use of the mutant viruses of the invention in immunogenic compositions, e.g., vaccine formulations. The immunogenic compositions may comprise either a live or inactivated mutant virus of the invention. The mutant virus can be inactivated by methods well known to those of skill in the art. Common methods use formalin and heat for inactivation. See, e.g., U.S. Pat. No. 6,635,246, which is herein incorporated by reference in its entirety. Other methods include those described in U.S. Pat. Nos. 5,891,705; 5,106,619 and 4,693,981, herein incorporated by reference in their entireties.

A live immunogenic composition may be preferred because multiplication in the subject leads to a prolonged stimulus of similar kind and magnitude to that occurring in natural infections, and therefore, confers substantial, long lasting immunity. Production of such live recombinant immunogenic formulations may be accomplished using conventional methods involving propagation of the mutant virus in cell culture or in embryonated eggs (e.g., chick embryonated eggs) followed by purification. Moreover, in some embodiments, the mutant viruses can induce a robust IFN response which has other biological consequences in vivo, affording protection against subsequent infections.

In some embodiments, the mutant viruses can induce a robust TNF$\alpha$ response which has other biological consequences in vivo, affording protection against subsequent infections. In certain embodiments, the expression and/or activity of TNF$\alpha$ or the TNF$\alpha$ pathway in a subject (host) or host cell infected with a mutant virus of the invention is increased 5-10%, 10-20%, 20-30%, 30-40%, 40-50%, 50-60%, 60-70%, 70-80%, 80-90% or more compared to a subject (host) or host cell infected with a wild-type virus. In certain embodiments, the expression and/or activity of TNF$\alpha$ or the TNF$\alpha$ pathway in a subject (host) or host cell infected with a mutant virus of the invention is increased approximately 1 to approximately 100 fold, approximately 5 to approximately 80 fold, approximately 20 to approximately 80 fold, approximately 1 to approximately 10 fold, or approximately 1 to approximately 5 fold, or approximately 40 to approximately 80 fold, or 1, 2, 3, 4, 5, 7, 10, 15, 20, 25, 30, 35, 40, 45, 50, 55, 60, 65, 70, 75, 80, 85, 90, 95 or 100 fold compared to a subject (host) or host cell infected with a wild-type virus.

In some embodiments, the mutant viruses can induce a robust NF-κB response which has other biological consequences in vivo, affording protection against subsequent infections. In certain embodiments, the activity of NF-κB, such as NF-κB signaling, in a subject (host) or host cell infected with a mutant virus of the invention is increased 5-10%, 10-20%, 20-30%, 30-40%, 40-50%, 50-60%, 60-70%, 70-80%, 80-90% or more compared to a subject (host) or host cell infected with a wild-type virus. In certain embodiments, the activity of NF-κB in a subject (host) or host cell infected with a mutant virus of the invention is increased approximately 1 to approximately 100 fold, approximately 5 to approximately 80 fold, approximately 20 to approximately 80 fold, approximately 1 to approximately 10 fold, or approximately 1 to approximately 5 fold, or approximately 40 to approximately 80 fold, or 1, 2, 3, 4, 5, 7, 10, 15, 20, 25, 30, 35, 40, 45, 50, 55, 60, 65, 70, 75, 80, 85, 90, 95 or 100 fold compared to a subject (host) or host cell infected with a wild-type virus.

In some embodiments, the mutant viruses can induce a robust interferon response which has biological consequences in vivo. In certain embodiments, the activity of interferon, such as interferon signaling, in a subject (host) or host cell infected with a mutant virus of the invention is increased 5-10%, 10-20%, 20-30%, 30-40%, 40-50%, 50-60%, 60-70%, 70-80%, 80-90% or more compared to a subject (host) or host cell infected with a wild-type virus. In certain embodiments, the activity of interferon in a subject (host) or host cell infected with a mutant virus of the invention is increased approximately 1 to approximately 100 fold, approximately 5 to approximately 80 fold, approximately 20 to approximately 80 fold, approximately 1 to approximately 10 fold, or approximately 1 to approximately 5 fold, or approximately 40 to approximately 80 fold, or 1, 2, 3, 4, 5, 7, 10, 15, 20, 25, 30, 35, 40, 45, 50, 55, 60, 65, 70, 75, 80, 85, 90, 95 or 100 fold compared to a subject (host) or host cell infected with a wild-type virus.

In a preferred embodiment, the immunogenic compositions of the present invention comprise an effective amount of a mutant virus of the invention, and a pharmaceutically acceptable carrier. The term "pharmaceutically acceptable" means approved by a regulatory agency of the Federal or a state government or listed in the U.S. Pharmacopeia or other generally recognized pharmacopeiae for use in animals, and more particularly in humans. The term "carrier" refers to a diluent, adjuvant, excipient, or vehicle with which the pharmaceutical formulation is administered. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Examples of suitable pharmaceutical carriers are described in "Remington's Pharmaceutical Sciences" by E. W. Martin. The formulation should suit the mode of administration. The particular composition may also depend on whether the mutant virus is live or inactivated.

The immunogenic compositions of the invention may be administered to a naïve subject, i.e., a subject that does not have a disease or has not been and is not currently infected with an infectious agent. In one embodiment, the immunogenic compositions are administered to a naïve subject, i.e., a subject that does not have a disease or has not been and is not currently infected with an infectious agent, but is predisposed of acquiring such disease (e.g., a viral infection). In one embodiment, the immunogenic compositions of the invention are administered to a subject that does not have a disease, or has not and is not infected with an infectious agent to which the mutant virus induces an immune response. The immunogenic compositions of the invention may also be administered to a subject that is and/or has been infected with an infectious agent or another type, subtype or strain of the agents to which the mutant virus induces an immune response.

Many methods may be used to introduce the immunogenic compositions, e.g., vaccine formulations described above, these include but are not limited to intranasal, intratracheal, oral, intradermal, intramuscular, intraperitoneal, intravenous, conjunctival and subcutaneous routes. In birds, the methods may further include choanal inoculation. As an alternative to parenteral administration, the invention also encompasses, routes of mass administration for agricultural purposes such as via drinking water or in a spray. It may be preferable to introduce the mutant virus of the invention via the natural route of infection of the agent from which the mutant is derived.

In certain embodiments, an immunogenic composition of the invention does not result in complete protection from an infection (e.g., a viral infection or infection by a non-viral infectious agent), but results in a lower titer or reduced number of the pathogen (e.g., a virus) compared to an untreated subject. Benefits include, but are not limited to, reduced severity of symptoms of the infection and a reduction in the length of the disease or condition associated with the infection In certain embodiments, an immunogenic composition of the invention is used to protect against a disease (e.g., an infection) in naïve subjects.

The prophylactic and/or therapeutic effect of the immunogenic compositions of the invention are based, in part, upon achieving or inducing an immune response (e.g., a humoral immune response). In one aspect, the immunogenic compositions induce a detectable serum titer of an antibody against antigens of the mutant virus in either the subject or an animal model thereof (e.g. mouse, rat, pig, goat, sheep or canine model). The serum titer of an antibody can be determined using techniques known to one of skill in the art, e.g., immunoassays such as ELISAs. In a specific embodiment, the antibodies generated by administering an immunogenic composition of the invention are neutralizing antibodies.

In one embodiment, administration of a mutant virus of the invention to a subject or animal model thereof results in a serum titer of about 1 μg/ml, about 2 μg/ml, about 5 μg/ml, about 6 μg/ml, about 10 μg/ml, about 15 μg/ml, about 20 μg/ml, about 25 μg/ml, about 50 μg/ml, about 75 μg/ml, about 100 μg/ml, about 125 μg/ml, about 150 μg/ml, about 175 μg/ml, about 200 μg/ml, about 225 μg/ml, about 250 μg/ml, about 275 μg/ml, or about 300 μg/ml or more of an antibody that specifically binds to an antigen of the mutant virus. The immune response may be determined in the subject or in a animal model, which response is then correlated or extrapolated to a predicted response in the subject, e.g., a human or livestock, such as a pig, sheep, goat, or cow.

In one embodiment, the present invention provides methods for preventing at least one disease (e.g., a viral infection) in a subject, the methods comprising administering to said subject a first dose of an effective amount of an immunogenic composition comprising a mutant virus of the invention. In some embodiments, the dose of the mutant virus administered to the subject or animal model is $10^2$, $5\times10^2$, $10^3$, $5\times10^3$, $10^4$, $5 \times 10^4$, $10^5$, $5 \times 10^5$, $10^6$, $5 \times 10^6$, $10^7$, $5 \times 10^7$, $10^8$, $5 \times 10^8$, $1 \times 10^9$, $5 \times 10^9$, $1 \times 10^{10}$, $5 \times 10^{10}$, $1 \times 10^{11}$, $5 \times 10^{11}$ or $10^{12}$ pfu.

In one embodiment, the present invention provides methods for managing and/or ameliorating at least one disease (e.g., a viral infection) in a subject, the methods comprising administering to said subject a dose of an effective amount of an immunogenic composition comprising a mutant virus of the invention. In some embodiments, the dose of the mutant virus administered to the subject or animal model is $10^2$, $5 \times 10^2$, $10^3$, $5 \times 10^3$, $10^4$, $5 \times 10^4$, $10^5$, $5 \times 10^5$, $10^6$, $5 \times 10^6$, $10^7$, $5 \times 10^7$, $10^8$, $5 \times 10^8$, $1 \times 10^9$, $5 \times 10^9$, $1 \times 10^{10}$, $5 \times 10^{10}$, $1 \times 10^{11}$, $5 \times 10^{11}$ or $10^{12}$ pfu.

The present invention also provides methods for preventing, treating and/or managing at least one disease, the methods comprising administering to said subject an effective amount of an immunogenic composition comprising a mutant virus of the invention, wherein the effective amount is the amount that results in a reduction in mortality, reduction in hospitalization, reduction in the severity of the disease and/or reduction in the clinical symptoms of the disease relative to a subject not administered the immunogenic formulation of the invention. In certain embodiments the subject is a human. In certain embodiments, the subject is a pig. In other embodiments, the subject is a cat, sheep, or goat. In some embodiments, the dose of the mutant virus administered to the subject is $10^2$, $5 \times 10^2$, $10^3$, $5 \times 10^3$, $10^4$, $5 \times 10^4$, $10^5$, $5 \times 10^5$, $10^6$, $5 \times 10^6$, $10^7$, $5 \times 10^7$, $10^8$, $5 \times 10^8$, $1 \times 10^9$, $5 \times 10^9$, $1 \times 10^{10}$, $5 \times 10^{10}$, $1 \times 10^{11}$, $5 \times 10^{11}$ or $10^{12}$ pfu.

The amount of the immunogenic composition of the invention which will be effective in the treatment, prevention and/or amelioration of a particular disease (e.g. viral infection) will depend on the nature of the disease, and can be determined by standard clinical techniques. In addition, in vitro assays may optionally be employed to help identify optimal dosage ranges. The precise dose to be employed in the formulation will also depend on the route of administration, and the seriousness of the infection or disorder, and should be decided according to the judgment of the practitioner and each subject's circumstances. However, suitable dosage ranges for administration are generally about $10^2$, $5 \times 10^2$, $10^3$, $5 \times 10^3$, $10^4$, $5 \times 10^4$, $10^5$, $5 \times 10^5$, $10^6$, $5 \times 10^6$, $10^7$, $5 \times 10^7$, $10^8$, $5 \times 10^8$, $1 \times 10^9$, $5 \times 10^9$, $1 \times 10^{10}$, $5 \times 10^{10}$, $1 \times 10^{11}$, $5 \times 10^{11}$ or $10^{12}$ pfu, and most preferably about $10^4$ to about $10^{12}$, and can be administered to a subject once, twice, three or more times with intervals as often as needed. Effective doses may be extrapolated from dose response curves derived from in vitro or animal model test systems.

In various embodiments, the immunogenic compositions of the invention or antibodies generated by the mutant viruses of the invention are administered to a subject in combination with one or more other therapies (e.g. antiviral or immunomodulatory therapies) for the prevention of at least one disease (e.g. a viral infection). In certain embodiments, the therapies (e.g., prophylactic or therapeutic agents) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In preferred embodiments, two or more therapies are administered within the same patient or subject visit. Non-limiting examples of agents that can be administered in combination with an immunogenic composition of the invention or an antibody generated in response to a viral mutant of the invention are found below.

5.8 Pharmaceutical Compositions

Any of the compounds identified by the methods of the invention, including the compounds described in Section 5.4 and derivatives and congeners of such compounds, may optionally be in the form of a composition comprising the compound or its pharmaceutically acceptable salt. In some embodiments, the invention provides compositions (including pharmaceutical compositions) comprising a compound and a pharmaceutically acceptable carrier, excipient, or diluent.

In certain embodiments, the invention provides a pharmaceutical composition comprising an effective amount of a compound and a pharmaceutically acceptable carrier, excipient, or diluent. The pharmaceutical compositions are suitable for veterinary and/or human administration.

The pharmaceutical compositions of the present invention can be in any form that allows for the composition to be administered to a subject, said subject preferably being an animal, including, but not limited to a human, mammal, or non-human animal, such as a cow, horse, sheep, pig, fowl, cat, dog, mouse, rat, rabbit, guinea pig, etc., and is more preferably a mammal, and most preferably a human.

In a specific embodiment and in this context, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Examples of suitable pharmaceutical carriers are described in "Remington's Pharmaceutical Sciences" by E. W. Martin.

Typical compositions and dosage forms comprise one or more excipients. Suitable excipients are well-known to those skilled in the art of pharmacy, and non-limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a patient and the specific active ingredients in the dosage form. The composition or single unit dosage form, if desired, can also contain minor amounts of wetting or emulsifying agents, or pH buffering agents.

Lactose free compositions of the invention can comprise excipients that are well known in the art and are listed, for example, in the U.S. Pharmacopeia (USP) SP (XXI)/NF (XVI). In general, lactose free compositions comprise an active ingredient, a binder/filler, and a lubricant in pharmaceutically compatible and pharmaceutically acceptable amounts. Preferred lactose free dosage forms comprise an active ingredient, microcrystalline cellulose, pre gelatinized starch, and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long term storage in order to determine characteristics such as shelf life or the stability of formulations over time. See, e.g., Jens T. Carstensen, Drug Stability: Principles & Practice, 2d. Ed., Marcel Dekker, NY, N.Y., 1995, pp. 379 80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous compositions and dosage forms of the invention can be prepared using anhydrous or low moisture containing ingredients and low moisture or low humidity conditions. Compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The compositions and single unit dosage forms can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain a prophylactically or therapeutically effective amount of a prophylactic or therapeutic agent preferably in purified form, together with a suitable amount of carrier so as to provide the form for proper administration to the patient. The formulation should suit the mode of administration. In a preferred embodiment, the compositions or single unit dosage forms are sterile and in suitable form for administration to a subject, preferably an animal subject, more preferably a mammalian subject, and most preferably a human subject.

A composition of the invention is formulated to be compatible with its intended route of administration. Examples of routes of administration include, but are not limited to, parenteral, e.g., intravenous, intradermal, subcutaneous, oral (e.g., inhalation), intranasal, transdermal (topical), transmucosal, intra-synovial and rectal administration. In a specific embodiment, the composition is formulated in accordance with routine procedures as a composition adapted for intravenous, subcutaneous, intramuscular, oral, intranasal or topical administration to human beings. In another embodiments, the composition is formulated for such administration to livestock. In a preferred embodiment, a composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non aqueous liquid suspensions, oil in water emulsions, or a water in oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient or subject.

The composition, shape, and type of dosage forms of the invention will typically vary depending on their use. For example, a dosage form used in the acute treatment of a disorder (e.g., a viral infection) may contain larger amounts of one or more of the active ingredients it comprises than a dosage form used in the chronic treatment of the same disorder. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., Remington's Pharmaceutical Sciences, 18th ed., Mack Publishing, Easton Pa. (1990).

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration. Typical dosage forms of the invention comprise a compound of the invention, or a pharmaceutically acceptable salt, solvate or hydrate thereof lie within the range of from about 1 mg to about 1000 mg per day, given as a single once-a-day dose in the morning but preferably as divided doses throughout the day taken with food.

Pharmaceutical compositions of the invention that are suitable for oral administration can be presented as discrete dosage forms, such as, but not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 18th ed., Mack Publishing, Easton Pa. (1990).

Typical oral dosage forms of the invention are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre gelatinized starch, and mixtures thereof. The binder or filler in pharmaceutical compositions of the invention is typically present in from about 50 to about 99 weight percent of the pharmaceutical composition or dosage form.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms of the invention include, but are not limited to, agar agar, alginic acid, calcium carbonate, microcrystalline cellulose, croscarmellose sodium, crospovidone, polacrilin potassium, sodium starch glycolate, potato or tapioca starch, pre gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W. R. Grace Co. of Baltimore, Md.), a coagulated aerosol of synthetic silica (marketed by Degussa Co. of Plano, Tex.), CAB 0 SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Active ingredients of the invention can be administered by controlled release means or by delivery devices that are well known to those of ordinary skill in the art. Examples include, but are not limited to, those described in U.S. Pat. Nos. 3,845, 770; 3,916,899; 3,536,809; 3,598,123; and 4,008,719, 5,674, 533, 5,059,595, 5,591,767, 5,120,548, 5,073,543, 5,639,476, 5,354,556, and 5,733,566, each of which is incorporated herein by reference. Such dosage forms can be used to provide slow or controlled release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled release.

All controlled release pharmaceutical products have a common goal of improving drug therapy over that achieved by their non controlled counterparts. Ideally, the use of an optimally designed controlled release preparation in medical treatment is characterized by a minimum of drug substance being employed to cure or control the condition in a minimum amount of time. Advantages of controlled release formulations include extended activity of the drug, reduced dosage frequency, and increased patient compliance. In addition, controlled release formulations can be used to affect the time of onset of action or other characteristics, such as blood levels of the drug, and can thus affect the occurrence of side (e.g., adverse) effects.

Most controlled release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled release of an active ingredient can be stimulated by various conditions including, but not limited to, pH, temperature, enzymes, water, or other physiological conditions or compounds.

Parenteral dosage forms can be administered to patients by various routes including, but not limited to, subcutaneous, intravenous (including bolus injection), intramuscular, and intraarterial. Because their administration typically bypasses patients' or subjects' natural defenses against contaminants, parenteral dosage forms are preferably sterile or capable of being sterilized prior to administration to a patient or subject. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

Transdermal, topical, and mucosal dosage forms of the invention include, but are not limited to, ophthalmic solutions, sprays, aerosols, creams, lotions, ointments, gels, solutions, emulsions, suspensions, or other forms known to one of skill in the art. See, e.g., Remington's Pharmaceutical Sciences, 16th and 18th eds., Mack Publishing, Easton Pa. (1980 & 1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane 1,3 diol, isopropyl myristate, isopropyl palmitate, mineral oil, and mixtures thereof to form lotions, tinctures, creams, emulsions, gels or ointments, which are non toxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences, 16th and 18th eds., Mack Publishing, Easton Pa. (1980 & 1990).

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery enhancing or penetration enhancing agent. Different salts, hydrates or solvates of the active ingredients can be used to further adjust the properties of the resulting composition.

In certain specific embodiments of the invention, the compositions are in oral, injectable, or transdermal dosage forms. In one specific embodiment, the compositions are in oral dosage forms. In another specific embodiment, the compositions are in the form of injectable dosage forms. In another specific embodiment, the compositions are in the form of transdermal dosage forms.

5.9 Uses of the Compounds of the Invention

In some embodiments, the compounds of the invention are useful as inhibitors of a viral OTU domain-containing protein. In certain embodiments, such compounds inhibit or reduce the deISGylation activity and deubiquitination activity and/or deNeddylation activity. In preferred embodiments, the compounds of the invention exhibit specificity for viral OTU domain-containing proteins compared to cellular OTU domain-containing proteins. In a specific embodiment, a compound of the invention is an inhibitor of viral replication. In another embodiment, a compound of the invention exhibits low cytotoxicity in eukaryotic cells, preferably mammalian cells.

In one embodiment, a compound of the invention reduces or inhibits a viral infection. In a specific embodiment, a compound eliminates or reduces the amount of virus by 75%, 80%, 85%, 90%, 95%, 98%, 99%, 75-99.5%, 85-99.5%, or 90-99.8% in a subject as determined by an assay described herein or known to one of skill in the art. Accordingly, the compounds of the invention are useful in methods of preventing, treating and/or managing viral infections. In a particular embodiment, a compound of the invention is useful in preventing, treating and/or managing a viral infection caused by a strain of virus that exhibits resistance to other antiviral agents.

In certain embodiments, a compound of the invention inhibits or reduces viral protein synthesis by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% as measured by a standard assay (e.g., an in vitro protein translation assay, or other inhibition assay) known to one of skill in the art, or an assay described herein.

In some embodiments, a compound of the invention inhibits or reduces the spread of virus from one organ, tissue or cell to another organ, tissue or cell as measured using a standard assay known to one of skill in the art, or an assay described herein. In some embodiments, a compound of the invention inhibits or reduces the ability of the virus to spread to other individuals in a population by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% as measured by the inability of the organism to cause infection or disease from one host to another, using a standard assay known to one of skill in the art, or an assay described herein.

Viral infections reduced or inhibited in accordance with the methods of the invention include infections caused by a nairovirus (e.g., CCHFV or DUGV), an arterivirus, or a herpes virus.

5.9.1 Prophylactic and Therapeutic Methods

The present invention provides methods of preventing, treating and/or managing a viral infection, said methods comprising administering to a subject in need thereof one or more compounds identified in accordance with the methods of the invention. In one embodiment, the invention provides a method of preventing, treating/and or managing a viral infection, said method comprising administering to a subject in need thereof a dose of a prophylactically or therapeutically effective amount of one or more compounds of the invention. In specific embodiments, a compound of the invention is not administered to prevent, treat and/or manage a viral infection, if such compound has been used previously to prevent, treat, manage or ameliorate said viral infection.

The invention also provides methods of preventing, treating and/or managing a viral infection, said methods comprising administering to a subject in need thereof one or more of the compounds of the invention, and one or more other therapies (e.g., prophylactic or therapeutic agents). In a specific embodiment, the other therapies are currently being used, have been used or are known to be useful in the prevention, treatment and/or management of a viral infection. Non-limiting examples of such prophylactic or therapeutic methods are provided in Section 5.10, infra.

The combination therapies of the invention can be administered sequentially or concurrently. In one embodiment, the combination therapies of the invention comprise a compound of the invention and at least one other therapy which has the same mechanism of action. In another embodiment, the combination therapies of the invention comprise a compound of the invention and at least one other therapy which has a different mechanism of action than the compound.

In a specific embodiment, the combination therapies of the present invention improve the prophylactic and/or therapeutic effect of a compound of the invention by functioning together with the compound to have an additive or synergistic effect. In another embodiment, the combination therapies of the present invention reduce the side effects associated with each therapy taken alone.

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

In a specific embodiment, a pharmaceutical composition comprising one or more compounds of the invention and a pharmaceutically acceptable carrier or excipient is administered to a subject, preferably a human, to prevent, treat and/or manage a viral infection. In accordance with the invention, the pharmaceutical compositions may also comprise one or more other prophylactic or therapeutic agents. In a specific embodiment, the other prophylactic or therapeutic agents are currently being used, have been used or are known to be useful in the prevention, treatment and/or management of a viral infection.

A compound of the invention may be used as any line of therapy, e.g., a first, second, third, fourth or fifth line therapy, for a viral infection. In some embodiments, the subject administered a compound of the invention in accordance with the invention has not received a therapy prior to the administration of the compound of the invention. In other embodiments, the subject administered a compound of the invention in accordance with the invention has received a therapy prior to administration of the compound of the invention. In some embodiments, the subject administered a compound of the invention in accordance with the invention was refractory to a prior therapy or experienced adverse side effects to the prior therapy or the prior therapy was discontinued due to unacceptable levels of toxicity to the subject.

The invention provides methods for treating and/or managing a viral infection, in a subject refractory to conventional therapies for such an infection, the methods comprising administering to said subject a dose of a prophylactically or therapeutically effective amount of a compound of the invention.

5.9.2 Use as Disinfectant

The present invention provides for the use of the compounds of the invention as active ingredients in products having antiviral properties or in products in which it is desirable to have antiviral activity. In one embodiment, one or more of the compounds of the invention is used as an additive in a cosmetic product, a personal hygiene product, or a household or industrial cleaning product. In another embodiment, one or more of the compounds of the invention is used as an additive in an antiviral ointment or cream. In another embodiment one or more compounds of the invention is used as an additive to soap.

5.10 Agents Useful in Combination with the Compounds or Viral Mutants of the Invention Therapeutic or prophylactic agents that can be used in combination with the compounds or viral mutants of the invention for the prevention, treatment and/or management of a viral infection include, but are not limited to, small molecules, synthetic drugs, peptides (including cyclic peptides), polypeptides, proteins, nucleic acids (e.g., DNA and RNA nucleotides including, but not limited to, antisense nucleotide sequences, triple helices, RNAi, and nucleotide sequences encoding biologically active proteins, polypeptides or peptides), antibodies, synthetic or natural inorganic molecules, mimetic agents, and synthetic or natural organic molecules. Specific examples of such agents include, but are not limited to, immunomodulatory agents (e.g., interferon), anti-inflammatory agents (e.g., adrenocorticoids, corticosteroids (e.g., beclomethasone, budesonide, flunisolide, fluticasone, triamcinolone, methylprednisolone, prednisolone, prednisone, hydrocortisone), glucocorticoids, steroids, and non-steriodal anti-inflammatory drugs (e.g., aspirin, ibuprofen, diclofenac, and COX-2 inhibitors), pain relievers, leukotreine antagonists (e.g., montelukast, methyl xanthines, zafirlukast, and zileuton), beta2-agonists (e.g., albuterol, biterol, fenoterol, isoetharie, metaproterenol, pirbuterol, salbutamol, terbutalin formoterol, salmeterol, and salbutamol terbutaline), anticholinergic agents (e.g., ipratropium bromide and oxitropium bromide), sulphasalazine, penicillamine, dapsone, antihistamines, anti-malarial agents (e.g., hydroxychloroquine), antiviral agents (e.g., nucleoside analogs (e.g., zidovudine, acyclovir, gangcyclovir, vidarabine, idoxuridine, trifluridine, and ribavirin), foscarnet, amantadine, rimantadine, saquinavir, indinavir, ritonavir, and AZT) and antibiotics (e.g., dactinomycin (formerly actinomycin), bleomycin, erythomycin, penicillin, mithramycin, and anthramycin (AMC)).

Any therapy which is known to be useful, or which has been used or is currently being used for the prevention, management, and/or treatment of a viral infection or can be used in combination with the compounds of the invention in accordance with the invention described herein. See, e.g., Gilman et al., Goodman and Gilman's: The Pharmacological Basis of Therapeutics, 10th ed., McGraw-Hill, New York, 2001; The Merck Manual of Diagnosis and Therapy, Berkow, M. D. et al. (eds.), 17th Ed., Merck Sharp & Dohme Research Laboratories, Rahway, N.J., 1999; Cecil Textbook of Medicine, 20th Ed., Bennett and Plum (eds.), W.B. Saunders, Philadelphia, 1996 for information regarding therapies (e.g., prophylactic or therapeutic agents) which have been or are currently being used for preventing, treating and/or managing viral infections.

5.10.1 Antibacterial Agents

Antibacterial agents, including antibiotics, that can be used in combination with the compounds or viral mutants of the invention include, but are not limited to, aminoglycoside antibiotics, glycopeptides, amphenicol antibiotics, ansamycin antibiotics, cephalosporins, cephamycins oxazolidinones, penicillins, quinolones, streptogamins, tetracycline, and analogs thereof.

In a specific embodiment, the compounds or viral mutants of the invention are used in combination with other protein synthesis inhibitors, including but not limited to, streptomycin, neomycin, erythromycin, carbomycin, and spiramycin.

In one embodiment, the antibacterial agent is selected from the group consisting of ampicillin, amoxicillin, ciprofloxacin, gentamycin, kanamycin, neomycin, penicillin G, streptomycin, sulfanilamide, and vancomycin. In another embodiment, the antibacterial agent is selected from the group consisting of azithromycin, cefonicid, cefotetan, cephalothin, cephamycin, chlortetracycline, clarithromycin, clindamycin, cycloserine, dalfopristin, doxycycline, erythromycin, linezolid, mupirocin, oxytetracycline, quinupristin, rifampin, spectinomycin, and trimethoprim Additional, non-limiting examples of antibacterial agents for use in combination with the compounds or viral mutants of the invention include the following: aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol, chloramphenicol, florfenicol, and thiamphenicol), ansamycin antibiotics (e.g., rifamide and rifampin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefmetazole, and cefminox), folic acid analogs (e.g., trimethoprim), glycopeptides (e.g., vancomycin), lincosamides (e.g., clindamycin, and lincomycin), macrolides (e.g., azithromycin, carbomycin, clarithomycin, dirithromycin, erythromycin, and erythromycin acistrate), monobactams (e.g., aztreonam, carumonam, and tigemonam), nitrofurans (e.g., furaltadone, and furazolium chloride), oxacephems (e.g., flomoxef, and moxalactam), oxazolidinones (e.g., linezolid), penicillins (e.g., amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o benethamine, penicillin 0, penicillin V, penicillin V benzathine, penicillin V hydrabamine, penimepicycline, and phencihicillin potassium), quinolones and analogs thereof (e.g., cinoxacin, ciprofloxacin, clinafloxacin, flumequine, grepagloxacin, levofloxacin, and moxifloxacin), streptogramins (e.g., quinupristin and dalfopristin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), and tetracyclines (e.g., apicycline, chlortetracycline, clomocycline, and demeclocycline). Additional examples include cycloserine, mupirocin, tuberin amphomycin, bacitracin, capreomycin, colistin, enduracidin, enviomycin, and 2,4 diaminopyrimidines (e.g., brodimoprim).

5.10.2 Antiviral Agents

Antiviral agents that can be used in combination with the compounds or viral mutants of the invention include, but are not limited to, non-nucleoside reverse transcriptase inhibitors, nucleoside reverse transcriptase inhibitors, protease inhibitors, and fusion inhibitors. In one embodiment, the antiviral agent is selected from the group consisting of amantadine, oseltamivir phosphate, rimantadine, and zanamivir. In another embodiment, the antiviral agent is a non-nucleoside reverse transcriptase inhibitor selected from the group consisting of delavirdine, efavirenz, and nevirapine. In another embodiment, the antiviral agent is a nucleoside reverse transcriptase inhibitor selected from the group consisting of abacavir, didanosine, emtricitabine, emtricitabine, lamivudine, stavudine, tenofovir DF, zalcitabine, and zidovudine. In another embodiment, the antiviral agent is a protease inhibitor selected from the group consisting of amprenavir, atazanavir, fosamprenav, indinavir, lopinavir, nelfinavir, ritonavir, and saquinavir. In another embodiment, the antiviral agent is a fusion inhibitor such as enfuvirtide.

Additional, non-limiting examples of antiviral agents for use in combination with the compounds or viral mutants of the invention include the following: rifampicin, nucleoside reverse transcriptase inhibitors (e.g., AZT, ddI, ddC, 3TC, d4T), non-nucleoside reverse transcriptase inhibitors (e.g., delavirdine efavirenz, nevirapine), protease inhibitors (e.g., aprenavir, indinavir, ritonavir, and saquinavir), idoxuridine, cidofovir, acyclovir, ganciclovir, zanamivir, amantadine, and palivizumab. Other examples of anti-viral agents include but are not limited to acemannan; acyclovir; acyclovir sodium; adefovir; alovudine; alvircept sudotox; amantadine hydrochloride (SYMMETREL™); aranotin; arildone; atevirdine mesylate; avridine; cidofovir; cipamfylline; cytarabine hydrochloride; delavirdine mesylate; desciclovir; didanosine; disoxaril; edoxudine; enviradene; enviroxime; famciclovir; famotine hydrochloride; fiacitabine; fialuridine; fosarilate; foscarnet sodium; fosfonet sodium; ganciclovir; ganciclovir sodium; idoxuridine; kethoxal; lamivudine; lobucavir; memotine hydrochloride; methisazone; nevirapine; oseltamivir phosphate (TAMIFLU™); penciclovir; pirodavir; ribavirin; rimantadine hydrochloride (FLUMADINE™); saquinavir mesylate; somantadine hydrochloride; sorivudine; statolon; stavudine; tilorone hydrochloride; trifluridine; valacyclovir hydrochloride; vidarabine; vidarabine phosphate; vidarabine sodium phosphate; viroxime; zalcitabine; zanamivir (RELENZA™); zidovudine; and zinviroxime.

5.11 Methods of Administering the Compounds of the Invention

Compounds of the invention can be administered to a patient, preferably a mammal, more preferably a human, suffering from a viral infection. In a specific embodiment, a compound of the invention or a pharmaceutically acceptable salt thereof, is administered to a patient, preferably a mammal, more preferably a human, as a preventative measure against a viral infection or to prevent the spread of a viral infection in a population. In another embodiment, a compound of the invention or a pharmaceutically acceptable salt thereof, is administered to a patient, preferably a human, to prevent or reduce the spread of the virus to other cells, tissues, or organs of the subject which have not yet been infected by the virus.

Compounds of the invention can be administered to a subject, preferably a livestock animal, more preferably a pig, cow, goat or sheep, suffering from a viral infection. In a specific embodiment, a compound of the invention or a pharmaceutically acceptable salt thereof, is administered to a subject, preferably a livestock animal, more preferably a pig, cow, goat or sheep, as a preventative measure against a viral infection or to prevent the spread of a viral infection in a population. In another embodiment, a compound of the invention or a pharmaceutically acceptable salt thereof, is administered to a subject, preferably a livestock animal, more preferably a pig, cow, goat or sheep, to prevent or reduce the spread of the virus to other cells, tissues, or organs of the subject which have not yet been infected by the virus.

When administered to a patient, a compound of the invention or a pharmaceutically acceptable salt thereof is preferably administered as component of a composition that optionally comprises a pharmaceutically acceptable vehicle. The composition can be administered orally, or by any other convenient route, for example, by infusion or bolus injection, by absorption through epithelial or mucocutaneous linings (e.g., oral mucosa, rectal, and intestinal mucosa) and may be administered together with another biologically active agent. Administration can be systemic or local. Various delivery systems are known, e.g., encapsulation in liposomes, microparticles, microcapsules, capsules, and can be used to administer the compound and pharmaceutically acceptable salts thereof.

Methods of administration include but are not limited to parenteral, intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The mode of administration is left to the discretion of the practitioner. In most instances, administration will result in the release of a compound of the invention or a pharmaceutically acceptable salt thereof into the bloodstream.

In specific embodiments, it may be desirable to administer the compound or a pharmaceutically acceptable salt thereof locally. This may be achieved, for example, and not by way of limitation, by local infusion, topical application, e.g., in conjunction with a wound dressing, by injection, by means of a catheter, by means of a suppository, or by means of an implant, said implant being of a porous, non-porous, or gelatinous material, including membranes, such as sialastic membranes, or fibers.

In certain embodiments, it may be desirable to introduce a compound of the invention or a pharmaceutically acceptable salt thereof into the central nervous system by any suitable route, including intraventricular, intrathecal and epidural injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, a compound of the invention or a pharmaceutically acceptable salt thereof is formulated as a suppository, with traditional binders and vehicles such as triglycerides.

In another embodiment, a compound of the invention or a pharmaceutically acceptable salt thereof is delivered in a vesicle, in particular a liposome (see Langer, 1990, Science 249:1527 1533; Treat et al., in Liposomes in the Therapy of Infectious Disease and Bacterial infection, Lopez-Berestein and Fidler (eds.), Liss, New York, pp. 353 365 (1989); Lopez Berestein, ibid., pp. 317 327; see generally ibid.).

In another embodiment, a compound of the invention or a pharmaceutically acceptable salt thereof is delivered in a controlled release system (see, e.g., Goodson, in Medical Applications of Controlled Release, supra, vol. 2, pp. 115 138 (1984)). Examples of controlled-release systems are discussed in the review by Langer, 1990, Science 249:1527 1533 may be used. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In a specific embodiment, a controlled-release system comprising a compound of the invention or a pharmaceutically acceptable salt thereof is placed in close proximity to the viral infection to be prevented, treated and/or managed. In accordance with this embodiment, the close proximity of the controlled-release system to the infection may result in only a fraction of the dose of the compound required if it is systemically administered.

5.11.1 Dosages and Frequency

The amount of a compound of the invention, or the amount of a composition comprising the compound, that will be effective in the prevention, treatment and/or management of a viral infection can be determined by standard clinical techniques. In vitro or in vivo assays may optionally be employed to help identify optimal dosage ranges. The precise dose to be employed will also depend, e.g., on the route of administration, the type of invention, and the seriousness of the infection, and should be decided according to the judgment of the practitioner and each patient's or subject's circumstances.

Exemplary doses of the compounds or compositions of the invention include milligram or microgram amounts per kilogram of subject or sample weight (e.g., about 1 microgram per kilogram to about 500 milligrams per kilogram, about 5 micrograms per kilogram to about 100 milligrams per kilogram, or about 1 microgram per kilogram to about 50 micrograms per kilogram). In specific embodiments, a daily dose is at least 50 mg, 75 mg, 100 mg, 150 mg, 250 mg, 500 mg, 750 mg, or at least 1 g.

In one embodiment, the dosage is a concentration of 0.01 to 5000 mM, 1 to 300 mM, 10 to 100 mM and 10 mM to 1 M. In another embodiment, the dosage is a concentration of at least 5 µM, at least 10 µM, at least 50 µM, at least 100 µM, at least 500 µM, at least 1 mM, at least 5 mM, at least 10 mM, at least 50 mM, at least 100 mM, or at least 500 mM.

In one embodiment, the dosage is a concentration of 0.01 to 5000 mM, 1 to 300 mM, 10 to 100 mM and 10 mM to 1 M. In another embodiment, the dosage is a concentration of at least 5 µM, at least 10 µM, at least 50 µM, at least 100 µM, at least 500 µM, at least 1 mM, at least 5 mM, at least 10 mM, at least 50 mM, at least 100 mM, or at least 500 mM. In a specific embodiment, the dosage is 0.25 µg/kg or more, preferably 0.5 µg/kg or more, 1 µg/kg or more, 2 µg/kg or more, 3 µg/kg or more, 4 µg/kg or more, 5 µg/kg or more, 6 µg/kg or more, 7 µg/kg or more, 8 µg/kg or more, 9 µg/kg or more, or 10 µg/kg or more, 25 µg/kg or more, preferably 50 µg/kg or more, 100 µg/kg or more, 250 µg/kg or more, 500 µg/kg or more, 1 mg/kg or more, 5 mg/kg or more, 6 mg/kg or more, 7 mg/kg or more, 8 mg/kg or more, 9 mg/kg or more, or 10 mg/kg or more of a patient's body weight.

In another embodiment, the dosage is a unit dose of 5 mg, preferably 10 mg, 50 mg, 100 mg, 150 mg, 200 mg, 250 mg, 300 mg, 350 mg, 400 mg, 500 mg, 550 mg, 600 mg, 650 mg, 700 mg, 750 mg, 800 mg or more. In another embodiment, the dosage is a unit dose that ranges from about 5 mg to about 100 mg, preferably about 100 mg to about 200 μg, about 150 mg to about 300 mg, about 150 mg to about 400 mg, 250 μg to about 500 mg, about 500 mg to about 800 mg, about 500 mg to about 1000 mg, or about 5 mg to about 1000 mg.

In certain embodiments, suitable dosage ranges for oral administration are about 0.001 milligram to about 500 milligrams of a compound of the invention, or a pharmaceutically acceptable salt thereof, per kilogram body weight per day. In specific embodiments of the invention, the oral dose is about 0.01 milligram to about 100 milligrams per kilogram body weight per day, about 0.1 milligram to about 75 milligrams per kilogram body weight per day or about 0.5 milligram to 5 milligrams per kilogram body weight per day. The dosage amounts described herein refer to total amounts administered; that is, if more than one compound is administered, then, in some embodiments, the dosages correspond to the total amount administered. In a specific embodiment, oral compositions contain about 10% to about 95% a compound of the invention by weight.

Suitable dosage ranges for intravenous (i.v.) administration are about 0.01 milligram to about 100 milligrams per kilogram body weight per day, about 0.1 milligram to about 35 milligrams per kilogram body weight per day, and about 1 milligram to about 10 milligrams per kilogram body weight per day. In some embodiments, suitable dosage ranges for intranasal administration are about 0.01 pg/kg body weight per day to about 1 mg/kg body weight per day. Suppositories generally contain about 0.01 milligram to about 50 milligrams of a compound of the invention per kilogram body weight per day and comprise active ingredient in the range of about 0.5% to about 10% by weight.

Recommended dosages for intradermal, intramuscular, intraperitoneal, subcutaneous, epidural, sublingual, intracerebral, intravaginal, transdermal administration or administration by inhalation are in the range of about 0.001 milligram to about 500 milligrams per kilogram of body weight per day. Suitable doses for topical administration include doses that are in the range of about 0.001 milligram to about 50 milligrams, depending on the area of administration. Effective doses may be extrapolated from dose-response curves derived from in vitro or animal model test systems. Such animal models and systems are well known in the art.

In another embodiment, a subject is administered one or more doses of a prophylactically or therapeutically effective amount of a compound of the invention or a composition of the invention, wherein the prophylactically or therapeutically effective amount is not the same for each dose. In another embodiment, a subject is administered one or more doses of a prophylactically or therapeutically effective amount of a compound of the invention or a composition of the invention, wherein the dose of a prophylactically or therapeutically effective amount administered to said subject is increased by, e.g., 0.01 μg/kg, 0.02 μg/kg, 0.04 μg/kg, 0.05 μg/kg, 0.06 μg/kg, 0.08 μg/kg, 0.1 μg/kg, 0.2 μg/kg, 0.25 μg/kg, 0.5 μg/kg, 0.75 μg/kg, 1 μg/kg, 1.5 μg/kg, 2 μg/kg, 4 μg/kg, 5 μg/kg, 10 μg/kg, 15 μg/kg, 20 μg/kg, 25 μg/kg, 30 μg/kg, 35 μg/kg, 40 μg/kg, 45 μg/kg, or 50 μg/kg, as treatment progresses. In another embodiment, a subject is administered one or more doses of a prophylactically or therapeutically effective amount of a compound or composition of the invention, wherein the dose is decreased by, e.g., 0.01 μg/kg, 0.02 μg/kg, 0.04 μg/kg, 0.05 μg/kg, 0.06 μg/kg, 0.08 μg/kg, 0.1 μg/kg, 0.2 μg/kg, 0.25 μg/kg, 0.5 μg/kg, 0.75 μg/kg, 1 μg/kg, 1.5 μg/kg, 2 μg/kg, 4 μg/kg, 5 μg/kg, 10 μg/kg, 15 μg/kg, 20 μg/kg, 25 μg/kg, 30 μg/kg, 35 μg/kg, 40 μg/kg, 45 μg/kg, or 50 μg/kg, as treatment progresses.

In certain embodiments, a subject is administered one or more doses of an effective amount of a compound of the invention or a composition of the invention, wherein the dose of an effective amount inhibits or reduces viral protein synthesis by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85%. In other embodiments, a subject is administered one or more doses of an effective amount of a compound of the invention or a composition of the invention, wherein the dose of an effective amount inhibits or reduces viral replication by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85%.

In other embodiments, a subject is administered one or more doses of an effective amount of a compound of the invention or a composition of the invention, wherein the dose of an effective amount inhibits or reduces viral infection by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85%. In other embodiments, a subject is administered one or more doses of an effective amount of a compound of the invention or a composition of the invention, wherein the dose of an effective amount inhibits or reduces the ability of the virus to spread to other individuals by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85%. In other embodiments, a subject is administered one or more doses of an effective amount of a compound of the invention or a composition of the invention, wherein the dose of an effective amount inhibits or reduces the ability of the virus to spread to other cells, tissues or organs in the subject by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85%.

The dosages of prophylactic or therapeutic agents other than a compound of the invention or composition of the invention which have been or are currently being used for the prevention, treatment and/or management of a viral infection can be determined using references available to a clinician such as, e.g., the Physicians' Desk Reference (55th ed. 2001). Preferably, dosages lower than those which have been or are currently being used to prevent, treat and/or manage the infection are utilized in combination with one or more compounds or compositions of the invention.

The above-described administration schedules are provided for illustrative purposes only and should not be considered limiting. A person of ordinary skill in the art will readily understand that all doses are within the scope of the invention.

5.12 Kits

The invention provides a pharmaceutical pack or kit comprising one or more containers filled with a compound or composition of the invention. The kits can be used in the above-described methods. In particular, the kits can be used for the prevention, treatment, and/or management of a viral infection.

In one embodiment, a kit comprises a compound or composition of the invention, in one or more containers. In another embodiment, a kit comprises a compound or composition of the invention, in one or more containers, and one or more other prophylactic or therapeutic agents, in one or more other containers. In a particular embodiment, the kit further comprises instructions for preventing, treating, and/or managing a viral infection, as well as side effects of the compound or composition and dosage information for a particular route of administration. Optionally associated with such container(s) can be a notice in the form prescribed by a governmental agency regulating the manufacture, use or sale of pharmaceuticals or biological products, which notice reflects approval by the agency of manufacture, use or sale for human administration.

5.13 Cloning, Expression and Characterization of OTU Domain-Containing Proteins

Techniques for practicing this specific aspect of this invention will employ, unless otherwise indicated, conventional techniques of molecular biology, microbiology, and recombinant DNA manipulation and production, which are routinely practiced by one of skill in the art. See, e.g., Sambrook, 1989, Molecular Cloning, A Laboratory Manual, Second Edition; DNA Cloning, Volumes I and II (Glover, Ed. 1985); Oligonucleotide Synthesis (Gait, Ed. 1984); Nucleic Acid Hybridization (Hames & Higgins, Eds. 1984); Transcription and Translation (Hames & Higgins, Eds. 1984); Animal Cell Culture (Freshney, Ed. 1986); Immobilized Cells and Enzymes (IRL Press, 1986); Perbal, A Practical Guide to Molecular Cloning (1984); Gene Transfer Vectors for Mammalian Cells (Miller & Calos, Eds. 1987, Cold Spring Harbor Laboratory); Methods in Enzymology, Volumes 154 and 155 (Wu & Grossman, and Wu, Eds., respectively), (Mayer & Walker, Eds., 1987); Immunochemical Methods in Cell and Molecular Biology (Academic Press, London, Scopes, 1987), Expression of Proteins in Mammalian Cells Using Vaccinia Viral Vectors in Current Protocols in Molecular Biology, Volume 2 (Ausubel et al., Eds., 1991).

5.13.1 Cloning and Expression of OTU Domain-Containing Proteins

The nucleotide sequences of various viral and cellular genes encoding OTU domain-containing proteins are known in the art and these sequences can be cloned into an expression vector for making the viral OTU domain-containing protein for use in the methods of the invention. Examples of such sequences can be found, e.g., in public sequence databases such as GENBANK, the EMBL and NCBI database. The genes encoding OTU domain-containing proteins can be cloned into a suitable expression vector using techniques commonly known in the art of molecular biology. For example, oligonucleotide primers which hybridize to the coding sequence of a gene encoding an OTU domain-containing viral protein can be designed using routine skill. Such primers are then used to amplify the gene using a polymerase chain reaction. The amplified gene product is purified using routine methods and subsequently cloned into a suitable vector. The genes from various organisms can be used to produce viral OTU domain-containing protein for use in the methods of the invention.

5.13.1.1 Expression Constructs

A variety of host-vector systems may be utilized to express a viral OTU domain-containing protein. Such relevant host-vector systems include, but are not limited to, mammalian cell systems infected with virus (e.g., vaccinia virus, adenovirus, Sindbis virus, etc.); insect cell systems infected with virus (e.g., baculovirus); microorganisms such as yeast containing yeast vectors, or bacteria transformed with bacteriophage, DNA, plasmid DNA, or cosmid DNA; and stable cell lines generated by transformation using a selectable marker. The expression elements of vectors vary in their strengths and specificities. Depending on the host-vector system utilized, any one of a number of suitable transcription and translation elements may be used.

Any of the methods known in the art for the insertion of DNA fragments into a vector may be used to construct expression vectors containing a nucleic acid consisting of appropriate transcriptional/translational control signals and the protein coding sequences. These methods may include in vitro recombinant DNA and synthetic techniques and in vivo recombinants (genetic recombination). Expression of the OTU domain-containing protein may be regulated by a second nucleic acid sequence so that the OTU domain-containing protein is expressed in a host transformed with the recombinant DNA molecule. For example, expression of a gene construct may be controlled by any promoter/enhancer element known in the art, such as a constitutive promoter, a tissue-specific promoter, or an inducible promoter. Specific examples of promoters which may be used to control gene expression include, but are not limited to, the SV40 early promoter region (Bernoist & Chambon, 1981, Nature 290: 304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42); prokaryotic expression vectors such as the β-lactamase promoter (Villa-Kamaroff et al., 1978, Proc. Natl. Acad. Sci. U.S.A. 75:3727-3731), or the tac promoter (DeBoer et al., 1983, Proc. Natl. Acad. Sci. U.S.A. 80:21-25); see also "Useful proteins from recombinant bacteria" in Scientific American, 1980, 242:74-94; plant expression vectors comprising the nopaline synthetase promoter region (Herrera-Estrella et al., Nature 303:209-213) or the cauliflower mosaic virus 35S RNA promoter (Gardner et al., 1981, Nucl. Acids Res. 9:2871), and the promoter of the photosynthetic enzyme ribulose biphosphate carboxylase (Herrera-Estrella et al., 1984, Nature 310:115-120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region, which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region, which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region, which is active in testicular, breast, lymphoid and mast cells (Leder et al., 1986, Cell 45:485-495), albumin gene control region, which is active in liver (Pinkert et al., 1987, Genes and Devel. 1:268-276), alpha-fetoprotein gene control region, which is active in liver (Krumlauf et al., 1985, Mol. Cell. Biol. 5:1639-1648; Hammer et al., 1987, Science 235:53-58; alpha 1-antitrypsin gene control region, which is active in the liver (Kelsey et al., 1987, Genes and Devel. 1:161-171), beta-globin gene control region, which is active in myeloid cells (Mogram et al., 1985, Nature 315:338-340; Kollias et al., 1986, Cell 46:89-94; myelin basic protein gene control region which is active in oligodendrocyte cells in the brain (Readhead et al., 1987, Cell 48:703-712); myosin light chain-2 gene control region which is active in skeletal muscle (Sani, 1985, Nature 314:283-286), and gonadotropic releasing hormone gene control region which is active in the hypothalamus (Mason et al., 1986, Science 234:1372-1378).

In a specific embodiment, a vector is used that comprises a promoter operably linked to a nucleic acid sequence encoding an OTU domain-containing viral protein, one or more origins of replication, and, optionally, one or more selectable markers (e.g., an antibiotic resistance gene).

Expression vectors containing the construct can be identified by three general approaches: (a) nucleic acid hybridization, (b) presence or absence of "marker" nucleic acid functions, (c) expression of inserted sequences, and (d) sequencing. In the first approach, the presence of the gene inserted in an expression vector can be detected by nucleic acid hybridization using probes comprising sequences that are homologous to the inserted gene. In the second approach, the recombinant vector/host system can be identified and selected based upon the presence or absence of certain "marker" nucleic acid functions (e.g., thymidine kinase activity, resistance to antibiotics, transformation phenotype, occlusion body formation in baculovirus, etc.) caused by the insertion of the nucleic acid of interest, i.e., the OTU domain-containing protein gene construct, in the vector. For example, if the nucleic acid of interest is inserted within the marker nucleic acid sequence of the vector, recombinants containing the insert can be identified by the absence of the marker nucleic acid function. In the third approach, recombinant expression vectors can be identified by assaying the gene product expressed by the recombinant. Such assays can be based, for example, on the physical or functional properties of the particular gene.

5.13.1.2 Expression Systems and Host Cells

Mammalian host cells include but are not limited to those derived from humans, pigs, monkeys and rodents, (see, for example, Kriegler M. in "Gene Transfer and Expression: A Laboratory Manual", New York, Freeman & Co. 1990), such as monkey kidney cell line transformed by SV40 (COS-7, ATCC Accession No. CRL 1651); human embryonic kidney cell lines (293, 293-EBNA, or 293 cells subcloned for growth in suspension culture, Graham et al., J. Gen. Virol., 36:59, 1977; baby hamster kidney cells (BHK, ATCC Accession No. CCL 10); Chinese hamster ovary-cells-DEFER (CHO, Umlaut and Chasing. Proc. Natl. Acad. Sci. 77; 4216, 1980); mouse sterol cells (Mother, Biol. Report. 23:243-251, 1980); mouse fibroblast cells (NIGH-3T3), monkey kidney cells (CIV ATCC Accession No. CCL 70); African green monkey kidney cells (VERO-76, ATCC Accession No. CRL-1587); human cervical carcinoma cells (HELA, ATCC Accession No. CCL 2); canine kidney cells (MDCK, ATCC Accession No. CCL 34); buffalo rat liver cells (BRL 3A, ATCC Accession No. CRL 1442); human lung cells (W138, ATCC Accession No. CCL 75); human liver cells (Hep G2, HB 8065); and mouse mammary tumor cells (MMT 060562, ATCC Accession No. CCL51).

A number of viral-based expression systems may also be utilized with mammalian cells to produce a viral OTU domain-containing protein. Vectors using DNA virus backbones have been derived from simian virus 40 (SV40) (Hamer et al., 1979, Cell 17:725), adenovirus (Van Doren et al., 1984, Mol Cell Biol 4:1653), adeno-associated virus (McLaughlin et al., 1988, J Virol 62:1963), and bovine papillomas virus (Zinn et al., 1982, Proc Natl Acad Sci 79:4897). In cases where an adenovirus is used as an expression vector, the donor DNA sequence may be ligated to an adenovirus transcription/translation control complex, e.g., the late promoter and tripartite leader sequence. This gene may then be inserted in the adenovirus genome by in vitro or in vivo recombination. Insertion in a non-essential region of the viral genome (e.g., region E1 or E3) will result in a recombinant virus that is viable and capable of expressing heterologous products in infected hosts. (See e.g., Logan and Shenk, 1984, Proc. Natl. Acad. Sci. (USA) 81:3655-3659). In a specific embodiment, the viral vector used lacks or is deficient in deISGylation activity, and in some embodiments, deubiquitination activity, deNeddylation activity and/or deSUMOylation activity.

Other useful eukaryotic host-vector system may include yeast and insect systems. In yeast, a number of vectors containing constitutive or inducible promoters may be used with *Saccharomyces cerevisiae* (Baker's yeast), *Schizosaccharomyces pombe* (fission yeast), *Pichia pastoris*, and *Hansenula polymorpha* (methylotropic yeasts). For a review see, Current Protocols in Molecular Biology, Vol. 2, 1988, Ed. Ausubel et al., Greene Publish. Assoc. & Wiley Interscience, Ch. 13; Grant et al., 1987, Expression and Secretion Vectors for Yeast, in Methods in Enzymology, Eds. Wu & Grossman, 1987, Acad. Press, N.Y., Vol. 153, pp. 516-544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673-684; and The Molecular Biology of the Yeast *Saccharomyces*, 1982, Eds. Strathern et al., Cold Spring Harbor Press, Vols. I and II.

In an insect system, *Autographa californica* nuclear polyhidrosis virus (AcNPV) a baculovirus, can be used as a vector to express the OTU domain-containing proteins in *Spodoptera frugiperda* cells. The sequences encoding an OTU domain-containing protein may be cloned into non-essential regions (for example the polyhedrin gene) of the virus and placed under control of an AcNPV promoter (for example the polyhedrin promoter). These recombinant viruses are then used to infect host cells in which the inserted DNA is expressed. (See e.g., Smith et al., 1983, J Virol 46:584; Smith, U.S. Pat. No. 4,215,051.)

Any of the cloning and expression vectors described herein may be synthesized and assembled from known DNA sequences by well known techniques in the art. The regulatory regions and enhancer elements can be of a variety of origins, both natural and synthetic. Some vectors and host cells may be obtained commercially. Non-limiting examples of useful vectors are described in Appendix 5 of Current Protocols in Molecular Biology, 1988, ed. Ausubel et al., Greene Publish. Assoc. & Wiley Interscience, which is incorporated herein by reference; and the catalogs of commercial suppliers such as Clontech Laboratories, Stratagene Inc., and Invitrogen, Inc.

Expression constructs containing a cloned nucleotide sequence encoding a viral OTU domain-containing protein can be introduced into the host cell by a variety of techniques known in the art, including but not limited to, for prokaryotic cells, viral transformation (Hanahan, 1985, in DNA Cloning, A Practical Approach, 1:109-136), and for eukaryotic cells, calcium phosphate mediated transfection (Wigler et al., 1977, Cell 11:223-232), liposome-mediated transfection (Schaefer-Ridder et al., 1982, Science 215:166-168), electroporation (Wolff et al., 1987, Proc Natl Acad Sci 84:3344), and microinjection (Cappechi, 1980, Cell 22:479-488).

5.13.1.3 Purification of Recombinant Proteins

Generally, a recombinant viral OTU domain-containing protein can be recovered and purified from cell cultures by known methods, including ammonium sulfate precipitation, acid extraction, anion or cation exchange chromatography, phosphocellulose chromatography, immunoaffinity chromatography, hydroxyapatite chromatography, and lectin chromatography.

In certain embodiments, the expression vector is engineered so that the viral OTU domain-containing protein is produced with a molecular tag at one end in order to facilitate purification. For example, the OTU domain-containing protein produced as a fusion with an affinity tag can be purified by affinity chromatography. Examples of affinity tags include the constant regions of immunoglobulins (purified using protein A or protein G affinity), a polyhistidine tag (purified using metal chelate chromatography), glutathione-S-transferase (purified using glutathione affinity), the maltose binding protein (MBP) of E. coli (purified using an amylose resin), and peptide tags that contain an epitope for which polyclonal or monoclonal antibodies are available (purified by immunoaffinity chromatography or immunoprecipitation using the appropriate antibody).

Methods of affinity purification using these tags are well known and routinely practiced in the art. For example, Protein-A or -G sepharose (Pharmacia or Biorad) can used as the solid phase for affinity purification of an OTU domain-containing protein fused to an immunoglobulin constant region fragment ("Fc"). Bound enzyme-Fc fusion protein can be eluted by various buffer systems known in the art, including a succession of citrate, acetate and glycine-HCl buffers which gradually lowers the pH. See, for example, Langone, 1982, J. Immunol. meth. 51:3; Wilchek et al., 1982, Biochem Intl. 4:629; Sjobring et al., 1991, J. Biol. Chem. 26:399; page 617-618, in Antibodies A Laboratory Manual, edited by Harlow and Lane, Cold Spring Harbor laboratory, 1988.

The polyhistidine tag, usually a sequence of six histidines, has a high affinity for divalent metal ions, such as nickel ions (Ni2+), which can be immobilized on a solid phase, such as nitrilotriacetic acid-matrices. Polyhistidine has a well characterized affinity for Ni2+-NTA-agarose, and can be eluted with either of two mild treatments: imidazole (0.1-0.2 M) will effectively compete with the resin for binding sites; or lowering the pH just below 6.0 will protonate the histidine sidechains and disrupt the binding. The purification method comprises loading the cell culture lysate onto the Ni2+-NTA-agarose column, washing the contaminants through, and eluting the OTU domain-containing protein subunit with imidazole or weak acid. Ni2+-NTA-agarose can be obtained from commercial suppliers such as Sigma (St. Louis) and Qiagen. Antibodies that recognize the polyhistidine tag are also available which can be used to detect and quantitate the OTU domain-containing protein.

A viral OTU domain-containing protein-GST fusion protein expressed in a prokaryotic host cell, such as E. coli, can be purified from the cell culture lysate by absorption with glutathione agarose beads, followed by elution in the presence of free reduced glutathione at neutral pH.

A peptidyl hydrolase enzyme fused to MBP binds to amylose resin while contaminants are washed away. The bound enzyme-MBP fusion is then eluted from the amylose resin by maltose. See, for example, Guan et al., 1987, Gene 67:21-30.

Examples of techniques for immunoaffinity purifications can be found, for example, in Chapter 13 of Antibodies A Laboratory Manual, edited by Harlow and Lane, Cold Spring Harbor laboratory, 1988; and Chapter 8, Sections I and II, in Current Protocols in Immunology, ed. by Coligan et al., John Wiley, 1991; the disclosure of which are both incorporated by reference herein.

In a specific embodiment, the OTU domain-containing protein is purified by chromatography over a metal affinity resin (Ni-NTA Superflow, Qiagen), followed by ion exchange chromatography. Preferably, the OTU domain-containing protein enzyme is greater than 95% pure and free of contaminating RNases. In certain embodiments, the OTU domain-containing protein enzyme is at least 80% pure, at least 85% pure, at least 90% pure, or at least 95% pure.

5.14 Viral OTU Domain-Containing Protein Compositions

In one aspect, the invention provides a composition comprising a viral OTU domain-containing protein, and an excipient, carrier or vehicle. Such compositions may be used in the assays described herein. For example, such compositions may be used in the assays described in Section 5.4.

6. EXAMPLE 1

Novel DeISGylation Activity of the CCHFV L Protein and Other Viral Proteases

This example demonstrates the deconjugating activity of viral OTU domain-containing proteins towards both ISG15 and ubiquitin (Ub) conjugates. This example also demonstrates the requirement for a cysteine at position 40 for the ISG15 and ubiquitin deconjugating activity of CCHFV L.

6.1 Materials and Methods

6.1.1 Cell Culture, Virus and Antibodies

The cells used in this study (293T, HeLa, BHK-21 and UBP43−/− MEF) were maintained in DMEM culture medium (Gibco, San Diego, Calif., USA) supplemented with 10% fetal calf serum (Hyclone, South Logan, Utah, USA), 100 U/ml of penicillin G sodium and 100 µg/ml of streptomycin sulfate (Gibco). Cells were maintained in a humidified 5% $CO_2$ atmosphere at 37° C.

CCHFV prototype strain IbAr10200, first isolated in 1976 from Hyalomma excavatum ticks from Nigeria, was grown in SW 13 cells and viral RNA was isolated from cells supernatants using Trizol (Gibco) following manufacturer's protocol.

Monoclonal antibodies to the FLAG (clone M2) and HA (clone HA.7) epitopes were purchased from Sigma (St. Louis, Mo., USA). Anti-HA antibody (clone HA.11) was purchased from Covance Research (Berkeley, Calif., USA) Ubiquitin (P4D1) mouse monoclonal antibody was obtained from Cell Signaling (Danvers, Mass., USA). Anti-mouse ISG15 monoclonal (3C2 and 2D12) and polyclonal antibodies have previously been described (Lenschow et al., 2005). Polyclonal antibody against Sindbis virus was provided by Dianne Griffin (Johns Hopkins University, Baltimore, Md.) (Levine et al., 1996). Anti-serum recognizing EAV nsp2 was previously described (Snijder et al., 1994).

6.1.2 Plasmid Construction and Mutagenesis

Viral Protein Expression Plasmids.

The pCAGGS vector for the expression of transcripts under control of chicken β-actin promoter has been described previously (Niwa et al., 1991). The cDNA for the full-length L-CCHFV gene was obtained by reverse transcription with specific oligonucleotides from RNA obtained from CCHFV-infected SW-13 cells. The HA-tagged L-CCHFV plasmid (HA-L-HA) was generated by multiple steps. First, the 5' and 3' ends of the L cDNA were introduced by trimolecular ligation between the NotI and BglII sites of the pCAGGS-MCSII vector. An N-terminal and C-terminal HA were introduced into the construct by PCR with 5' and 3' gene-specific primers possessing the tag sequences (pCAGGS #12). In parallel, the complete L cDNA was being assembled in the pGEMT vector (Promega, Madison, Wis., United States). A total of eight fragments, not longer that 2.3 kb, were obtained by RT-PCR, ligated into pGEMT vector and sequenced. These small fragments of the L gene were ligated one after the other until the full length clone was obtained. Once L cDNA was assembled in the pGEMT vector, it was transferred to the pCAGGS #12 vector using the DraIII restriction site. The deletion mutants of CCHFV were all constructed in the pCAGGS-MCSII background. The HA-L(1-1300) cDNA was introduced into the NotI and BglII sites of the vector. The L(1300-2600) HA cDNA was introduced into the pCAGGS-MCSII using the NotI and NheI restriction sites. The L(2600-3900), the HA-L (1-169) and the HA-L(1-354) cDNAs were cloned between the NotI and XhoI sites of the same vector. The N-terminal or C-terminal HA tag was introduced into each construct by PCR with gene-specific primers possessing the tag sequences.

The L(1-169) cDNA was cloned into the pGEX6P-1 vector (Amersham, Little Chalfont, United Kingdom) for bacterial expression of the GST fusion protein.

To generate catalytically inactive variants of L(1-169) a single mutation of the Cys40 to Ala or a double mutation Cys40 and His151 to Ala were generated in the pGEX-GST-L(1-169) or pCAGGS-HA-L(1-169) plasmids, respectively. In all cases, the mutagenesis was carried on using the QuikChange XL Site-Directed Mutagenesis Kit (Stratagene, La Jolla, Calif., USA). Sequences of each constructed plasmid were confirmed by automated sequencing performed at the Mount Sinai sequencing core facility.

The plasmid pcDNA 3.1+ (HA-Ub) was kindly provided by Dr. Tortorella (Mount Sinai School of Medicine, NY, USA). Plasmids pCAGGS.MCS-6HismISG15 pCAGGS-hUBE1L-HA, pFLAGCMV2-UbcM8 and pcDNA3.1 UbcM8 were kindly provided by Dong-Er Zhang (Scripps Research Institute, La Jolla, Calif., USA).

The plasmid encoding the nsp2 of PRRSV was generated by subcloning into the NotI and NheI restriction sites of the pCAGGS-MCSII vector. An N-terminal HA epitope tag was introduced by PCR. EAV nsp2N was synthesized by Top Gene Technologies (Montreal, QC, Canada) and subcloned into pFLAGCMV2. EAV nsp2 was expressed from pcDNA3-nsp2/3-GFP, which was kindly provided by Dr. Eric Snijder (Leiden University Medical Center, The Netherlands).

Mammalian Protein Expression Plasmids

Plasmids pCAGGS.MCS-6HismISG15, pCAGGS-hUbe1L-HA, pFLAGCMV2-UbcM8 and pcDNA3.1-UbcM8 were kindly provided by Dong-Er Zhang (Scripps Research Institute, La Jolla, Calif., USA) (Giannakopoulos et al., 2005). Plasmid encoding Herc5 was provided by Motoaki Ohtsubo (Kurume University, Fukuoka-ken, Japan). Mouse Ube1L (mUbe1L) and mUBP43 were PCR-amplified from an IFNβ-induced bone marrow macrophage cDNA library (Kim et al., 2004). mUbe1L was subcloned between the EcoRI and XhoI sites of the pCAGGS.MCS vector. An N-terminal HA epitope tag was introduced by PCR. UBP43 was subcloned into the HindIII and EcoRI sites of pFLAGCMV2. The plasmid pcDNA 3.1+ (HA-Ub) was generously provided by Dr. Tortorella (Mount Sinai School of Medicine, NY, USA) (Treier et al., 1994).

Expression constructs encoding eukaryotic OTU domain-containing proteins were generated by subcloning indicated sequences into pFLAGCMV2 vector (restriction sites are in parenthesis): nucleotides 1-816 of mouse otubain 1 (HindIII/KpnI), 1-705 of mouse otubain 2 (HindIII/KpnI) and 1-2532 of human cezanne. peak10-FLAG-A20 plasmid was kindly provided by Dr. Ting (Mount Sinai School of Medicine).

Expression constructs encoding eukaryotic OTU domains were generated by subcloning indicated sequences into pFLAGCMV2 (restriction sites are in parenthesis): nucleotides 238-816 of mouse otubain 1 (HindIII/KpnI), 118-690 of mouse otubain 2 (HindIII/KpnI), 1-2261 of valosin containing protein (p97)/p47 complex interacting protein 1 (VCIP) (NotI/EcoRI), 271-840 of mouse A20 (HindIII/EcoRI), 541-1140 of mouse cezanne (NotI/KpnI) and 541-1140 of human cezanne (NotI/XbaI).

Recombinant Sindbis Virus Plasmids

To generate recombinant Sindbis viruses 169 and MT, CCHFV-L(1-169) and L(1-169)2A were amplified by PCR and subcloned into the BstEII restriction site of the dstE12Q vector. The N-terminal HA epitope tag present in the original constructs was maintained. The 169GG and MTGG constructs, expressing ISG15 and FLAG-tagged L(1-169) or L(1-169)2A cDNAs were cloned into the BstEII restriction site of the dstE12Q vector by multiple steps.

Sequences of each generated construct were confirmed by automated sequencing performed at the Mount Sinai sequencing core facility and Massachusetts General Hospital DNA Sequencing Core Facility.

6.1.3 Immunofluorescence and Immunoprecipitation

For the immunofluorescence experiment, HeLa cells grown on coverslips were transfected in 24-well dishes with 2 μg of HA-L-HA plasmid using Lipofectamine™ 2000 (Invitrogen, Carlsbad, USA) according to the manufacturer's instructions. After 48 h, the cells were fixed with methanol-acetone (1:1 ratio), permeabilized with 0.5% NP-40 and blocked with 1×PBG (0.5% BSA, 0.2% Fish gel in 1×PBS). Cells were probed with primary anti-HA antibody for 2 h at room temperature, washed, and labeled with secondary antibody anti-mouse FITC (DakoCytomation, Glostrup, Denmark). The tagged CCHFV-L protein was visualized by laser scanning confocal microscopy at the Mount Sinai Microscopy Shared Resource Facility.

For the immunoprecipitation experiment to test CCHFV-L expression, 293T cells in 10-cm dishes were transfected with 2 μg of HA-tagged CCHFV-L plasmids using Lipofectamine™ 2000. Cells were collected 48 h post-transfection and lysed in lysis buffer (1% NP-40, 150 mM NaCl, 50 mM Tris-HCl pH 7.4, 1 mM EDTA, 0.25% Na-Deoxycholate and protease inhibitor cocktail). Proteins were incubated at 4° C. overnight with 1 μg of the HA antibody, and protein complexes were precipitated with protein G agarose beads for 2 h. Beads were washed five times in lysis buffer and resuspended in protein sample buffer. Proteins were subsequently separated by 4-20% SDS-PAGE and detected by Western blot using anti-HA antibody.

To generate 293T lysates enriched in ISGylated proteins a total of fourteen 10-cm dishes were transfected with 6 μg of pCAGGS.MCS-6HismISG15 along with 3 μg of pCAGGS-hUbe1L-HA and 3 μg of pFLAGCMV2-UbcM8 plasmids. 24 h later, the cells were harvested, lysed by freezing and thawing three times in 20 mM Tris-HCl pH 8.0 containing 300 mM NaCl and centrifuged for 15 min at 14000 rpm. The His-tagged ISG15 conjugates were purified through a His-Select Spin Column (SIGMA), following manufacturer's indications. The column bound conjugates were washed extensively with washing buffer (20 mM Tris-HCl, pH 8.0, 300 mM NaCl and 5 mM imidazole) and then eluted with elution buffer (20 mM Tris-HCl, pH 8.0, 300 mM NaCl and 250 mM imidazole). Total protein concentration was measured by Bradford assay (Bio-Rad).

6.1.4 Purification of CCHFV L(1-169) from *E. coli*

Competent BL-21 cells (Stratagene, La Jolla, Calif., USA) transformed with pGEX-L(1-169) or pGEX-L(1-169)1A CCHFV vectors were cultured to an $OD_{600}$ of 0.6 in 2×YT medium. The cells were induced for 6 h at 30° C. with 1 mM isopropyl-1-thio-β-D-galactopyranoside (IPTG) and collected in lysis buffer (50 mM Tris-HCl, 5 mM EDTA, 1 mM DTT, 200 mM NaCl and 0.1% NP-40). Purification of the GST fusion proteins was performed using the GSH Sepharose resin (Amersham) according to the manufacturer's protocol. Purified protein was then cleaved from GST with PreScission™ Protease (Pharmacia, Uppsala, Sweden) in cleavage buffer (50 mM Tris-HCl pH 7.6, 150 mM NaCl, 1 mM EDTA and 1 mM DTT). The protein was aliquoted and stored at −80° C.

6.1.5 Assays for DeISGylation in Cultured Cells

Initial experiments were performed in 293T cells cultured in 12-well dishes and co-transfected with 0.4 µg of pCAGGS.MCS-6HismISG15, 0.4 µg of pCAGGS-hUbe1L-HA, and 0.2 µg of pFLAGCMV2-UbcM8 along with various OTU domain expression plasmids or empty pCAGGS plasmid using Lipofectamine™ 2000. For experiments testing eukaryotic and viral OTU constructs, 293T cells in 12-well dishes were co-transfected with OTU domain expression plasmids and 0.5 µg pCAGGS.MCS-6His mISG15, 0.5 µg pCAGGS.MCS mUbe1L HA, 0.5 µg of plasmid encoding Herc5 and 0.2 µg pFLAGCMV2 UbcM8 or pCDNA3.1 UbcM8. 24 h post-transfection, the cells were lysed in Laemmli sample buffer and boiled for 10 min before Western blot analysis. Total amounts of ISGylated proteins were visualized by using anti-ISG15 mAb 3C2 as previously described (Lenschow et al., 2005). Each transfection experiment was performed a minimum of three times.

6.1.6 Assay for Deubiquitination in Cultured Cells 293T cells cultured in either 12 dishes were co-transfected with 0.5 µg of pcDNA3.1-HA-ubiquitin and various OTU domain expression plasmids or empty pCAGGS plasmid using Lipofectamine™ 2000, following the manufacturer's recommendations. 24 hours post transfection, the cells were harvested and lysed in Laemmli sample and boiled for 10 min. Total amounts of ubiquitinated proteins were visualized by Western blot using anti-HA antibody. Each transfection experiment was performed a minimum of three times.

6.1.7 In Vitro Isopeptidase Assays

Hydrolysis of Ub Chains.

2.5 µg of either poly-ubiquitin chains Ub2-7, K48-linked or Ub2-7, K63-linked were incubated in reaction buffer (50 mM Tris-HCl pH 7.6, 5 mM $MgCl_2$ and 2 mM DTT) with 1000 to 1 ng of the L(1-169) or L(1-169)1A recombinant protein at 37° C. for 2 hr. The USP5 (IsoT) commercially available protein was used as positive control for the assay. The reactions were terminated by addition of Laemmli sample buffer and separated by 4-20% SDS-PAGE (BioRad). Proteins were visualized by Coomassie staining.

Hydrolysis of SUMO Chains.

2.5 µg of either poly-SUMO-2 chains$_{(2-8)}$ or poly-SUMO-3 chains$_{(2-8)}$ were incubated in reaction buffer (50 mM Tris-HCl pH 7.6, 5 mM $MgCl_2$ and 2 mM DTT) with 1000 to 1 ng of the L(1-169) or L(1-169)1A recombinant protein at 37° C. for 2 hr. His6-SENP2$_{CD}$ recombinant protein was used as positive control for the assay. The reactions were terminated by addition of Laemmli sample buffer and separated by 4-20% SDS-PAGE (BioRad). Proteins were visualized by Coomassie staining.

The Ub and SUMO chains and their specific recombinant isopeptidases were purchased from Boston Biochem (Cambridge, Mass., USA).

Hydrolysis of ISG15 Conjugates.

Cell extracts of IFNβ-treated UBP43$^{-/-}$ MEFs or 3 µg of ISG15 and ISG15-conjugates enriched fraction from 293T transfected cells was incubated with serial 10-fold dilutions of the recombinant L(1-169) or L(1-169)1A proteins under the same experimental conditions as described for Ub and SUMO hydrolysis assays. Total amounts of ISG15 conjugates were evaluated by Western blot using anti-ISG15 mAb 3C2.

6.1.8 Sindbis Virus Studies

Double sub-genomic Sindbis virus dsTE12Q and their derivatives were generated from a cDNA clone by in vitro transcription and RNA transfection of BHK-21 cells as previously described (Hardwick and Levine, 2000), (Lenschow et al., 2005). Recombinant virus stocks were produced and titered on BHK-21 cells as previously described (Lenschow et al., 2005). Single-step growth curves were performed in BHK-21 cells at MOI of 5 as described (Heise et al., 2000).

6.1.9 Mouse Studies

IFNαβR1$^{-/-}$ mice on the 129/SV/Pas background were initially obtained from M. Aguet, Swiss Institute of Experimental Cancer Research (Epalinges, Switzerland) (Muller et al., 1994), (Dunn et al., 2005). 8 to 10-week-old male IFNαβR1$^{-/-}$ mice were infected subcutaneously (s.c.) in the left hind footpad with 5×10$^6$ PFU of virus diluted in 50 µl of Hank's balanced salt solution (HBSS). Mice were bred and maintained at Washington University School of Medicine in accordance with all federal and university guidelines.

6.1.10 Sequence Analysis

Database searches and sequence comparisons were performed using the National Center for Biotechnology Information (NCBI) BLAST search programs. Web-based bioinformatics programs, such a Match-Box (Depiereux et al., 1997) and Multalin were also utilized in the analysis of conserved regions and other primary structure analysis.

6.1.11 Statistical Analysis

All data were analyzed with Prism software (GraphPad, San Diego, Calif.). Survival data were analyzed by the Mantel-Haenzsel test, with death as the primary variable. Single-step growth curves were analyzed by one way analysis of variance 6.2 Results 6.2.1 The L Protein of CCHFV is a 450 kDa Protein With Cytoplasmic Localization To obtain the full sequence of the L segment of CCHFV, primers for initial RT-PCR amplifications were designed based on the Dugbe virus (DUGV) L segment nucleotide sequence. Alignment of DUGV and CCHFV M and S segments established an overall identity of 86 and 83%, respectively, and showed that the nucleotides at the termini of the segments are highly conserved between the two viruses. In addition to this, two domains with high identity with other proteins were found in the DUGV-L segment sequence: the conserved RNA dependent RNA polymerase motif and an OTU-like cysteine protease domain (NCBI Conserved Domain Search). Degenerate primers to reverse transcribe and amplify regions of the CCHFV L segment were designed based on these two conserved regions of the DUGV-L segment, along with primers based on the 5' and 3' conserved terminal nucleotides. These primers were used to reverse transcribe viral RNA extracted from supernatants of SW-13 cells infected with CCHFV, strain IbAr10200. Amplicons were sequenced and permitted the subsequent design of specific primers for the CCHFV-L gene. Successive reactions of reverse transcription and amplification ("primer walking" strategy) in conjunction with the rapid amplification of cDNA ends (RACE) method for sequencing the untranslated regions (UTR) allowed the complete sequence of the L segment of CCHFV to be obtained. The L segment contains 12,160 nucleotides, with a 76 and 246-nucleotide long 3' and 5' UTR, respectively. A single open reading frame (ORF) was identified, encoding a 3,945 amino acid protein. This sequence is 99% identical at the nucleotide level to a consensus sequence obtained from the four complete CCHFV-L IbAr10200 sequences deposited in NCBI (Altschul et al., 1997). At the amino acid level, only two differences were found between this L sequence (CCHFV-L USAMRIID (SEQ ID NO:3)) and the consensus sequence (SEQ ID NO:4) of all available sequences for the same strain.

TABLE 3

| | Encoded Amino acid position in L protein | | | | | | |
|---|---|---|---|---|---|---|---|
| Accession number | 1047 | 1467 | 1660 | 1675 | 2675 | 2678 | 3230 |
| Acc # AAQ98866 | E | N | T | N | A | T | V |
| Acc # AY389508 | E | N | T | N | V | A | V |
| Acc # AY389361 | G | N | P | T | V | A | V |
| Acc # AAY24690 | E | N | T | N | V | A | I |
| CCHFV-L USAMRIID | E | S | T | N | V | A | I |
| *Consensus* | *E* | *N* | *T* | *N* | *V* | *A* | *V* |

Table 3 depicts the amino acid variation observed between published sequences of IbAr10200 CCHFV-L protein. In italics, the consensus sequence made from the available complete L sequences, including the one obtained in this study (CCHFV-L USAMRIID). In bold, the residues from the CCHFV-L USAMRIID sequence differing from the consensus.

As in DUGV-L, the CCHFV-L protein contains the core polymerase motif characteristic of the RdRp of segmented negative-stranded viruses, and an OTU-like protease motif in the amino terminal portion (FIG. 1A).

Figure 1B:
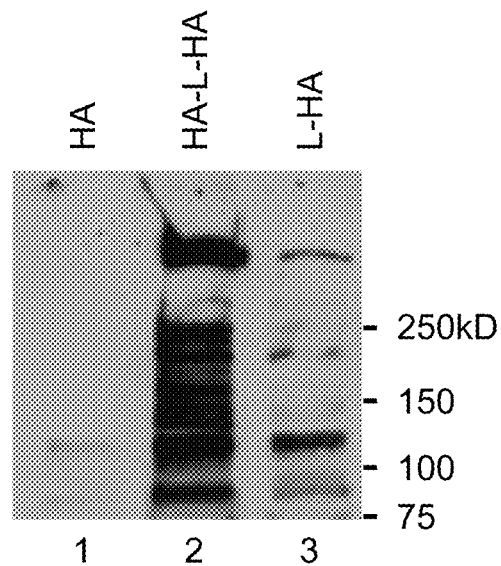
Figure 1C:
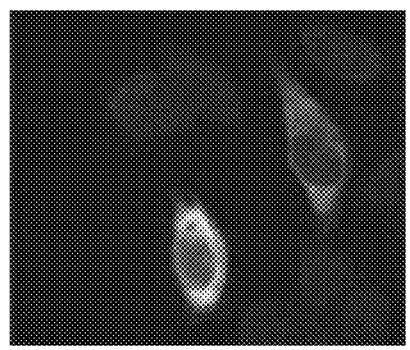

The L cDNA was cloned from viral RNA into HA-tagged mammalian expression vectors. Two approaches were used to test expression of the full length L protein in tissue culture: (i) transfection of 293T cells followed by immunoprecipitation and Western blot using anti-HA antibodies and (ii) transfection of Vero and HeLa cells followed by indirect immunofluorescence and confocal microscopy. The first approach showed the expression of a protein with an approximate molecular weight of 450 kDa, as expected from the primary sequence analysis (FIGS. 1B and 1C). Immunofluorescence analyses revealed that the L protein has cytoplasmic localization in HeLa (FIG. 1C) and Vero (data not shown) cells. This is the first full length L protein of a nairovirus reported to be expressed from transfected plasmids.

Figure 2B:
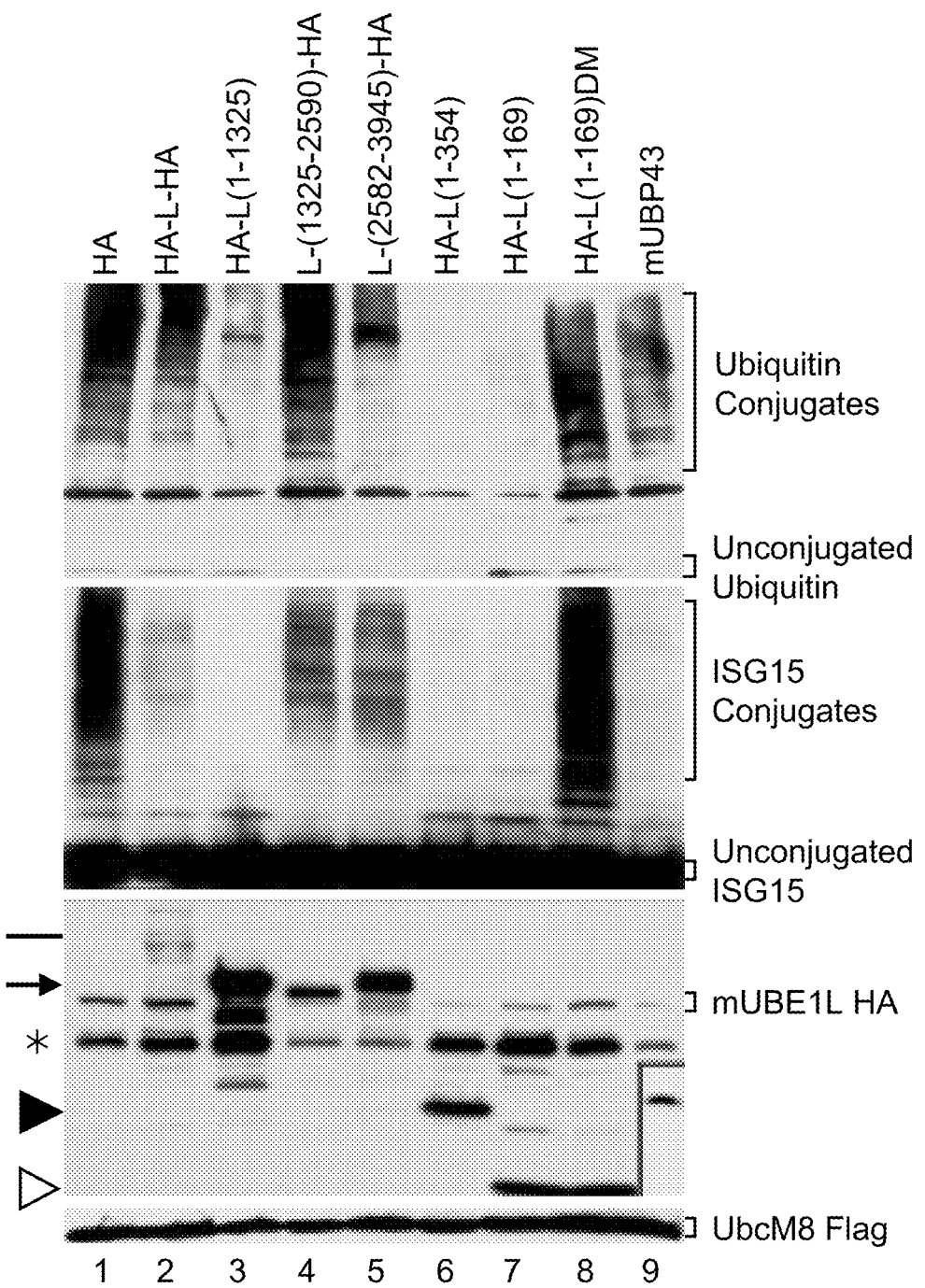

6.2.2 Analysis of Protein ISGylation and Ubiquitination in Full Length CCHFV-L Transfected Cells Transfection experiments were designed to determine the ability of CCHFV-L to inhibit the buildup of cellular ubiquitinated proteins. In these assays, L expression plasmid (HA-L-HA) or empty (HA) plasmid was co-transfected into 293T cells, along with an HA-Ub plasmid. Total levels of ubiquitinated proteins were detected by Western blotting against HA (FIG. 2B, upper panel). In this experiment, no differences in the total level of cellular protein ubiquitination were detected between empty plasmid and full length CCHFV-L transfected lysates (FIG. 2B, compare lane 2 to 1, upper panel).

The effect of the full length L protein on ISGylation was then tested. Since endogenous levels of ISGylation are not easy to detect, 293T cells were co-transfected with CCHFV-L expression plasmid (HA-L-HA) or empty plasmid (HA) along with expression plasmids for ISG15, UBE1L and UbcM8. Total levels of ISGylated proteins were tested by Western blotting with an anti-ISG15 antibody (FIG. 2B, middle panel). Cell lysates expressing the CCHFV-L protein showed a clear decrease in the total level of ISG15-conjugated proteins as compared to cell lysates transfected with an empty plasmid (FIG. 2B, compare lane 2 to 1, middle panel). The decrease in total ISGylation was comparable to the effect of UBP43 (lane 9). Expression of CCHFV-L did not affect levels of expression of UBE1L or UbcM8 (FIG. 2B, lane 2, lower panel). The same inhibition of total ISGylation was observed when the carboxy-terminus HA tagged L plasmid (L-HA) was tested in this assay (data not shown). These data suggest that the full length CCHFV-L has the ability to either inhibit the ISG15 conjugation or to de-conjugate ISGylated proteins.

6.2.3 ISGylation Inhibition by CCHFV-L Maps to the OTU Domain

In order to determine the region of the L protein responsible for the deISGylation activity, different deletion mutants of the L protein were constructed (FIG. 2A). In this assay, only the amino terminal portion, HA-L(1-1325), showed inhibition of total protein ISGylation (FIG. 2B, lane 3, middle panel). The region of CCHFV-L that showed deISGylation activity contained the putative OTU domain. To further map the deISGylation activity to the OTU domain, additional deletion mutants of the L protein expressing only the first 354 or 169 amino acids (referred as L(1-354) or L(1-169), respectively) were generated. Both truncation mutants, the latter expressing the core sequence of the OTU domain, were next tested in transfection-based experiments and inhibited the accumulation of ISGylated proteins (FIG. 2B, lanes 6 and 7, middle panel). In contrast to full length CCHFV-L, the deletion mutants L(1-354) and L(1-169) also inhibited the accumulation of ubiquitinated proteins (FIG. 2B, lanes 3, 6 and 7, upper panel). As longer CCHFV-L constructs were expressed, there was less of a decrease in the levels of ubiquitin conjugates (FIG. 2B, compare lanes 7 to 3 and 2, upper panel). These results indicate that the CCHFV-L OTU domain has the ability to inhibit the buildup of ISGylated and ubiquitinated proteins in transfected cells and the latter activity seems to be reduced when this domain is in the context of the full length L protein.

6.2.4 The Core OTU Domain of CCHFV-L Hydrolyzes ISG15 Conjugates In Vitro

Figure 3A:
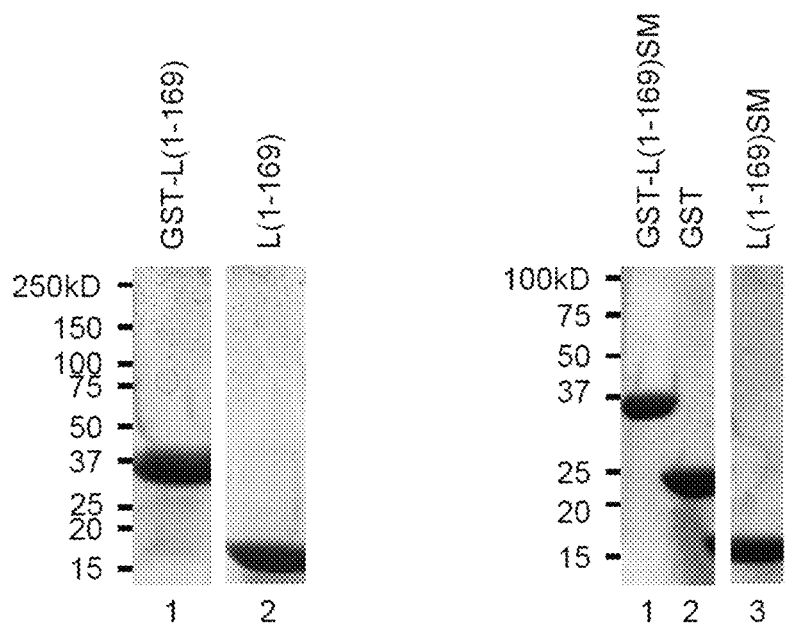
Figure 3B:
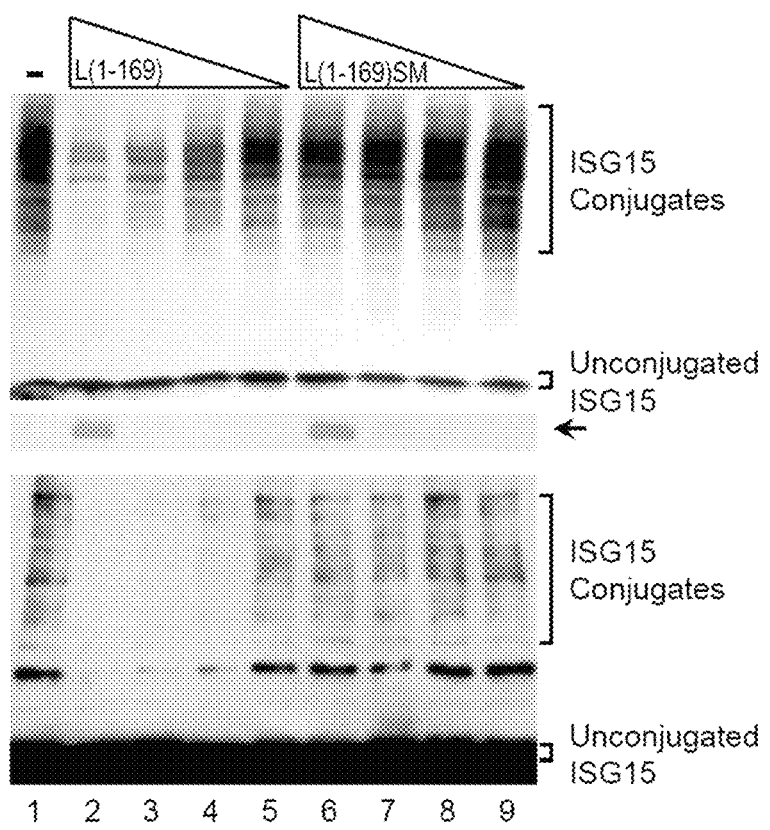

To further characterize the activity of the core OTU domain, the L(1-169) deletion mutant was subcloned into a bacteria expression plasmid and purified from E. coli (FIG. 3A). The L(1-169) recombinant protein was tested for its ability to deconjugate ISGylated proteins. As a source of ISGylated proteins, cell lysates from IFNβ-treated murine embryonic fibroblasts (MEFs) derived from Ubp43−/− mice (Malakhov et al., 2003) were prepared. Ubp43−/− cells show an accumulation of ISGylated proteins, which can be further increased by IFN treatment. Incubation of ISG15 conjugates with recombinant L(1-169) protein led to a significant decrease of ISGylated protein as detected by anti-ISG15 Western blot (FIG. 3B, lanes 2 to 5, upper panel). The decrease in ISG15 conjugates is proportional to the amount of L(1-169) added to the reaction. This result suggests that the core OTU domain is able to deconjugate cellular ISG15 conjugates.

To further determine if the deconjugating activity of the L(1-169) protein was associated directly with the OTU domain and not due to activation of a cellular deconjugating activity, His-tagged ISG15, UBE1L and UbcM8 were overexpressed in 293T cells and the ISG15 conjugates were enriched using Ni-NTA affinity columns. Enriched ISG15 conjugates were next incubated with increasing amounts of L(1-169) recombinant protein and the total level of ISGylated proteins was detected by Western blot. As observed in FIG. 3B, L(1-169) was able to deconjugate ISGylated proteins (FIG. 3B, lanes 2 to 5, lower panel). This experiment confirms that the recombinant OTU domain can deconjugate ISGylated proteins in a concentration dependent manner and suggests that no other cellular proteins are involved in the observed deISGylation.

6.2.5 CCHFV-L Core OTU Domain Cleaves Polyubiquitin Chains but has no Effect on SUMO Chains To prove that the CCHFV-L OTU domain is a deconjugating enzyme, the ability of the L(1-169) recombinant protein to cleave commercially available polyubiquitin chains was tested. In vitro hydrolysis experiments demonstrated that bacteria-purified L(1-169) protein cleaved both K48 and K63-linked ubiquitin chains into monomers (FIG. 4A, lanes 2 to 5), similar to the activity seen with a known deubiquitinating enzyme, Isopeptidase-T (FIG. 4A, lane 10). These results confirm that the core OTU domain has proteolytic activity in the absence of any other cellular partner and it can function as a deconjugating enzyme.

Figure 4B:
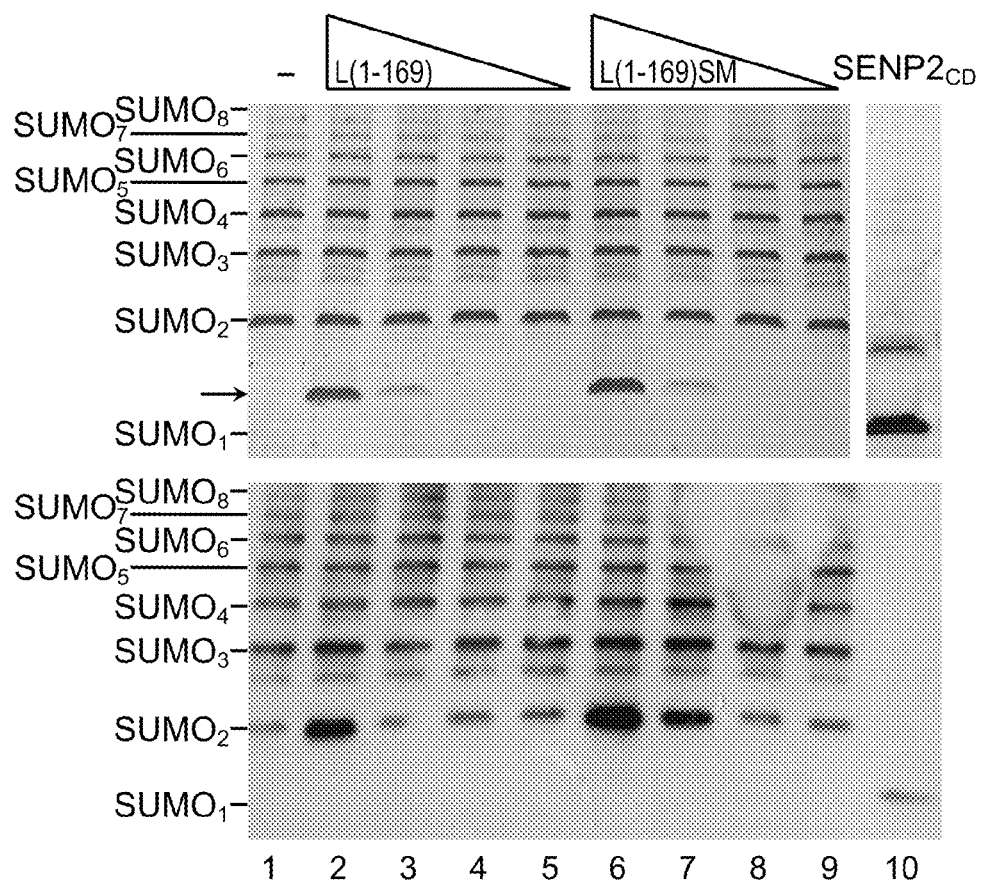

To gain further insight into the specificity of the OTU domain, the ability of L(1-169) to deconjugate SUMO chains in vitro was assessed. Poly-SUMO-2 chains$_{(2-8)}$ were incubated with the recombinant L (1-169) and hydrolysis was analyzed by SDS-PAGE and Coomassie staining (FIG. 4B, upper panel). As positive control, the catalytic domain of SENP2, a SUMO-specific protease (SENP2$_{CD}$), was used. In this in vitro assay, the core OTU domain was not able to hydrolyze the branched poly-SUMO-2 chains while SENP2 reduced the chains to monomers. An identical result was obtained when poly-SUMO-3$_{(2-8)}$ chains were tested and analyzed by Western blotting using an anti-SUMO-3 antibody (FIG. 4B, lower panel). These results indicate that the core OTU domain shows deconjugating activity towards ubiquitin in vitro and it is not able to hydrolyze SUMO isopeptide bonds.

6.2.6 Point Mutation in Cys40 Abolishes the Catalytic Activity of the CCHFV-L OTU Domain Bioinformatics approaches used to analyze the primary sequence of the CCHFV-L protein predicted that the Cys at position 40 and the His at position 151 might be involved in the catalytic activity of the OTU domain (FIGS. 1A, 5 and 9). To test that these amino acids constitute the catalytic residues, either single mutants (SM) or double mutants (DM) of the CCHFV-L OTU domain were constructed by changing Cys40 and His151 to Ala (FIG. 2A). As shown in FIG. 2B, the double mutant L(1-169)DM completely lost the Ub and ISG15 deconjugating activity in transfection based assays (FIG. 2B lane 8, upper and middle panels). The recombinant L(1-169)SM protein purified from E. coli only contains the Cys40Ala mutation and was tested in in vitro experiments. This single point mutation was sufficient to abolish the hydrolyzing activity of the bacteria-purified core OTU domain in in vitro deISGylation (FIG. 3B, lanes 6 to 9) and deubiquitination (FIG. 4A, lanes 6 to 9) experiments, suggesting that the sole replacement of the Cys to Ala resulted in a catalytically impaired protein. These experiments demonstrate the role of the residue Cys40 as an essential amino acid for the deconjugating activity of the CCHFV-L protein towards ISG15 and Ub conjugates.

6.2.7 Additional Viral OTU Domains can Mediate Deubiquitination and DeISGylation As the ability to deconjugate proteins in a virally-infected cell may represent a novel immune evasion strategy, other viral OTU domains were tested to determine if they possess this enzymatic activity. Representative examples of viral and cellular proteins containing an OTU domain are shown in FIGS. 5 and 9 (and Table 2, infra). The OTU domain from DUGV, a related nairovirus, also deubiquitinated and deISGylated conjugates in 293T cells (FIG. 6, lane 3). The deconjugating activity of OTU domain-containing proteins found in the arteriviruses EAV and PRRSV was also tested. During infection, PRRSV and EAV express a polypeptide that is processed into non-structural proteins (nsp). Nsp2 from both PRRSV and EAV contains an N-terminal OTU domain; in EAV, nsp2 can further be processed in certain cell types into N- (nsp2N) and C-terminal (nsp2C) fragments (Snijder et al., 2001). PRRSV nsp2, EAV nsp2 and nsp2N were each able to cleave ISG15 and ubiquitin conjugates (FIG. 6, lanes 4-6), indicating that deconjugation may be an immune strategy shared by different viral families.

6.2.8 Expression of CCHFV OTU Domain Inhibits ISG15-Mediated Protection From Sindbis Virus-Induced Lethality In vivo anti-viral function of ISG15 is dependent on the presence of a C-terminal LRLRGG (SEQ ID NO:1) motif (Lenschow et al., 2005; Lenschow et al., 2007). Mutation of LRLRGG (SEQ ID NO:1) to LRLRAA abolishes both protein ISGylation and ISG15-mediated protection from Sindbis-induced lethality. As ISGylation is critical for the anti-viral function of ISG15, the ability of viral OTU domain-containing proteins to antagonize the anti-viral activity of ISG15 by cleaving ISG15 conjugates that are generated during a cell's innate immune response to viral infection was assessed. The CCHFV-L OTU domain was expressed from a double subgenomic Sindbis virus, dsTE12Q. As expression of ISG15 from dsTE12Q can protect adult Ifnar$^{-/-}$ mice from Sindbis virus induced lethality (Lenschow et al., 2005) it was predicted that expression of CCHFV-L(1-169) would abrogate the anti-viral action of ISG15, while expression of the catalytically inactive mutant L(1-169)2A would have no effect on mouse survival.

Figure 7A:
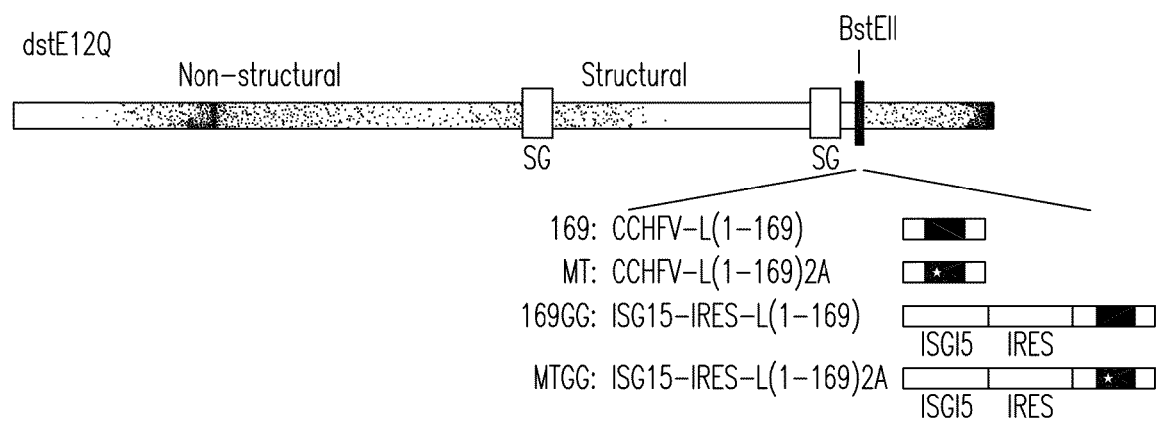
Figure 7B:
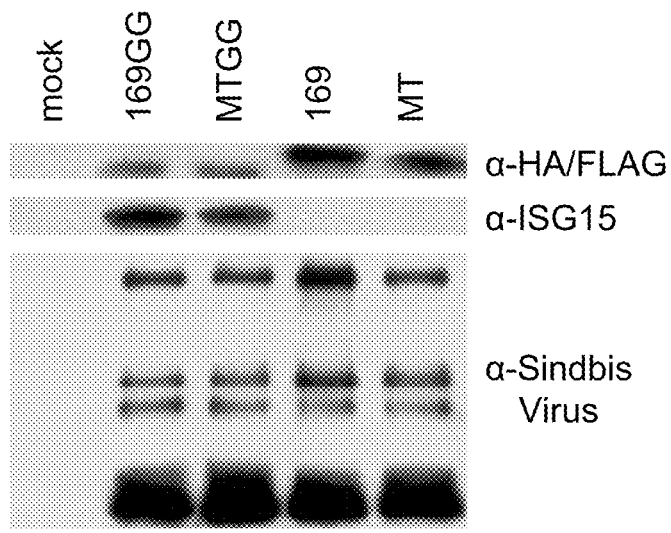
Figure 7C:
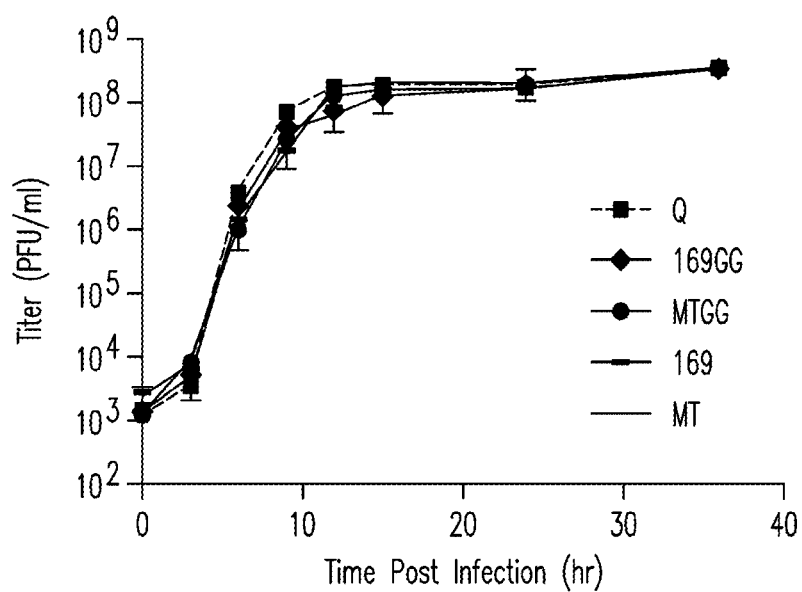

Four recombinant Sindbis viruses were generated (FIG. 7A). Two of the viruses both expressed ISG15 and contained an IRES element, which drives translation of either L(1-169) (169GG) or L(1-169)2A (MTGG). To demonstrate that L(1-169) expression did not increase the virulence of dsTE12Q, control viruses that expressed either L(1-169) (169) or L(1-169)2A (MT) were generated. The viruses expressed the tagged OTU domain and ISG15 appropriately (FIG. 7B, top and middle panels) and expressed similar levels of Sindbis virus proteins (FIG. 7B, bottom panel). All viruses grew with similar kinetics to similar final titers under single-step growth conditions in BHK-21 cells (FIG. 7C).

Figure 8A:
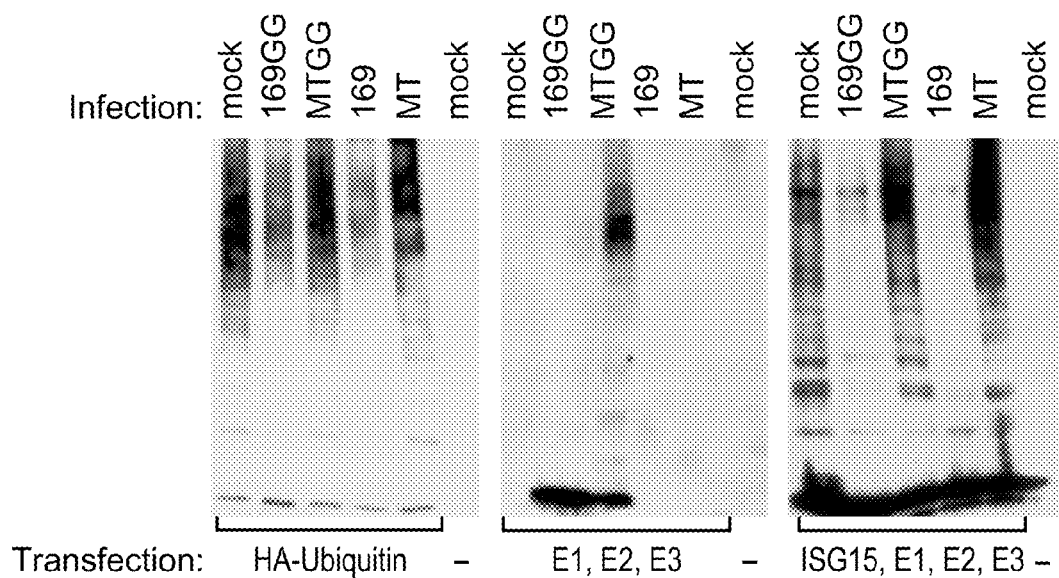
Figure 8B:
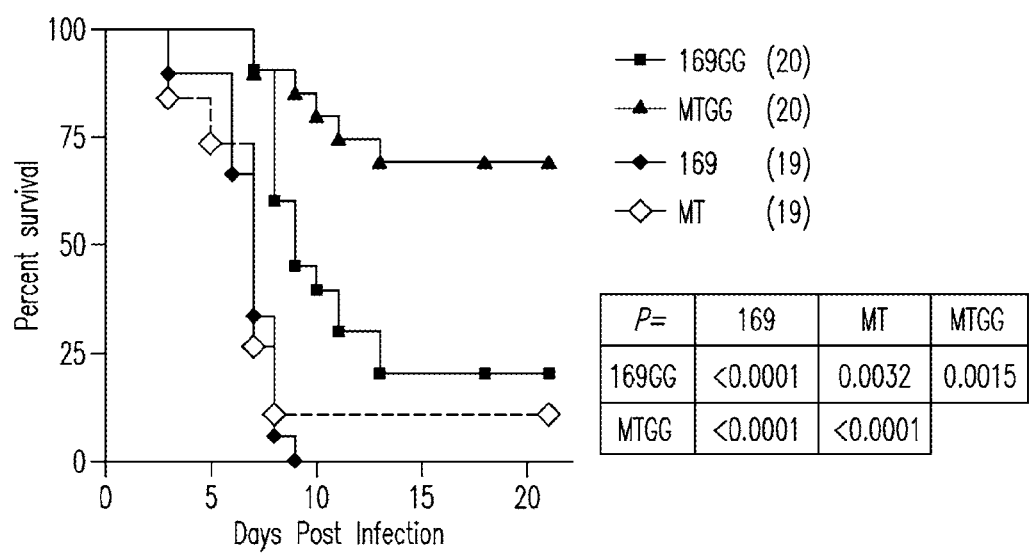

The ability of the recombinant Sindbis viruses to deISGylate and deubiquitinate proteins was assessed by infecting BHK-21 cells that had been previously transfected with components of the ISG15 conjugation system or HA-tagged ubiquitin (FIG. 8A). After transfection of HA-ubiquitin, infection with 169GG or 169—but not MTGG or MT—reduced the amount of ubiquitin conjugates detected in cells (FIG. 8A, first panel). This decrease in ubiquitin conjugates was not as drastic as observed in 293T transfection experiments (compare FIG. 2B, lane 7 to FIG. 8A). When BHK-21 cells were transfected with only the enzymes necessary for ISGylation (but not ISG15 itself), unconjugated ISG15 was detected following 169GG and MTGG infection, but ISG15 conjugates were only observed following MTGG infection (FIG. 8A, middle panel). This observation confirms that ISG15 expressed from dsTE12Q is capable of ISGylating proteins (FIG. 8A, middle panel, lane 3) and suggests that the OTU domain deconjugates ISGylated proteins (FIG. 8A, middle panel, lane 2). Following transfection with ISG15 and its E1, E2 and E3 enzymes, ISGylated proteins can be detected in BHK-21 cells (FIG. 8A, right panel, lane 1). Infection with 169GG or 169 greatly reduces detectable ISG15 conjugates, confirming that OTU domain expression from dsTE12Q results in a loss of ISGylated proteins.

To determine whether OTU domain expression counters the anti-viral effect of ISG15, Ifnar$^{-/-}$ mice were infected s.c. with 5×10$^6$ PFU of recombinant Sindbis virus (FIG. 8B). 70% of mice infected with MTGG survived as compared to only 20% survival following 169GG infection (P=0.0015), with a median survival time of 9 days. Mice infected with 169 or MT died with similar kinetics and had a median survival time of 7 days, demonstrating that the expression of 169 did not increase the virulence of dsTE12Q. There was a statistical difference between the survival curves of 169 and 169GG (P<0.0001) and MT and 169GG (P=0.0191) and a slight difference in median survival time (7 days vs. 9 days). These data suggest that the OTU domain is capable of inhibiting the majority of the anti-viral function of ISG15. The slight differences in survival between 169GG and 169 or MT suggests that ISG15 may have another (non-conjugating) anti-viral function or that the OTU domain cannot deconjugate all ISGylated proteins in a cell.

6.3 Discussion

This example demonstrates that CCHFV-L is a viral protease of 450 kDa with deISGylating activity. This activity was mapped to the OTU domain present in the amino-terminal end of the CCHFV-L protein. In vitro assays and transfection-based experiments showed that the core OTU domain of CCHFV-L is not only able to recognize and process ISGylated but also ubiquitinated substrates. In the experiments described in this example, deISGylation activity but not deubiquitination activity was observed with the full length CCHFV-L in transfection-based cell assays. This outcome was unexpected because of the in vitro data showing that the core OTU domain has DUB activity. Without being bound to a particular mechanism, one possible explanation for this difference is that low expression levels of the full-length L protein (as compared to the OTU domain alone) may be sufficient to mediate deISGylation, but not deubiquitination. The deconjugating activity of the full length CCHFV-L protein toward specific ubiquitinated substrates cannot be excluded based on these results.

To further investigate the specificity of the core OTU domain, in vitro assays using SUMO-2 or SUMO-3 poly chains were employed as substrates. However, no hydrolysis by CCHFV-L OTU was observed with these substrates. Ubiquitin, ISG15 and SUMO are synthesized as longer precursors that are processed into the mature form by exposing a carboxy-terminal LRLRGG (SEQ ID NO:1) motif (Ub and ISG15) or a QQQTGG (SEQ ID NO:5) motif (SUMO). The observation that CCHFV-L OTU is not able to hydrolyze SUMO chains indicates that the LRLRGG (SEQ ID NO:1) sequence may play an important role in substrate recognition and specific cleavage by CCHFV-L OTU.

Sequence alignment between different OTU domain-containing proteins reveals two motifs, each containing a predicted catalytic residue (cysteine 40 and histidine 151). Their fundamental role in the catalytic activity of the protein was demonstrated by mutating these residues to Ala resulting in a catalytically dead OTU domain. In addition to demonstrating deconjugating activity of CCHFV-L towards both ubiquitin and ISG15, this example demonstrates that the DUGV L OTU domain and nsp2 from PRRSV and EAV have deISGylating and DUB activities.

ISG15 is a known target of immune evasion strategies, as the NS1 protein of influenza B inhibits the ISG15-UBE1L interaction (Yuan and Krug, 2001). An OTU domain expressed from a Sindbis virus was capable of deconjugating ISG15 and ubiquitin conjugates in transfected BHK cells. When mice were infected with OTU domain-expressing Sindbis viruses, deISGylation of cellular proteins inhibited ISG15-mediated protection from Sindbis virus lethality and demonstrates in vivo consequences of this enzymatic activity.

7. EXAMPLE 2

Novel DeISGylation Activity of the CCHFV L Protein and Other Viral Proteases as Compared to Cellular OTU Domain-Containing Proteins and Role in Immune Evasion This example demonstrates that the OTU domain-containing proteases from nairoviruses and arteriviruses, two unrelated groups of RNA viruses, hydrolyze Ub and ISG15 from cellular target proteins. These viral OTU domains, in contrast to known mammalian OTU proteases, display a broad deconjugating activity towards ubiquitinated and ISGylated products and consequently inhibit innate immunity pathways that are dependent on Ub and ISG15. The viral OTU domain-containing proteases inhibit TNFα and NF-κB dependent signaling.

7.1 Materials and Methods 7.1.1 Expression Plasmids.

Plasmids pCAGGS.-6HismISG15, pCAGGS-hUBE1L-HA, pFLAGCMV2-UbcM8 and pcDNA3.1-UbcM8 were provided by Dong-Er Zhang (Scripps Research Institute, La Jolla, Calif., USA) (Giannakopoulos et al., 2005). Herc5 was provided by Motoaki Ohtsubo (Kurume University, Fukuoka-ken, Japan). pcDNA 3.1+-HA-Ub was provided by Dr. Domenico Tortorella (Mount Sinai School of Medicine, NY, USA) (Treier et al., 1994). Peak10-Flag-A20 plasmid was provided by Dr. Adrian Ting (Mount Sinai School of Medicine).

Viral Protein Expression Plasmids.

The pCAGGS vector expresses transcripts under the control of a chicken β-actin promoter (Niwa et al., 1991). The multi-cloning site of this original vector was modified in order to facilitate the cloning strategy generating a pCAGGS-MCSII vector (AGS data not shown). CCHFV prototype strain IbAr10200, first isolated in 1976 from *Hyalomma excavatum* ticks from Nigeria, was grown in SW13 cells and viral RNA was isolated from cells supernatants using Trizol (Gibco) following manufacturer's protocol. Full-length CCHFV-L cDNAs was obtained by reverse transcription with specific primers from RNA obtained from CCHFV-infected cells. The single and double HA-tagged CCHFV-L plasmid (L-HA and HA-L-HA) was generated through multiple cloning steps. First, the 5' and 3' ends of the L cDNA were introduced by trimolecular ligation between the NotI and BglII sites of the pCAGGS-MCSII vector. An N-terminal and C-terminal HA were introduced into the construct by PCR with 5' and 3' gene-specific primers possessing the tag sequences (pCAGGS #12). In parallel, the complete L cDNA was assembled in the pGEMT vector (Promega, Madison, Wis., United States). A total of eight fragments, (not longer that 2.3 kb) were obtained by RT-PCR, ligated into pGEMT vector and sequenced. These fragments of the L gene were ligated one after the other until the full length clone was obtained. Once L cDNA was assembled in the pGEMT vector, it was transferred to the pCAGGS #12 vector using the DraIII restriction site.

cDNAs encoding deletion mutants of CCHFV-L, HA-L(1-1325), L(1325-2590)HA, L(2590-3945)HA, HA-L(1-169) and HA-L(1-354) were all cloned into the pCAGGS-MCSII vector. N-terminal or C-terminal HA tags were introduced into each construct by PCR with gene-specific primers possessing the tag sequence. HA-tagged DUGV L(1-169) was subcloned from DUGV-L cDNA (Anne Bridgen, University of Ulster, unpublished data) into pCAGGS-MCSII. A bacteria expression plasmid to generate recombinant CCHFV OTU domain was made by subcloning L(1-169) cDNA into the pGEX6P-1 vector (Amersham, Little Chalfont, United Kingdom). To generate catalytically inactive variants of L(1-169), a single mutation of C40 to A or a double mutation of C40 and H151 to A were generated in the pGEX-GST-L(1-169) or pCAGGS-HA-L(1-169) plasmids, respectively. To generate the CCHFV-L 1A single mutant, the C40 to A mutation was generated in the pCAGGS#12 vector (see above), cleaved with DraIII and then a DraIII cleavage product derived from pGEMT-L was inserted into it. In all cases, mutagenesis was performed using the QuikChange XL Site-Directed Mutagenesis Kit (Stratagene, La Jolla, Calif., USA). PRRSV-nsp2 cDNA was subcloned into the pCAGGS-MCSII vector. An N-terminal HA epitope tag was introduced by PCR.

EAV nsp2N was synthesized by Top Gene Technologies (Montreal, QC, Canada) and subcloned into pFLAGCMV2. pCDNA3-nsp2/3-GFP was derived from Sindbis virus expression vector pSRE-nsp2+3GFP, a derivative of pSRE-nsp2+3His vector (Snijder et al., 2001). In brief, using a smaller shuttle construct, the SmaI restriction site at the junction of the nsp3- and His-tag-coding sequences of pSRE-nsp2+3His was digested to insert the eGFP gene. The latter was derived from vector pEGFP-N1 (Clontech) from which it was cut using BamHI and XbaI, followed by filling of sticky ends. Using MluI and NotI, the nsp2/3-GFP sequence was transferred from pSRE-nsp2+3GFP to pCDNA3 (Invitrogen), where it was placed downstream of the CMV promoter. Compared to native nsp2-3, the expression construct carried an additional N-terminal Methionine and a G-1064→P substitution at the C-terminal position of nsp3.

Mammalian Protein Expression Plasmids

Mouse UBE1L (mUBE1L) and mouse UBP43 were PCR-amplified from an IFNβ-induced bone marrow macrophage cDNA library (Kim et al., 2004). mUBE1L was subcloned into the pCAGGS.MCS and an N-terminal HA epitope tag was introduced by PCR. UBP43 was subcloned into pFLAGCMV2. Expression constructs encoding eukaryotic OTU-domain containing proteins were generated by subcloning indicated sequences into pFLAGCMV2 vector: nucleotides 1-816 of mouse otubain 1, 1-705 of mouse otubain 2 and 1-2532 of human Cezanne.

Recombinant Sindbis Virus Plasmids

To generate recombinant Sindbis viruses 169 and MT, CCHFV-L(1-169) and L(1-169)2A, along with N-terminal HA tags, were PCR-amplified and subcloned into the BstEII restriction site of the dstE12Q vector. The 169GG and MTGG constructs, expressing ISG15 and Flag-tagged L(1-169) or L(1-169)2A cDNAs were cloned into the BstEII restriction site of the dstE12Q vector by multiple steps.

ISG15-IRES-L(1-169) and ISG15-IRES-L(1-169)2A were generated by cloning ISG15 into pMIG and replacing the GFP ORF in pMIG with either L(1-169) or L(1-169)2A. To facilitate cloning, the N-terminal HA tags of L(1-169) and L(1-169)2A were replaced with a N-terminal FLAG tag. L(1-169) or L(1-169)2A were PCR amplified with primers containing a 5' HindIII site and 3' BstEII and ClaI sites and subcloned into pFLAGCMV2. The resulting constructs were digested with NcoI and ClaI to generate FLAG-L(1-169) or FLAG-L(1-169)2A, which was subcloned into NcoI/ClaI-digested pMIG to replace the GFP ORF. Nucleotides 1-465 of murine ISG15 was PCR amplified with primers containing 5'

EcoRI and BstEII sites and a 3' BamHI site and cloned into the EcoRI/BamHI sites of pMIG-L(1-169) and pMIG-L(1-169)2A. pMIG-ISG15-L(1-169) and pMIG-ISG15-L(1-169)2A were digested with BstEII to yield ISG15-IRES-L(1-169) and ISG15-IRES-L(1-169)2A which were subcloned into dsTE12Q.

Sequences of each generated construct were confirmed by automated sequencing performed at the Massachusetts General Hospital DNA Sequencing Core Facility.

7.1.2 Antibodies.

Antibodies against Flag (M2 and rabbit polyclonal, Sigma, St. Louis, Mo.), HA [HA.7 (Sigma) HA.11 (Covance Research, Berkeley, Calif.)], Ub (P4D1, Cell Signaling, Danvers, Mass.,) NF-κB p65 (F-6, Santa Cruz Biotech, Santa Cruz, Calif.) and actin (AC-74, Sigma) were used following manufacturer's protocol. Anti-mouse ISG15 monoclonal (3C2 and 2D12) and polyclonal antibodies (Lenschow et al., 2005) and antiserum recognizing EAV-nsp2 (Snijder et al., 1994) have been previously described.

7.1.3 Purification of CCHFV L(1-169) from *E. coli*.

BL-21 cells (Stratagene, La Jolla, Calif., USA) were transformed with pGEX-L(1-169) or pGEX-L(1-169)1A CCHFV, cultured to an OD600 of 0.6 in 2×YT medium and induced for 6 h at 30° C. with 1 mM IPTG. Bacteria were resuspended in lysis buffer (50 mM Tris-HCl, 5 mM EDTA, 1 mM DTT, 200 mM NaCl and 0.1% NP-40) and purification of the GST fusion proteins was performed using GSH Sepharose resin (Amersham) according to the manufacturer's protocol. GST was cleaved using PreScission™ Protease (Pharmacia, Uppsala, Sweden) in cleavage buffer (50 mM Tris-HCl pH 7.6, 150 mM NaCl, 1 mM EDTA and 1 mM DTT).

7.1.4 Assays for DeISGylation in Cultured Cells.

Initially, 293T cells cultured in 12-well dishes were co-transfected with 0.4 µg of pCAGGS.-6HismISG15, 0.4 µg of pCAGGS-hUBE1L-HA, and 0.2 µg of pFLAGCMV2-UbcM8 along with OTU-domain expression plasmids or empty pCAGGS plasmid using Lipofectamine™ 2000. In subsequent experiments testing eukaryotic and viral OTU constructs, 293T cells in 12-well dishes were co-transfected with OTU-domain expression plasmids and 0.5 µg pCAGGS-6His mISG15, 0.5 µg pCAGGS-mUBE1L HA, 0.5 µg of plasmid encoding Herc5 and 0.2 µg pFLAGCMV2 UbcM8 or pCDNA3.1-UbcM8. 24 h post-transfection, cells were lysed in Laemmli sample buffer, boiled and analyzed by immunoblot using anti-ISG15 mAb 3C2 as previously described (Lenschow et al., 2005). Each transfection experiment was performed a minimum of three times.

7.1.5 Assay for Deubiquitination in Cultured Cells.

293T cells cultured in 12-well dishes were co-transfected with 0.5 µg of pcDNA3.1-HA-Ub and various OTU-domain expression plasmids or empty pCAGGS plasmid using Lipofectamine™ 2000. 24 hours post transfection, the cells were lysed in Laemmli sample buffer, boiled and immunoblotted with anti-HA antibody. Each transfection experiment was performed a minimum of three times.

7.1.6 Generation of ISG15 Conjugates.

Fourteen 10 cm dishes of 293T cells were transfected with 6 µg pCAGGS.MCS-6HismISG15, 3 µg pCAGGS-hUBE1L-HA and 3 µg pFLAGCMV2-UbcM8. 24 h later, cells were harvested, resuspended in 20 mM Tris-HCl pH 8.0 with 300 mM NaCl, and lysed by three cycles of freeze-thaw. Lysates were centrifuged for 15 min at 14000 rpm. His-tagged ISG15 conjugates were purified over a His-Select Spin Column (SIGMA) following manufacturer's directions. Column bound conjugates were washed extensively with washing buffer (20 mM Tris-HCl, pH 8.0, 300 mM NaCl and 5 mM Imidazole) and eluted with 20 mM Tris-HCl, pH 8.0, 300 mM NaCl and 250 mM Imidazole. Protein concentration was measured by Bradford assay (Bio Rad).

7.1.7 In Vitro Deconjugation Assays.

K48 Ub2-7, K63 Ub3-7, SUMO-22-8, SUMO-32-8, pro-ISG15, pro-Nedd8, pro-SUMO-1, USP5/Isopeptidase T, NEDP1, UBP43, A20CD and His6-SENP2CD were purchased from Boston Biochem (Cambridge, Mass., USA). All reactions were performed in 50 mM Tris-HCl pH 7.6, 5 mM MgCl2 and 2 mM DTT at 37° C. for 2 hr. Serial 10-fold dilutions of L(1-169) or L(1-169)1A (ranging from 2.5 μM-2.5 nM) were incubated with either 2.5 μg Ub chains or SUMO chains, 2.5 μg pro-ISG15, pro-Nedd8 or pro-SUMO-1, 10 μl Ubp43−/− lysate or 3 μg of 6HisISG15 conjugates. Positive control for deconjugation was incubation with 100 mM USP5 (Ub), SENP2CD (SUMO), NEDP1 (Nedd8) or UBP43 (ISG15). Negative control was incubation of chains or conjugates in assay buffer alone. Reactions were terminated by addition of Laemmli sample buffer and separated by SDS-PAGE electrophoresis on a 4-20% gradient gel (Bio-Rad). Proteins were visualized by SimplyBlue Safestain (Invitrogen) staining (Ub and SUMO) or by anti-ISG15 Western blot.

7.1.8 Viruses.

Sindbis viruses were generated from a cDNA clone by in vitro transcription and RNA transfection of BHK-21 cells as previously described (Levine et al., 1996), (Lenschow et al., 2005). Recombinant virus stocks were produced and titered on BHK-21 cells as previously described (Lenschow et al., 2005). Sindbis virus AR86 was a kind gift of Dr. Mark Heise (University of North Carolina, Chapel Hill) (Heise et al., 2000)

7.1.9 NF-κB Reporter Gene Assay.

293T cells were co-transfected with 3.3-fold dilutions (starting at 100 ng) of A20, CCHFV-L(1-169), CCHFV-L(1-169)2A, EAV-nsp2N or empty plasmid along with the firefly luciferase gene construct under the control of the NF-κB binding sites) (Wang et al., 2000) and pRL-TK (Renilla luciferase; Promega, Wis., USA). The total amount of transfected DNA was kept constant by adding the pCAGGS empty vector. 24 hours post-transfection, the cells were stimulated with TNFα (10 ng/ml) for 6 h, and luciferase activities were measured using the Dual-Luciferase Reporter (DLR™) Assay System (Promega). Final NF-κB luciferase values were normalized with the Renilla luciferase values as internal control.

7.1.10 Immunofluorescence.

200 ng of empty plasmid or Flag-tagged L(1-169) and L(1-169)2A were transfected into A549 cells. 24 hours later, cells were stimulated with 10 ng/ml TNFα for 2 h. Cells were fixed and permeabilized for 30 min at room temperature with 2.5% formaldehyde and 0.5% Triton X-100, washed extensively with PBS and stained with anti-p65 and anti-Flag antibodies. Following PBS washes, cells were stained with anti-mouse (p65) or anti-rabbit (Flag) and secondary antibodies, and then mounted in medium containing an antifade reagent. Nuclear localization of p65 was scored in 100 to 400 transfected cells for each experimental condition.

7.1.11 Mouse Studies.

IFNαβR−/− mice on the 129/SV/Pas background were initially obtained from M. Aguet, Swiss Institute of Experimental Cancer Research (Epalinges, Switzerland) (Behr et al., 2001; Dunn et al., 2005). CCHFV-L(1-1325) transgenic mice were generated at the WUSM Pathology Microinjection Core by microinjecting a linearized construct derived from pCAGGS-HA-L(1-1325) into B6 oocytes. Oocytes were implanted into pseudo-pregnant mice and resulting litters were genotyped using PCR (primer sequences available upon request). Individual embryo MEFs from transgenic lines 1836, 1854, and 2929 were generated as described previously (Weck et al., 1999). Uninfected transgenic brain was homogenized in 1 ml of DMEM with protease inhibitors using 100 μl 1.0-mm-diameter zirconia-silica beads in a MagNa Lyser (Roche, Indianapolis, Ind.). To assess transgene expression, 4×105 MEFs or 12 μl of brain homogenate were immunoblotted with HA.11 and anti-actin antibodies. Eight to 10-week-old male IFNαβR−/− mice were infected subcutaneously (s.c.) in the left hind footpad with 5×106 PFU of virus diluted in 50 μl of Hank's balanced salt solution (HBSS). Four to 5-week old L(1-1325) transgenic mice were infected s.c. in the left hind footpad with 5000 PFU of Sindbis virus AR86 diluted in 50 μl of HBSS. Mice were bred and maintained at Washington University School of Medicine in accordance with all federal and university guidelines.

7.1.12 Statistical Analysis.

All data were analyzed with Prism software (GraphPad, San Diego, Calif.). Survival data were analyzed by the log rank (Mantel-Haenzsel) test, with death as the primary variable. Single-step growth curves were analyzed by one way analysis of variance (ANOVA).

7.2 Results 7.2.1 OTU Domains in Viral and Mammalian Proteins.

Sequencing of the L gene of the highly pathogenic human virus CCHFV (NFS and AGS, data not shown) (Honig et al., 2004; Kinsella et al., 2004) led to the identification of an OTU domain in the N-terminal region of the viral protein (FIG. 10). This domain was also present in the L proteins of the nairoviruses Dugbe virus (DUGV) and Nairobi sheep disease virus (Honig et al., 2004), but has not been found in the L proteins of any other genus in the Bunyaviridae family. An alignment of the OTU domains present in nairoviruses, arteriviruses and mammalian proteins A20, Cezanne, VCIP135, Otubain 1 and Otubain 2 revealed limited identity; however a strong conservation of D37, G38, N39, C40, W71, H151 and an aromatic amino acid at position 152 (numbering based on the CCHFV-L sequence) was observed (FIG. 10, black boxes). Among these amino acids, C40 and H151 (FIG. 10, black arrows) were predicted to be the catalytic residues present in the putative protease active site (Balakirev et al., 2003; Makarova et al., 2000; Nanao et al., 2004).

7.2.2 Impact of CCHFV-L Expression on Protein Ubiquitination and ISGylation.

The deISGylating and deubiquitinating activity of the L protein of CCHFV (CCHFV-L) was tested (FIG. 11). To test the effect of CCHFV-L expression on protein ubiquitination, cells were transfected with plasmids expressing CCHFV-L and the expression of Ub-conjugated proteins was assessed. The level of Ub-conjugated protein detected was slightly decreased in CCHFV-L-transfected cells relative to controls (FIG. 11B, lanes 1 and 2, panel A, FIG. 11C, lanes 1, 4 and 5, panel A). To test the effect of CCHFV-L expression on protein ISGylation, ISG15 conjugates were generated by transfecting plasmids expressing ISG15 and its specific E1 (UBE1L) (Yuan and Krug, 2001) and E2 (UbcM8) (Kim et al., 2004; Zhao et al., 2004) enzymes since endogenous levels of ISGylated proteins are low in the absence of IFN stimulation. Co-transfection of CCHFV-L resulted in a clear decrease in the level of ISGylated proteins (FIG. 11B, lanes 1 and 2, panel B; FIG. 11C, lanes 1, 4 and 5, panel B). This decrease was also observed when CCHFV-L was untagged (data not shown). The decrease in total ISGylation was comparable to the effect of UBP43, a known ISG15 deconjugating enzyme (FIG. 11B, lane 9, panel B). Expression of CCHFV-L did not affect levels of expression of UBE1L or UbcM8 (FIG. 11B, lane 2, panels C and D; FIG. 11C, lanes 4 and 5, panel C), consistent with CCHFV-L acting via inhibition of ubiquitination and ISGylation reactions or by directly deubiquitinating or deISGylating proteins.

Figure 13B:
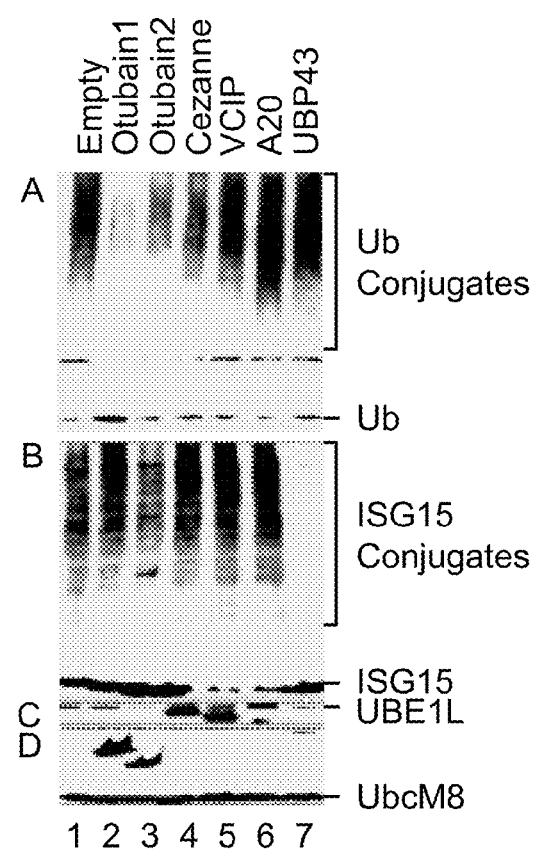

7.2.3 The OTU Domain of CCHFV-L Decreases the Levels of Ubiquitinated and ISGylated Proteins.

To determine the region of the L protein responsible for decreasing ubiquitinated and ISGylated proteins, plasmids expressing three portions of the L protein were constructed (FIG. 11A). Expression of the OTU-domain containing N-terminal portion, L(1-1325), resulted in the greatest decrease of Ub and ISG15 conjugates (FIG. 11B, lane 3, panels A and B). To further map this region, truncation mutants of the L protein expressing only the first 354, L(1-354), or 169 amino acids, L(1-169), were tested. The results indicate that the region responsible for the decreased levels of Ub and ISG15 conjugates mapped to the OTU domain, L-(1-169) (FIG. 11B, lanes 6 and 7, panels A and B; FIG. 11C, lane 2, panels A and B).

7.2.4 The Predicted Protease Active Site of the CCHFV-L OTU Domain is Required for Reducing Ub and ISG15 Conjugates.

To test whether the amino acids C40 and H151 (FIG. 10, black arrows) were critical for the observed reduction in ubiquitinated and ISGylated proteins by the CCHFV-L OTU domain, a full length L protein with a C40 to A40 mutation (L 1A) and a mutant L(1-169) protein in which both amino acids were replaced by alanines (L(1-169)2A) were expressed (FIG. 11A). Expression of L 1A and L(1-169)2A proteins did not decrease levels of ubiquitinated or ISGylated proteins (FIG. 11B, lane 8, panels A and B; FIG. 11C, lanes 6 and 7, panels A and B), strongly suggesting that the OTU domain contains a cysteine protease activity that mediates the decrease in ubiquitinated and ISGylated proteins.

7.2.5 The OTU Domain of CCHFV-L is a Deconjugating Enzyme With Specificity for Poly-Ub Conjugates and ISG15.

To determine whether the CCHFV-L OTU domain directly deconjugates Ub and ISG15 from target proteins, L(1-169) and a catalytic C40 to A40 mutant, L(1-169)1A, were expressed and purified for in vitro deconjugation assays (FIG. 12A). Recombinant L(1-169) cleaved both K48- and K63-linked poly-Ub chains into monomers (FIG. 12B, lanes 2 to 5), similarly to isopeptidase T, a known DUB enzyme (FIG. 12B, lane 10). This activity was markedly decreased by mutating the amino acid C40 (FIG. 12B, lanes 6 to 9), indicating that this residue is required for optimal protease activity. The small amount of deconjugation observed with L(1-169)1A is not unexpected, as mutation of Cezanne's catalytic cysteine yielded similar data where most, but not all, catalytic activity was impaired (Evans et al., 2003). This result shows that the OTU domain of CCHFV-L has bona fide DUB activity in the absence of other cellular proteins.

Next, the ability of L(1-169) to deconjugate ISGylated proteins was assessed. For this, cell lysates from IFNβ-treated UBP43−/− murine embryonic fibroblasts (MEFs) that are rich in ISG15 conjugates (Malakhov et al., 2003) were generated. Incubation of these lysates with recombinant L(1-169) protein, but not L(1-169)1A, appreciably decreased ISGylated proteins (FIG. 12C, top panel) in a L(1-169) concentration-dependent manner. This result suggests that the CCHFV OTU domain has C40-dependent ISG15 deconjugating activity but does not exclude the possibility that the protease activity of the viral OTU domain was activating another deISGylating enzyme present in cell lysates. To address this possibility, 6× HisISG15 conjugates were enriched using affinity chromatography. Incubation of ISG15 conjugates with increasing amounts of L(1-169) resulted in ISG15 deconjugation (FIG. 12C, lanes 2 to 5, bottom panel). No deconjugation was detected with the mutant L(1-169)1A protein (FIG. 12C, lanes 6 to 9, bottom panel). In addition, L(1-169) processed a pro-ISG15 protein into its mature form (FIG. 12E, lane 2, panel A). These data suggest that the CCHFV-L OTU domain directly deconjugates ISGylated proteins through its predicted cysteine protease activity.

To gain further insights on the specificity of the OTU domain, the ability of L(1-169) and L(1-169)1A to hydrolyze poly-SUMO-2 (FIG. 12D, top panel) and poly-SUMO-3 chains (FIG. 12D, bottom panel), pro-SUMO-1 (FIG. 12E, panel C) and pro-Nedd8 (FIG. 12E, panel B) was assessed. While the catalytic domain of SENP2 (SENP2CD), a SUMO-specific protease, could hydrolyze SUMO chains to monomers (FIG. 12D, lane 10) and process pro-SUMO-1 (FIG. 12E, lane 5, panel C), neither L(1-169) nor L(1-169)1A was able to cleave SUMO chains or a pro-SUMO-1 precursor. However, similar to its ability to process pro-ISG15 (FIG. 12E, lane 2, panel A), L(1-169) hydrolyzed pro-Nedd8 into a mature form (FIG. 12E, lane 2, panel B). In summary, the OTU domain of CCHFV-L hydrolyzes Ub and ISG15, but not SUMO2 or SUMO3, from conjugates in vitro, suggesting that viral OTU domains have the unique ability to recognize Ub and specific Ub1 molecules.

7.2.6 Additional Viral OTU Domains Mediate Deubiquitination and DeISGylation.

In addition to CCHFV, viral OTU domains are found in the L proteins of other nairoviruses and in the nsp2 proteins of arteriviruses such as EAV and PRRSV (FIG. 10). The arterivirus nsp2 cysteine protease cleaves the nsp2/nsp3 site within the large viral polyprotein during replicase maturation. In the case of EAV, this process is known to be mediated by the 166 N-terminal residues of nsp2 which contains the OTU domain (Snijder et al., 1995). In this study, a slightly larger N-terminal EAV-nsp2 domain (175 amino acids; nsp2N) was used in addition to the full-length protein. The OTU domain of the L protein of DUGV, a nairovirus related to CCHFV, as well as EAV-nsp2, EAV-nsp2N and PRRSV-nsp2, decreased Ub and ISG15 conjugates when expressed in 293T cells (FIG. 13A, lanes 3-6), indicating that deconjugation may be an immune evasion strategy shared by these viral families.

Previous studies have demonstrated that the OTU domain-containing mammalian proteins Otubain1, Otubain 2, Cezanne. VCIP135 and A20 cleave poly-Ub chains in vitro (Balakirev et al., 2003; Evans et al., 2004; Evans et al., 2003; Wang et al., 2004). In contrast, only over-expression of Otubain 1 and Cezanne moderately decreased cellular global Ub conjugate levels, while expression of A20 or Otubain 2 had no effect on total levels of ubiquitinated proteins (Balakirev et al., 2003; Evans et al., 2004; Evans et al., 2003). Otubain 1, Otubain2, Cezanne, VCIP135 and A20 were tested for their ability to decrease overall protein ubiquitination and ISGylation in transfected cells (FIG. 13B). Expression of Otubain 1 resulted in a significant decrease in Ub conjugate levels, while Otubain 2 and Cezanne had a lesser effect (FIG. 13B, lanes 2-4, panel A). Consistent with their specificity for particular ubiquitinated substrates, expression of VCIP135 and A20 did not result in a decrease in overall ubiquitination. None of the OTU-containing mammalian proteins tested decreased global levels of ISG15 conjugates (FIG. 13B, lanes 2-6, panel B). Similar results were obtained when truncation mutants expressing the OTU domains of Otubain 1, Otubain 2, Cezanne and A20 were tested (data not shown). In addition, the OTU-containing catalytic domain of A20 (A20CD) was unable to process either ISG15 or Nedd8 (FIG. 12E, lane 4, panels A and B) even though it cleaved K48-linked Ub chains (FIG. 12F, lane 4). By contrast, over-expression of the mammalian deISGylating enzyme UBP43 decreased overall levels of ISG15 conjugates but not Ub-conjugates (FIG. 13B, lane 7). Thus, viral OTU proteases appear to be unique in their ability to target both ISG15 and Ub conjugates.

7.2.7 Transgenic Mice Expressing CCHFV-L(1-1325) Have Increased Susceptibility to Sindbis Virus Infection.

Figure 14A:
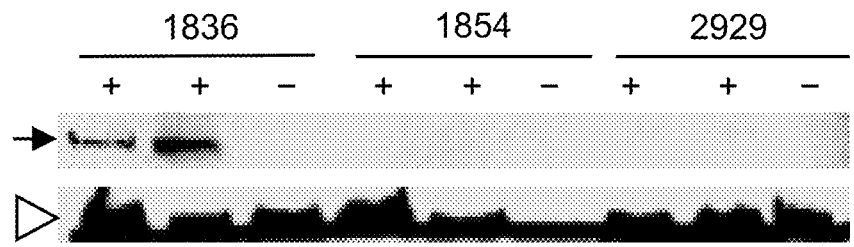
Figure 14B:
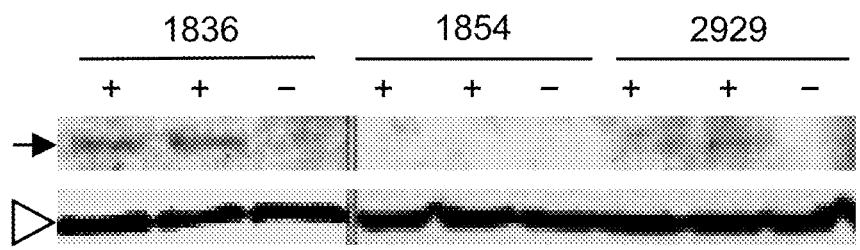
Figure 14C:
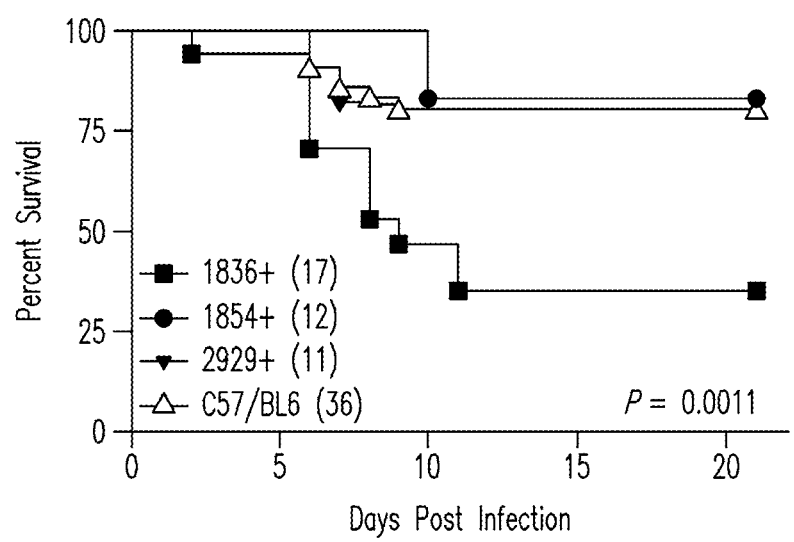

To assess the effect of expressing an OTU domain during viral infection, transgenic mice expressing the CCHFV-L(1-1325) OTU domain-containing protein, which exhibits DUB and deISGylating activities (FIG. 11B, lane 3), were generated. Germ line transgene transmission was obtained in three lines designated 1836, 1854, and 2929 and L(1-1325) expression in both MEFs and brain lysates from these transgenic lines was evaluated. MEF cells and brain tissue from 1836 transgenic mice contained detectable L(1-1325) protein while protein expression from the 1854 and 2929 lines was either undetectable or very low (FIGS. 14A and 14B). Next, the sensitivity of L(1-1325) transgenic mice to infection with the virulent Sindbis virus strain AR86, an alphavirus that causes lethal encephalitis in young mice and is sensitive to ISG15-mediated antiviral effects (Lenschow et al., 2005), was evaluated. Susceptibility to Sindbis virus infection tracked with expression of the L(1-1325) protein (FIG. 14C). Thirty five percent of mice from the 1836 transgenic line survived infection compared to ≥80% survival in C57/BL6 littermate controls or transgenic mice expressing low or undetectable levels of transgene-encoded protein. The decreased survival of 1836 transgenic mice following AR86 infection suggests that the CCHFV-L OTU domain enhances susceptibility to viral disease in vivo.

7.2.8 The OTU Domain of CCHFV Overcomes ISG15-Mediated Protection From Sindbis Virus Induced Lethality.

The increased pathogenicity of Sindbis virus observed in L(1-1325)-expressing mice suggested that the CCHFV-L OTU domain might counteract the antiviral activities of ISG15 in vivo. It was previously shown that expression of ISG15 from the chimeric Sindbis virus dsTE12Q protects adult IFNαβR−/− mice from Sindbis virus-induced lethality (Lenschow et al., 2005). To determine whether expression of CCHFV-L OTU domain would antagonize this protective effect of ISG15, four recombinant chimeric Sindbis viruses (FIG. 15A) were engineered. Two viruses expressed ISG15 followed by an IRES element to drive translation of either L(1-169) (169GG) or enzymatically inactive L(1-169)2A (MTGG). Control viruses that expressed either L(1-169) (169) or L(1-169)2A (MT) in the absence of ISG15 were also generated.

The recombinant viruses expressed the viral OTU domains and ISG15 as expected (FIG. 17, panels A and B) as well as similar levels of Sindbis virus proteins in infected cells (FIG. 17, panel C). All four viruses grew with similar kinetics to similar final titers under single-step growth conditions in BHK-21 cells (FIG. 18).

Figures 15A, 15B, 15C:
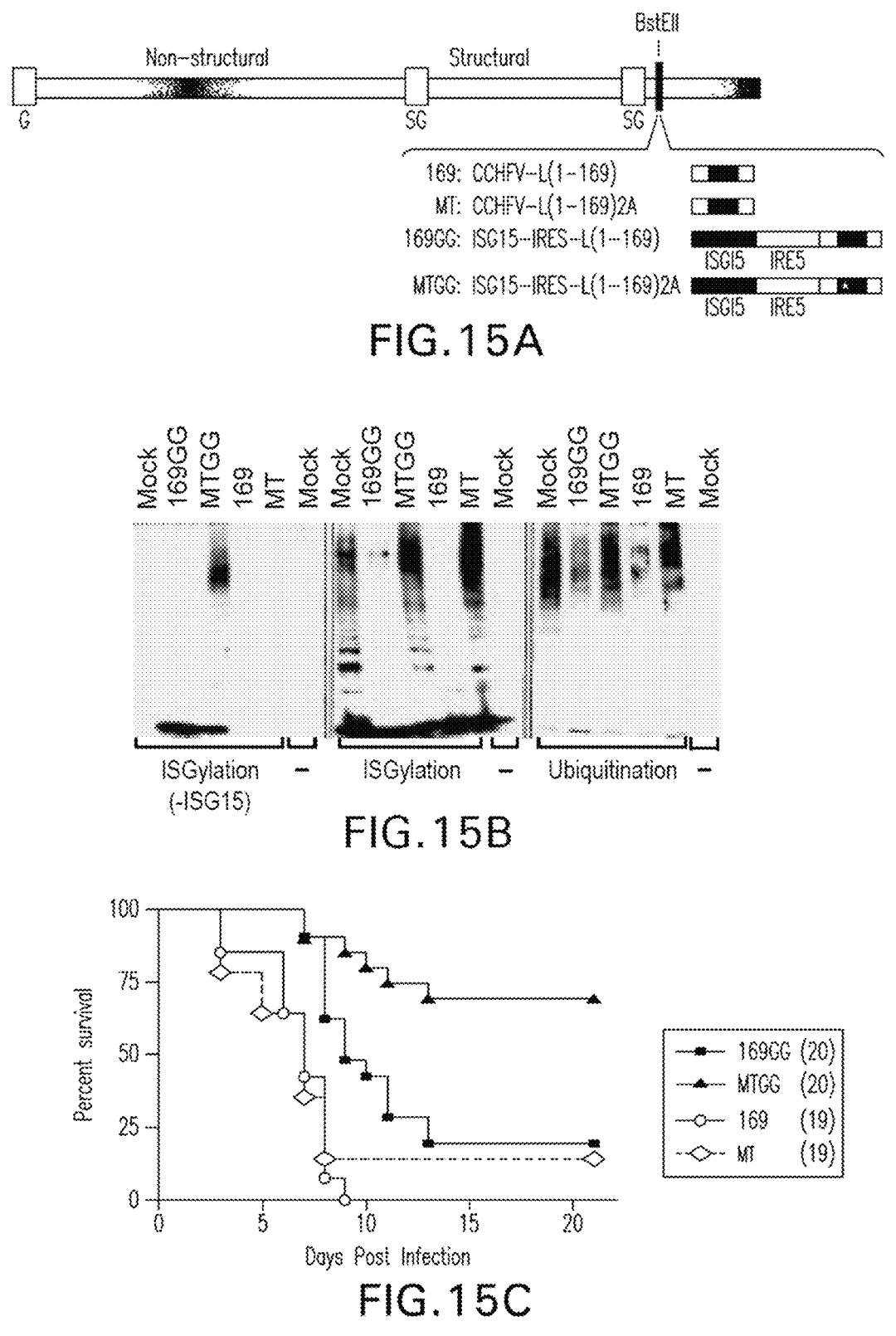

The ability of the L(1-169) protein expressed from within the Sindbis virus genome to deISGylate and deubiquitinate proteins by infecting BHK-21 cells was assessed (FIG. 15B). Infection with 169GG or 169, but not MTGG or MT, reduced the amount of Ub conjugates detected in cells (FIG. 15B, right panel), indicating that the viral OTU domain functions as a DUB enzyme when expressed from a Sindbis virus. Following transfection with ISG15 and its E1, E2 and E3 enzymes, ISGylated proteins can be detected in BHK-21 cells (FIG. 15B, lane 1, middle panel). Infection with 169GG or 169 greatly reduced ISG15 conjugates, confirming that OTU expression results in deconjugation of ISGylated proteins. When cells were transfected with the E1, E2, and E3 enzymes but not ISG15, ISG15 conjugates were observed only following MTGG infection (FIG. 15B, left panel). This shows that ISG15 expressed from dsTE12Q is capable of ISGylating proteins in the presence of the relevant conjugating enzymes but that this is only seen in the presence of a catalytically inactive form of the co-expressed L(1-169) protein (FIG. 15B, lane 3, left panel).

The ability of viral OTU domain expression to counter ISG15's in vivo antiviral effect was then assessed. In order to exclude effects due to IFNαβ stimulated genes other than ISG15, IFNαβR−/− mice were infected (FIG. 15C). Seventy percent of mice infected with a virus expressing ISG15 and the mutant viral OTU domain (MTGG) survived, consistent with previous observations that expression of ISG15 protects mice from lethality following Sindbis virus infection (Lenschow et al., 2005). In contrast, only 20% of mice infected with a virus expressing ISG15 and a functional viral OTU domain (169GG) survived infection (P=0.0015). These data also correlate with the in vitro data demonstrating that L(1-169), but not L(1-169)2A, can deISGylate proteins following infection (FIG. 15B). Mice infected with 169 or MT died with similar kinetics, demonstrating that the expression of L(1-169) did not increase the virulence of dsTE12Q in the absence of the IFN-mediated antiviral response.

7.2.9 Negative Regulation of the NF-κB Pathway by Viral OTU Domains.

The data above indicate that a viral OTU domain protease can counter the antiviral activities of ISG15. To assess whether the DUB activity of these proteins may also play a role in immune evasion, the effects of the CCHFV-L and EAV-nsp2 OTU domains on the NF-κB signaling pathway were evaluated. Expression of the OTU domains of CCHFV-L and of EAV-nsp2 decreased in a dose-dependent manner the activation of an NF-κB responsive promoter (Fujita et al., 1992) after TNFα treatment. This inhibition was similar to that mediated by A20, an OTU-domain containing inhibitor of the NF-κB pathway (FIG. 16A). Inhibition was about 10-fold greater in the presence of the L(1-169) domain than the L(1-169)2A mutant, indicating a role for the OTU domain protease activity. These results were further confirmed by the ability of CCHFV-L(1-169) to inhibit NF-κB activation as measured by the inhibition of endogenous p65 nuclear translocation upon TNFα treatment (FIGS. 16B and 16C). The p65 nuclear translocation inhibition by the L(1-169) protein was significantly higher when compared to its mutant counterpart (P=0.0044). Overall, these results demonstrate the ability of viral OTU domains to affect immune pathways that are regulated by ubiquitination.

7.3 Discussion

This example shows that viral OTU domain-containing proteins are proteases that hydrolyze Ub and ISG15 from conjugated proteins. This dual deconjugating activity provides an elegant example of the economy of viral evolution since both Ub and ISG15 rely on a conserved conjugation motif. Furthermore, the protease activity by the viral OTU domains has the physiologic capacity to evade two different cytokine pathways, IFNαβ and TNFα, which are fundamentally important for antiviral immunity.

7.3.1 Viral DUB and DeISGylating Enzymes as a Unique Strategy for Immune Evasion Biochemical and genetic evidence indicates that protein ubiquitination plays a critical role in the induction of both the innate and the adaptive cellular immune system (Liu et al., 2005). For example, in addition to NF-κB signaling, Ub regulates several aspects of antiviral immunity such as MHC class I and II antigen presentation (Loureiro and Ploegh, 2006; Shin et al., 2006), TLR/IL1 signaling (Chen, 2005) and induction of type I IFN by the cellular viral sensor RIGI (Gack et al., 2007). Inhibition of protein ubiquitination might also affect other cellular processes that can be subverted by viruses for their own advantage, such as the proteasome-mediated protein degradation system, multiple signal transduction events or cell cycle progress. The results above demonstrate that viral OTU domain-containing proteins affect the NF-κB signaling pathway. Given the effects observed on NF-κB signaling, the viral OTU domain-containing proteins likely target other Ub-dependent pathways as well.

While the biochemical effects of ISGylation have been studied far less extensively than those of Ub, ISG15 is an antiviral protein (Lenschow et al., 2005; Lenschow et al., 2007; Okumura et al., 2006) that now appears to use multiple strategies to counter the antiviral effects of ISG15. This example demonstrates that viral OTU domain-containing proteins deISGylate ISG15 conjugates in cells. This deISGylation activity in cells contributes to the virus' ability to counteract the host antiviral response. The NS 1 protein of influenza B virus has been shown to inhibit protein ISGylation by blocking the ISG15-UBE1L interaction (Yuan et al., 2002; Yuan and Krug, 2001).

7.3.2 OTU Domain Specificity and Deconjugating Activity as a Target for Antiviral Drug Development This example demonstrates that the CCHFV-L OTU domain processes Ub and ISG15 conjugates and pro-ISG15 and pro-Nedd8 in vitro. The results suggest that the CCHFV-L domain does not have activity against any SUMO isoforms. Ub, ISG15 and Nedd8 differ from SUMO in their exposed C-terminal motifs: LRLRGG (SEQ ID NO:1) for Ub and ISG15 and LALRGG (SEQ ID NO:6) for Nedd8 versus QQQTGG (SEQ ID NO:5) for SUMO2 and SUMO3. Without being bound by a particular theory or mechanism, sequences similar to the LRLRGG (SEQ ID NO:1) motif may play an important role in substrate recognition and specific cleavage by CCHFV-L OTU and perhaps other viral OTU domain-containing proteases. The nsp2 of arteriviruses cleaves the nsp2/3 junction at FRLIGG (SEQ ID NO:7) (EAV) or GRLLGG (SEQ ID NO:8) (PRSSV) (Allende et al., 1999; Snijder et al., 1996; Ziebuhr et al., 2000), sequences similar to the LRLRGG (SEQ ID NO:1) motif. Thus, arterivirus OTU proteases have dual functions: performing essential viral polyprotein processing and targeting host substrates to modulate the anti-viral response.

7.3.3 Physiologic Importance of Viral OTU Domain Protease DUB and DeISGylating Activities This example shows that in transgenic mice, recombinant chimeric Sindbis viruses, and transfected cells, viral OTU domain-containing proteases have significant effects on Ub- and ISG15-dependent host processes of known importance for innate immunity. Therefore, these proteins have bona fide immune evasion properties.

8. EXAMPLE 3

Deubiquitinating and DeISGylating Activity of CCHFV-L OTU

This example demonstrates that the deubiquitinating and deISGylating activity of viral OTU domain-containing proteins may be assessed in assays amenable to high throughput.

Ubiquitin or ISG15 is fused in its carboxy-terminus to the fluorogenic substrate 7-amido-4-methylcoumarin (AMC) (Dang et al., 1998; Stein et al., 1995). These substrates are highly sensitive and allow for monitoring continuous enzymatic activity. Alternatively, ubiquitin or ISG15 fused to 7-amino-4-trifluoromethylcoumarin (AFC) can be used as substrate. This latter fluorophore has a larger Stokes radius than AMC which is useful to reduce compound interference in high-throughput assays.

The AMC- or AFC-based enzymatic assays allow the substrate specificity of the viral OTU domain-containing proteins to be tested. Such assays may include inhibitors, such as Ub/ISG15-aldehyde or Ub/ISG15-vinyl sulfone. Quantifying the rate of release of the fluorophore from the substrate using a luminescence spectrometer permits the calculation of the amount of the deISGylating and/or deubiquitinating enzymatic activity. The use of inhibitors can allow calculations of Ki as well, thereby revealing the binding constants of ubiquitin and ISG15 substrates and inhibitors. The advantages of these assays include the small amounts of deISGylating enzyme or deubiquitinating enzyme required, the strong signal obtained from the AMC or AFC fluorophore, and the rapid and specific inhibition by the aldehyde and vinyl sulfone inhibitors.

To determine the enzymatic activity of recombinant purified CCHFV-L OTU, standard steady-state kinetic analysis was carried out with the AMC derivatives. Ub-AMC (FIG. 19) and ISG15-AMC (data not shown) were efficiently hydrolyzed by CCHFV-L OTU enzyme with liberation of highly fluorescent AMC. Hydrolysis of Ub-AMC or ISG15-AMC substrates was determined spectrofluorometrically in a final volume of 200 μl. The assays contained Ub-AMC (or ISG15-AMC) at different concentrations, 50 mM Tris HCl, pH 7.6, 2 mM DTT, 50 μg/ml BSA, and CCHFV-L OTU at a concentration of 1.3 nm. The excitation wavelength was 380 nm, and emission was monitored at 440 nm. Absolute concentrations were determined by reference to a standard curve of fluorescence versus concentration of AMC.

The in vitro assays for enzymatic activity described here will facilitate high-throughput screening for inhibitors of viral OTU domain-containing proteins, such as CCHFV-L. In particular, such assays will facilitate the identification of an inhibitor that binds specifically to the viral protease without blocking cellular deISGylating enzymes and/or cellular deubiquitinating enzymes.

REFERENCES

Allende, R., Lewis, T. L., Lu, Z., Rock, D. L., Kutish, G. F., Ali, A., Doster, A. R., and Osorio, F. A. (1999). North American and European porcine reproductive and respiratory syndrome viruses differ in non-structural protein coding regions. J Gen Virol 80, 307-315.

Altschul, S. F., Madden, T. L., Schaffer, A. A., Zhang, J., Zhang, Z., Miller, W., and Lipman, D. J. (1997). Gapped BLAST and PSI-BLAST: a new generation of protein database search programs. Nucleic Acids Res 25, 3389-3402.

Balakirev, M. Y., Jaquinod, M., Haas, A. L., and Chroboczek, J. (2002). Deubiquitinating function of adenovirus proteinase. J Virol 76, 6323-6331.

Balakirev, M. Y., Tcherniuk, S. O., Jaquinod, M., and Chroboczek, J. (2003). Otubains: a new family of cysteine proteases in the ubiquitin pathway. EMBO Rep 4, 517-522.

Barretto, N., Jukneliene, D., Ratia, K., Chen, Z., Mesecar, A. D., and Baker, S. C. (2005). The papain-like protease of severe acute respiratory syndrome coronavirus has deubiquitinating activity. J Virol 79, 15189-15198.

Behr, M., Schieferdecker, K., Buhr, P., Buter, M., Petsophonsakul, W., Sirirungsi, W., Redmann-Muller, I., Muller, U., Prempracha, N., and Jungwirth, C. (2001). Interferon stimulated response element (ISRE)-binding protein complex DRAF1 is activated in Sindbis virus (HR)-infected cells. J Interferon Cytokine Res 21, 981-990.

Blanchard, J. E., Elowe, N. H., Huitema, C., Fortin, P. D., Cechetto, J. D., Eltis, L. D., and Brown, E. D. (2004). High-throughput screening identifies inhibitors of the SARS coronavirus main proteinase. Chem Biol 11, 1445-1453.

Blomstrom, D. C., Fahey, D., Kutny, R., Korant, B. D., and Knight, E., Jr. (1986). Molecular characterization of the interferon-induced 15-kDa protein. Molecular cloning and nucleotide and amino acid sequence. J Biol Chem 261, 8811-8816.

Boone, D. L., Tureri, E. E., Lee, E. G., Ahmad, R. C., Wheeler, M. T., Tsui, C., Hurley, P., Chien, M., Chai, S., Hitotsumatsu, O., et al. (2004). The ubiquitin-modifying enzyme A20 is required for termination of Toll-like receptor responses. Nat Immunol 5, 1052-1060.

Chen, Z. J. (2005). Ubiquitin signaling in the NF-kappaB pathway. Nat Cell Biol 7, 758-765.

Dastur, A., Beaudenon, S., Kelley, M., Krug, R. M., and Huibregtse, J. M. (2006). Herc5, an interferon-induced HECT E3 enzyme, is required for conjugation of ISG15 in human cells. J Biol Chem 281, 4334-4338.

Depiereux, E., Baudoux, G., Briffeuil, P., Reginster, I., De Bolle, X., Vinals, C., and Feytmans, E. (1997). Match-Box server: a multiple sequence alignment tool placing emphasis on reliability. Comput Appl Biosci 13, 249-256.

Dunn, G. P., Bruce, A. T., Sheehan, K. C., Shankaran, V., Uppaluri, R., Bui, J. D., Diamond, M. S., Koebel, C. M., Arthur, C., White, J. M., and Schreiber, R. D. (2005). A critical function for type I interferons in cancer immunoediting. Nat Immunol 6, 722-729.

Evans, P. C., Ovaa, H., Hamon, M., Kilshaw, P. J., Hamm, S., Bauer, S., Ploegh, H. L., and Smith, T. S. (2004). Zinc-finger protein A20, a regulator of inflammation and cell survival, has de-ubiquitinating activity. Biochem J 378, 727-734.

Evans, P. C., Smith, T. S., Lai, M. J., Williams, M. G., Burke, D. F., Heyninck, K., Kreike, M. M., Beyaert, R., Blundell, T. L., and Kilshaw, P. J. (2003). A novel type of deubiquitinating enzyme. J Biol Chem 278, 23180-23186.

Flick, R., and Whitehouse, C. A. (2005). Crimean-Congo hemorrhagic fever virus. Curr Mol Med 5, 753-760.

Fujita, T., Nolan, G. P., Ghosh, S., and Baltimore, D. (1992). Independent modes of transcriptional activation by the p50 and p65 subunits of NF-kappa B. Genes Dev 6, 775-787.

Gack, M. U., Shin, Y. C., Joo, C. H., Urano, T., Liang, C., Sun, L., Takeuchi, O., Akira, S., Chen, Z., Inoue, S., and Jung, J. U. (2007). TRIM25 RING-finger E3 ubiquitin ligase is essential for RIG-I-mediated antiviral activity. Nature 446, 916-920.

Giannakopoulos, N. V., Luo, J. K., Papov, V., Zou, W., Lenschow, D. J., Jacobs, B. S., Borden, E. C., Li, J., Virgin, H. W., and Zhang, D. E. (2005). Proteomic identification of proteins conjugated to ISG15 in mouse and human cells. Biochem Biophys Res Commun 336, 496-506.

Haas, A. L., Ahrens, P., Bright, P. M., and Ankel, H. (1987). Interferon induces a 15-kilodalton protein exhibiting marked homology to ubiquitin. J Biol Chem 262, 11315-11323.

Haller, O., Frese, M., Rost, D., Nuttall, P. A., and Kochs, G. (1995). Tick-borne thogoto virus infection in mice is inhibited by the orthomyxovirus resistance gene product Mx1. J Virol 69, 2596-2601.

Hardwick, J. M., and Levine, B. (2000). Sindbis virus vector system for functional analysis of apoptosis regulators. Methods Enzymol 322, 492-508.

Heise, M. T., Simpson, D. A., and Johnston, R. E. (2000). A single amino acid change in nsP1 attenuates neurovirulence of the Sindbis-group alphavirus S.A.AR86. J Virol 74, 4207-4213.

Honig, J. E., Osborne, J. C., and Nichol, S. T. (2004). Crimean-Congo hemorrhagic fever virus genome L RNA segment and encoded protein. Virology 321, 29-35.

Karin, M., and Ben-Neriah, Y. (2000). Phosphorylation meets ubiquitination: the control of NF-[kappa]B activity. Annu Rev Immunol 18, 621-663.

Kim, K. I., Giannakopoulos, N. V., Virgin, H. W., and Zhang, D. E. (2004). Interferon-inducible ubiquitin E2, Ubc8, is a conjugating enzyme for protein ISGylation. Mol Cell Biol 24, 9592-9600.

Kinsella, E., Martin, S. G., Grolla, A., Czub, M., Feldmann, H., and Flick, R. (2004). Sequence determination of the Crimean-Congo hemorrhagic fever virus L segment. Virology 321, 23-28.

Kirkin, V., and Dikic, I. (2007). Role of ubiquitin- and Ub1-binding proteins in cell signaling. Curr Opin Cell Biol 19, 199-205.

Korant, B. D., Blomstrom, D. C., Jonak, G. J., and Knight, E., Jr. (1984). Interferon-induced proteins. Purification and characterization of a 15,000-dalton protein from human and bovine cells induced by interferon. J Biol Chem 259, 14835-14839.

Lenschow, D. J., Giannakopoulos, N. V., Gunn, L. J., Johnston, C., O'Guin, A. K., Schmidt, R. E., Levine, B., and Virgin, H. W. t. (2005). Identification of interferon-stimulated gene 15 as an antiviral molecule during Sindbis virus infection in vivo. J Virol 79, 13974-13983.

Lenschow, D. J., Lai, C., Frias-Staheli, N., Giannakopoulos, N. V., Lutz, A., Wolff, T., Osiak, A., Levine, B., Schmidt, R. E., Garcia-Sastre, A., et al. (2007). IFN-stimulated gene 15 functions as a critical antiviral molecule against influenza, herpes, and Sindbis viruses. Proc Natl Acad Sci USA 104, 1371-1376.

Levine, B., Goldman, J. E., Jiang, H. H., Griffin, D. E., and Hardwick, J. M. (1996). Bcl-2 protects mice against fatal alphavirus encephalitis. Proc Natl Acad Sci USA 93, 4810-4815.

Loeb, K. R., and Haas, A. L. (1992). The interferon-inducible 15-kDa ubiquitin homolog conjugates to intracellular proteins. J Biol Chem 267, 7806-7813.

Loureiro, J., and Ploegh, H. L. (2006). Antigen presentation and the ubiquitin-proteasome system in host-pathogen interactions. Adv Immunol 92, 225-305.

Lindner, H. A., Fotouhi-Ardakani, N., Lytvyn, V., Lachance, P., Sulea, T., and Menard, R. (2005). The papain-like protease from the severe acute respiratory syndrome coronavirus is a deubiquitinating enzyme. J Virol 79, 15199-15208.

Liu, Y. C., Penninger, J., and Karin, M. (2005). Immunity by ubiquitylation: a reversible process of modification. Nat Rev Immunol 5, 941-952.

Makarova, K. S., Aravind, L., and Koonin, E. V. (2000). A novel superfamily of predicted cysteine proteases from eukaryotes, viruses and Chlamydia pneumoniae. Trends Biochem Sci 25, 50-52.

Malakhov, M. P., Kim, K. I., Malakhova, O. A., Jacobs, B. S., Borden, E. C., and Zhang, D. E. (2003). High-throughput immunoblotting. Ubiquitin-like protein ISG15 modifies key regulators of signal transduction. J Biol Chem 278, 16608-16613.

Malakhov, M. P., Malakhova, O. A., Kim, K. I., Ritchie, K. J., and Zhang, D. E. (2002). UBP43 (USP18) specifically removes ISG15 from conjugated proteins. J Biol Chem 277, 9976-9981.

Meurs, E. F., Watanabe, Y., Kadereit, S., Barber, G. N., Katze, M. G., Chong, K., Williams, B. R., and Hovanessian, A. G. (1992). Constitutive expression of human double-stranded RNA-activated p68 kinase in murine cells mediates phosphorylation of eukaryotic initiation factor 2 and partial resistance to encephalomyocarditis virus growth. J Viro 166, 5805-5814.

Muller, U., Steinhoff, U., Reis, L. F., Hemmi, S., Pavlovic, J., Zinkernagel, R. M., and Aguet, M. (1994). Functional role of type I and type II interferons in antiviral defense. Science 264, 1918-1921.

Nanao, M. H., Tcherniuk, S. O., Chroboczek, J., Dideberg, O., Dessen, A., and Balakirev, M. Y. (2004). Crystal structure of human otubain 2. EMBO Rep 5, 783-788.

Narasimhan, J., Potter, J. L., and Haas, A. L. (1996). Conjugation of the 15-kDa interferon induced ubiquitin homolog is distinct from that of ubiquitin. J Biol Chem 271, 324-330.

Narasimhan, J., Wang, M., Fu, Z., Klein, J. M., Haas, A. L., and Kim, J. J. (2005). Crystal structure of the interferon-induced ubiquitin-like protein ISG15. J Biol Chem 280, 27356-27365.

Nijman, S. M., Luna-Vargas, M. P., Velds, A., Brummelkamp, T. R., Dirac, A. M., Sixma, T. K., and Bernards, R. (2005). A genomic and functional inventory of deubiquitinating enzymes. Cell 123, 773-786.

Niwa, H., Yamamura, K., and Miyazaki, J. (1991). Efficient selection for high-expression transfectants with a novel eukaryotic vector. Gene 108, 193-199.

Nyman, T. A., Matikainen, S., Sareneva, T., Julkunen, I., and Kalkkinen, N. (2000). Proteome analysis reveals ubiquitin-conjugating enzymes to be a new family of interferon-alpha-regulated genes. Eur J Biochem 267, 4011-4019.

Okumura, A., Lu, G., Pitha-Rowe, I., and Pitha, P. M. (2006). Innate antiviral response targets HIV-1 release by the induction of ubiquitin-like protein ISG15. Proc Natl Acad Sci USA 103, 1440-1445.

Osiak, A., Utermohlen, O., Niendorf, S., Horak, I., and Knobeloch, K. P. (2005). ISG15, an interferon-stimulated ubiquitin-like protein, is not essential for STAT1 signaling and responses against vesicular stomatitis and lymphocytic choriomeningitis virus. Mol Cell Bio125, 6338-6345.

Ritchie, K. J., and Zhang, D. E. (2004). ISG15: the immunological kin of ubiquitin. Semin Cell Dev Biol 15, 237-246.

Shin, J. S., Ebersold, M., Pypaert, M., Delamarre, L., Hartley, A., and Mellman, I. (2006). Surface expression of MHC class II in dendritic cells is controlled by regulated ubiquitination. Nature 444, 115-118.

Snijder, E. J., Wassenaar, A. L., Spaan, W. J., and Gorbalenya, A. E. (1995). The arterivirus Nsp2 protease. An unusual cysteine protease with primary structure similarities to both papain like and chymotrypsin-like proteases. J Biol Chem 270, 16671-16676.

Snijder, E. J., Wassenaar, A. L., van Dinten, L. C., Spaan, W. J., and Gorbalenya, A. E. (1996). The arterivirus nsp4 protease is the prototype of a novel group of chymotrypsin-like enzymes, the 3C-like serine proteases. J Biol Chem 271, 4864-4871.

Snijder, E. J., van Tol, H., Roos, N., and Pedersen, K. W. (2001). Non-structural proteins 2 and 3 interact to modify host cell membranes during the formation of the arterivirus replication complex. J Gen Virol 82, 985-994.

Snijder, E. J., Wassenaar, A. L., and Spaan, W. J. (1994). Proteolytic processing of the replicase ORF1a protein of equine arteritis virus. J Virol 68, 5755-5764.

Sudo, K., Yamaji, K., Kawamura, K., Nishijima, T., Kojima, N., Aibe, K., Shimotohno, K., and Shimizu, Y. (2005). High-throughput screening of low molecular weight N53-NS4A protease inhibitors using a fluorescence resonance energy transfer substrate. Antivir Chem Chemother 16, 385-392.

Tergaonkar, V. (2006). NFkappaB pathway: a good signaling paradigm and therapeutic target. Int J Biochem Cell Biol 38, 1647-1653.

Treier, M., Staszewski, L. M., and Bohmann, D. (1994). Ubiquitin-dependent c-Jun degradation in vivo is mediated by the delta domain. Cell 78, 787-798.

Wang, X., Li, M., Zheng, H., Muster, T., Palese, P., Beg, A. A., and Garcia-Sastre, A. (2000). Influenza A virus NS1 protein prevents activation of NF-kappaB and induction of alpha/beta interferon. J Virol 74, 11566-11573.

Wang, Y., Satoh, A., Warren, G., and Meyer, H. H. (2004). VCIP135 acts as a deubiquitinating enzyme during p97-p47-mediated reassembly of mitotic Golgi fragments. J Cell Biol 164, 973-978.

Weck, K. E., Kim, S. S., Virgin, H. I., and Speck, S. H. (1999). B cells regulate murine gammaherpesvirus 68 latency. J Virol 73, 4651-4661.

Welchman, R. L., Gordon, C., and Mayer, R. J. (2005). Ubiquitin and ubiquitin-like proteins as multifunctional signals. Nat Rev Mol Cell Biol 6, 599-609.

Wertz, I. E., O'Rourke, K. M., Zhou, H., Eby, M., Aravind, L., Seshagiri, S., Wu, P., Wiesmann, C., Baker, R., Boone, D. L., et al. (2004). Deubiquitination and ubiquitin ligase domains of A20 downregulate NF-kappaB signaling. Nature 430, 694-699.

Whitehouse, C. A. (2004). Crimean-Congo hemorrhagic fever. Antiviral Res 64, 145-160.

Yoneyama, M., Kikuchi, M., Natsukawa, T., Shinobu, N., Imaizumi, T., Miyagishi, M., Taira, K., Akira, S., and Fujita, T. (2004). The RNA helicase RIG-I has an essential function in double-stranded RNA-induced innate antiviral responses. Nat Immunol 5, 730-737.

Yuan, W., Aramini, J. M., Montelione, G. T., and Krug, R. M. (2002). Structural basis for ubiquitin-like ISG 15 protein binding to the NS1 protein of influenza B virus: a protein-protein interaction function that is not shared by the corresponding N-terminal domain of the NS1 protein of influenza A virus. Virology 304, 291-301.

Yuan, W., and Krug, R. M. (2001). Influenza B virus NS1 protein inhibits conjugation of the interferon (IFN)-induced ubiquitin-like ISG15 protein. Embo J 20, 362-371.

Zhao, C., Beaudenon, S. L., Kelley, M. L., Waddell, M. B., Yuan, W., Schulman, B. A., Huibregtse, J. M., and Krug, R. M. (2004). The UbcH8 ubiquitin E2 enzyme is also the E2 enzyme for ISG15, an IFN-alpha/beta-induced ubiquitin-like protein. Proc Natl Acad Sci USA 101, 7578-7582.

Zhao, C., Denison, C., Huibregtse, J. M., Gygi, S., and Krug, R. M. (2005). Human ISG15 conjugation targets both IFN-induced and constitutively expressed proteins functioning in diverse cellular pathways. Proc Natl Acad Sci USA 102, 10200-10205.

Ziebuhr, J., Snijder, E. J., and Gorbalenya, A. E. (2000). Virus-encoded proteinases and proteolytic processing in the Nidovirales. J Gen Virol 81, 853-879.

Zou, W., and Zhang, D. E. (2006). The interferon-inducible ubiquitin-protein isopeptide ligase (E3) EFP also functions as an ISG15 E3 ligase. J Biol Chem 281, 3989-3994.

Dang, L. C., Melandri, F. D., and Stein, R. L. (1998). Kinetic and mechanistic studies on the hydrolysis of ubiquitin C-terminal 7-amido-4-methylcoumarin by deubiquitinating enzymes. Biochemistry 37, 1868-1879.

Frias-Staheli, N., Giannakopoulos, N. V., Kikkert, M., Taylor, S. L., Bridgen, A., Paragas, J., Richt, J. A., Rowland, R. R., Schmaljohn, C. S., Lenschow, D. J., et al. (2007). Ovarian tumor domain-containing viral proteases evade ubiquitin- and ISG15-dependent innate immune responses. Cell Host Microbe 2, 404-416.

Stein, R. L., Chen, Z., and Melandri, F. (1995). Kinetic studies of isopeptidase T: modulation of peptidase activity by ubiquitin. Biochemistry 34, 12616-12623.

9. EQUIVALENTS

Those skilled in the art will recognize or be able to ascertain, using no more than routine experimentation, many equivalents to the specific embodiments of the invention described herein. Such equivalents are intended to be encompassed by the following claims.

All references cited herein are incorporated herein by reference in their entirety and for all purposes to the same extent as if each individual publication or patent or patent application was specifically and individually indicated to be incorporated by reference in its entirety for all purposes.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed:

1. A method for identifying a compound that modulates the deISGylation activity of a viral OTU domain-containing protein or fragment thereof comprising the OTU domain, comprising:
   a. contacting a compound with a composition comprising ISG15 conjugated protein and the viral OTU domain-containing protein or fragment thereof, and
   b. determining the amount of ISG15 conjugated protein in the composition, wherein an alteration in the amount of ISG15 conjugated protein relative to a negative control indicates that the compound modulates the deISGylation activity of the viral OTU domain-containing protein or fragment thereof.

2. The method of claim 1, wherein a compound with antiviral activity is identified if there is an increase in the amount of ISG15 conjugated protein.

3. The method of claim 1, wherein the compound decreases the deISGylation or deubiquitination activity of the viral OTU domain-containing protein.

4. The method of claim 1, wherein the viral OTU domain-containing protein is a nairovirus OTU domain-containing protein.

5. The method of claim 1, wherein the viral OTU domain-containing protein is the L protein of a nairovirus.

6. The method of claim 5, wherein the nairovirus is Crimean Congo Hemorrhagic Fever Virus (CCHFV) or Dugbe virus.

7. The method of claim 1, wherein the viral OTU domain-containing protein is an arterivirus or herpes virus OTU domain-containing protein.

8. A method for identifying a compound that modulates the deISGylation activity of a viral OTU domain-containing protein, comprising:
   a. contacting a compound with a composition comprising an artificial substrate that mimics ISG15 cleavage from a protein to which it is conjugated and the viral OTU domain-containing protein, and
   b. measuring the amount of cleavage of the artificial substrate, wherein an alteration in the cleavage of the artificial substrate relative to a negative control indicates that the compound modulates the deISGylation activity of the viral OTU domain-containing protein.

9. A method for identifying a compound that reduces the deISGylation activity of a viral OTU domain-containing protein, comprising:
   a. contacting a compound with a composition comprising an artificial substrate that mimics ISG15 cleavage from a protein to which it is conjugated and the viral OTU domain-containing protein, and
   b. measuring the amount of cleavage of the artificial substrate, wherein a decrease in the cleavage of the artificial substrate relative to a negative control indicates that the compound reduces the deISGylation activity of the viral OTU domain-containing protein.

10. The method of claim 8, wherein the artificial substrate is ISG15 fused in its carboxy-terminus to a fluorogenic substrate.

11. The method of claim 9, wherein the artificial substrate is ISG15 fused in its carboxy-terminus to a fluorogenic substrate.

12. The method of claim 10, wherein the fluorogenic substrate is 7-amido-4-methylcoumarin (AMC).

13. The method of claim 11, wherein the fluorogenic substrate is 7-amido-4-methylcoumarin (AMC).

14. The method of claim 8, wherein the artificial substrate is a synthetic AMC substrate that incorporates the carboxy-terminal six residues found in ISG15 (LRLRGG; SEQ ID NO:1).

15. The method of claim 9, wherein the artificial substrate is a synthetic AMC substrate that incorporates the carboxy-terminal six residues found in ISG15 (LRLRGG; SEQ ID NO:1).

16. The method of claim 8, wherein the artificial substrate comprises DABCYL or EDANS moieties on opposite ends of a 12 amino acid peptide which contains the cleavage site LRLRGG (SEQ ID NO:1).

17. The method of claim 9, wherein the artificial substrate comprises DABCYL or EDANS moieties on opposite ends of a 12 amino acid peptide which contains the cleavage site LRLRGG (SEQ ID NO:1).

18. The method of claim 8, wherein the viral OTU domain-containing protein is a nairovirus OTU domain-containing protein.

19. The method of claim 8, wherein the viral OTU domain-containing protein is the L protein of a nairovirus.

20. The method of claim 9, wherein the viral OTU domain-containing protein is the L protein of a nairovirus.

21. The method of claim 19, wherein the nairovirus is Crimean Congo Hemorrhagic Fever Virus (CCHFV) or Dugbe virus.

22. The method of claim 20, wherein the nairovirus is Crimean Congo Hemorrhagic Fever Virus (CCHFV) or Dugbe virus.

23. The method of claim 8, wherein the viral OTU domain-containing protein is an arterivirus or herpes virus OTU domain-containing protein.

24. The method of claim 9, wherein the viral OTU domain-containing protein is an arterivirus or herpes virus OTU domain-containing protein.

25. The method of claim 9, wherein the viral OTU domain-containing protein is a nairovirus OTU domain-containing protein.

* * * * *

UNITED STATES PATENT AND TRADEMARK OFFICE
CERTIFICATE OF CORRECTION

PATENT NO. : 8,709,730 B2
APPLICATION NO. : 12/594774
DATED : April 29, 2014
INVENTOR(S) : Garcia-Sastre et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 833 days.

Signed and Sealed this

Twenty-ninth Day of September, 2015

Michelle K. Lee
*Director of the United States Patent and Trademark Office*